(12) United States Patent
Cook et al.

(10) Patent No.: US 11,813,311 B2
(45) Date of Patent: Nov. 14, 2023

(54) TREATMENT AND PREVENTION OF METABOLIC DISEASES

(71) Applicants: Singapore Health Services PTE LTD., Singapore (SG); National University of Singapore, Singapore (SG)

(72) Inventors: Stuart Alexander Cook, Singapore (SG); Sebastian Schaefer, Singapore (SG); Brijesh Kumar Singh, Singapore (SG); Anissa Widjaja, Singapore (SG)

(73) Assignees: Singapore Health Services PTE LTD., Singapore (SG); National University of Singapore, Singapore (SG)

(*) Notice: Subject to any disclaimer, the term of this patent is extended or adjusted under 35 U.S.C. 154(b) by 234 days.

(21) Appl. No.: 16/865,259

(22) Filed: May 1, 2020

(65) Prior Publication Data

US 2020/0384083 A1 Dec. 10, 2020
US 2021/0177940 A2 Jun. 17, 2021

(30) Foreign Application Priority Data

May 3, 2019 (GB) .................................. 1906291
Jan. 24, 2020 (GB) .................................. 2001013
Feb. 12, 2020 (GB) .................................. 2001896
Feb. 14, 2020 (GB) .................................. 2002030

(51) Int. Cl.
*A61K 39/395* (2006.01)
*A61K 38/20* (2006.01)
*A61P 3/00* (2006.01)
*C12N 15/113* (2010.01)
*C07K 16/24* (2006.01)

(52) U.S. Cl.
CPC ............ *A61K 38/2073* (2013.01); *A61P 3/00* (2018.01); *C07K 16/244* (2013.01); *C12N 15/1136* (2013.01); *A61K 39/3955* (2013.01)

(58) Field of Classification Search
None
See application file for complete search history.

(56) References Cited

U.S. PATENT DOCUMENTS

| | | | |
|---|---|---|---|
| 9,334,331 B2 * | 5/2016 | Igawa | C07K 16/36 |
| 10,421,807 B2 * | 9/2019 | Gonzales | A61P 17/08 |
| 10,865,240 B2 * | 12/2020 | Cook | A61P 1/16 |
| 10,870,696 B2 * | 12/2020 | Cook | C07K 14/7155 |
| 10,889,642 B2 * | 1/2021 | Cook | C07K 14/5428 |
| 10,894,826 B2 * | 1/2021 | Cook | C12N 15/1138 |
| 2014/0193402 A1 | 7/2014 | Wiegand et al. | |
| 2015/0376271 A1 | 12/2015 | Perlroth et al. | |
| 2016/0038589 A1 | 2/2016 | Patel | |
| 2021/0238272 A1 | 8/2021 | Cook et al. | |

FOREIGN PATENT DOCUMENTS

| | | |
|---|---|---|
| WO | WO 2002/007747 A1 | 1/2002 |
| WO | WO 2003/049693 A2 | 6/2003 |
| WO | WO 2014/121325 A1 | 8/2014 |
| WO | WO 2017/103108 A1 | 6/2017 |
| WO | WO 2017/141032 A1 | 8/2017 |
| WO | WO 2018/109168 A1 | 6/2018 |

OTHER PUBLICATIONS

Justice et al. Using the mouse to model human disease: increasing validity and reproducibility. Disease, Models & Mechanisms 9: 101-103, 2016.*
Korinkova et al., 2020, Front. Endocrinol. 11:597583; pp. 1-19.*
Fong et al., 2004, Diabetes Care 27(Suppl. 1): S84-S87.*
Bell et al., 2010, BMC Medical Genomics 3:33; pp. 1-11.*
Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Dearment, "Singapore biotech could get more than $1B from Boehringer Ingelheim under partnership" https://medcitynews.com/2020/01/singapore-biotech-could-get-more-than-1b-from-boehringer-ingelheim-under-partnership/; accessed Oct. 27, 2022.*
Casset et al. (2003, Biochem Biophys Res Comm. 307:198-205).*
MacCallum et al. (1996, J Mol Biol. 262:732-745).*
Lamminmaki et al. (2001, J. Biol. Chem. 276:36687-36694).*
Chen et al. (1994, EMBO J. 14(12):2784-2794).*
International Search Report and Written Opinion for Application No. PCT/EP2020/062193, dated Jun. 23, 2020.
Cook et al., Hiding in Plain Sight: Interleukin-11 Emerges as a Master Regulator of Fibrosis, Tissue Integrity, and Stromal Inflammation. Annu Rev Med. Jan. 27, 2020;71:263-276. doi: 10.1146/annurev-med-041818-011649.
Negahdaripour et al., A panoramic review and in silico analysis of IL-11 structure and function. Cytokine Growth Factor Rev. Dec. 2016;32:41-61. doi: 10.1016/j.cytogfr.2016.06.002. Epub Jun. 4, 2016.
Underhill-Day et al., Functional characterization of W147A: a high-affinity interleukin-11 antagonist. Endocrinology. 2003;144(8):3406-3414. doi:10.1210/en.2002-0144.
Widjaja et al., Inhibiting Interleukin 11 Signaling Reduces Hepatocyte Death and Liver Fibrosis, Inflammation, and Steatosis in Mouse Models of Nonalcoholic Steatohepatitis. Gastroenterology. Sep. 2019; 157(3):777-792.e14. doi: 10.1053/j.gastro.2019.05.002. Epub May 9, 2019.
International Search Report and Written Opinion for Application No. PCT/EP2019/060772, dated Jul. 10, 2019.

(Continued)

*Primary Examiner* — Elizabeth C. Kemmerer

(57) ABSTRACT

Methods of treating and preventing metabolic disease through inhibiting interleukin 11 (IL-11)-mediated signalling are disclosed, as well as agents for use in such methods.

8 Claims, 151 Drawing Sheets

Specification includes a Sequence Listing.

(56) References Cited

OTHER PUBLICATIONS

International Preliminary Report on Patentability for Application No. PCT/EP2019/060772, dated Nov. 5, 2020.
International Preliminary Report on Patentability for Application No. PCT/EP2020/062193, dated Nov. 18, 2021.
Arons et al., Immunoglobulin light chain repertoire in hairy cell leukemia. Leuk Res. Sep. 2007;31(9):1231-6. doi: 10.1016/j.leukres.2006.11.019. Epub Apr. 25, 2007.
D'Angelo et al., Many Routes to an Antibody Heavy-Chain CDR3: Necessary, Yet Insufficient, for Specific Binding. Front Immunol. Mar. 8, 2018;9:395. doi: 10.3389/fimmu.2018.00395.
Schafer et al., IL-11 is a crucial determinant of cardiovascular fibrosis. Nature. Dec. 7, 2017;552(7683):110-115. oi: 10.1038/nature24676. Epub Nov. 13, 2017.
Xu et al., Diversity in the CDR3 region of V(H) is Sufficient for Most Antibody Specificities. Immunity. Jul. 2000; 13(1):37-45. doi: 10.1016/s1074-7613(00)00006-6. PMID: 10933393.

\* cited by examiner

TREATMENT AND PREVENTION OF METABOLIC DISEASES

RELATED APPLICATIONS

This application claims priority from GB2002030.1, filed Feb. 14, 2020, GB2001896.6, filed Feb. 12, 2020, GB 2001013.8, filed Jan. 24, 2020, GB1906597.8, filed May 10, 2019, and GB 1906291.8, filed May 3, 2019, the contents of each of these applications are incorporated herein by reference in their entireties.

FIELD OF THE INVENTION

The present invention relates to the diagnosis, treatment and prophylaxis of metabolic diseases.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 11, 2020, is named E060170009US00-SUBSEQ-JOB and is 62 kilobytes in size.

BACKGROUND TO THE INVENTION

Obesity, Diabetes and Related Conditions

Obesity is defined by the WHO as excessive fat accumulation that might impair health, and diagnosed at a BMI≥kg/m$^2$. Obesity substantially increases the risk of metabolic diseases (including type 2 diabetes mellitus (T2D) and fatty liver disease), cardiovascular diseases (including hypertension, myocardial infarction and stroke), musculoskeletal diseases (e.g. osteoarthritis), Alzheimer disease, depression and some types of cancer (breast, ovarian, prostate, liver, kidney and colon)—see e.g. Bluher, et al., Nat Rev Endocrinol. (2019) 15:288-298 and Prospective Studies Collaboration, Lancet. (2009) 373(9669):1083-96. In addition, obesity might lead to reduced quality of life, unemployment, lower productivity and social disadvantages Berrington de Gonzalez et al., N Engl J Med (2010) 363:2211-2219. Obesity is also associated with decreased life expectancy, with an estimated 5-20 years lost depending on the severity of the condition and comorbid disorders Fontaine et al., JAMA (2003) 289: 187-193.

Over the past 50 years, obesity prevalence has increased to pandemic levels. Worldwide prevalence of obesity has also increased at an alarming rate in children and adolescents from 0.7% to 5.6% in boys and 0.9% to 7.8% in girls between 1975 and 2016 (NCD-RisC, Lancet (2017) 390 (10113):26227-2642). 'Westernization' of lifestyles and hypercaloric food have been shown to be the leading cause of obesity.

One other the most important threats to global human health is the increasing incidences of type 2 diabetes with obesity. Menke et al., JAMA (2015) 314: 1021-1029 examined trends by BMI categories, and diabetes only increased amongst obese subjects (18.0% to 20.1%), suggesting that much of the increase in the prevalence of diabetes is due to the increasing prevalence of obesity. Of particular concern is the high prevalence of diabetes among Asians, who despite having a lower BMI are 30%-50% more likely to develop diabetes than their white counterparts (Lee et al., Diabetes Care (2011) 34, 353-357).

Metformin has demonstrated therapeutic potential, and has been used as first line treatment for diabetes along with adopting a healthy lifestyle that also includes regular exercise to get its anti-obesity benefits (Yerevanian et al., Curr Obes Rep (2019)). Recently, interleukin-1 has also been shown to be a therapeutic target for diabetes to regulate low grade inflammation in T2D (Kataria et al., Semin Immunopathol. (2010)).

Non-Alcoholic Steatohepatitis (NASH)

The global prevalence of non-alcoholic fatty liver disease (NAFLD) is estimated at 25% (Friedman et al., Nat Med. (2018) 24(7): 908-922) and while NAFLD is reversible, it can progress to nonalcoholic steatohepatitis (NASH). NASH is characterized by steatosis-driven inflammation, hepatocyte death and liver fibrosis that eventually leads to liver failure. Hepatic stellate cells (HSCs) are pivotal in the pathogenesis of NASH and give rise to up to 95% of liver myofibroblasts (Mederacke et al. Nat Commun (2013) 4:2823), which drive many of the key pathologies in NASH, namely liver fibrosis, inflammation and parenchymal dysfunction (Friedman, Physiol Rev (2008) 88:125-172; Friedman, J Biol Chem (2000) 275:2247-2250; Higashi et al., Adv Drug Deliv Rev (2017) 121:27-42).

A number of factors are implicated in HSC activation and transformation, including the canonical pro-fibrotic factors transforming growth factor-β1 (TGFβ1) and platelet-derived growth factor (PDGF; Hellerbrand J Hepatol (1999) 30:77-87; Tsuchida and Friedman Nat Rev Gastroenterol Hepatol (2017) 14:397-411) and also pro-inflammatory factors such as CCL2, TNFα and CCL5 (Friedman, J Biol Chem (2000) 275:2247-2250; Tsuchida and Friedman Nat Rev Gastroenterol Hepatol (2017) 14:397-411; Kim et al., Sci Rep (2018) 8:7499). Perhaps reflecting this complexity and implicit redundancy, no single upstream initiating factor has been targeted successfully in NASH and there are no approved NASH drugs. Currently, there are a number of drugs in clinical trials for NASH but many of these target metabolism and it is not clear if they will improve liver fibrosis, which predicts clinical outcomes (Friedman et al., Nat Med. (2018) 24(7): 908-922; Banini et al., Curr Opin Gastroenterol (2017) 33:134-141).

Quiescent HSCs are vitamin A storing cells and very distinct from fibroblasts. However, common factors activate both cell types and stimulate their transition to myofibroblasts with shared features (Mederacke et al. Nat Commun (2013) 4:2823; Iwaisako et al., Proc Natl Acad Sci USA 2014; 111:E3297-305). IL-11 has recently been identified as a crucial factor for cardiovascular and pulmonary fibroblast-to-myofibroblast transformation (Schafer et al., Nature 2017; 552:110-115; Cook et al., (2018) https://doi.org/10.1101/336537). There are very limited insights into IL-11 in the liver but recombinant human IL-11 has been reported to have protective effects when injected to rodents at very high doses (Zhu et al., PLoS One (2015) 10:e0126296; Yu et al., Clin Res Hepatol Gastroenterol (2016) 40:562-570) and was trialled in humans in an attempt to reduce inflammation in advanced hepatitis (Lawitz et al., Am J Gastroenterol 2004; 99:2359-2364).

Wasting Diseases

Wasting can be defined as loss of muscle, with or without loss of fat mass that can manifest as a loss in body weight. A variety of acute and chronic diseases, as well as ageing, are frequently associated with wasting. Wasting may lead to deterioration of nutritional status, loss of muscle mass and function, impaired quality of life and increased risk for morbidity and mortality. Muscle wasting is the most common denominator of wasting, although fat tissue wasting may also occur in isolation or combination with muscle wasting. Examples of wasting disorders include cachexia, sarcopenia (e.g. ageing-related or lack-of-use loss of skeletal muscle mass and strength), anorexia (lack or loss of appetite for food), myopenia (a term suggested to describe muscle wasting generally), lipodystrophy (specific wasting of fat deposits) and lipoatrophy. The currently-accepted definition of cachexia is: "a multifactorial syndrome characterised by an ongoing loss of skeletal muscle mass (with or without loss of fat mass) that cannot be fully reversed by conventional nutritional support and leads to progressive functional impairment" (Evans et al. Clin Nutr. 2008 (6):793-9).

Wasting is highly prevalent in patients with late-stage chronic illnesses. Approximately 5-15% of patients with chronic heart failure or chronic obstructive pulmonary disease display a wasting disorder, while wasting disorders are experienced by 60-80% of patients with advanced cancer, according to the Society on Sarcopenia, Cachexia and Wasting Disorders (SCWS). Cachexia is directly attributable for 20% of cancer deaths (Skipworth et al, Clin Nutr. 2007; 26:667-76). Wasting has been noted in patients with infectious disease, such as HIV/AIDS, malaria and tuberculosis, as well as in chronic conditions such as cystic fibrosis, liver cirrhosis, renal failure, Crohn's disease, rheumatoid arthritis, stroke, and neurological degenerative disease. Traumatic injury, post-surgery, weightlessness, chronic alcoholism and sepsis are also associated with the onset of wasting (Farkas et al. J Cachexia Sarcopenia Muscle (2013) 4:173-178).

Wasting and wasting disorders often have a negative impact on the treatment of underlying diseases: they can impair patient response to treatment for the underlying disease, harm the immune system and lead to worsened symptoms of the underlying condition. Therefore, treatments that improve wasting may increase the efficacy of treatments for underlying diseases/conditions and improve prognosis for patients.

For example, advanced cancer-associated cachexia often leads to poor prognosis with respect to anti-cancer treatments. Cancer patients experiencing weight loss leading up to and during chemotherapy receive a lower initial dose and experience more frequent and severe dose-limiting toxicity when compared to weight-stable patients, and thus receive significantly less treatment or indeed may be excluded from a treatment regime from the outset (Vaughan et al. J Cachexia Sarcopenia Muscle (2013) 4:95-109). An effective treatment for wasting would result in more positive outcomes for such patients.

Presently, treatment for wasting includes appetite stimulants and exercise to build up muscle mass. However, nutritional supplementation or pharmacological manipulation of appetite alone is often unable to reverse the wasting process, particularly when severe or at a late stage. Eicosapentaenoic acid (EPA; an omega-3 fatty acid from fish oils) has been tested for its effect in improving cachexia in a cancer context, but results from trials have been contradictory (Jatoi et al, J Clin Oncol. 2004; 22:2469-76). Antioxidants and non-steroidal anti-inflammatories have been trialled and combinations of these treatments with e.g. EPA, oxidative stress inhibitors and/or appetite stimulants are thought to have potential in treating wasting. Inhibition of the ubiquitin proteolytic pathway (UPP) is of particular interest. Inhibition of muscle inhibiting substances such as myostatin have not been successful in clinical trials.

The multi-factorial nature of wasting in combination with underlying diseases means that there is no globally effective or accepted treatment for wasting, or even any approved drug therapies. Indeed, it is generally accepted that the only way to treat disease-associated wasting is to cure the underlying disease (Vaughan et al. J Cachexia Sarcopenia Muscle (2013) 4:95-109). Thus, new therapies for wasting are needed.

SUMMARY OF THE INVENTION

The present invention provides an agent capable of inhibiting interleukin 11 (IL-11)-mediated signalling for use in a method of treating or preventing a metabolic disease.

Also provided is the use of an agent capable of inhibiting interleukin 11 (IL-11)-mediated signalling in the manufacture of a medicament for use in a method of treating or preventing a metabolic disease.

Also provided is a method of treating or preventing a metabolic disease, comprising administering a therapeutically or prophylactically effective amount of an agent capable of inhibiting interleukin 11 (IL-11)-mediated signalling to a subject.

In some embodiments the metabolic disease is, or comprises, obesity, type 2 diabetes (T2D), type 1 diabetes (T1D), pre-diabetes, being overweight, metabolic syndrome, pregnancy-associated hyperglycemia, cholestatic liver disease, hyperglycaemia, hyperlipidaemia, hypertriglyceridemia, hypercholesterolemia, wasting, cachexia, chemotherapy-associated weight loss, pancreatic insufficiency, pancreatitis, acute pancreatitis, chronic pancreatitis, steatosis, lipotoxicity, non-alcoholic fatty liver disease (NAFLD), non-alcoholic fatty liver (NAFL), non-alcoholic steatohepatitis (NASH), lipodystrophy, lipohypertrophy, lipoatrophy, insulin resistance or hyperglucagonemia.

In some embodiments the agent is an agent capable of preventing or reducing the binding of interleukin 11 (IL-11) to a receptor for interleukin 11 (IL-11R).

In some embodiments the agent is capable of binding to interleukin 11 (IL-11) or a receptor for interleukin 11 (IL-11R).

In some embodiments the agent is selected from the group consisting of: an antibody or an antigen-binding fragment thereof, a polypeptide, a peptide, a nucleic acid, an oligonucleotide, an aptamer or a small molecule.

In some embodiments the agent is an antibody or an antigen-binding fragment thereof.

In some embodiments the agent is a decoy receptor.

In some embodiments, the agent is an anti-IL-11 antibody antagonist of IL-11-mediated signalling, or an antigen-binding fragment thereof. In some embodiments, the agent is an anti-IL-11 Rα antibody antagonist of IL-11-mediated signalling, or an antigen-binding fragment thereof.

In some embodiments, the agent is a decoy receptor for IL-11. In some embodiments the decoy receptor for IL-11 comprises: (i) an amino acid sequence corresponding to the cytokine binding module of gp130 and (ii) an amino acid sequence corresponding to the cytokine binding module of IL-11 Rα.

In some embodiments the agent is an IL-11 mutein. In some embodiments the IL-11 mutein is W147A.

In some embodiments the agent is capable of preventing or reducing the expression of interleukin 11 (IL-11) or a receptor for interleukin 11 (IL-11R).

In some embodiments the agent is an oligonucleotide or a small molecule.

In some embodiments the agent is an antisense oligonucleotide capable of preventing or reducing the expression of IL-11. In some embodiments the antisense oligonucleotide capable of preventing or reducing the expression of IL-11 is siRNA targeted to IL11 comprising the sequence of SEQ ID NO:12, 13, 14 or 15. In some embodiments the agent is an antisense oligonucleotide capable of preventing or reducing the expression of IL-11Rα. In some embodiments the antisense oligonucleotide capable of preventing or reducing the expression of IL-11Rα is siRNA targeted to IL11RA comprising the sequence of SEQ ID NO:16, 17, 18 or 19.

In some embodiments the interleukin 11 receptor is or comprises IL-11Rα.

In some embodiments the method comprises administering the agent to a subject in which expression of interleukin 11 (IL-11) or a receptor for IL-11 (IL-11R) is upregulated.

In some embodiments the method comprises administering the agent to a subject in expression of interleukin 11 (IL-11) or a receptor for interleukin 11 (IL-11R) has been determined to be upregulated.

In some embodiments the method comprises determining whether expression of interleukin 11 (IL-11) or a receptor for IL-11 (IL-11R) is upregulated in the subject and administering the agent to a subject in which expression of interleukin 11 (IL-11) or a receptor for IL-11 (IL-11R) is upregulated.

DESCRIPTION

Interleukin 11 and Receptors for IL-11

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types. IL-11 genomic sequences have been mapped onto chromosome 19 and the centromeric region of chromosome 7, and is transcribed with a canonical signal peptide that ensures efficient secretion from cells. The activator protein complex of IL-11, cJun/AP-1, located within its promoter sequence is critical for basal transcriptional regulation of IL-11 (Du and Williams., Blood 1997, Vol 89: 3897-3908). The immature form of human IL-11 is a 199 amino acid polypeptide whereas the mature form of IL-11 encodes a protein of 178 amino acid residues (Garbers and Scheller., Biol. Chem. 2013; 394(9):1145-1161). The human IL-11 amino acid sequence is available under UniProt accession no. P20809 (P20809.1 GI:124294; SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. In preferred embodiments the species is human (*Homo sapiens*). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 60, 70, 80, 90, 100, 110, 120, 130, 140, 150, 160, 170, 180, 190 or 195 amino acids.

IL-11 signals through a homodimer of the ubiquitously expressed glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual interleukin 11 receptor subunit alpha (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt Q14626; SEQ ID NO:3) and shares ~85% nucleotide and amino acid sequence identity with the murine IL-11Rα. Two isoforms of IL-11Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification a receptor for IL-11 (IL-11R) refers to a polypeptide or polypeptide complex capable of binding IL-11. In some embodiments an IL-11 receptor is capable of binding IL-11 and inducing signal transduction in cells expressing the receptor.

An IL-11 receptor may be from any species and includes isoforms, fragments, variants or homologues of an IL-11 receptor from any species. In preferred embodiments the species is human (*Homo sapiens*).

In some embodiments the IL-11 receptor may be IL-11Rα. In some embodiments a receptor for IL-11 may be a polypeptide complex comprising IL-11Rα. In some embodiments the IL-11 receptor may be a polypeptide complex comprising IL-11Rα and gp130. In some embodiments the IL-11 receptor may be gp130 or a complex comprising gp130 to which IL-11 binds.

Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

IL-11 Signalling

IL-11 binds to IL-11Rα with low affinity (Kd~10 nmol/L), and interaction between these binding partners alone is insufficient to transduce a biological signal. The generation of a high affinity receptor (Kd~400 to 800 pmol/L) capable of signal transduction requires co-expression of the IL-11Rα and gp130 (Curtis et al Blood 1997; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT5 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be important for disease pathogenesis, yet its role in human disease has not yet been studied.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling". In preferred embodiments, inhibition of IL-11-mediated signalling is achieved by disrupting IL-11-mediated cis signalling.

IL-11-mediated signalling has been shown to stimulate hematopoiesis and thrombopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells (Du and Williams, supra).

The physiological role of Interleukin 11 (IL-11) remains unclear. IL-11 has been most strongly linked with activation of haematopoetic cells and with platelet production. IL-11 has also been shown to confer protection against graft-vs-host-disease, inflammatory arthritis and inflammatory bowel disease, leading to IL-11 being considered an anti-inflammatory cytokine (Putoczki and Ernst, J Leukoc Biol 2010, 88(6):1109-1117). However, it is suggested that IL-11 is pro-inflammatory as well as anti-inflammatory, pro-angiogenic and important for neoplasia. Recent studies have shown that IL-11 is readily detectable during viral-induced inflammation in a mouse arthritis model and in cancers, suggesting that the expression of IL-11 can be induced by pathological stimuli. IL-11 is also linked to Stat3-dependent activation of tumour-promoting target genes in neoplastic gastrointestinal epithelium (Putoczki and Ernst, supra).

As used herein, "IL-11 signalling" and "IL-11-mediated signalling" refers to signalling mediated by binding of IL-11, or a fragment thereof having the function of the mature IL-11 molecule, to a receptor for IL-11. It will be appreciated that "IL-11 signalling" and "IL-11 mediated signalling" refer to signalling initiated by IL-11/functional fragment thereof, e.g. through binding to a receptor for IL-11. "Signalling" in turn refers to signal transduction and other cellular processes governing cellular activity.

Metabolic Diseases

The present invention is concerned with the treatment and/or prevention of metabolic diseases.

As used herein, a "metabolic disease" refers to any disease or condition which is caused by, or which is characterised by, abnormal metabolism. "Metabolism" in this context refers to the bodily conversion/processing of sources of energy, e.g. substances consumed to provide nutrition, into energy and/or for storage.

"Normal metabolism" may be the metabolism of a healthy subject not having a disease, e.g. not having a metabolic disease, or not possessing a symptom/correlate of a metabolic disease.

A subject having a metabolic disease may display abnormal metabolism. A subject having a metabolic disease may have a symptom/correlate of abnormal metabolism. A subject having a metabolic disease may have been diagnosed as having metabolic disease. A subject may satisfy the diagnostic criteria for the diagnosis of a metabolic disease.

In some embodiments the metabolic disease is, or comprises (e.g. is characterised by), obesity, type 2 diabetes (T2D), type 1 diabetes (T1 D), pre-diabetes, being overweight, metabolic syndrome, pregnancy-associated hyperglycemia (i.e. gestational diabetes), cholestatic liver disease, hyperglycaemia, hyperlipidaemia, hypertriglyceridemia, hypercholesterolemia, wasting, cachexia, chemotherapy-associated weight loss, pancreatic insufficiency, pancreatitis, acute pancreatitis, chronic pancreatitis, steatosis, lipotoxicity, non-alcoholic fatty liver disease (NAFLD), non-alcoholic fatty liver (NAFL), non-alcoholic steatohepatitis (NASH), lipodystrophy, lipohypertrophy, lipoatrophy, insulin resistance and hyperglucagonemia.

Aspects of the present invention are concerned with the treatment and/or prevention of aberrant and/or insufficient function of cells/tissue(s)/organ(s)/organ systems having a role in metabolism. In particular, treatment and/or prevention of aberrant function and/or insufficient function of cells of the pancreas/pancreatic tissue/the pancreas is contemplated herein, as is the treatment and/or prevention of aberrant function and/or insufficient function of cells of the liver/hepatic tissue/the liver.

In some embodiments the metabolic disease is, or comprises, obesity. Obesity is characterised by excess body fat. The diagnosis of obesity is reviewed e.g. in Orzano and Scott, J Am Board Fam Pract (2004) 17(5): 359-369, which is hereby incorporated by reference in its entirety. Obese subjects have a body mass index (BMI; calculated by dividing a person's weight by the square of their height) which is over 30 kg/m$^2$. In some embodiments the metabolic disease is, or comprises, being overweight. Being overweight is characterised by having a BMI of greater than 25 kg/m$^2$, and less than 30 kg/m$^2$ (Fact sheet No 311", WHO (2015)). Obesity and being overweight are commonly caused by a combination of excessive food intake, lack of physical activity, and genetic susceptibility.

In some embodiments the metabolic disease is, or comprises, diabetes mellitus (often also referred to as simply as 'diabetes'). Diabetes refers to a group of metabolic diseases characterised by high blood sugar levels over a prolonged period (Diabetes Fact sheet No 312". WHO, (2013)). Diagnosis of diabetes according to the American Diabetes Association (ADA) requires the detection of hemoglobin A1c level of 6.5%, a fasting plasma glucose (FPG) level (defined as no caloric intake for at least 8 hours) ≥126 mg/dl (7.0 mmol/l), 2-h plasma glucose after ingestion of 75 g of oral glucose load of ≥200 mg/dl (11.1 mmol/l), or detection in a patient with classic symptoms of hyperglycemia or hyperglycemic crisis, a random plasma glucose ≥200 mg/dl (11.1 mmol/l) (American Diabetes Association, Diabetes Care (2010) 33(Suppl 1): S62-S69). Symptoms of diabetes include frequent urination, increased thirst, and increased hunger. The underlying cause of diabetes is usually insufficient insulin production by the pancreas, or the cells of the body not responding properly to the insulin produced.

There are three main types of diabetes, which are described e.g. in Diabetes Fact sheet No 312". WHO, (2013). Type 1 diabetes (T1 D) results from failure of the pancreas to produce sufficient insulin due to insufficient numbers of insulin-producing β cells from pancreatic islets. T1 D and its diagnosis is reviewed e.g. by Kahanovitz et al., Point Care. (2017) 16(1): 37-40, which is hereby incorporated by reference in its entirety. Type 2 diabetes (T2D) results from failure of a subject's cells to respond to insulin properly, and may progress to also include insufficient insulin production. T2D is most commonly caused by excess body weight and insufficient exercise. T2D is reviewed by DeFronzo, Nature Reviews Disease Primers (2015) 1:15019, which is hereby incorporated by reference in its entirety. Gestational diabetes (also referred to as pregnancy-associated hyperglycemia) occurs when pregnant women develop high blood sugar levels. Gestational diabetes is caused by insufficient production of the extra insulin required during pregnancy, in the context of insulin resistance which is associated with pregnancy. Gestational diabetes is reviewed e.g. in Kampmann et al., World J Diabetes. (2015) 6(8):1065-1072, which is hereby incorporated by reference in its entirety.

In some embodiments the metabolic disease is, or comprises, insulin deficiency. In some embodiments the metabolic disease is, or comprises, insulin resistance. In some embodiments the metabolic disease is, or comprises, hyperglycaemia. In some embodiments the metabolic disease is, or comprises, type 2 diabetes (T2D). In some embodiments the metabolic disease is, or comprises, type 1 diabetes (T1 D). In some embodiments the metabolic disease is, or comprises, pregnancy-associated hyperglycemia.

In some embodiments the metabolic disease is, or comprises, pre-diabetes. Pre-diabetes refers to a state of hyperglycemia, in which blood sugar levels are elevated for a prolonged period of time, but to a level below that required for diagnosis of diabetes. Pre-diabetes and its diagnosis is reviewed e.g. by Bansal World J Diabetes. (2015) 6(2):296-303, which is hereby incorporated by reference in its entirety. The WHO defines prediabetes as a state of intermediate hyperglycemia, diagnosed by the determination of a FPG level of 6.1-6.9 mmol/L (110 to 125 mg/dL), and 2 h plasma glucose level of 7.8-11.0 mmol/L (140-200 mg/dL) after ingestion of 75 g of oral glucose load. Diagnosis of prediabetes according to the ADA requires 2 h plasma glucose level of 7.8-11.0 mmol/L (140-200 mg/dL) after ingestion of 75 g of oral glucose load, FPG level of 100-125 mg/dL, and hemoglobin A1c level of 5.7% to 6.4%.

In some embodiments the metabolic disease is, or comprises, metabolic syndrome. Metabolic syndrome is reviewed e.g. by Rochlani et al., Cardiovascular Disease (2017) 215-225, which is hereby incorporated by reference in its entirety. The WHO define metabolic syndrome as the presence of insulin resistance (impaired fasting glucose, impaired glucose tolerance, or T2D) in addition to two of: obesity, hyperlipidemia (hypertriglyceridemia or low high-density lipoprotein (HDL) cholesterol), hypertension, or microalbuminuria. Several other definitions for metabolic syndrome exist, and are summarised in Table 1 of Rochlani et al., supra.

In some embodiments the metabolic disease is, or comprises, cholestasis. Cholestasis refers to a reduced flow of bile from the liver to the duodenum. In some embodiments the metabolic disease is, or comprises, cholestatic liver disease. Cholestatic liver disease results from the insufficient bile synthesis, secretion and/or flow through the biliary tract, and is reviewed e.g. in Jansen et al., Hepatology (2017) 65(2):722-738 and Pollock and Minuk, J Gastroenterol Hepatol (2017) 32(7):1303-1309, both of which are hereby incorporated by reference in their entirety. Cholestatic liver diseases include primary biliary cholangitis (PBC) and primary sclerosing cholangitis (PSC), In some embodiments the metabolic disease is, or comprises, hyperlipidaemia. Hyperlipidaemia refers to an elevated level of lipid or lipoprotein in the blood. Hyperlipidaemia includes hypertriglyceridemia, hypercholesterolemia and combined hyperlipidaemia (combination of hypertriglyceridemia and hypercholesterolemia). Hyperlipidaemia is associated e.g. with atherosclerosis and cardiovascular disease.

In some embodiments the metabolic disease is, or comprises, hypertriglyceridemia. Hypertriglyceridemia is described e.g. in Berglund et al., J. Clin. Endocrinol. Metab. (2012) 97(9):2969-89, and is defined by blood triglyceride level ≥50 mg/dL (≥1.7 mmol/L).

In some embodiments the metabolic disease is, or comprises, hypercholesterolemia. Hypercholesterolemia is described e.g. in Bhatnagar et al., BMJ (2008) 337:a993. The UK NHS defines hypercholesterolemia as blood total cholesterol level of ≥5 mmol/L or blood low-density lipoprotein (LDL) level of mmol/L. The US NIH defines hypercholesterolemia as blood total cholesterol level of 240 mg/dL.

In some embodiments the metabolic disease is, or comprises, pancreatic insufficiency. Pancreatic insufficiency may be endocrine or exocrine. Endocrine pancreatic insufficiency may be charaterised by insufficient production of one or more of insulin, amylin, glucagon, somatostatin, ghrelin and pancreatic polypeptide (PP). Exocrine pancreatic insufficiency may be charaterised by insufficient production of one or more of pancreatic juice, digestive enzymes, trypsinogen, chymotrypsinogen, elastase, carboxypeptidase, pancreatic lipase, nucleases and amylase, and consequent inability to properly digest food. Pancreatic insufficiency is generally caused by the loss of pancreatic cells that produce the relevant factors, e.g. islet cells in the case of endocrine function, and acinar cells in the case of exocrine function. Exocrine pancreatic insufficiency is described e.g. in Struyvenberg et al., BMC Med (2017) 15:29, which is hereby incorporated by reference in its entirety. The most common cause of pancreatic insufficiency is pancreatitis, but it can also be caused by cystic fibrosis, surgery, celiac disease and diabetes.

In some embodiments the metabolic disease is, or comprises, pancreas injury. Herein, 'injury' refers to damage to the relevant organ and/or tissue or cells of the organ. Damage to a cell/tissue/organ may result from insult to the cell/tissue/organ, e.g. chemical or physical treatment/experience. In some embodiments injury may be a consequence of chemical insult, e.g. in the case of drug-induced injury. In some embodiments injury may arise from physical insult, e.g. injury as a result of surgical damage, which may occur e.g. during surgery to treat a disease and/or for transplantation (e.g. the injury may have iatrogenic causes). In some embodiments injury may be a consequence of hypoxia, e.g. as a consequence of ischaemia, or may result from reperfusion. In some embodiments injury may arise from infection, immune response to infection, cancer and/or autoimmunity. Damage may be reversible or irreversible. Damage to a cell/tissue/organ may be characterised by a change to the structure and/or function of the cell/tissue/organ. For example, damage to a cell/tissue/organ may be characterised by a reduction in the level of a correlate of normal function of the cell/tissue/organ, and/or an increase in a correlate of impaired function of the cell/tissue/organ. Damage to a cell/tissue/organ may be characterised by cell death, e.g. death of cells of the damaged organ/tissue. The cell death may result from apoptosis (i.e. programmed cell death) or necrosis (premature cell death as a consequence of damage).

In some embodiments the metabolic disease is, or comprises, pancreatitis. Pancreatitis is characterised by inflammation of the pancreas. Pancreatitis may be acute or chronic. Acute pancreatitis is reviewed e.g. in Shah et al., J Inflamm Res (2018) 11:77-85, which is hereby incorporated by reference in its entirety. Acute pancreatitis is most commonly caused by gallstones, but can also be caused by alcohol and metabolic diseases amongst others. Chronic pancreatitis is reviewed e.g. in Pham et al Version 1. F1000Res (2018) 7: F1000 Faculty Rev-607, which is hereby incorporated by reference in its entirety. Chronic pancreatitis is a syndrome involving chronic inflammation, fibrosis, and loss of acinar and islet cells which can manifest in exocrine and endocrine insufficiency.

In some embodiments the metabolic disease is, or comprises, steatosis. Steatosis refers to the abnormal retention of lipid within a cell/tissue/organ. Steatosis may be macrovesicular or microvesicular.

In some embodiments, the metabolic disease is characterised by accumulation of molecules containing lipid moieties (or derivatives thereof) in non-adipose tissue. In some embodiments the metabolic disease is, comprises, is characterised by or is associated with lipotoxicity.

As used herein, lipotoxicity refers to damage, dysfunction or and/or death of cells/tissue resulting from accumulation of molecules containing lipid moieties (or derivatives thereof) in non-adipose tissue. In some embodiments in accordance with the present disclosure, lipotoxicity is of cells of the liver, kidney, heart and/or skeletal muscle. In some embodiments lipotoxicity is of cells of the liver (e.g. hepatocytes).

Metabolic diseases characterised by/associated with lipotoxicity include e.g. non-alcoholic fatty liver disease (NAFLD) and NASH. Accumulation of lipid in hepatocytes and its relevance to NAFLD and in particular NASH is described in Friedman et al., Nat. Med. (2018) 24(7):908-922 and Farrell et al., Adv. Exp. Med. Biol. (2018) 1061: 19-44 (both of which are hereby incorporated by reference in their entirety).

NAFLD such as NASH is thought to arise as a consequence of lipotoxicity to hepatocytes. Lipotoxic factors are thought to include free (unesterified) cholesterol, saturated free fatty acids (e.g. palmitic acid), diacylglycerols, lysophosphatidyl-choline, sphingolipids and ceramide. Hepatocytes are unable to sequester such chemically-reactive lipid molecules, resulting in mitochondrial injury, endoplasmic reticulum (ER) stress and autophagy. Lipotoxicity results in hepatocyte apoptosis, and also necrosis, necroptosis and pyroptosis which activate the innate immune system and trigger expression of proinflammatory factors. Proinflammatory cytokines and chemokines in turn recruits inflammatory cells such as macrophages and neutrophils.

In the present Examples (in particular Example 5), the inventors demonstrate that autocrine IL-11-mediated signalling is an important component of lipotoxic signalling (e.g. in hepatocytes), and that lipototxicity (and its downstream consequences) can be inhibited by antagonising IL-11-mediated signalling. Accordingly, aspects of the present disclosure provide for the treatment/prevention of lipotoxicity or diseases characterised by, or associated with, lipotoxicity, through antagonising IL-11 mediated signalling.

Importantly, the inventors demonstrate herein at Example 5.3.5 that IL-11 mediated-signalling is an important component of lipotoxicity in hepatocytes associated with NAFL and leading to NASH upstream of and separately to IL-11-mediated activation of HSCs to myofibroblasts. Accordingly, aspects of the present disclosure provide for the treatment/prevention of NAFLD (e.g. NASH) comprising inhibition of lipotoxicity in hepatocytes through antagonising IL-11 mediated signalling.

In some embodiments the metabolic disease non-alcoholic fatty liver disease (NAFLD). NAFLD is reviewed e.g. in Benedict and Zhang, World J Hepatol. (2017) 9(16): 715-732 and Albhaisi et al., Version 1. F1000Res. (2018) 7: F1000 Faculty Rev-720, both of which are hereby incorporated by reference in their entirety. NAFLD is characterised by steatosis of the liver, and in particular of hepatocytes. NAFLD includes non-alcoholic fatty liver (NAFL) and non-alcoholic steatohepatitis (NASH). NAFL is characterized by steatosis of the liver, involving greater than 5% of parenchyma, with no evidence of hepatocyte injury. NAFL may progress to NASH, which is steatosis combined with inflammation and/or fibrosis (steatohepatitis).

In some embodiments the metabolic disease is, or comprises, lipodystrophy. Lipodystrophy is reviewed e.g. in Fiorenza et al., Nature Reviews Endocrinology (2011) 7: 137-150, which is hereby incorporated by reference in its entreity. Lipodystrophy refers to the inability to produce and/or maintain healthy fat tissue, and encompasses complete or partial loss of adipose tissue (lipoatrophy), that can occur in conjunction with pathological accumulation of adipose tissue (lipohypertrophy). Lipodystrophy can be inherited or acquired, although inherited lipodystrophy syndromes are rare. In some embodiments the metabolic disease is, or comprises, lipoatrophy. In some embodiments the metabolic disease is, or comprises, lipohypertrophy.

In some embodiments the metabolic disease is, or comprises, hyperglucagonemia. Hyperglucagonemia is described e.g. in Wewer Albrechtsen et al., Biomark Med. (2016) (11):1141-1151, which is hereby incorporated by reference in its entirety.

In some embodiments the metabolic disease is, or comprises, wasting. As used herein, the term "wasting" refers to involuntary weight loss, which may be progressive and/or degenerative. Wasting can be defined as loss of muscle with or without loss of fat mass, and typically involves significant, usually involuntary, loss of body mass (including skeletal muscle), and may or may not include loss of adipose tissue. In some instances, adipose tissue wasting can occur in isolation, as seen in lipodystrophy diseases. Wasting may be characterised by a negative protein and energy balance driven by a variable combination of reduced food intake and abnormal metabolism (Fearon et al. Lancet Oncol. (2011) 12(5):489-95). Wasting can lead to progressive functional impairment, impaired quality of life, increased risk for morbidity and mortality. In some cases, wasting leads to asthenia (abnormal physical weakness or lack of energy) and/or anaemia (deficiency of red cells or haemoglobin in the blood). In some cases, wasting cannot be fully reversed by conventional nutritional support or by therapeutic interventions that have been trialled to date. Death usually occurs once weight loss has reached 30% of the patient's historic stable body weight (Tisdale, Nature Reviews Cancer, 2, 862-871 (2002)).

Diseases/conditions characterised by wasting include cachexia (non-age-related loss of muscle mass), sarcopenia (loss of muscle mass: e.g. age-related, disuse, space travel or denervation), anorexic disorders (protein-energy malnutrition), muscular dystrophies, lipodystrophies (e.g. abnormal or degenerative condition of adipose tissue), lipoatrophy (age-related loss of subcutaneous fat in the face and other tissues) and myopenia (muscle wasting in any chronic illness; proposed by Fearon et al. J Cachexia Sarcopenia Muscle. 2011; 2:1-3). Herein, diseases/conditions characterised by wasting are also referred to as "wasting disorders". In some embodiments a wasting disorder according to the present disclosure is cachexia, pre-cachexia, refractory cachexia, sarcopenia, anorexia, lipodystrophy, lipoatrophy and/or myopenia. In some embodiments according to the various aspects described herein, the wasting disorder is cachexia, pre-cachexia and/or refractory cachexia.

Wasting disorders arising due to chronic illness may include "mild muscle wasting disease" (with or without frailty), "moderate muscle wasting disease" (with or without frailty; sometimes known as "pre-cachexia"), or "severe muscle wasting disease" (sometimes called "cachexia", often with frailty present).

Cachexia is a complex inflammatory/metabolic syndrome associated with underlying illness (which may be an acute or chronic illness) and characterised by wasting. The prominent clinical feature of cachexia is weight loss in adults (corrected for fluid retention) or growth failure in children (excluding endocrine disorders). Anorexia, inflammation, insulin resistance, increased muscle protein breakdown and increased basal metabolic rate are frequently associated with cachexia. Low lipid levels and fatty livers in cachexia patients suggest a role for hepatic metabolism in the pathogenesis of cachexia. Thus, therapies targeting the liver and preventing fatty liver, liver damage or liver metabolism may have a direct relevance for cachexia. Cachexia is distinct from starvation, age-related loss of muscle mass, primary depression, malabsorption and hyperthyroidism and is associated with increased morbidity (Evans et al. Clin Nutr. 2008 (6):793-9).

Cachexia can be defined as involuntary weight loss of >5% from historical stable weight, a body mass index (BMI) of <20 kg/m$^2$ (person younger than 65) or <22 kg/m$^2$ (person aged 65 or older) with any degree of weight loss >2%, or a skeletal muscle index consistent with sarcopenia with any degree of weight loss >2%. The subject may also display <10% body fat and/or a low blood albumin level of <35 g/l. These criteria may also help to identify populations 'at-risk' of developing a wasting disorder (Fearon et al. Lancet Oncol. 2011; 12(5):489-95).

A three-step classification of cachexia has been proposed, with severity classified according to degree of depletion of energy stores and body protein (BMI) in combination with degree of ongoing weight loss.
1. Pre-cachexia—when a patient has weight loss <5%, but has not yet developed serious complications.
2. Cachexia—where the syndrome is progressing, with weight loss exceeding the above-mentioned parameters, but still potentially able to be treated.
3. Refractory cachexia—the point at which the disease is no longer responsive to treatment or when treatment benefits are outweighed by burden and risk (Fearon et al, supra). Often, the refractory stage is dictated by the overall stage of an underlying illness, described below, and the condition of the patient.

Metabolic diseases may be present in acute or chronic disease settings. Aspects of the present invention provide for the treatment/prevention of diseases/conditions associated with metabolic diseases. Disease/conditions associated with metabolic diseases include diseases/conditions that are positively associated with the onset of a metabolic disease. In some embodiments, the disease/condition associated with a metabolic disease is one which can cause/causes/has caused (i.e. can lead to, leads to or has led to) a metabolic disease.

Disease/conditions associated with metabolic diseases also include diseases/conditions which are caused and/or exacerbated (made worse, progressed and/or complicated) by a metabolic disease. In some embodiments a disease/condition associated with a metabolic disease, may be positively associated with the onset of a metabolic disease and may also be exacerbated by a metabolic disease. An "associated" disease/condition may be one comprising a metabolic disease-related pathology.

In embodiments of the invention, a metabolic disease, or a disease/condition associated with a metabolic disease may be present in or affect any organ/tissue, such as the heart, liver, kidney, brain, skin, muscular system, stomach, small intestine, large intestine, pancreas, mouth, salivary glands, pharynx, esophagus, gallbladder, trachea, larynx, bladder, ovary, uterus, testes, glands of the endocrine system e.g. pituitary or thyroid, the lymphatic system e.g. spleen.

In embodiments of the invention, a disease/condition associated with a metabolic disease may be one or more of cancer, cardiac disease, kidney disease, lung disease, liver disease, chronic infection, neurological degenerative diseases, acute injury, traumatic injury/trauma, post-operative conditions, or ageing/senescence.

In some embodiments, a metabolic disease may be recognised/identified/diagnosed using one or more biomarkers or correlates of the metabolic disease.

Agents Capable of Inhibiting the Action of IL-11

Aspects of the present invention involve inhibition of IL-11-mediated signalling.

Herein, 'inhibition' refers to a reduction, decrease or lessening relative to a control condition. For example, inhibition of the action of IL-11 by an agent capable of inhibiting IL-11-mediated signalling refers to a reduction, decrease or lessening of the extent/degree of IL-11-mediated signalling in the absence of the agent, and/or in the presence of an appropriate control agent.

Inhibition may herein also be referred to as neutralisation or antagonism. That is, an agent capable of inhibiting IL-11-mediated signalling (e.g. interaction, signalling or other activity mediated by IL-11 or an IL-11-containing complex) may be said to be a 'neutralising' or 'antagonist' agent with respect to the relevant function or process. For example, an agent which is capable of inhibiting IL-11-mediated signalling may be referred to as an agent which is capable of neutralising IL-11-mediated signalling, or may be referred to as an antagonist of IL-11-mediated signalling.

The IL-11 signalling pathway offers multiple routes for inhibition of IL-11 signalling. An agent capable of inhibiting IL-11-mediated signalling may do so e.g. through inhibiting the action of one or more factors involved in, or necessary for, signalling through a receptor for IL-11.

For example, inhibition of IL-11 signalling may be achieved by disrupting interaction between IL-11 (or an IL-11 containing complex, e.g. a complex of IL-11 and IL-11Rα) and a receptor for IL-11 (e.g. IL-11Rα, a receptor complex comprising IL-11Rα, gp130 or a receptor complex comprising IL-11Rα and gp130). In some embodiments, inhibition of IL-11-mediated signalling is achieved by inhibiting the gene or protein expression of one or more of e.g. IL-11, IL-11Rα and gp130.

In embodiments, inhibition of IL-11-mediated signalling is achieved by disrupting IL-11-mediated cis signalling but not disrupting IL-11-mediated trans signalling, e.g. inhibition of IL-11-mediated signalling is achieved by inhibiting gp130-mediated cis complexes involving membrane bound IL-11Rα. In embodiments, inhibition of IL-11-mediated signalling is achieved by disrupting IL-11-mediated trans signalling but not disrupting IL-11-mediated cis signalling, i.e. inhibition of IL-11-mediated signalling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling. Any agent as described herein may be used to inhibit IL-11-mediated cis and/or trans signalling.

In other examples, inhibition of IL-11 signalling may be achieved by disrupting signalling pathways downstream of IL-11/IL-11Rα/gp130. That is, in some embodiments inhibition/antagonism of IL-11-mediated signalling comprises inhibition of a signalling pathway/process/factor downstream of signalling through the IL-11/IL-11 receptor complex.

In some embodiments inhibition/antagonism of IL-11-mediated signalling comprises inhibition of signalling through an intracellular signalling pathway which is activated by the IL-11/IL-11 receptor complex. In some embodiments inhibition/antagonism of IL-11-mediated signalling comprises inhibition of one or more factors whose expression/activity is upregulated as a consequence of signalling through the IL-11/IL-11 receptor complex.

In some embodiments, the methods of the present invention employ agents capable of inhibiting JAK/STAT signalling. In some embodiments, agents capable of inhibiting JAK/STAT signalling are capable of inhibiting the action of JAK1, JAK2, JAK3, TYK2, STAT1, STAT2, STAT3, STAT4, STAT5A, STAT5B and/or STATE. For example, agents may be capable of inhibiting activation of JAK/STAT proteins, inhibiting interaction of JAK or STAT proteins with cell surface receptors e.g. IL-11Rα or gp130, inhibiting phosphorylation of JAK proteins, inhibiting interaction between JAK and STAT proteins, inhibiting phosphorylation of STAT proteins, inhibiting dimerization of STAT proteins, inhibiting translocation of STAT proteins to the cell nucleus, inhibiting binding of STAT proteins to DNA, and/or promoting degradation of JAK and/or STAT proteins. In some embodiments, a JAK/STAT inhibitor is selected from Ruxolitinib (Jakafi/Jakavi; Incyte), Tofacitinib (Xeljanz/Jakvinus; NIH/Pfizer), Oclacitinib (Apoquel), Baricitinib (Olumiant; Incyte/Eli Lilly), Filgotinib (G-146034/GLPG-0634; Galapagos NV), Gandotinib (LY-2784544; Eli Lilly), Lestaurtinib (CEP-701; Teva), Momelotinib (GS-0387/CYT-387; Gilead Sciences), Pacritinib (SB1518; CTI), PF-04965842 (Pfizer), Upadacitinib (ABT-494; AbbVie), Peficitinib (ASP015K/JNJ-54781532; Astellas), Fedratinib (SAR302503; Celgene), Cucurbitacin I (JSI-124) and CHZ868.

In some embodiments, the methods of the present invention employ agents capable of inhibiting MAPK/ERK signalling. In some embodiments, agents capable of inhibiting MAPK/ERK signalling are capable of inhibiting the action of GRB2, inhibiting the action of RAF kinase, inhibiting the action of MEK proteins, inhibiting the activation of MAP3K/MAP2K/MAPK and/or Myc, and/or inhibiting the phosphorylation of STAT proteins. In some embodiments, agents capable of inhibiting ERK signalling are capable of inhibiting ERK p42/44. In some embodiments, an ERK inhibitor is selected from SCH772984, SC1, VX-11e, DEL-22379, Sorafenib (Nexavar; Bayer/Onyx), SB590885, PLX4720, XL281, RAF265 (Novartis), encorafenib (LGX818/Braftovi; Array BioPharma), dabrafenib (Tafinlar; GSK), vemurafenib (Zelboraf; Roche), cobimetinib (Cotellic; Roche), CI-1040, PD0325901, Binimetinib (MEK162/MEKTOVI; Array BioPharma), selumetinib (AZD6244; Array/AstraZeneca) and Trametinib (GSK1120212/Mekinist; Novartis). In some embodiments, the methods of the present invention employ agents capable of inhibiting c-Jun N-terminal kinase (JNK) signalling/activity. In some embodiments, agents capable of inhibiting JNK signalling/activity are capable of inhibiting the action and/or phosphorylation of a JNK (e.g. JNK1, JNK2). In some embodiments, a JNK inhibitor is selected from SP600125, CEP 1347, TCS JNK 6o, c-JUN peptide, SU3327, AEG 3482, TCS JNK 5a, BI78D3, IQ3, SR3576, IQ1S, JIP-1 (153-163) and CC401 dihydrochloride.

In the present Examples the inventors demonstrate that NOX4 expression and activity is upregulated by signalling through IL-11/IL-11Rα/gp130. NOX4 is an NADPH oxidase, and a source of reactive oxygen species (ROS). Expression of Nox4 is upregulated in transgenic mice with hepatocyte-specific Il11 expression, and primary human hepatocytes stimulated with IL11 upregulate NOX4 expression.

In some embodiments, the present invention employs agents capable of inhibiting NOX4 expression (gene or protein expression) or function. In some embodiments, the present invention employs agents capable of inhibiting IL-11-mediated upregulation of NOX4 expression/function. Agents capable of inhibiting NOX4 expression or function may be referred to herein as NOX4 inhibitors. For example, a NOX4 inhibitor may be capable of reducing expression (e.g. gene and/or protein expression) of NOX4, reducing the level of RNA encoding NOX4, reduce the level of NOX4 protein, and/or reducing the level of a NOX4 activity (e.g. reducing NOX4-mediated NADPH oxidase activity and/or NOX4-mediated ROS production).

NOX4 inhibitors include a NOX4-binding molecules and molecules capable of reducing NOX4 expression. NOX4-binding inhibitors include peptide/nucleic acid aptamers, antibodies (and antibody fragments) and fragments of interaction partners for NOX4 which behave as antagonists of NOX4 function, and small molecules inhibitors of NOX4. Molecules capable of reducing NOX4 expression include antisense RNA (e.g. siRNA, shRNA) to NOX4. In some embodiments, a NOX4 inhibitor is selected from a NOX4 inhibitor described in Altenhofer et al., Antioxid Redox Signal. (2015) 23(5): 406-427 or Augsburder et al., Redox Biol. (2019) 26: 101272, such as GKT137831.

Binding Agents

In some embodiments, agents capable of inhibiting IL-11-mediated signalling may bind to IL-11. In some embodiments, agents capable of inhibiting IL-11-mediated signalling may bind to a receptor for IL-11 (e.g. IL-11Rα, gp130, or a complex containing IL-11Rα and/or gp130). Binding of such agents may inhibit IL-11-mediated signalling by reducing/preventing the ability of IL-11 to bind to receptors for IL-11, thereby inhibiting downstream signalling. Binding of such agents may inhibit IL-11 mediated cis and/or trans-signalling by reducing/preventing the ability of IL-11 to bind to receptors for IL-11, e.g. IL-11Rα and/or gp130, thereby inhibiting downstream signalling. Agents may bind to trans-signalling complexes such as IL-11 and soluble IL-11Rα and inhibit gp130-mediated signalling.

Agents capable of binding to IL-11/an IL-11 containing complex or a receptor for IL-11 may be of any kind, but in some embodiments the agent may be an antibody, an antigen-binding fragment thereof, a polypeptide, a peptide, a nucleic acid, an oligonucleotide, an aptamer or a small molecule. The agents may be provided in isolated or purified form, or may be formulated as a pharmaceutical composition or medicament.

Antibodies and Antigen-Binding Fragments

In some embodiments, an agent capable of binding to IL-11/an IL-11 containing complex or a receptor for IL-11 is an antibody, or an antigen-binding fragment thereof. In some embodiments, an agent capable of binding to IL-11/an IL-11 containing complex or a receptor for IL-11 is a polypeptide, e.g. a decoy receptor molecule. In some embodiments, an agent capable of binding to IL-11/an IL-11 containing complex or a receptor for IL-11 may be an aptamer.

In some embodiments, an agent capable of binding to IL-11/an IL-11 containing complex or a receptor for IL-11 is an antibody, or an antigen-binding fragment thereof. An "antibody" is used herein in the broadest sense, and encompasses monoclonal antibodies, polyclonal antibodies, monospecific and multispecific antibodies (e.g., bispecific antibodies), and antibody fragments, as long as they display binding to the relevant target molecule.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799). Monoclonal antibodies (mAbs) are particularly useful in the methods of the invention, and are a homogenous population of antibodies specifically targeting a single epitope on an antigen.

Polyclonal antibodies are also useful in the methods of the invention. Monospecific polyclonal antibodies are preferred. Suitable polyclonal antibodies can be prepared using methods well known in the art.

Antigen-binding fragments of antibodies, such as Fab and Fab2 fragments may also be used/provided as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

Antibodies and antigen-binding fragments according to the present disclosure comprise the complementarity-determining regions (CDRs) of an antibody which is capable of binding to the relevant target molecule (i.e. IL-11/an IL-11 containing complex/a receptor for IL-11).

Antibodies capable of binding to IL-11 include e.g. monoclonal mouse anti-human IL-11 antibody clone #22626; Catalog No. MAB218 (R&D Systems, MN, USA), used e.g. in Bockhorn et al. Nat. Commun. (2013) 4(0):1393, clone 6D9A (Abbiotec), clone KT8 (Abbiotec), clone M3103F11 (BioLegend), clone 1F1 (Abnova Corporation), clone 3C6 (Abnova Corporation), clone GF1 (LifeSpan Biosciences), clone 13455 (Source BioScience), 11 h3/19.6.1 (Hermann et al., Arthritis Rheum. (1998) 41(8):1388-97), AB-218-NA (R&D Systems), X203 (Ng et al., Sci Transl Med. (2019) 11(511) pii: eaaw1237) and anti-IL-11 antibodies disclosed in US 2009/0202533 A1, WO 99/59608 A2, WO 2018/109174 A2 and WO 2019/238882 A1.

In particular, anti-IL-11 antibody clone 22626 (also known as MAB218) has been shown to be an antagonist of IL-11 mediated signalling, e.g. in Schaefer et al., Nature (2017) 552(7683):110-115. Monoclonal antibody 11 h3/19.6.1 is disclosed in Hermann et al., Arthritis Rheum. (1998) 41(8):1388-97 to be a neutralising anti-IL-11 IgG1. AB-218-NA from R&D Systems, used e.g. in McCoy et al., BMC Cancer (2013) 13:16, is another example of neutralizing anti-IL-11 antibody. WO 2018/109174 A2 and WO 2019/238882 A1 disclose yet further exemplary anti-IL-11 antibody antagonists of IL-11 mediated signalling. X203 (also referred to as Enx203) disclosed in Ng, et al., "IL-11 is a therapeutic target in idiopathic pulmonary fibrosis." bioRxiv 336537; doi: https://doi.org/10.1101/336537 and WO 2019/238882 A1 is an anti-IL-11 antibody antagonist of IL-11-mediated signalling, and comprises the VH region according to SEQ ID NO:92 of WO 2019/238882 A1 (SEQ ID NO:22 of the present disclosure), and the VL region according to SEQ ID NO:94 of WO 2019/238882 A1 (SEQ ID NO:23 of the present disclosure). Humanised versions of the X203 are described in WO 2019/238882 A1, including hEnx203 which comprises the VH region according to SEQ ID NO:117 of WO 2019/238882 A1 (SEQ ID NO:30 of the present disclosure), and the VL region according to SEQ ID NO:122 of WO 2019/238882 A1 (SEQ ID NO:31 of the present disclosure). Enx108A is a further example of an anti-IL-11 antibody antagonist of IL-11-mediated signalling, and comprises the VH region according to SEQ ID NO:8 of WO 2019/238882 A1 (SEQ ID NO:26 of the present disclosure), and the VL region according to SEQ ID NO:20 of WO 2019/238882 A1 (SEQ ID NO:27 of the present disclosure).

Antibodies capable of binding to IL-11Rα include e.g. monoclonal antibody clone 025 (Sino Biological), clone EPR5446 (Abcam), clone 473143 (R & D Systems), clones 8E2, 8D10 and 8E4 and the affinity-matured variants of 8E2 described in US 2014/0219919 A1, the monoclonal antibodies described in Blanc et al (J. Immunol Methods. 2000 Jul. 31; 241(1-2); 43-59), X209 (Widjaja et al., Gastroenterology (2019) 157(3):777-792, which is also published as Widjaja, et al., "IL-11 neutralising therapies target hepatic stellate cell-induced liver inflammation and fibrosis in NASH." bioRxiv 470062; doi: https://doi.org/10.1101/470062) antibodies disclosed in WO 2014121325 A1 and US 2013/0302277 A1, and anti-IL-11Rα antibodies disclosed in US 2009/0202533 A1, WO 99/59608 A2, WO 2018/109170 A2 and WO 2019/238884 A1.

In particular, anti-IL-11Rα antibody clone 473143 (also known as MAB1977) has been shown to be an antagonist of IL-11 mediated signalling, e.g. in Schaefer et al., Nature (2017) 552(7683):110-115. US 2014/0219919 A1 provides sequences for anti-human IL-11Rα antibody clones 8E2, 8D10 and 8E4, and discloses their ability to antagonise IL-11 mediated signalling—see e.g. [0489] to [0490] of US 2014/0219919 A1. US 2014/0219919 A1 moreover provides sequence information for an additional 62 affinity-matured variants of clone 8E2, 61 of which are disclosed to antagonise IL-11 mediated signalling—see Table 3 of US 2014/0219919 A1. WO 2018/109170 A2 and WO 2019/238884 A1 disclose yet further exemplary anti-IL-11Rα antibody antagonists of IL-11 mediated signalling. X209 (also referred to as Enx209) disclosed in Widjaja, et al., "IL-11 neutralising therapies target hepatic stellate cell-induced liver inflammation and fibrosis in NASH." bioRxiv 470062; doi: https://doi.org/10.1101/470062 and WO 2019/238884 A1 is an anti-IL-11Rα antibody antagonist of IL-11-mediated signalling, and comprises the VH region according to SEQ ID NO:7 of WO 2019/238884 A1 (SEQ ID NO:24 of the present disclosure), and the VL region according to SEQ ID NO:14 of WO 2019/238884 A1 (SEQ ID NO:25 of the present disclosure). Humanised versions of the X209 are described in WO 2019/238884 A1, including hEnx209 which comprises the VH region according to SEQ ID NO:11 of WO 2019/238884 A1 (SEQ ID NO:32 of the present disclosure), and the VL region according to SEQ ID NO:17 of WO 2019/238884 A1 (SEQ ID NO:33 of the present disclosure).

The skilled person is well aware of techniques for producing antibodies suitable for therapeutic use in a given species/subject. For example, procedures for producing antibodies suitable for therapeutic use in humans are described in Park and Smolen Advances in Protein Chemistry (2001) 56: 369-421 (hereby incorporated by reference in its entirety).

Antibodies to a given target protein (e.g. IL-11 or IL-11Rα) can be raised in model species (e.g. rodents, lagomorphs), and subsequently engineered in order to improve their suitability for therapeutic use in a given species/subject. For example, one or more amino acids of monoclonal antibodies raised by immunisation of model species can be substituted to arrive at an antibody sequence which is more similar to human germline immunoglobulin sequences (thereby reducing the potential for anti-xenogenic antibody immune responses in the human subject treated with the antibody). Modifications in the antibody variable domains may focus on the framework regions in order to preserve the antibody paratope. Antibody humanisation is a matter of routine practice in the art of antibody technology, and is reviewed e.g. in Almagro and Fransson, Frontiers in Bioscience (2008) 13:1619-1633, Safdari et al., Biotechnology and Genetic Engineering Reviews (2013) 29(2): 175-186 and Lo et al., Microbiology Spectrum (2014) 2(1), all of which are hereby incorporated by reference in their entirety. The requirement for humanisation can be circumvented by raising antibodies to a given target protein (e.g. IL-11 or IL-11Rα) in transgenic model species expressing human immunoglobulin genes, such that the antibodies raised in such animals are fully-human (described e.g. in Brüggemann et al., Arch Immunol Ther Exp (Warsz) (2015) 63(2): 101-108, which is hereby incorporated by reference in its entirety).

Phage display techniques may also be employed to the identification of antibodies to a given target protein (e.g. IL-11 or IL-11Rα), and are well known to the skilled person. The use of phage display for the identification of fully human antibodies to human target proteins is reviewed e.g. in Hoogenboom, Nat. Biotechnol. (2005) 23, 1105-1116 and Chan et al., International Immunology (2014) 26(12): 649-657, which are hereby incorporated by reference in their entirety.

The antibodies/fragments may be antagonist antibodies/fragments that inhibit or reduce a biological activity of IL-11. The antibodies/fragments may be neutralising antibodies that neutralise the biological effect of IL-11, e.g. its ability to stimulate productive signalling via an IL-11 receptor. Neutralising activity may be measured by ability to neutralise IL-11 induced proliferation in the T11 mouse plasmacytoma cell line (Nordan, R. P. et al. (1987) J. Immunol. 139:813).

IL-11- or IL-11Rα-binding antibodies can be evaluated for the ability to antagonise IL-11-mediated signalling, e.g. using the assay described in US 2014/0219919 A1 or Blanc et al (J. Immunol Methods. 2000 Jul. 31; 241(1-2); 43-59. Briefly, IL-11- and IL-11Rα-binding antibodies can be evaluated in vitro for the ability to inhibit proliferation of Ba/F3 cells expressing IL-11Rα and gp130 from the appropriate species, in response to stimulation with IL-11 from the appropriate species. Alternatively, IL-11- and IL-11Rα-binding antibodies can be analysed in vitro for the ability to inhibit the fibroblast-to-myofibroblast transition following stimulation of fibroblasts with TGFβ1, by evaluation of αSMA expression (as described e.g. in WO 2018/109174 A2 (Example 6) and WO 2018/109170 A2 (Example 6), Ng et al., Sci Transl Med. (2019) 11(511) pii: eaaw1237 and Widjaja et al., Gastroenterology (2019) 157(3):777-792).

Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. The VH region and VL region comprise framework regions (FRs) either side of each CDR, which provide a scaffold for the CDRs. From N-terminus to C-terminus, VH regions comprise the following structure: N term-[HC-FR1]-[HC- CDR1HHC-FR2HHC-CDR2HHC-FR3HHC-CDR3HHC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, Md. (1991), Chothia et al., *J. Mol. Biol.* 196:901-917 (1987), and VBASE2, as described in Retter et al., *Nucl. Acids Res.* (2005) 33 (suppl 1): D671-D674. The CDRs and FRs of the VH regions and VL regions of the antibodies described herein are defined according to the Kabat system.

In some embodiments an antibody, or an antigen-binding fragment thereof, according to the present disclosure is derived from an antibody which binds specifically to IL-11 (e.g. Enx108A, Enx203 or hEnx203). In some embodiments an antibody, or an antigen-binding fragment thereof, according to the present disclosure is derived from an antibody which binds specifically to IL-11Rα (e.g. Enx209 or hEnx209).

Antibodies and antigen-binding fragments according to the present disclosure preferably inhibit IL-11-mediated signalling. Such antibodies/antigen-binding fragments may be described as being antagonists of IL-11-mediated signalling, and/or may be described as having the ability to neutralise IL-11-mediated signalling.

In some embodiments, the antibody/antigen-binding fragment comprises the CDRs of an antibody which binds to IL-11. In some embodiments the antibody/antigen-binding fragment comprises the CDRs of, or CDRs derived from, the CDRs of an IL-11-binding antibody described herein (e.g. Enx108A, Enx203 or hEnx203).

In some embodiments the antibody/antigen-binding fragment comprises a VH region incorporating the following CDRs:

(1)
HC-CDR1 having the amino acid sequence of SEQ ID NO:34
HC-CDR2 having the amino acid sequence of SEQ ID NO:35
HC-CDR3 having the amino acid sequence of SEQ ID NO:36,
or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:

(2)
LC-CDR1 having the amino acid sequence of SEQ ID NO:37
LC-CDR2 having the amino acid sequence of SEQ ID NO:38
LC-CDR3 having the amino acid sequence of SEQ ID NO:39,
or a variant thereof in which one or two or three amino acids in one or more of LC-CDR1, LC-CDR2, or LC-CDR3 are substituted with another amino acid.

In some embodiments the antibody/antigen-binding fragment comprises a VH region incorporating the following CDRs:

(3)
HC-CDR1 having the amino acid sequence of SEQ ID NO:40
HC-CDR2 having the amino acid sequence of SEQ ID NO:41
HC-CDR3 having the amino acid sequence of SEQ ID NO:42,
or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:

(4)
LC-CDR1 having the amino acid sequence of SEQ ID NO:43
LC-CDR2 having the amino acid sequence of SEQ ID NO:44
LC-CDR3 having the amino acid sequence of SEQ ID NO:45,
or a variant thereof in which one or two or three amino acids in one or more of LC-CDR1, LC-CDR2, or LC-CDR3 are substituted with another amino acid.

In some embodiments the antibody/antigen-binding fragment comprises a VH region incorporating the CDRs according to (1), and a VL region incorporating the CDRs according to (2). In some embodiments the antibody/antigen-binding fragment comprises a VH region incorporating the CDRs according to (3), and a VL region incorporating the CDRs according to (4).

In some embodiments the antibody/antigen-binding fragment comprises the VH region and the VL region of an antibody which binds to IL-11. In some embodiments the antibody/antigen-binding fragment comprises the VH region and VL region of, or a VH region and VL region derived from, the VH region and VL region of an IL-11-binding antibody described herein (e.g. Enx108A, Enx203 or hEnx203).

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27.

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:22. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:22 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23.

In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30. In some embodiments the antibody/antigen-binding fragment comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31. In some embodiments the antibody/antigen-binding fragment comprises a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30 and a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31.

In some embodiments, the antibody/antigen-binding fragment comprises the CDRs of an antibody which binds to IL-11Rα. In some embodiments the antibody/antigen-binding fragment comprises the CDRs of, or CDRs derived from, the CDRs of an IL-11Rα-binding antibody described herein (e.g. Enx209 or hEnx209).

In some embodiments the antibody/antigen-binding fragment comprises a VH region incorporating the following CDRs:
(5)
  HC-CDR1 having the amino acid sequence of SEQ ID NO:46
  HC-CDR2 having the amino acid sequence of SEQ ID NO:47
  HC-CDR3 having the amino acid sequence of SEQ ID NO:48,
  or a variant thereof in which one or two or three amino acids in one or more of HC-CDR1, HC-CDR2, or HC-CDR3 are substituted with another amino acid.

In some embodiments the antibody/antigen-binding fragment comprises a VL region incorporating the following CDRs:
(6)
  LC-CDR1 having the amino acid sequence of SEQ ID NO:49
  LC-CDR2 having the amino acid sequence of SEQ ID NO:50
  LC-CDR3 having the amino acid sequence of SEQ ID NO:51,
  or a variant thereof in which one or two or three amino acids in one or more of LC-CDR1, LC-CDR2, or LC-CDR3 are substituted with another amino acid.

In some embodiments the antibody/antigen-binding fragment comprises a VH region incorporating the CDRs according to (5), and a VL region incorporating the CDRs according to (6).

In some embodiments the antibody/antigen-binding fragment comprises the VH region and the VL region of an antibody which binds to IL-11Rα. In some embodiments the antibody/antigen-binding fragment comprises the VH region and VL region of, or a VH region and VL region derived from, the VH region and VL region of an IL-11Rα-binding antibody described herein (e.g. Enx209 or hEnx209).

In embodiments in accordance with the present invention in which one or more amino acids of a reference amino acid sequence (e.g. a CDR sequence, VH region sequence or VL region sequence described herein) are substituted with another amino acid, the substitutions may conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
|---|---|---|
|  |  | I L V |
|  | Polar - uncharged | C S T M |
|  |  | N Q |
|  | Polar - charged | D E |
|  |  | K R |
| AROMATIC |  | H F W Y |

In some embodiments, substitution(s) may be functionally conservative. That is, in some embodiments the substitution may not affect (or may not substantially affect) one or more functional properties (e.g. target binding) of the antibody/fragment comprising the substitution relative to the equivalent unsubstituted molecule.

In some embodiments, substitution(s) relative to a reference VH region or VL region sequence may be focussed in a particular region or regions of the VH region or VL region sequence. For example, variation from a reference VH region or VL region sequence may be focussed in one or more of the framework regions (FR1, FR2, FR3 and/or FR4).

Antibodies and antigen-binding fragments according to the present disclosure may be designed and prepared using the sequences of monoclonal antibodies (mAbs) capable of binding to the relevant target molecule. Antigen-binding regions of antibodies, such as single chain variable fragment (scFv), Fab and Fab2 fragments may also be used/provided. An 'antigen-binding region' or 'antigen binding fragment' is any fragment of an antibody which is capable of binding to the target for which the given antibody is specific.

In some embodiments the antibodies/fragments comprise the VL and VH regions of an antibody which is capable of binding to IL-11, an IL-11 containing complex, or a receptor for IL-11. The VL and VH region of an antigen-binding region of an antibody together constitute the Fv region. In some embodiments the antibodies/fragments comprise or consist of the Fv region of an antibody which is capable of binding to IL-11, an IL-11 containing complex, or a receptor for IL-11. The Fv region may be expressed as a single chain wherein the VH and VL regions are covalently linked, e.g. by a flexible oligopeptide. Accordingly, antibodies/fragments may comprise or consist of an scFv comprising the VL and VH regions of an antibody which is capable of binding to IL-11, an IL-11 containing complex, or a receptor for IL-11.

The VL and light chain constant (CL) region, and the VH region and heavy chain constant 1 (CH1) region of an antigen-binding region of an antibody together constitute the Fab region. In some embodiments the antibodies/fragments comprise or consist of the Fab region of an antibody which is capable of binding to IL-11, an IL-11 containing complex, or a receptor for IL-11.

In some embodiments, antibodies/fragments comprise, or consist of, whole antibody capable of binding to IL-11, an IL-11 containing complex, or a receptor for IL-11. A "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety. Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprises a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments the antibody/antigen-binding fragment of the present disclosure comprises an immunoglobulin heavy chain constant sequence. In some embodiments, an immunoglobulin heavy chain constant sequence may be a human immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM, e.g. a human IgG (e.g. hIgG1, hIgG2, hIgG3, hIgG4), hIgA (e.g. hIgA1, hIgA2), hIgD, hIgE or IgM. In some the immunoglobulin heavy chain constant sequence is, or is derived from, the heavy chain constant sequence of a human IgG1 allotype (e.g. G1 m1, G1 m2, G1 m3 or G1 m17).

In some embodiments the immunoglobulin heavy chain constant sequence is, or is derived from, the constant region sequence of human immunoglobulin G 1 constant (IGHG1; UniProt: P01857-1, v1). In some embodiments the immunoglobulin heavy chain constant sequence is, or is derived from, the constant region sequence of human immunoglobulin G 1 constant (IGHG1; UniProt: P01857-1, v1) comprising substitutions K214R, D356E and L358M (i.e. the G1 m3 allotype). In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:52.

In some embodiments the immunoglobulin heavy chain constant sequence is, or is derived from, the constant region sequence of human immunoglobulin G 4 constant (IGHG4; UniProt: P01861, v1). In some embodiments the immunoglobulin heavy chain constant sequence is, or is derived from, the constant region sequence of human immunoglobulin G 4 constant (IGHG4; UniProt: P01861, v1) comprising substitutions S241P and/or L248E. The S241P mutation is hinge stabilising while the L248E mutation further reduces the already low ADCC effector function of IgG4 (Davies and Sutton, Immunol Rev. 2015 November; 268(1):139-159; Angal et al Mol Immunol. 1993 January; 30(1):105-8). In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:53.

In some embodiments the antibody/antigen-binding fragment of the present disclosure comprises an immunoglobulin light chain constant sequence. In some embodiments, an immunoglobulin light chain constant sequence may be a human immunoglobulin light chain constant sequence. In some embodiments the immunoglobulin light chain constant sequence is, or is derived from, a kappa (κ) or lambda (λ) light chain, e.g. human immunoglobulin kappa constant (IGKC; Cκ; UniProt: P01834-1, v2), or human immunoglobulin lambda constant (IGLC; Cλ), e.g. IGLC1 (UniProt: P0CG04-1, v1), IGLC2 (UniProt: P0DOY2-1, v1), IGLC3 (UniProt: P0DOY3-1, v1), IGLC6 (UniProt: P0CF74-1, v1) or IGLC7 (UniProt: A0M8Q6-1, v3).

In some embodiments the antibody/antigen-binding fragment comprises an immunoglobulin light chain constant sequence. In some embodiments the immunoglobulin light chain constant sequence is, or is derived from human immunoglobulin kappa constant (IGKC; Cκ; UniProt: P01834-1, v2; SEQ ID NO:90). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:54. In some embodiments the antibody/antigen-binding fragment comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:55.

In some embodiments, the antibody/antigen-binding fragment comprises: (i) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:28, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:29.

In some embodiments, the antibody/antigen-binding fragment comprises: (i) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:56, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:57.

In some embodiments, the antibody/antigen-binding fragment comprises: (i) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:58, and (ii) a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:59.

Fab, Fv, ScFv and dAb antibody fragments can all be expressed in and secreted from *E. coli*, thus allowing the facile production of large amounts of the said fragments.

Whole antibodies, and F(ab')2 fragments are "bivalent". By "bivalent" we mean that the said antibodies and F(ab')2 fragments have two antigen combining sites. In contrast, Fab, Fv, ScFv and dAb fragments are monovalent, having only one antigen combining site. Synthetic antibodies capable of binding to IL-11, an IL-11 containing complex, or a receptor for IL-11 may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Rio/Technology 10:779-783 (1992); Barbas et al. *Proc Nat. Acad. Sci. USA* 91:3809-3813 (1994); Schier et al. Gene 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies/fragments include bi-specific antibodies, e.g. composed of two different fragments of two different antibodies, such that the bi-specific antibody binds two types of antigen. The bispecific antibody comprises an antibody/fragment as described herein capable of binding to IL-11, an IL-11 containing complex, or a receptor for IL-11. The antibody may contain a different fragment having affinity for a second antigen, which may be any desired antigen. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297), and Baeuerle, P A et al., (2009 *Cancer Res* 69 (12): 4941-4944). Bispecific antibodies and bispecific antigen-binding fragments may be provided in any suitable format, such as those formats described in Kontermann MAbs 2012, 4(2): 182-197, which is hereby incorporated by reference in its entirety. For example, a bispecific antibody or bispecific antigen-binding fragment may be a bispecific antibody conjugate (e.g. an IgG2, F(ab')2 or CovX-Body), a bispecific IgG or IgG-like molecule (e.g. an IgG, scFv4-Ig, IgG-scFv, scFv-IgG, DVD-Ig, IgG-sVD, sVD-IgG, 2 in 1-IgG, mAb2, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')2-scFv2), a bispecific Fc and CH3 fusion protein (e.g. a taFv-Fc, Di-diabody, scDb-CH3, scFv-Fc-scFv, HCAb-VHH, scFv-kih-Fc, or scFv-kih-CH3), or a bispecific fusion protein (e.g. a scFv2-albumin, scDb-albumin, taFv-toxin, DNL-Fab3, DNL-Fab4-IgG, DNL-Fab4-IgG-cytokine2). See in particular FIG. 2 of Kontermann MAbs 2012, 4(2): 182-19.

Methods for producing bispecific antibodies include chemically crosslinking antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(–2-pyridyldithio)-propionate (SPDP) can be used to chemically crosslink e.g. Fab fragments via hinge region SH-groups, to create disulfide-linked bispecific F(ab)2 heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen-binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339.

For example, a DNA construct encoding the light and heavy chain variable domains for the two antigen binding domains (i.e. the light and heavy chain variable domains for the antigen binding domain capable of binding to IL-11, an IL-11 containing complex, or a receptor for IL-11, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Decoy Receptors

Peptide or polypeptide based agents capable of binding to IL-11 or IL-11 containing complexes may be based on the IL-11 receptor, e.g. an IL-11 binding fragment of an IL-11 receptor.

In some embodiments, the binding agent may comprise an IL-11-binding fragment of the IL-11Rα chain, and may preferably be soluble and/or exclude one or more, or all, of the transmembrane domain(s). In some embodiments, the binding agent may comprise an IL-11-binding fragment of gp130, and may preferably be soluble and/or exclude one or more, or all, of the transmembrane domain(s). Such molecules may be described as decoy receptors. Binding of such agents may inhibit IL-11 mediated cis and/or trans-signalling by reducing/preventing the ability of IL-11 to bind to receptors for IL-11, e.g. IL-11Rα or gp130, thereby inhibiting downstream signalling.

Curtis et al (*Blood* 1997 Dec. 1; 90 (11):4403-12) report that a soluble murine IL-11 receptor alpha chain (sIL-11R) was capable of antagonizing the activity of IL-11 when tested on cells expressing the transmembrane IL-11R and gp130. They proposed that the observed IL-11 antagonism by the sIL-11R depends on limiting numbers of gp130 molecules on cells already expressing the transmembrane IL-11R.

The use of soluble decoy receptors as the basis for inhibition of signal transduction and therapeutic intervention has also been reported for other signalling molecule:receptor pairs, e.g. VEGF and the VEGF receptor (De-Chao Yu et al., Molecular Therapy (2012); 20 5, 938-947; Konner and Dupont Clin Colorectal Cancer 2004 October; 4 Suppl 2:S81-5).

As such, in some embodiments a binding agent may be a decoy receptor, e.g. a soluble receptor for IL-11 and/or IL-11 containing complexes. Competition for IL-11 and/or IL-11 containing complexes provided by a decoy receptor has been reported to lead to IL-11 antagonist action (Curtis et al., supra). Decoy IL-11 receptors are also described in WO 2017/103108 A1 and WO 2018/109168 A1, which are hereby incorporated by reference in their entirety.

Decoy IL-11 receptors preferably bind IL-11 and/or IL-11 containing complexes, and thereby make these species unavailable for binding to gp130, IL-11Rα and/or gp130:IL-11Rα receptors. As such, they act as 'decoy' receptors for IL-11 and IL-11 containing complexes, much in the same way that etanercept acts as a decoy receptor for TNFα. IL-11-mediated signalling is reduced as compared to the level of signalling in the absence of the decoy receptor.

Decoy IL-11 receptors preferably bind to IL-11 through one or more cytokine binding modules (CBMs). The CBMs are, or are derived from or homologous to, the CBMs of naturally occurring receptor molecules for IL-11. For example, decoy IL-11 receptors may comprise, or consist of, one or more CBMs which are from, are derived from or homologous to the CBM of gp130 and/or IL-11Rα.

In some embodiments, a decoy IL-11 receptor may comprise, or consist of, an amino acid sequence corresponding to the cytokine binding module of gp130. In some embodiments, a decoy IL-11 receptor may comprise an amino acid sequence corresponding to the cytokine binding module of IL-11Rα. Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%, 95%, 96%, 97%, 98% or 99% sequence identity to the amino acid sequence of the reference region/sequence.

In some embodiments a decoy receptor may be able to bind IL-11, e.g. with binding affinity of at least 100 μM or less, optionally one of 10 μM or less, 1 μM or less, 100 nM or less, or about 1 to 100 nM. In some embodiments a decoy receptor may comprise all or part of the IL-11 binding domain and may optionally lack all or part of the transmembrane domains. The decoy receptor may optionally be fused to an immunoglobulin constant region, e.g. IgG Fc region.

Inhibitors

The present invention contemplates the use of inhibitor molecules capable of binding to one or more of IL-11, an IL-11 containing complex, IL-11Rα, gp130, or a complex containing IL-11Rα and/or gp130, and inhibiting IL-11 mediated signalling.

In some embodiments the agent is a peptide- or polypeptide-based binding agent based on IL-11, e.g. mutant, variant or binding fragment of IL-11. Suitable peptide or polypeptide based agents may bind to a receptor for IL-11 (e.g. IL-11Rα, gp130, or a complex containing IL-11Rα and/or gp130) in a manner that does not lead to initiation of signal transduction, or which produces sub-optimal signalling. IL-11 mutants of this kind may act as competitive inhibitors of endogenous IL-11.

For example, W147A is an IL-11 antagonist in which the amino acid 147 is mutated from a tryptophan to an alanine, which destroys the so-called 'site III' of IL-11. This mutant can bind to IL-11Rα, but engagement of the gp130 homodimer fails, resulting in efficient blockade of IL-11 signalling (Underhill-Day et al., 2003; *Endocrinology* 2003 August; 144(8):3406-14). Lee et al (*Am J respire Cell Mol Biol.* 2008 December; 39(6):739-746) also report the generation of an IL-11 antagonist mutant (a "mutein") capable of specifically inhibiting the binding of IL-11 to IL-11Rα. IL-11 muteins are also described in WO 2009/052588 A1.

Menkhorst et al (Biology of Reproduction May 1, 2009 vol. 80 no. 5 920-927) describe a PEGylated IL-11 antagonist, PEGIL11A (CSL Limited, Parkvill, Victoria, Australia) which is effective to inhibit IL-11 action in female mice.

Pasqualini et al. *Cancer* (2015) 121(14):2411-2421 describe a ligand-directed, peptidomimetic drug, bone metastasis-targeting peptidomimetic-11 (BMTP-11) capable of binding to IL-11Rα.

In some embodiments a binding agent capable of binding to a receptor for IL-11 may be provided in the form of a small molecule inhibitor of one of IL-11Rα, gp130, or a complex containing IL-11Rα and/or gp130. In some embodiments a binding agent may be provided in the form of a small molecule inhibitor of IL-11 or an IL-11 containing complex, e.g. IL-11 inhibitor described in Lay et al., Int. J. Oncol. (2012); 41(2): 759-764, which is hereby incorporated by reference in its entirety.

Aptamers

In some embodiments, an agent capable of binding to IL-11/an IL-11 containing complex or a receptor for IL-11 (e.g. IL-11Rα, gp130, or a complex containing IL-11Rα and/or gp130) is an aptamer. Aptamers, also called nucleic acid/peptide ligands, are nucleic acid or peptide molecules characterised by the ability to bind to a target molecule with high specificity and high affinity. Almost every aptamer identified to date is a non-naturally occurring molecule.

Aptamers to a given target (e.g. IL-11, an IL-11 containing complex or a receptor for IL-11) may be identified and/or produced by the method of Systematic Evolution of Ligands by EXponential enrichment (SELEX™), or by developing SOMAmers (slow off-rate modified aptamers) (Gold L et al. (2010) *PLoS ONE* 5(12):e15004). Aptamers and SELEX are described in Tuerk and Gold, *Science* (1990) 249(4968):505-10, and in WO 91/19813. Applying the SELEX and the SOMAmer technology includes for instance adding functional groups that mimic amino acid side chains to expand the aptamer's chemical diversity. As a result high affinity aptamers for a target may be enriched and identified.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). Tetrahedron 48 (12): 2223).

Suitable nucleic acid aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Suitable nucleic acid aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Suitable nucleic acid aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Aptamers may be peptides selected or engineered to bind specific target molecules. Peptide aptamers and methods for their generation and identification are reviewed in Reverdatto et al., *Curr Top Med Chem.* (2015) 15(12):1082-101, which is hereby incorporated by reference in its entirety. Peptide aptamers may optionally have a minimum length of one of 2, 3, 4, 5, 6, 7, 8, 9 or 10 amino acids. Peptide aptamers may optionally have a maximum length of one of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. Suitable peptide aptamers may optionally have a length of one of 2-30, 2-25, 2-20, 5-30, 5-25 or 5-20 amino acids.

Aptamers may have $K_D$'s in the nM or pM range, e.g. less than one of 500 nM, 100 nM, 50 nM, 10 nM, 1 nM, 500 pM, 100 pM.

Properties of IL-11 Binding Agents

Agents capable of binding to IL-11/an IL-11 containing complex or a receptor for IL-11 according to the present invention may exhibit one or more of the following properties:

Specific binding to IL-11/IL-11 containing complex or a receptor for IL-11;
Binding to IL-11/IL-11 containing complex, or a receptor for IL-11, with a KD of 10 μM or less, preferably one of ≤5 μM≤1 μM, ≤500 nM, ≤100 nM, ≤10 nM, ≤1 nM or ≤100 pM;
Inhibition of interaction between IL-11 and IL-11Rα;
Inhibition of interaction between IL-11 and gp130;
Inhibition of interaction between IL-11 and IL-11Rα:gp130 receptor complex;
Inhibition of interaction between IL-11:IL-11Rα complex and gp130.

These properties can be determined by analysis of the relevant agent in a suitable assay, which may involve comparison of the performance of the agent to suitable control agents. The skilled person is able to identify an appropriate control conditions for a given assay.

For example, a suitable negative control for the analysis of the ability of a test antibody/antigen-binding fragment to bind to IL-11/an IL-11 containing complex/a receptor for IL-11 may be an antibody/antigen-binding fragment directed against a non-target protein (i.e. an antibody/antigen-binding fragment which is not specific for IL-11/an IL-11 containing complex/a receptor for IL-11). A suitable positive control may be a known, validated (e.g. commercially available) IL-11- or IL-11 receptor-binding antibody. Controls may be of the same isotype as the putative IL-11/IL-11 containing complex/IL-11 receptor-binding antibody/antigen-binding fragment being analysed, and may e.g. have the same constant regions.

In some embodiments, the agent may be capable of binding specifically to IL-11 or an IL-11 containing complex, or a receptor for IL-11 (e.g. IL-11Rα, gp130, or a complex containing IL-11Rα and/or gp130). An agent which specifically binds to a given target molecule preferably binds the target with greater affinity, and/or with greater duration than it binds to other, non-target molecules.

In some embodiments the agent may bind to IL-11 or an IL-11 containing complex with greater affinity than the affinity of binding to one or more other members of the IL-6 cytokine family (e.g. IL-6, leukemia inhibitory factor (LIF), oncostatin M(OSM), cardiotrophin-1 (CT-1), ciliary neurotrophic factor (CNTF) and cardiotrophin-like cytokine (CLC)). In some embodiments the agent may bind to a receptor for IL-11 (e.g. IL-11Rα, gp130, or a complex containing IL-11Rα and/or gp130) with greater affinity than the affinity of binding to one or more other members of the IL-6 receptor family. In some embodiments the agent may bind with greater affinity to IL-11Rα than the affinity of binding to one or more of IL-6Rα, leukemia inhibitory factor receptor (LIFR), oncostatin M receptor (OSMR), ciliary neurotrophic factor receptor alpha (CNTFRα) and cytokine receptor-like factor 1 (CRLF1).

In some embodiments, the extent of binding of a binding agent to an non-target is less than about 10% of the binding of the agent to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the binding agent binds to IL-11, an IL-11 containing complex or a receptor for IL-11 with a $K_D$ that is at least 0.1 order of magnitude (i.e. 0.1×10n, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity for a given binding agent for its target is often described in terms of its dissociation constant ($K_D$). Binding affinity can be measured by methods known in the art, such as by ELISA, Surface Plasmon Resonance (SPR; see e.g. Hearty et al., *Methods Mol Biol* (2012) 907:411-442; or Rich et al., *Anal Biochem.* 2008 Feb. 1; 373(1):112-20), Bio-Layer Interferometry (see e.g. Lad et al., (2015) *J Biomol Screen* 20(4): 498-507; or Concepcion et al., *Comb Chem High Throughput Screen.* 2009 September; 12(8):791-800), MicroScale Thermophoresis (MST) analysis (see e.g. Jerabek-Willemsen et al., *Assay Drug Dev Technol.* 2011 August; 9(4): 342-353), or by a radiolabelled antigen binding assay (RIA).

In some embodiments, the agent is capable of binding to IL-11 or an IL-11 containing complex, or a receptor for IL-11 with a $K_D$ of 50 μM or less, preferably one of ≤10 μM, ≤5 μM, ≤4 μM, ≤3 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM≤3 nM, ≤2 nM, ≤1 nM, ≤500 pM, ≤400 pM, ≤300 pM, ≤200 pM, or ≤100 pM.

In some embodiments, the agent binds to IL-11, an IL-11 containing complex or a receptor for IL-11 with an affinity of binding (e.g. as determined by ELISA) of EC50=10,000 ng/ml or less, preferably one of ≤5,000 ng/ml, ≤1000 ng/ml, ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml. Such ELISAs can be performed e.g. as described in Antibody Engineering, vol. 1 (2nd Edn), Springer Protocols, Springer (2010), Part V, pp 657-665.

In some embodiments, the agent binds to IL-11 or an IL-11-containing complex in a region which is important for binding to a receptor for the IL-11 or IL-11-containing complex, e.g. gp130 or IL-11Rα, and thereby inhibits interaction between IL-11 or an IL-11-containing complex and a receptor for IL-11, and/or signalling through the receptor. In some embodiments, the agent binds to a receptor for IL-11 in a region which is important for binding to IL-11 or an IL-11-containing complex, and thereby inhibits interaction between IL-11 or an IL-11-containing complex and a receptor for IL-11, and/or signalling through the receptor.

The ability of a given binding agent (e.g. an agent capable of binding IL-11/an IL-11 containing complex or a receptor for IL-11) to inhibit interaction between two proteins can be determined for example by analysis of interaction in the presence of, or following incubation of one or both of the interaction partners with, the binding agent. An example of a suitable assay to determine whether a given binding agent is capable of inhibiting interaction between two interaction partners is a competition ELISA.

A binding agent which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the binding agent, as compared to the level of interaction in the absence of the binding agent (or in the presence of an appropriate control binding agent). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the binding agent may be labelled or used in conjunction with a detectable entity for the purposes of detecting and/or measuring the level of interaction. For example, the agent may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding agent may be directly labelled with a detectable label or it may be indirectly labelled. For example, the binding agent may be unlabelled, and detected by another binding agent which is itself labelled. Alternatively, the second binding agent may have bound to it biotin and binding of labelled streptavidin to the biotin may be used to indirectly label the first binding agent.

Ability of a binding agent to inhibit interaction between two binding partners can also be determined by analysis of the downstream functional consequences of such interaction, e.g. IL-11-mediated signalling. For example, downstream functional consequences of interaction between IL-11 and IL-11Rα:gp130 or between IL-11:IL-11Rα and gp130 may include e.g. a process mediated by IL-11, or gene/protein expression of e.g. collagen or IL-11.

Inhibition of interaction between IL-11 or an IL-11 containing complex and a receptor for IL-11 can be analysed using 3H-thymidine incorporation and/or Ba/F3 cell proliferation assays such as those described in e.g. Curtis et al. *Blood,* 1997, 90(11) and Karpovich et al. *Mol. Hum. Reprod.* 2003 9(2): 75-80. Ba/F3 cells co-express IL-11Rα and gp130.

In some embodiments, the binding agent may be capable of inhibiting interaction between IL-11 and IL-11Rα to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the binding agent (or in the presence of an appropriate control binding agent). In some embodiments, the binding agent may be capable of inhibiting interaction between IL-11 and IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the binding agent (or in the presence of an appropriate control binding agent).

In some embodiments, the binding agent may be capable of inhibiting interaction between IL-11 and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the binding agent (or in the presence of an appropriate control binding agent). In some embodiments, the binding agent may be capable of inhibiting interaction between IL-11 and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the binding agent (or in the presence of an appropriate control binding agent).

In some embodiments, the binding agent may be capable of inhibiting interaction between IL-11 and IL-11Rα:gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the binding agent (or in the presence of an appropriate control binding agent). In some embodiments, the binding agent may be capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the binding agent (or in the presence of an appropriate control binding agent).

In some embodiments, the binding agent may be capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the binding agent (or in the presence of an appropriate control binding agent). In some embodiments, the binding agent is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the binding agent.

Agents Capable of Reducing Expression of IL-11 or an IL-11 Receptor

In aspects of the present invention the agent capable of inhibiting IL-11-mediated signalling may be capable of preventing or reducing the expression of one or more of IL-11, IL-11Rα or gp130.

Expression may be gene or protein expression, and may be determined as described herein or by methods in the art that will be well known to a skilled person. Expression may be by a cell/tissue/organ/organ system of a subject.

Suitable agents may be of any kind, but in some embodiments an agent capable of preventing or reducing the expression of one or more of IL-11, IL-11Rα or gp130 may be a small molecule or an oligonucleotide.

An agent capable of preventing or reducing of the expression of one or more of IL-11, IL-11Rα or gp130 may do so e.g. through inhibiting transcription of the gene encoding IL-11, IL-11Rα or gp130, inhibiting post-transcriptional processing of RNA encoding IL-11, IL-11Rα or gp130, reducing the stability of RNA encoding IL-11, IL-11Rα or gp130, promoting degradation of RNA encoding IL-11, IL-11Rα or gp130, inhibiting post-translational processing of IL-11, IL-11Rα or gp130 polypeptide, reducing the stability of IL-11, IL-11Rα or gp130 polypeptide or promoting degradation of IL-11, IL-11Rα or gp130 polypeptide. Taki et al. *Clin Exp Immunol* (1998) April; 112(1): 133-138 reported a reduction in the expression of IL-11 in rheumatoid synovial cells upon treatment with indomethacin, dexamethasone or interferon-gamma (IFNγ).

The present invention contemplates the use of antisense nucleic acid to prevent/reduce expression of IL-11, IL-11Rα or gp130. In some embodiments, an agent capable of preventing or reducing the expression of IL-11, IL-11Rα or gp130 may cause reduced expression by RNA interference (RNAi).

In some embodiments, the agent may be an inhibitory nucleic acid, such as antisense or small interfering RNA, including but not limited to shRNA or siRNA.

In some embodiments the inhibitory nucleic acid is provided in a vector. For example, in some embodiments the agent may be a lentiviral vector encoding shRNA for one or more of IL-11, IL-11Rα or gp130.

Oligonucleotide molecules, particularly RNA, may be employed to regulate gene expression. These include antisense oligonucleotides, targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single-stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for IL-11, IL-11Rα and gp130 (e.g. the known mRNA sequences available from GenBank under Accession No.s: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the IL-11, IL-11Rα or gp130 mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of expression of IL-11, IL-11Rα or gp130 will preferably result in a decrease in the quantity of IL-11, IL-11Rα or gp130 expressed by a cell/tissue/organ/organ system/subject. For example, in a given cell the repression of IL-11, IL-11Rα or gp130 by administration of a suitable nucleic acid will result in a decrease in the quantity of IL-11, IL-11Rα or gp130 expressed by that cell relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of IL-11, IL-11Rα or gp130. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of IL-11, IL-11Rα or gp130.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, or kidney specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of IL-11, IL-11Rα or gp130 repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (Nature 2009 Jan. 22; 457 (7228):426-433), adenovirus (Shen et al., *FEBS Lett* 2003 Mar. 27; 539(1-3)111-4) and retroviruses (Barton and Medzhitov *PNAS* Nov. 12, 2002 vol. 99, no. 23 14943-14945).

In other embodiments a vector may be configured to assist delivery of the therapeutic oligonucleotide to the site at which repression of IL-11, IL-11Rα or gp130 expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., *AAPS* J. 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR$_6$; CO; or CONR'2 wherein R is H (or a salt) or alkyl (1-12C) and R6 is alkyl (1-9C) is joined to adjacent nucleotides through-O-or-S-.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3'position and other than a phosphate group at the 5'position. Thus modified nucleotides may also include 2'substituted sugars such as 2'-O-methyl-; 2'-O-alkyl; 2'-O-allyl; 2'-S-alkyl; 2'-5-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine,5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methylthio-N6-isopentenyladenine, uracil-5-oxyacetic acid methyl ester, pseudouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in *C. elegans, Drosophila*, plants, and mammals are known in the art (Fire A, et al., 1998 *Nature* 391:806-811; Fire A. *Trends Genet.* 15, 358-363 (1999); Sharp, P. A. *RNA interference* 2001. Genes Dev. 15, 485-490 (2001); Hammond, S. M., et al., *Nature Rev. Genet.* 2, 110-1119 (2001); Tuschl, T. *Chem. Biochem.* 2, 239-245 (2001); Hamilton, A. et al., *Science* 286, 950-952 (1999); Hammond, S. M., et al., *Nature* 404, 293-296 (2000); Zamore, P. D., et al., *Cell* 101, 25-33 (2000); Bernstein, E., et al., *Nature* 409, 363-366 (2001); Elbashir, S. M., et al., *Genes Dev.* 15, 188-200 (2001); WO0129058; WO9932619, and Elbashir S M, et al., 2001 *Nature* 411:494-498).

Accordingly, the invention provides nucleic acid that is capable, when suitably introduced into or expressed within a mammalian, e.g. human, cell that otherwise expresses IL-11, IL-11Rα or gp130, of suppressing IL-11, IL-11Rα or gp130 expression by RNAi.

Nucleic acid sequences for IL-11, IL-11Rα and gp130 (e.g. the known mRNA sequences available from GenBank under Accession No.s: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

The nucleic acid may have substantial sequence identity to a portion of IL-11, IL-11Rα or gp130 mRNA, e.g. as defined in GenBank accession no. NM_000641.3 GI:391353405 (IL-11), NM_001142784.2 GI:391353394 (IL-11Rα), NM_001190981.1 GI:300244534 (gp130) or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridise with each other. In a mammalian cell, the hairpin structure may be cleaved from the molecule by the enzyme DICER, to yield two distinct, but hybridised, RNA molecules.

In some preferred embodiments, the nucleic acid is generally targeted to the sequence of one of SEQ ID NOs 4 to 7 (IL-11) or to one of SEQ ID NOs 8 to 11 (IL-11Rα).

Only single-stranded (i.e. non self-hybridised) regions of an mRNA transcript are expected to be suitable targets for RNAi. It is therefore proposed that other sequences very close in the IL-11 or IL-11Rα mRNA transcript to the sequence represented by one of SEQ ID NOs 4 to 7 or 8 to 11 may also be suitable targets for RNAi. Such target sequences are preferably 17-23 nucleotides in length and preferably overlap one of SEQ ID NOs 4 to 7 or 8 to 11 by at least 1, 2, 3, 4, 5, 6, 7, 8, 9, 10, 11, 12, 13, 14, 15, 16, 17, 18 or all 19 nucleotides (at either end of one of SEQ ID NOs 4 to 7 or 8 to 11).

Accordingly, the invention provides nucleic acid that is capable, when suitably introduced into or expressed within a mammalian cell that otherwise expresses IL-11 or IL-11Rα, of suppressing IL-11 or IL-11Rα expression by RNAi, wherein the nucleic acid is generally targeted to the sequence of one of SEQ ID NOs 4 to 7 or 8 to 11.

By "generally targeted" the nucleic acid may target a sequence that overlaps with SEQ ID NOs 4 to 7 or 8 to 11. In particular, the nucleic acid may target a sequence in the mRNA of human IL-11 or IL-11Rα that is slightly longer or shorter than one of SEQ ID NOs 4 to 7 or 8 to 11 (preferably from 17-23 nucleotides in length), but is otherwise identical to one of SEQ ID NOs 4 to 7 or 8 to 11.

It is expected that perfect identity/complementarity between the nucleic acid of the invention and the target sequence, although preferred, is not essential. Accordingly, the nucleic acid of the invention may include a single mismatch compared to the mRNA of IL-11 or IL-11Rα. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences shown in SEQ ID NOs 12 to 15. In another embodiment, the nucleic acid (herein referred to as double-stranded siRNA) includes the double-stranded RNA sequences shown in SEQ ID NOs 16 to 19.

However, it is also expected that slightly shorter or longer sequences directed to the same region of IL-11 or IL-11Rα mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czauderna et al. 2003).

Any dinucleotide overhang may therefore be used in the antisense strand of the siRNA. Nevertheless, the dinucleotide is preferably -UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The invention also provides single-stranded nucleic acids (herein referred to as single-stranded siRNAs) respectively consisting of a component strand of one of the aforementioned double-stranded nucleic acids, preferably with the 3'-overhangs, but optionally without. The invention also provides kits containing pairs of such single-stranded nucleic acids, which are capable of hybridising with each other in vitro to form the aforementioned double-stranded siRNAs, which may then be introduced into cells.

The invention also provides DNA that, when transcribed in a mammalian cell, yields an RNA (herein also referred to as an shRNA) having two complementary portions which are capable of self-hybridising to produce a double-stranded motif, e.g. including a sequence selected from the group consisting of SEQ ID NOs: 12 to 15 or 16 to 19 or a sequence that differs from any one of the aforementioned sequences by a single base pair substitution.

The complementary portions will generally be joined by a spacer, which has suitable length and sequence to allow the two complementary portions to hybridise with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridise with each other, e.g. elongating the double-stranded motif beyond the exact sequences of SEQ ID NOs 12 to 15 or 16 to 19 by a small number (e.g. 1 or 2) of base pairs.

Similarly, the transcribed RNA preferably includes a 3' overhang from the downstream complementary portion. Again, this is preferably —UU or -UG, more preferably -UU.

Such shRNA molecules may then be cleaved in the mammalian cell by the enzyme DICER to yield a double-stranded siRNA as described above, in which one or each strand of the hybridised dsRNA includes a 3' overhang.

Techniques for the synthesis of the nucleic acids of the invention are of course well known in the art.

The skilled person is well able to construct suitable transcription vectors for the DNA of the invention using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-Ill promoter (H1) and a T5 transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the invention may be introduced into mammalian cells in vitro or in vivo using known techniques, as described below, to suppress expression of IL-11 or a receptor for IL-11.

Similarly, transcription vectors containing the DNAs of the invention may be introduced into tumour cells in vitro or in vivo using known techniques, as described below, for transient or stable expression of RNA, again to suppress expression of IL-11 or a receptor for IL-11.

Accordingly, the invention also provides a method of suppressing expression of IL-11 or a receptor for IL-11 in a mammalian, e.g. human, cell, the method comprising administering to the cell a double-stranded siRNA of the invention or a transcription vector of the invention.

Similarly, the invention further provides a method of treating a metabolic disease, the method comprising administering to a subject a double-stranded siRNA of the invention or a transcription vector of the invention.

The invention further provides the double-stranded siRNAs of the invention and the transcription vectors of the invention, for use in a method of treatment, preferably a method of treating a metabolic disease.

The invention further provides the use of the double-stranded siRNAs of the invention and the transcription vectors of the invention in the preparation of a medicament for the treatment of a metabolic disease.

The invention further provides a composition comprising a double-stranded siRNA of the invention or a transcription vector of the invention in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the invention are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE, dextran and calcium phosphate precipitation. In vivo gene transfer techniques include transfection with viral (typically retroviral) vectors and viral coat protein-liposome mediated transfection (Dzau et al. (2003) Trends in Biotechnology 11, 205-210).

In particular, suitable techniques for cellular administration of the nucleic acids of the invention both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in US patent numbers 6,649,1928 and 5,843,509B.

Inhibition of IL-11-Mediated Signalling

In embodiments of the present invention, agents capable of inhibiting the action of IL-11 may possess one or more of the following functional properties:

Inhibition of signalling mediated by IL-11;
Inhibition of signalling mediated by binding of IL-11 to IL-11Rα:gp130 receptor complex;
Inhibition of signalling mediated by binding of IL-11:IL-11Rα complex to gp130 (i.e. IL-11 trans signalling);
Inhibition of a process mediated by IL-11;
Inhibition of gene/protein expression of IL-11 and/or IL-11Rα.

These properties can be determined by analysis of the relevant agent in a suitable assay, which may involve comparison of the performance of the agent to suitable control agents. The skilled person is able to identify an appropriate control conditions for a given assay.

IL-11-mediated signalling and/or processes mediated by IL-11 includes signalling mediated by fragments of IL-11 and polypeptide complexes comprising IL-11 or fragments thereof. IL-11-mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, an agent may be capable of inhibiting the biological activity of IL-11 or an IL-11-containing complex.

In some embodiments, the agent is an antagonist of one or more signalling pathways which are activated by signal transduction through receptors comprising IL-11Rα and/or gp130, e.g. IL-11Rα:gp130. In some embodiments, the agent is capable of inhibiting signalling through one or more immune receptor complexes comprising IL-11Rα and/or gp130, e.g. IL-11Rα:gp130. In various aspects of the present invention, an agent provided herein is capable of inhibiting IL-11-mediated cis and/or trans signalling. In some embodiments in accordance with the various aspects of the present invention an agent provided herein is capable of inhibiting IL-11-mediated cis signalling.

In some embodiments, the agent may be capable of inhibiting IL-11-mediated signalling to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the agent (or in the presence of an appropriate control agent). In some embodiments, the agent is capable of reducing IL-11-mediated signalling to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the agent (or in the presence of an appropriate control agent).

In some embodiments, the IL-11-mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for an agent for inhibition of IL-11-mediated signalling may be determined, e.g. by culturing Ba/F3 cells expressing IL-11Rα and gp130 in the presence of human IL-11 and the agent, and measuring 3H-thymidine incorporation into DNA. In some embodiments, the agent may exhibit an $IC_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11-mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα, e.g. hyper IL-11. Hyper IL-11 was constructed using fragments of IL-11Rα (amino acid residues 1 to 317 consisting of domain 1 to 3; UniProtKB: Q14626) and IL-11 (amino acid residues 22 to 199 of UniProtKB: P20809) with a 20 amino acid long linker (SEQ ID NO:20). The amino acid sequence for Hyper IL-11 is shown in SEQ ID NO:21.

In some embodiments, the agent may be capable of inhibiting signalling mediated by binding of IL-11:IL-11Rα complex to gp130, and is also capable of inhibiting signalling mediated by binding of IL-11 to IL-11Rα:gp130 receptor.

In some embodiments, the agent may be capable of inhibiting a process mediated by IL-11.

In some embodiments, the agent may be capable of inhibiting gene/protein expression of IL-11 and/or IL-11Rα. Gene and/or protein expression can be measured as described herein or by methods in the art that will be well known to a skilled person.

In some embodiments, the agent may be capable of inhibiting gene/protein expression of IL-11 and/or IL-11Rα to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of expression in the absence of the agent (or in the presence of an appropriate control agent). In some embodiments, the agent is capable of inhibiting gene/protein expression of IL-11 and/or IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of expression in the absence of the agent (or in the presence of an appropriate control agent).

Treatment/Prevention of Metabolic Diseases

The present invention provides methods and articles (agents and compositions) for the treatment and/or prevention of metabolic diseases, e.g. metabolic diseases as described herein.

Treatment is achieved by inhibition of IL-11-mediating signalling (i.e. antagonism of IL-11-mediated signalling). That is, the present invention provides for the treatment/prevention of metabolic diseases through inhibition of IL-11 mediated signalling, in e.g. a cell, tissue/organ/organ system/subject. In some embodiments, inhibition of IL-11-mediated signalling in accordance with the present disclosure comprises inhibition of IL-11-mediated signalling in cells of the liver (e.g. hepatocytes).

Accordingly, the present invention provides an agent capable of inhibiting interleukin 11 (IL-11)-mediated signalling for use in a method of treating or preventing a metabolic disease.

Also provided is the use of an agent capable of inhibiting interleukin 11 (IL-11)-mediated signalling for use in the manufacture of a medicament for use in a method of treating or preventing a metabolic disease.

Further provided is a method of treating or preventing a metabolic disease, the method comprising administering to a subject in need of treatment a therapeutically effective amount of an agent capable of inhibiting interleukin 11 (IL-11)-mediated signalling.

The utility of the present invention extends to the treatment/prevention of any metabolic disease. The present invention also provides for the treatment/prevention of diseases/conditions that are caused or exacerbated by a metabolic disease. In some embodiments, the present invention provides for the treatment/prevention of diseases/conditions in a subject for which a metabolic disease provides a poor prognosis.

In some embodiments, a metabolic disease to be treated/prevented may be characterised by an increase in the expression of IL-11 and/or IL-11Rα (i.e. gene and/or protein expression) in an organ/tissue/subject affected by the metabolic disease e.g. as compared to normal organ/tissue/subject (i.e. in the absence of the metabolic disease).

Treatment/prevention of a metabolic disease according to the present invention may be of a metabolic disease that is associated with an upregulation of IL-11, e.g. an upregulation of IL-11 in cells or tissue in which the symptoms of the disease manifests or may occur, or upregulation of extracellular IL-11 or IL-11Rα.

The metabolic disease may affect any tissue or organ or organ system. In some embodiments, the metabolic disease may affect several tissues/organs/organ systems.

In some embodiments, the metabolic disease affects one or more of: the liver, pancreas, cardiovascular system, digestive system, the excretory system, the respiratory system, the renal system, the reproductive system, the circulatory system, the muscular system, the endocrine system, the exocrine system, the lymphatic system, the immune system, the nervous system, and/or the skeletal system.

In accordance with the various aspects disclosed herein, in some embodiments the metabolic disease is characterised by reduced function of the liver, or reduced function of cells of the liver (e.g. hepatocytes), relative to function in the absence of the metabolic disease. In some embodiments, the metabolic disease is characterised by increased levels of ALT and/or AST, and/or reduced levels of GSH (e.g. in the serum), relative to levels in the absence of the metabolic disease.

In some embodiments the metabolic disease is characterised by inflammation and/or fibrosis of the liver. In some embodiments, the metabolic disease is characterised by increased gene/protein expression of pro-inflammatory and/or pro-fibrotic factors (e.g. IL-11, IL-6, CCL2 and/or CCL5) by cells of the liver (e.g. hepatocytes) relative to levels in the absence of the metabolic disease. In some embodiments, the metabolic disease is characterised by increased gene/protein expression of collagen by cells of the liver and/or increased collagen content of the liver relative to levels in the absence of the metabolic disease.

In some embodiments the metabolic disease is characterised by and increased number/proportion of myofibroblasts in the liver relative to the number/proportion myofibroblasts in the liver in the absence of the metabolic disease.

In some embodiments the metabolic disease is characterised by increased apoptosis and/or necrosis of cells of the liver (e.g. hepatocytes) relative to the level in the absence of the metabolic disease. In some embodiments the metabolic disease is characterised by an increase in the number/proportion of apoptotic and/or necrotic liver cells relative to the number/proportion in the absence of the metabolic disease.

In some embodiments the metabolic disease is characterised by increased gene/protein expression of fatty acid synthase (FASN) by cells of the liver (e.g. hepatocytes) relative to levels in the absence of the metabolic disease. In some embodiments the metabolic disease is characterised by increased levels of reactive oxygen species (ROS) in cells of the liver (e.g. hepatocytes) relative to levels in the absence of the metabolic disease. In some embodiments the metabolic disease is characterised by increased gene/protein expression of NOX4 by cells of the liver (e.g. hepatocytes) relative to levels in the absence of the metabolic disease. In some embodiments the metabolic disease is characterised by increased levels of ERK and/or JNK activation in cells of the liver (e.g. hepatocytes) relative to levels in the absence of the metabolic disease.

In some embodiments the metabolic disease is characterised by increased triglyceride levels in the liver, or in cells of the liver (e.g. hepatocytes), relative to levels in the absence of the metabolic disease. In some embodiments the metabolic disease is characterised by hyperglycemia. In some embodiments the metabolic disease is characterised by hypertriglyceridemia. In some embodiments the metabolic disease is characterised by hypercholesterolemia. In some embodiments the metabolic disease is characterised by increased body weight relative to body weight in the absence of the metabolic disease. In some embodiments the metabolic disease is characterised by increased liver weight relative to liver weight in the absence of the metabolic disease.

Treatment may be effective to reduce/delay/prevent the development or progression of a metabolic disease. Treatment may be effective to reduce/delay/prevent the worsening of one or more symptoms of a metabolic disease. Treatment may be effective to improve one or more symptoms of a metabolic disease. Treatment may be effective to reduce the severity of and/or reverse one or more symptoms of a metabolic disease. Treatment may be effective to reverse the effects of a metabolic disease.

Prevention may refer to prevention of development of a metabolic disease, and/or prevention of worsening of a metabolic disease, e.g. prevention of progression of a metabolic disease, e.g. to a later/chronic stage.

In accordance with various aspects of the present invention, a method of treating and/or preventing a metabolic disease according to the present invention may comprise one or more of the following:

Reducing blood lipid level;
Reducing blood glucose level;
Increasing glucose tolerance (e.g. of a glucose intolerant subject);
Increasing insulin tolerance (e.g. of an insulin resistant subject);
Increasing pancreatic function
Reducing body weight (e.g. of an overweight/obese subject);
Reducing body fat mass;
Increasing lean mass;
Reducing fasting blood glucose level;
Reducing serum triglyceride level;
Reducing serum cholesterol level;
Increasing glucose tolerance;
Increasing pancreatic function (e.g. exocrine and/or endocrine function);
Increasing the growth of pancreatic tissue;
Regenerating pancreatic tissue;
Increasing pancreas weight;
Inhibiting PSC-to-myofibroblast transition by PSCs;
Reducing the number/proportion of myofibroblasts in the pancreas;
Reducing pancreas hydroxyproline level;
Reducing pancreas collagen level;
Reducing pancreas damage;
Reducing pancreatic islet cell hyperplasia;
Reducing glucagon expression;
Increasing insulin expression;
Increasing body weight (e.g. of a subject having a wasting disease, e.g. cachexia);
Reducing expression of IL-11 protein in the liver;
Reducing Erk activation in the liver;
Reducing JNK activation in the liver;
Reducing caspase-3 cleavage in the liver;
Reducing levels of ROS in the liver;
Reducing NOX4 expression in the liver;
Reducing steatosis, e.g. of the liver;
Reducing liver triglyceride level;
Reducing fatty acid synthase expression;
Reducing serum ALT and/or AST level;
Reducing expression of a pro-inflammatory factor (e.g. TNFα, CCL2, CCL5, IL-6, CXCL5, and/or CXCL1);
Reducing expression of a pro-fibrotic factor (e.g. IL-11, TIMP1, ACTA2, TGFβ1, MMP2, TIMP2, MMP9, COL1A2, COL1A1 and/or COL3A1);
Reducing serum TGFβ1 level;
Reducing expression/production by HSCs of IL-11, ACTA2, MMP2, TGFβ1, PDGF, ANG II, bFGF, CCL2 and/or $H_2O_2$;
Inhibiting HSC-to-myofibroblast transition by HSCs;
Reducing the number/proportion of myofibroblasts in the liver;
Reducing liver hydroxyproline level;
Reducing liver collagen level;
Increasing liver function;
Increasing serum GSH level;
Increasing the function of an organ/tissue affected by a metabolic disease;
Reducing liver damage;
Reducing hepatocyte death;
Reducing cell death as a consequence of lipotoxicity;
Reducing IL-11-mediated signalling in hepatocytes; and
Reducing the number/proportion of CD45+ cells in the liver.

In accordance with various aspects and embodiments described herein, treatment/prevention of a metabolic disease specifically comprises inhibition, reduction or prevention of lipotoxicity, e.g. in a given organ system/organ/tissue/cell type. In some embodiments treatment/prevention of a metabolic disease comprises inhibition/reduction/prevention of lipotoxicity in the liver, e.g. in hepatocytes.

Administration

Administration of an agent capable of inhibiting IL-11-mediated signalling is preferably in a "therapeutically effective" or "prophylactically effective" amount, this being sufficient to show benefit to the subject.

The actual amount administered, and rate and time-course of administration, will depend on the nature and severity of the disease and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Multiple doses of the agent may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In therapeutic applications, agents capable of inhibiting IL-11-mediated signalling are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium. The formulation and mode of administration may be selected according to the agent and disease to be treated.

Detection of IL-11 and Receptors for IL-11

Some aspects and embodiments of the present invention concern detection of expression of IL-11 or a receptor for IL-11 (e.g. IL-11Rα, gp130, or a complex containing IL-11Rα and/or gp130) in a sample obtained from a subject.

In some aspects and embodiments the present invention concerns the upregulation of expression (overexpression) of IL-11 or a receptor for IL-11 (as a protein or oligonucleotide encoding the respective IL-11 or receptor for IL-11) and detection of such upregulation as an indicator of suitability for treatment with an agent capable of inhibiting the action of IL-11 or with an agent capable of preventing or reducing the expression of IL-11 or a receptor for IL-11.

Upregulated expression comprises expression at a level that is greater than would normally be expected for a cell or tissue of a given type. Upregulation may be determined by measuring the level of expression of the relevant factor in a cell or tissue. Comparison may be made between the level of expression in a cell or tissue sample from a subject and a reference level of expression for the relevant factor, e.g. a value or range of values representing a normal level of expression of the relevant factor for the same or corresponding cell or tissue type. In some embodiments reference levels may be determined by detecting expression of IL-11 or a receptor for IL-11 in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of IL-11 or a receptor for IL-11 (e.g. IL-11Rα, gp130, or a complex containing IL-11Rα and/or gp130) may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of IL-11 or a receptor for IL-11 in a sample by contacting the sample with an agent capable of binding IL-11 or a receptor for IL-11 and detecting the formation of a complex of the agent and IL-11 or receptor for IL-11. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4- methyl coumarin, Cy3, Cy5), isotope markers, radioisotopes (e.g. 32P, 33P, 35S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of IL-11 or receptor for IL-11 in a sample. Quantified amounts of IL-11 or receptor for IL-11 from a test sample may be compared with reference values, and the comparison used to determine whether the test sample contains an amount of IL-11 or receptor for IL-11 that is higher or lower than that of the reference value to a selected degree of statistical significance.

Quantification of detected IL-11 or receptor for IL-11 may be used to determine up- or down-regulation or amplification of genes encoding IL-11 or a receptor for IL-11. In cases where the test sample contains fibrotic cells, such up-regulation, down-regulation or amplification may be compared to a reference value to determine whether any statistically significant difference is present.

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate. Samples may be stored and/or processed for subsequent determination of IL-11 expression levels.

Samples may be used to determine the upregulation of IL-11 or receptor for IL-11 in the subject from which the sample was taken.

In some preferred embodiments a sample may be a tissue sample, e.g. biopsy, taken from a tissue/organ affected by a metabolic disease. A sample may contain cells.

A subject may be selected for therapy/prophylaxis in accordance with the present invention based on determination that the subject has an upregulated level of expression of IL-11 or of a receptor for IL-11 (e.g. IL-11Rα, gp130, or a complex containing IL-11Rα and/or gp130). Upregulated expression of IL-11 or of a receptor for IL-11 may serve as a marker of a metabolic disease suitable for treatment with an agent capable of inhibiting IL-11 mediated signalling.

Upregulation may be in a given tissue or in selected cells from a given tissue. A preferred tissue may be liver tissue or pancreatic tissue. Upregulation of expression of IL-11 or of a receptor for IL-11 may also be determined in a circulating fluid, e.g. blood, or in a blood derived sample. Upregulation may be of extracellular IL-11 or IL-11Rα. In some embodiments expression may be locally or systemically upregulated.

Following selection, a subject may be administered with an agent capable of inhibiting IL-11 mediated signalling.

Diagnosis and Prognosis

Detection of upregulation of expression of IL-11 or a receptor for IL-11 (e.g. IL-11Rα, gp130, or a complex containing IL-11Rα and/or gp130) may also be used in a method of diagnosing a metabolic disease, identifying a subject at risk of developing a metabolic disease, and in methods of prognosing or predicting a subject's response to treatment with an agent capable of inhibiting IL-11 mediated signalling.

"Developing", "development" and other forms of "develop" may refer to the onset of a disorder/disease, or the continuation or progression of a disorder/disease.

In some embodiments a subject may be suspected of having or suffering from a metabolic disease, e.g. based on the presence of other symptoms indicative of a metabolic disease in the subject's body or in selected cells/tissues of the subject's body, or be considered at risk of developing a metabolic disease, e.g. because of genetic predisposition or exposure to environmental conditions, known to be risk factors for a metabolic disease. Determination of upregulation of expression of IL-11 or a receptor for IL-11 may confirm a diagnosis or suspected diagnosis, or may confirm that the subject is at risk of developing a metabolic disease. The determination may also diagnose a metabolic disease or predisposition as one suitable for treatment with an agent capable of inhibiting IL-11-mediated signalling.

As such, a method of providing a prognosis for a subject having, or suspected of having a metabolic disease may be provided, the method comprising determining whether the expression of IL-11 or a receptor for IL-11 is upregulated in a sample obtained from the subject and, based on the determination, providing a prognosis for treatment of the subject with an agent capable of inhibiting IL-11-mediated signalling.

In some aspects, methods of diagnosis or methods of prognosing or predicting a subject's response to treatment with an agent capable of inhibiting IL-11-mediated signalling may not require determination of the expression of IL-11 or a receptor for IL-11, but may be based on determining genetic factors in the subject that are predictive of upregulation of expression or activity. Such genetic factors may include the determination of genetic mutations, single nucleotide polymorphisms (SNPs) or gene amplification in IL-11, IL-11Rα and/or gp130 which are correlated with and/or predictive of upregulation of expression or activity and/or IL-11 mediated signalling. The use of genetic factors to predict predisposition to a disease state or response to treatment is known in the art, e.g. see Peter Stärkel Gut 2008; 57:440-442; Wright et al., Mol. Cell. Biol. March 2010 vol. 30 no. 6 1411-1420.

Genetic factors may be assayed by methods known to those of ordinary skill in the art, including PCR based assays, e.g. quantitative PCR, competitive PCR. By determining the presence of genetic factors, e.g. in a sample obtained from a subject, a diagnosis may be confirmed, and/or a subject may be classified as being at risk of developing a metabolic disease, and/or a subject may be identified as being suitable for treatment with an agent capable of inhibiting IL-11 mediated signalling.

Some methods may comprise determination of the presence of one or more SNPs linked to secretion of IL-11 or susceptibility to development of a metabolic disease. SNPs are usually bi-allelic and therefore can be readily determined using one of a number of conventional assays known to those of skill in the art (e.g. see Anthony J. Brookes. The essence of SNPs. Gene Volume 234, Issue 2, 8 Jul. 1999, 177-186; Fan et al., Highly Parallel SNP Genotyping. Cold Spring Harb Symp Quant Biol 2003. 68: 69-78; Matsuzaki et al., Parallel Genotyping of Over 10,000 SNPs using a one-primer assay on a high-density oligonucleotide array. Genome Res. 2004. 14: 414-425).

The methods may comprise determining which SNP allele is present in a sample obtained from a subject. In some embodiments determining the presence of the minor allele may be associated with increased IL-11 secretion or susceptibility to development of a metabolic disease.

Accordingly, in one aspect of the present invention a method for screening a subject is provided, the method comprising:

obtaining a nucleic acid sample from the subject;
determining which allele is present in the sample at the polymorphic nucleotide position of one or more of the SNPs listed in FIG. 33, FIG. 34, or FIG. 35 of WO 2017/103108 A1 (incorporated by reference herein), or a SNP in linkage disequilibrium with one of the listed SNPs with an $r^2 \leq 0.8$.

The determining step may comprise determining whether the minor allele is present in the sample at the selected polymorphic nucleotide position. It may comprise determining whether 0, 1 or 2 minor alleles are present.

The screening method may be, or form part of, a method for determining susceptibility of the subject to development of a metabolic disease, or a method of diagnosis or prognosis as described herein.

The method may further comprise the step of identifying the subject as having susceptibility to, or an increased risk of, developing a metabolic disease, e.g. if the subject is determined to have a minor allele at the polymorphic nucleotide position. The method may further comprise the step of selecting the subject for treatment with an agent capable of inhibiting IL-11 mediated signalling and/or administering an agent capable of inhibiting IL-11 mediated signalling to the subject in order to provide a treatment for a metabolic disease in the subject or to prevent development or progression of a metabolic disease in the subject.

In some embodiments, a method of diagnosing a metabolic disease, identifying a subject at risk of developing a metabolic disease, and methods of prognosing or predicting a subject's response to treatment with an agent capable of inhibiting IL-11 mediated signalling employs an indicator that is not detection of upregulation of expression of IL-11 or a receptor for IL-11, or genetic factors.

In some embodiments, a method of diagnosing a metabolic disease, identifying a subject at risk of developing a metabolic disease, and methods of prognosing or predicting a subject's response to treatment with an agent capable of inhibiting IL-11 mediated signalling is based on detecting, measuring and/or identifying one or more indicators of metabolic function.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practiced on the human or animal body. The sample obtained from a subject may be of any kind, as described herein above.

Other diagnostic or prognostic tests may be used in conjunction with those described here to enhance the accuracy of the diagnosis or prognosis or to confirm a result obtained by using the tests described here.

Subjects

Subjects may be animal or human. Subjects are preferably mammalian, more preferably human. The subject may be a non-human mammal, but is more preferably human. The subject may be male or female. The subject may be a patient.

The patient may have a metabolic disease as described herein. A subject may have been diagnosed with a metabolic disease requiring treatment, may be suspected of having such a metabolic disease, or may be at risk from developing a metabolic disease.

In embodiments according to the present invention the subject is preferably a human subject. In embodiments according to the present invention, a subject may be selected for treatment according to the methods based on characterisation for certain markers of a metabolic disease.

Further Methods and Uses Provided

The present invention also provides an agent capable of inhibiting IL-11-mediated signalling for use, or the use of an agent capable of inhibiting IL-11-mediated signalling, in a method of: reducing blood lipid level, reducing blood glucose level, increasing glucose tolerance (e.g. of a glucose intolerant subject), increasing insulin tolerance (e.g. of an insulin resistant subject), increasing pancreatic function reducing body weight (e.g. of an overweight/obese subject), reducing body fat mass, increasing lean mass, reducing fasting blood glucose level, reducing serum triglyceride level, reducing serum cholesterol level, increasing glucose tolerance, increasing pancreatic function (e.g. exocrine and/or endocrine function), increasing the growth of pancreatic tissue, regenerating pancreatic tissue, increasing pancreas weight, inhibiting PSC-to-myofibroblast transition by PSCs, reducing the number/proportion of myofibroblasts in the pancreas, reducing pancreas hydroxyproline level, reducing pancreas collagen level, reducing pancreas damage, reducing pancreatic islet cell hyperplasia, reducing glucagon expression, increasing insulin expression, increasing body weight (e.g. of a subject having a wasting disease, e.g. cachexia), reducing expression of IL-11 protein in the liver, Reducing Erk activation in the liver, reducing JNK activation in the liver; reducing caspase-3 cleavage in the liver; reducing levels of ROS in the liver; reducing NOX4 expression in the liver reducing steatosis, e.g. of the liver, reducing liver triglyceride level, reducing fatty acid synthase expression, reducing serum ALT and/or AST level, reducing expression of a pro-inflammatory factor (e.g. TNFα, CCL2, CCL5, IL-6, CXCL5, and/or CXCL1), reducing expression of a pro-fibrotic factor (e.g. IL-11, TIMP1, ACTA2, TGFβ1, MMP2, TIMP2, MMP9, COL1A2, COL1A1 and/or COL3A1), reducing serum TGFβ1 level, reducing expression/production by HSCs of IL-11, ACTA2, MMP2, TGFβ1, PDGF, ANG II, bFGF, CCL2 and/or $H_2O_2$, inhibiting HSC-to-myofibroblast transition by HSCs, reducing the number/proportion of myofibroblasts in the liver, reducing liver hydroxyproline level, reducing liver collagen level, increasing liver function, increasing serum GSH level, increasing the function of an organ/tissue affected by a metabolic disease, reducing liver damage, reducing hepatocyte death; reducing cell death (e.g. of hepatocytes) as a consequence of lipotoxicity; reducing IL-11-mediated signalling in hepatocytes or reducing the number/proportion of CD45+ cells in the liver.

The present invention also provides use of an agent capable of inhibiting IL-11-mediated signalling for use in the manufacture of a composition for use in a method of: reducing blood lipid level, reducing blood glucose level, increasing glucose tolerance (e.g. of a glucose intolerant subject), increasing insulin tolerance (e.g. of an insulin resistant subject), increasing pancreatic function reducing body weight (e.g. of an overweight/obese subject), reducing body fat mass, increasing lean mass, reducing fasting blood glucose level, reducing serum triglyceride level, reducing serum cholesterol level, increasing glucose tolerance, increasing pancreatic function (e.g. exocrine and/or endocrine function), increasing the growth of pancreatic tissue, regenerating pancreatic tissue, increasing pancreas weight, reducing pancreatic islet cell hyperplasia, reducing glucagon expression, increasing insulin expression, increasing body weight (e.g. of a subject having a wasting disease, e.g. cachexia), reducing expression of IL-11 protein in the liver, Reducing Erk activation in the liver, reducing JNK activation in the liver; reducing caspase-3 cleavage in the liver; reducing levels of ROS in the liver; reducing NOX4 expression in the liver reducing steatosis, e.g. of the liver, reducing liver triglyceride level, reducing fatty acid synthase expression, reducing serum ALT and/or AST level, reducing expression of a pro-inflammatory factor (e.g. TNFα, CCL2, CCL5, IL-6, CXCL5, and/or CXCL1), reducing expression of a pro-fibrotic factor (e.g. IL-11, TIMP1, ACTA2, TGFβ1, MMP2, TIMP2, MMP9, COL1A2, COL1A1 and/or COL3A1), reducing serum TGFβ1 level, reducing expression/production by HSCs of IL-11, ACTA2, MMP2, TGFβ1, PDGF, ANG II, bFGF, CCL2 and/or $H_2O_2$, inhibiting HSC-to-myofibroblast transition by HSCs, reducing the number/proportion of myofibroblasts in the liver, reducing liver hydroxyproline level, reducing liver collagen level, increasing liver function, increasing serum GSH level, increasing the function of an organ/tissue affected by a metabolic disease, reducing liver damage, reducing hepatocyte death; reducing cell death (e.g. of hepatocytes) as a consequence of lipotoxicity; reducing IL-11-mediated signalling in hepatocytes or reducing the number/proportion of CD45+ cells in the liver.

The present invention also provides method of: reducing blood lipid level, reducing blood glucose level, increasing glucose tolerance (e.g. of a glucose intolerant subject), increasing insulin tolerance (e.g. of an insulin resistant subject), increasing pancreatic function reducing body weight (e.g. of an overweight/obese subject), reducing body fat mass, increasing lean mass, reducing fasting blood glucose level, reducing serum triglyceride level, reducing serum cholesterol level, increasing glucose tolerance, increasing pancreatic function (e.g. exocrine and/or endocrine function), increasing the growth of pancreatic tissue, regenerating pancreatic tissue, increasing pancreas weight, reducing pancreatic islet cell hyperplasia, reducing glucagon expression, increasing insulin expression, increasing body weight (e.g. of a subject having a wasting disease, e.g. cachexia), reducing expression of IL-11 protein in the liver, Reducing Erk activation in the liver, reducing JNK activation in the liver; reducing caspase-3 cleavage in the liver; reducing levels of ROS in the liver; reducing NOX4 expression in the liver reducing steatosis, e.g. of the liver, reducing liver triglyceride level, reducing fatty acid synthase expression, reducing serum ALT and/or AST level, reducing expression of a pro-inflammatory factor (e.g. TNFα, CCL2, CCL5, IL-6, CXCL5, and/or CXCL1), reducing expression of a pro-fibrotic factor (e.g. IL-11, TIMP1, ACTA2, TGFβ1, MMP2, TIMP2, MMP9, COL1A2, COL1A1 and/or COL3A1), reducing serum TGFβ1 level, reducing expression/production by HSCs of IL-11, ACTA2, MMP2, TGFβ1, PDGF, ANG II, bFGF, CCL2 and/or $H_2O_2$, inhibiting HSC-to-myofibroblast transition by HSCs, reducing the number/proportion of myofibroblasts in the liver, reducing liver hydroxyproline level, reducing liver collagen level, increasing liver function, increasing serum GSH level, increasing the function of an organ/tissue affected by a metabolic disease, reducing liver damage, reducing hepatocyte death; reducing cell death (e.g. of hepatocytes) as a consequence of lipotoxicity; reducing IL-11-mediated signalling in hepatocytes or reducing the number/proportion of CD45+ cells in the liver.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, *Bioinformatics* 21, 951-960), T-coffee (Notredame et al. 2000, *J. Mol. Biol.* (2000) 302, 205-217), Kalign (Lassmann and Sonnhammer 2005, *BMC Bioinformatics,* 6(298)) and MAFFT (Katoh and Standley 2013, *Molecular Biology and Evolution,* 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human IL-11 (UniProt P20809) | MNCVCRLVLVVLSLWPDTAVAPGPPPGPPRVSPDPRAELDSTVLLTRSLLADTRQLA AQLRDKFPADGDHNLDSLPTLAMSAGALGALQLPGVLTRLRADLLSYLRHVQWLRR AGGSSLKTLEPELGTLQARLDRLLRRLQLLMSRLALPQPPPDPPAPPLAPPSSAWG GIRAAHAILGGLHLTLDWAVRGLLLLKTRL |
| 2 | Human gp130 (UniProt P40189-1) | MLTLQTWLVQALFIFLTTESTGELLDPCGYISPESPVVQLHSNFTAVCVLKEKCMDYF HVNANYIVWKTNHFTIPKEQYTIINRTASSVTFTDIASLNIQLTCNILTFGQLEQNVY GITIISGLPPEKPKNLSCIVNEGKKMRCEWDGGRETHLETNFTLKSEWATHKFADCKA KRDTPTSCTVDYSTVYFVNIEVWVEAENALGKVTSDHINFDPVYKVKPNPPHNLSVIN SEELSSILKLTWTNPSIKSVIILKYNIQYRTKDASTWSQIPPEDTASTRSSFTVQDLK PFTEYVFRIRCMKEDGKGYWSDWSEEASGITYEDRPSKAPSFWYKIDPSHTQGYRTVQ LVWKTLPPFEANGKILDYEVTLTRWKSHLQNYTVNATKLTVNLTNDRYLATLTVRNLV GKSDAAVLTIPACDFQATHPVMDLKAFPKDNMLWVEWTTPRESVKKYILEWCVLSDK APCITDWQQEDGTVHRTYLRGNLAESKCYLITVTPVYADGPGSPESIKAYLKQAPPS KGPTVRTKKVGKNEAVLEWDQLPVDVQNGFIRNYTIFYRTIIGNETAVNVDSSHTEYT LSSLTSDTLYMVRMAAYTDEGGKDGPEFTFTTPKFAQGEIEAIVVPVCLAFLLTTLLG VLFCFNKRDLIKKHIWPNVPDPSKSHIAQWSPHTPPRHNFNSKDQMYSDGNFTDVS VVEIEANDKKPPPEDLKSLDLFKKEKINTEGHSSGIGGSSCMSSSRPSISSSDENESS QNTSSTVQYSTVVHSGYRHQVPSVQVFSRSESTQPLLDSEERPEDLQLVDHVDGG DGILPRQQYFKQNCSQHESSPDISHFERSKQVSSVNEEDFVRLKQQISDHISQSCGS GQMKMFQEVSAADAFGPGTEGQVERFETVGMEAATDEGMPKSYLPQTVRQGGYM PQ |

| SEQ ID NO: | DESCRIPTION | SEQUENCE |
|---|---|---|
| 3 | Human IL11RA (UniProt O14626) | MSSSCSGLSRVLVAVATALVSASSPCPQAWGPPGVQYGQPGRSVKLCCPGVTAGD PVSWFRDGEPKLLQGPDSGLGHELVLAQADSTDEGTYICQTLDGALGGTVTLQLGY PPARPVVSCQAADYENFSCTWSPSQISGLPTRYLTSYRKKTVLGADSQRRSPSTGP WPCPQDPLGAARCVVHGAEFWSQYRINVTEVNPLGASTRLLDVSLQSILRPDPPQG LRVESVPGYPRRLRASWTYPASWPCQPHFLLKFRLQYRPAQHPAWSTVEPAGLEE VITDAVAGLPHAVRVSARDFLDAGTWSTANSPEAWGTPSTGTIPKEIPAWGQLHTQP EVEPQVDSPAPPRPSLQPHPRLLDHRDSVEQVAVLASLGILSFLGLVAGALALGLWL RLRRGGKDGSPKPGFLASVIPVDRRPGAPNL |
| 4 | siRNA target IL-11 | CCTTCCAAAGCCAGATCTT |
| 5 | siRNA target IL-11 | GCCTGGGCAGGAACATATA |
| 6 | siRNA target IL-11 | CCTGGGCAGGAACATATAT |
| 7 | siRNA target IL-11 | GGTTCATTATGGCTGTGTT |
| 8 | siRNA target IL-11Rα | GGACCATACCAAAGGAGAT |
| 9 | siRNA target IL-11Rα | GCGTCTTTGGGAATCCTTT |
| 10 | siRNA target IL-11Rα | GCAGGACAGTAGATCCCT |
| 11 | siRNA target IL-11Rα | GCTCAAGGAACGTGTGTAA |
| 12 | siRNA to IL-11 (NM_000641.3) | CCUUCCAAAGCCAGAUCUUdTdT-AAGAUCUGGCUUUGGAAGGdTdT |
| 13 | siRNA to IL-11 (NM_000641.3) | GCCUGGGCAGGAACAUAUAdTdT-UAUAUGUUCCUGCCCAGGCdTdT |
| 14 | siRNA to IL-11 (NM_000641.3) | CCUGGGCAGGAACAUAUAUdTdT-AUAUAUGUUCCUGCCCAGGdTdT |
| 15 | siRNA to IL-11 (NM_000641.3) | GGUUCAUUAUGGCUGUGUUdTdT-AACACAGCCAUAAUGAACCdTdT |
| 16 | siRNA to IL-11Rα (U32324.1) | GGACCAUACCAAAGGAGAUdTdT-AUCUCCUUUGGUAUGGUCCdTdT |
| 17 | siRNA to IL-11Rα (U32324.1) | GCGUCUUUGGGAAUCCUUUdTdT-AAAGGAUUCCCAAAGACGCdTdT |
| 18 | siRNA to IL-11Rα (U32324.1) | GCAGGACAGUAGAUCCCUAdTdT-UAGGGAUCUACUGUCCUGCdTdT |
| 19 | siRNA to IL-11Rα (U32324.1) | GCUCAAGGAACGUGUGUAAdTdT-UUACACACGUUCCUUGAGCdTdT |
| 20 | 20 amino acid linker | GPAGQSGGGGSGGGSGGGSV |
| 21 | Hyper IL-11 (IL-11RA: IL-11 fusion) | MSSSCSGLSRVLVAVATALVSASSPCPQAWGPPGVQYGQPGRSVKLCCPGVTAGD PVSWFRDGEPKLLQGPDSGLGHELVLAQADSTDEGTYICQTLDGALGGTVTLQLGY PPARPVVSCQAADYENFSCTWSPSQISGLPTRYLTSYRKKTVLGADSQRRSPSTGP WPCPQDPLGAARCVVHGAEFWSQYRINVTEVNPLGASTRLLDVSLQSILRPDPPQG LRVESVPGYPRRLRASWTYPASWPCQPHFLLKFRLQYRPAQHPAWSTVEPAGLEE VITDAVAGLPHAVRVSARDFLDAGTWSTANSPEAWGTPSTGPAGQSGGGGSGGG SGGGSVPGPPPGPPRVSPDPRAELDSTVLLTRSLLADTRQLAAQLRDKFPADGDHN LDSLPTLAMSAGALGALQLPGVLTRLRADLLSYLRHVQWLRRAGGSSLKTLEPELGT LQARLDRLLRRLQLLMSRLALPQPPPDPPAPPLAPPSSAWGGIRAAHAILGGLHLTLD WAVRGLLLLKTRL |
| 22 | Enx203 VH | EVQLQQSGPELVKPGASVKIPCKASGYTFTDYNMDWVKQSHGKSLEWIGDINPHNG GPIYNQKFTGKATLTVDKSSSTAYMELRSLTSEDTAVYYCARGELGHWYFDVWGTG TTVTVSS |
| 23 | Enx203 VL | DIVLTQSPASLAVSLGQRATISCRASKSVSTGYSYIHWYQQKPGQPPKLLIYLASNL DSGVPARFSGSGSGTDFTLNIHPVEEEDAATYYCQHSRDLPPTFGGGTKLEIK |
| 24 | Enx209 VH | QVQLQQPGAELVRPGSSVKLSCKASGYTFTNYWMHWLKQRPVQGLEWIGNIGPSD SKTHYNQKFKDKATLTVDKSSSTAYMQLNSLTSEDSAVYYCARGDYVLFTYWGQGT LVTVSA |

| SEQ ID NO: | DESCRIPTION | SEQUENCE |
|---|---|---|
| 25 | Enx209 VL | DIVLTQSPATLSLSPGERATLSCRASQSISNNLHWYQQKSHEAPRLLIKYASQSIS GIPARFSGSGSGTDFTLSFSSLETEDFAVYFCQQSYSWPLTFGQGTKLEIK QVQLVQSGGGVVQPGRSLRLSCAASGFTSSYGMHWVRQAPGKGLEWVAVISYD |
| 26 | Enx108A VH | GSNKYYADSVKGRFTISRDNSKNTLYLQMNSLRAEDTAVYYCAKIGATDPLDYWGQ GTLVTVSS |
| 27 | Enx108A VL | QSALTQPRSVSGSPGQSVTLSCTGTSSDVGGYNYVSWYQHYPGKAPKLMIFDVNE RSSGVPDRFSGSKSGNTASLTISGLQAEDEADYYCASYAGRYTWMFGGGTKVTVL G |
| 28 | Enx108A hIgG4 (L248E, S241 P) HC | QVQLVQSGGGVVQPGRSLRLSCAASGFTSSYGMHWVRQAPGKGLEWVAVISYD GSNKYYADSVKGRFTISRDNSKNTLYLQMNSLRAEDTAVYYCAKIGATDPLDYWGQ GTLVTVSSASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVESKYGPPC PPCPAPEFEGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTISKA KGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK |
| 29 | Enx108A lambda LC | QSALTQPRSVSGSPGQSVTLSCTGTSSDVGGYNYVSWYQHYPGKAPKLMIFDVNE RSSGVPDRFSGSKSGNTASLTISGLQAEDEADYYCASYAGRYTWMFGGGTKVTVL GQPKAAPSVTLFPPSSEELQANKATLVCLISDFYPGAVTVAWKADSSPVKAGVETTT PSKQSNNKYAASSYLSLTPEQWKSHRSYSCQVTHEGSTVEKTVAPTECS |
| 30 | hEnx203 VH | EVQLVQSGAEVKKPGASVKISCKASGYTFTDYNMDWVKQAPGQRLEWIGDINPHNG GPIYNQKFTGRATLTVDKSASTAYMELSSLRSEDTAVYYCARGELGHWYFDVWGQ GTTVTVSS |
| 31 | hEnx203 VL | DIVLTQSPASLALSPGERATLSCRASKSVSTSGYSYIHWYQQKPGQAPRLLIYLASNL DSGVPARFSGSGSGTDFTLTISSLEEEDFATYYCQHSRDLPPTFGQGTKLEIK QVQLVQSGAEVKKPGASVKVSCKASGYTFTNYWMHWLRQRPGQGLEWIGNIGPSD |
| 32 | hEnx209 VH | SKTHYNQKFKDRVTMTVDKSTSTAYMELSSLRSEDTAVYYCARGDYVLFTYWGQG TLVTVSS |
| 33 | hEnx209 VL | DIVLTQSPATLSLSPGERATLSCRASQSISNNLHWYQQKPGQAPRLLIKYASQSISGI PARFSGSGSGTDFTLTISSLEPEDFAVYYCQQSYSWPLTFGQGTKLEIK |
| 34 | Enx108A VH CDR1 | SYGMH |
| 35 | Enx108A VH CDR2 | VISYDGSNKYYADSVKG |
| 36 | Enx108A VH CDR3 | IGATDPLDY |
| 37 | Enx108A VL CDR1 | TGTSSDVGGYNYVS |
| 38 | Enx108A VL CDR2 | DVNERSS |
| 39 | Enx108A VL CDR3 | ASYAGRYTWM |
| 40 | Enx203, hEnx203 VH CDR1 | DYNMD |
| 41 | Enx203, hEnx203 VH CDR2 | DINPHNGGPIYNQKFTG |
| 42 | Enx203, hEnx203 VH CDR3 | GELGHWYFDV |
| 43 | Enx203, hEnx203 VL CDR1 | RASKSVSTSGYSYIH |
| 44 | Enx203, hEnx203 VL CDR2 | LASNLDS |
| 45 | Enx203, hEnx203 VL CDR3 | QHSRDLPPT |
| 46 | Enx209, hEnx209 VH CDR1 | NYWMH |
| 47 | Enx209, hEnx209 VH CDR2 | NIGPSDSKTHYNQKFKD |

| SEQ ID NO: | DESCRIPTION | SEQUENCE |
|---|---|---|
| 48 | Enx209, hEnx209 VH CDR3 | GDYVLFTY |
| 49 | Enx209, hEnx209 VL CDR1 | RASQSISNNLH |
| 50 | Enx209, hEnx209 VL CDR2 | YASQSIS |
| 51 | Enx209, hEnx209 VL CDR3 | QQSYSWPLT |
| 52 | Human IGHG1 constant (K214R, D356E, L358M) | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTCPPCPA PELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDS DGSFFLYSKLTVDKSRWQQGNVFSCSVMHEALHNHYTQKSLSLSPGK |
| 53 | Human IGHG4 constant (L248E, S241 P) | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPE FEGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| 54 | Human IGKC constant | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 55 | Human IGLC2 constant | GQPKAAPSVTLFPPSSEELQANKATLVCLISDFYPGAVTVAWKADSSPVKAGVETTT PSKQSNNKYAASSYLSLTPEQWKSHRSYSCQVTHEGSTVEKTVAPTECS |
| 56 | hEnx203 hIgG1 HC | EVQLVQSGAEVKKPGASVKISCKASGYTFTDYNMDWVKQAPGQRLEWIGDINPHNG GPIYNQKFTGRATLTVDKSASTAYMELSSLRSEDTAVYYCARGELGHWYFDVWGQ GTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSCDK THTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPGK |
| 57 | hEnx203 kappa LC | DIVLTQSPASLALSPGERATLSCRASKSVSTSGYSYIHWYQQKPGQAPRLLIYLASNL DSGVPARFSGSGSGTDFTLTISSLEEEDFATYYCQHSRDLPPTFGQGTKLEIKRTVA APSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC |
| 58 | hEnx209 hIgG4 (L248E, S241P) HC | QVQLVQSGAEVKKPGASVKVSCKASGYTFTNYWMHWLRQRPGQGLEWIGNIGPSD SKTHYNQKFKDRVTMTVDKSTSTAYMELSSLRSEDTAVYYCARGDYVLFTYWGQG TLVTVSSASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVESKYGPPCP PCPAPEFEGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGK |
| 59 | hEnx209 kappa LC | DIVLTQSPATLSLSPGERATLSCRASQSISNNLHWYQQKPGQAPRLLIKYASQSISGI PARFSGSGSGTDFTLTISSLEPEDFAVYYCQQSYSWPLTFGQGTKLEIKRTVAAPSV FIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Methods disclosed herein may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. In some embodiments, methods performed in vivo may be performed on non-human animals. "Ex vivo" refers to something present or taking place outside an organism, e.g. outside the human or animal body, which may be on tissue (e.g. whole organs) or cells taken from the organism.

Where a nucleic acid sequence is disclosed herein, the reverse complement thereof is also expressly contemplated.

For standard molecular biology techniques, see Sambrook, J., Russel, D. W. Molecular Cloning, A Laboratory Manual. 3 ed. 2001, Cold Spring Harbor, N.Y.: Cold Spring Harbor Laboratory Press Aspects and embodiments of the present invention will now be discussed with reference to the accompanying figures. Further aspects and embodiments will be apparent to those skilled in the art. All documents mentioned in this text are incorporated herein by reference in their entirety. While the invention has been described in conjunction with the exemplary embodiments described below, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

BRIEF DESCRIPTION OF THE FIGURES

Embodiments and experiments illustrating the principles of the invention will now be discussed with reference to the accompanying figures.

EXAMPLES

Figure 1A:
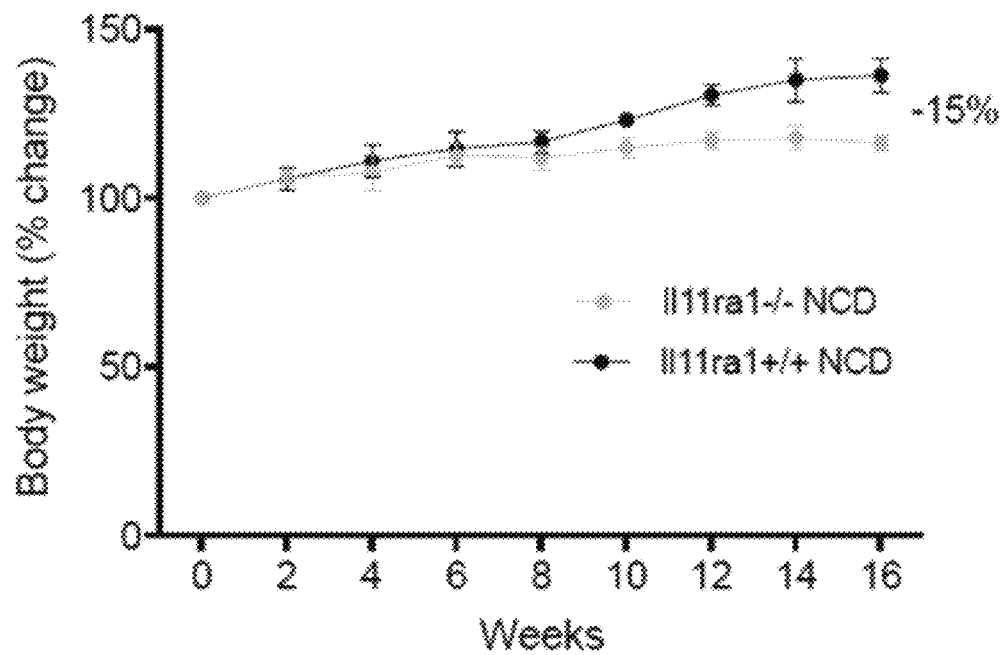
FIGS. 1A and 1B. Graphs showing percentage change in body weight over time for IL-11 RA knockout (Il11ra1−/−) or wildtype, IL-11 RA expressing (Il11ra1+/+) mice fed (1A) a normal chow diet (NCD), or (1B) a Western diet along with fructose (WDF).

In the following Examples, the inventors demonstrate that inhibition of IL-11-mediated signalling reduces the severity and reverses the symptoms of a range of metabolic diseases.

Example 1: General Methods for Examples 1 to 4

IL-11-RA-Knockout Mice

Mice lacking functional alleles for Il11rα (Il11rα-/-) were on C576I/6J genetic background (B6.129S1-Il11rαtm1Wehi/J, Jackson's Laboratory).

Treatment with Anti-IL-11 or Anti-IL-11Rα Antibody

Mice were injected intraperitoneally with 10 mg/kg of an antagonist anti-IL-11 antibody, an antagonist anti-IL-11Rα antibody, or an identical amount of isotype-matched IgG control antibody. The anti-IL-11 and anti-IL-11Rα antibodies bind to mouse IL-11 and mouse IL-11Rα respectively, and inhibit IL-11 mediated signalling.

Specifically, the anti-IL-11 antibody used in the present examples is mouse anti-mouse IL-11 IgG X203, which is described e.g. in Ng et al., Sci Transl Med. (2019) 11(511) pii: eaaw1237 (also published as Ng, et al., "IL-11 is a therapeutic target in idiopathic pulmonary fibrosis." bioRxiv 336537; doi: https://doi.org/10.1101/336537). X203 is also referred to as "Enx203", and comprises the VH region according to SEQ ID NO:92 of WO 2019/238882 A1 (SEQ ID NO:22 of the present disclosure), and the VL region according to SEQ ID NO:94 of WO 2019/238882 A1 (SEQ ID NO:23 of the present disclosure).

The anti-IL-11Rα antibody used in the present examples is mouse anti-mouse IL-11Rα IgG X209, which is described e.g. in Widjaja et al., Gastroenterology (2019) 157(3):777-792 (also published as Widjaja, et al., "IL-11 neutralising therapies target hepatic stellate cell-induced liver inflammation and fibrosis in NASH." bioRxiv 470062; doi: https://doi.org/10.1101/470062). X209 is also referred to as "Enx209", and comprises the VH region according to SEQ ID NO:7 of WO 2019/238884 A1 (SEQ ID NO:24 of the present disclosure), and the VL region according to SEQ ID NO:14 of WO 2019/238884 A1 (SEQ ID NO:25 of the present disclosure).

Diets

Western diet along with fructose (WDF) was used to establish metabolic disorders that closely resemble those in humans during obesity, T2D and NAFLD (Baena et al., Sci Rep (2016) 6: 26149, Machado et al., PLoS One (2015) 10:e0127991).

In order to establish metabolic diseases such as obesity and T2D, mice were fed Western diet (D12079B, Research Diets), supplemented with 15% weight/volume fructose in drinking water (WDF) for 16 weeks, from 12 weeks of age.

High fat methionine choline deficient diet (HFMCD) was used to establish cachexia-like metabolic disorder. In order to establish cachexia weight loss and lean mass loss, C57BL/6N mice were fed with methionine and choline deficient (HFMCD) diet supplemented with 60 kcal % fat (A06071301B, Research Diets).

Control subjects were fed normal chow (NC, Specialty Feeds) and drinking water.

Echo MRI Analysis for Body Composition

Total body fat and lean mass measurements were performed every two weeks by EchoMRI analysis using 4in1 Body Composition Analyzer for Live Small Animals.

Fasting Blood Glucose Measurements

For fasting blood glucose measurements, mice were fasted for 6 hours prior to blood collection (via tail snip), and Accu-Chek blood glucose meter was used to obtain fasting glucose measurements.

Intraperitoneal Glucose Tolerance Test (ipGTT)

For intraperitoneal glucose tolerance tests, mice were fasted for 6 h prior to being subjected to ipGTT. Basal fasting glucose was measured by tail snip using Accu-Chek blood glucose meter. 2 g/kg lean mass glucose was injected intraperitoneally, and glucose measurements were taken every 15 min for 2 hours. The area under the curve (AUC) was calculated, and plotted as bar graphs.

Histology of Pancreas for Islet of Langerhans, Glucagon and Insulin

For histological analysis, pancreas samples were excised and fixed for 24 hours at RT in 4% neutral-buffered formalin (NBF), and stored in 30% sucrose. 5 µm cryosections were stained with either glucagon or insulin antibodies overnight, and visualized with ImmPRESS HRP IgG polymer detection kit (Vector Laboratories) with ImmPACT DAB Peroxidase Substrate (Vector Laboratories) according to standard protocols, and examined by light microscopy.

Example 2: Antagonism of IL-11-Mediated Signalling in Obesity-Related Disorders

To investigate the effect of antagonism of IL-11-mediated signalling on obesity and related disorders like T2D, in vivo experiments were performed using diet-induced mouse models of these metabolic diseases using IL-11 receptor alpha knock out (IL11-RA–/–) mice, or by treatment of mice with antagonist anti-mouse IL-11 antibody, or antagonist anti-mouse IL11-RA antibody.

IL11RA knockout mice fed on normal chow diet (NCD) or WDF displayed an improved metabolic phenotype as compared to wildtype IL11RA-expressing littermates.

Figure 1B:
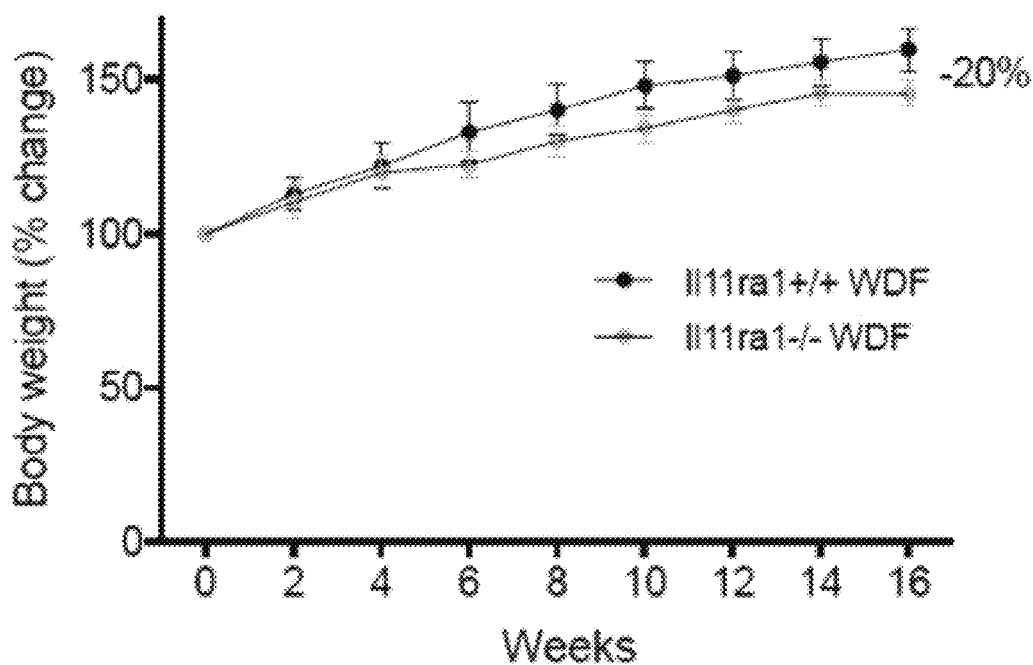
Figure 2A:
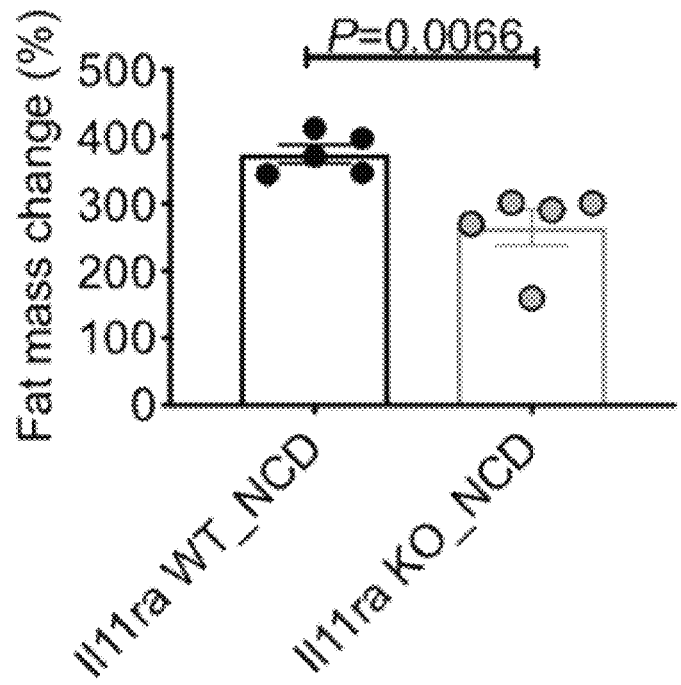
FIGS. 2A and 2B. Bar charts showing percentage total body fat mass change for IL-11 RA knockout (Il11ra1KO) or wildtype, IL-11 RA expressing (Il11raWT) mice fed (2A) a normal chow diet (NCD), or (2B) a Western diet along with fructose (WDF).
Figure 2B:
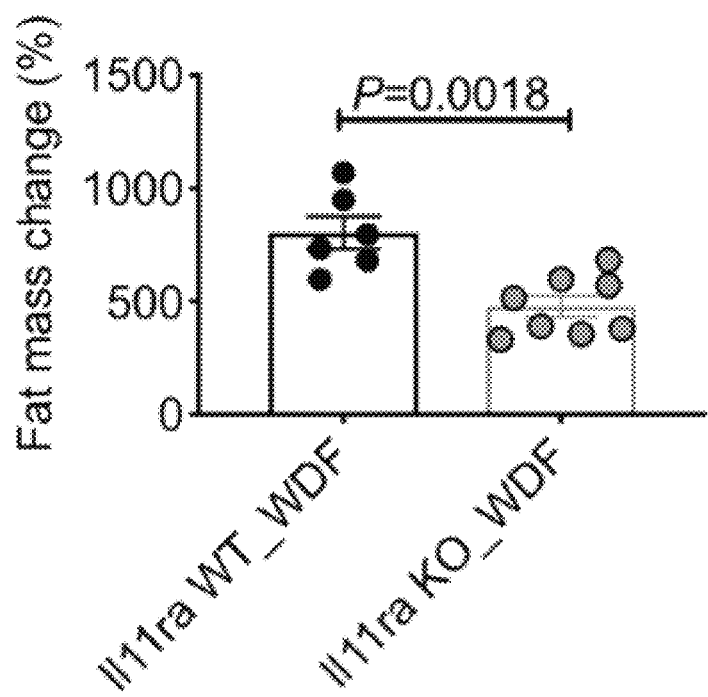
Figure 3:
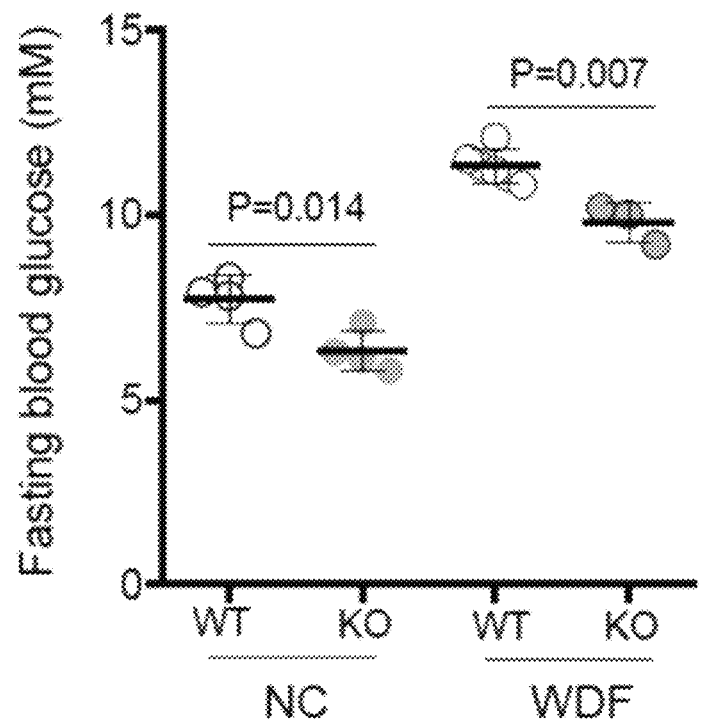
FIG. 3. Graph showing fasting blood glucose levels (mM) for IL-11 RA knockout (KO) or wildtype, IL-11 RA expressing (WT) mice fed a normal chow diet (NC), or a Western diet along with fructose (WDF).
Figure 4:
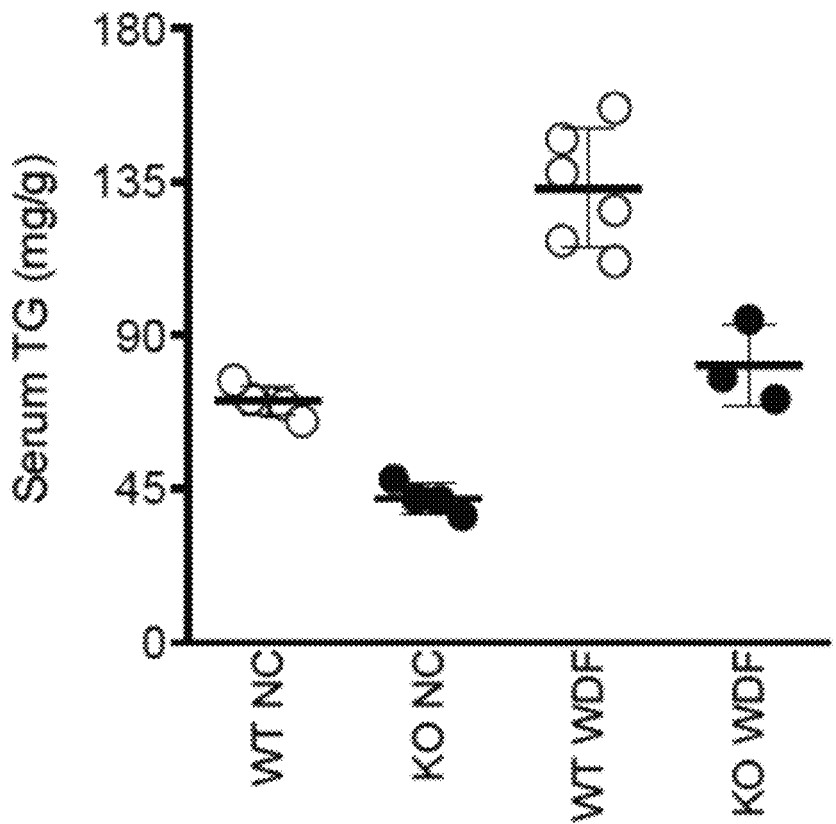
FIG. 4. Graph showing serum triglyceride levels (mg/g) for IL-11 RA knockout (KO) or wildtype, IL-11 RA expressing (WT) mice fed a normal chow diet (NC), or a Western diet along with fructose (WDF).
Figure 5A:
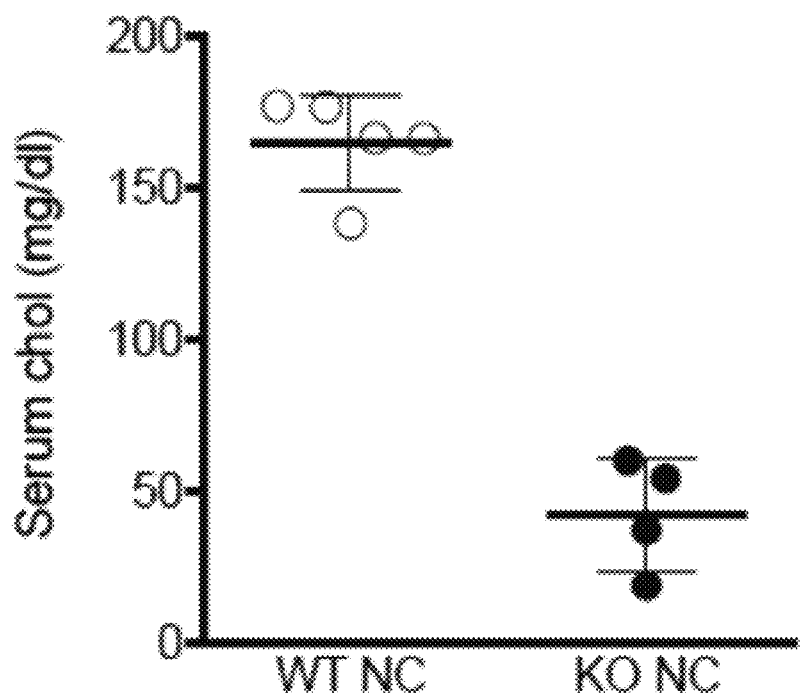
FIGS. 5A and 5B. Graphs showing serum cholesterol levels (mg/dl) for IL-11 RA knockout (KO) or wildtype, IL-11 RA expressing (WT) mice fed (5A) a normal chow diet (NC), or (5B) a Western diet along with fructose (WDF).
Figure 5B:
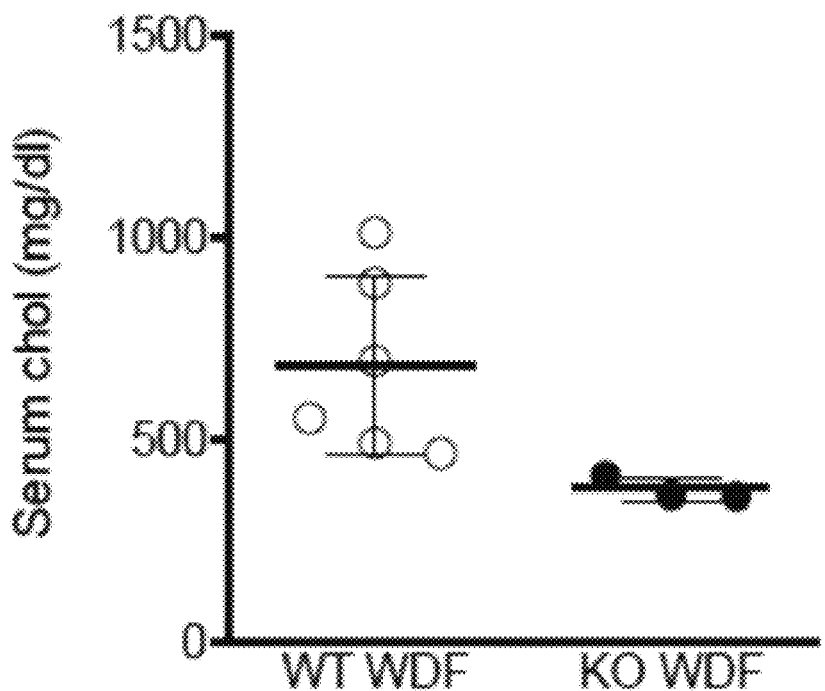

FIGS. 1A and 1B show that the body weight increased more for wildtype mice than for IL11RA knockout mice. FIGS. 2A and 2B show that IL11RA knockout mice had significantly lower total body fat mass compared to wildtype mice. FIG. 3 shows that IL11RA knockout mice had significantly lower fasting blood glucose levels compared to wildtype mice. FIG. 4 shows that IL11RA knockout mice had significantly lower serum triglyceride levels compared to wildtype mice. FIGS. 5A and 5B show that IL11RA knockout mice had significantly lower serum cholesterol levels compared to wildtype mice.

The results suggested that reduction of IL-11 mediated signalling has beneficial effects in metabolism.

The inventors next investigated the effect of an antagonist anti-IL-11 RA antibody or control IgG antibody on mice fed on WDF.

Figure 6A:
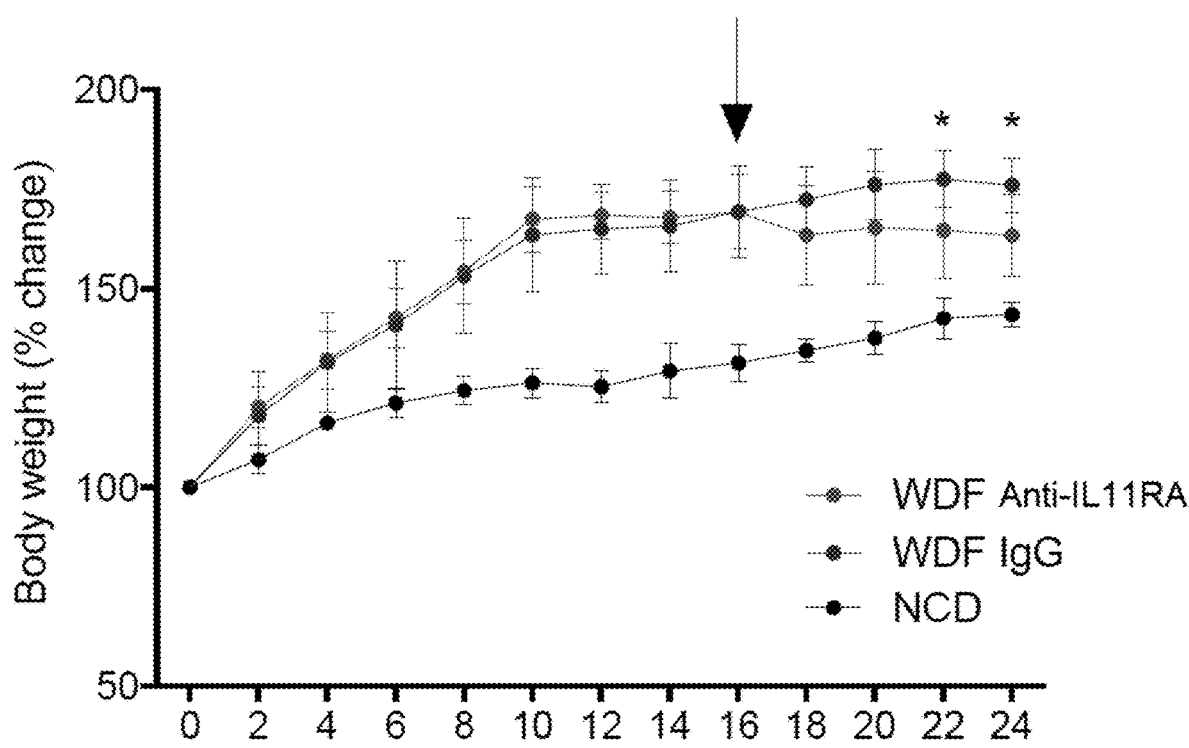
FIGS. 6A and 6B. Graph and box plot showing change in body weight for mice fed normal chow (NC) or a Western diet with fructose (WDF), and treated with anti-IL-11 RA antibody or IgG control. (6A) shows percentage change in body weight over time (weeks). (6B) shows percentage difference between total body fat mass and lean mass. *P<0.05.
Figure 6B:
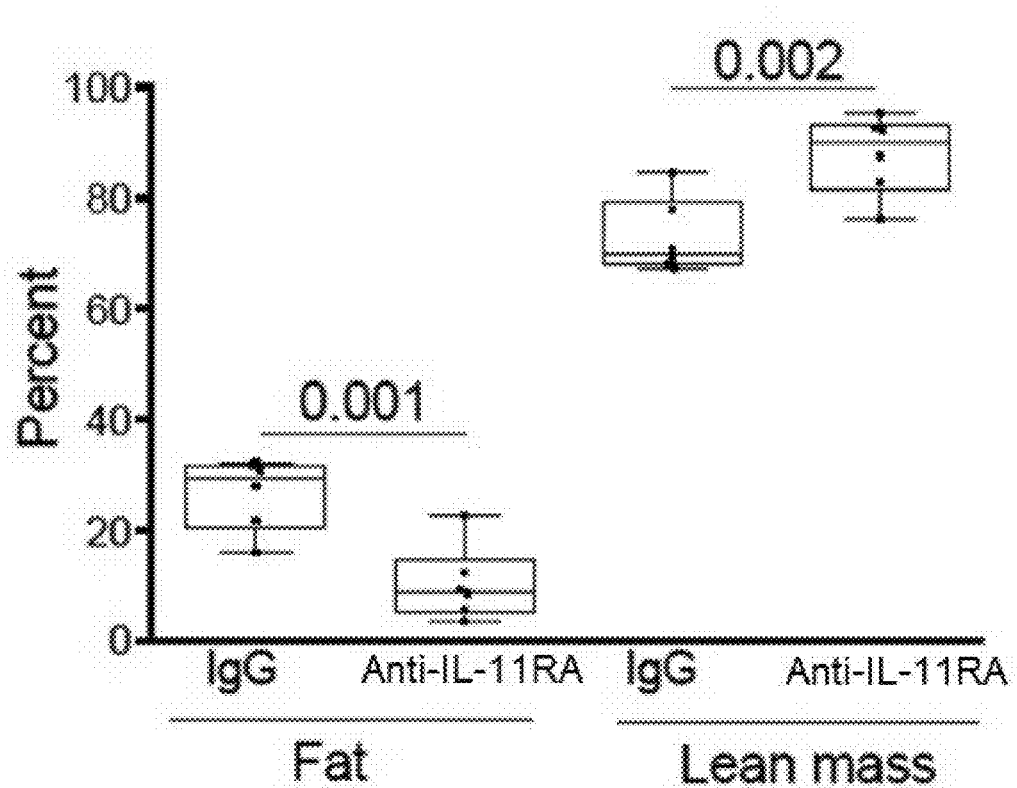

Strikingly, anti-IL-11 RA antibody-treated mice fed on WDF showed significant reduction in body weight when compared to control IgG anybody-treated mice fed on WDF (FIG. 6A). Similar to IL11RA KO mice (FIG. 3), these anti-IL-11 RA antibody-treated mice also showed significantly reduced fat mass (FIG. 6B).

Figure 7A:
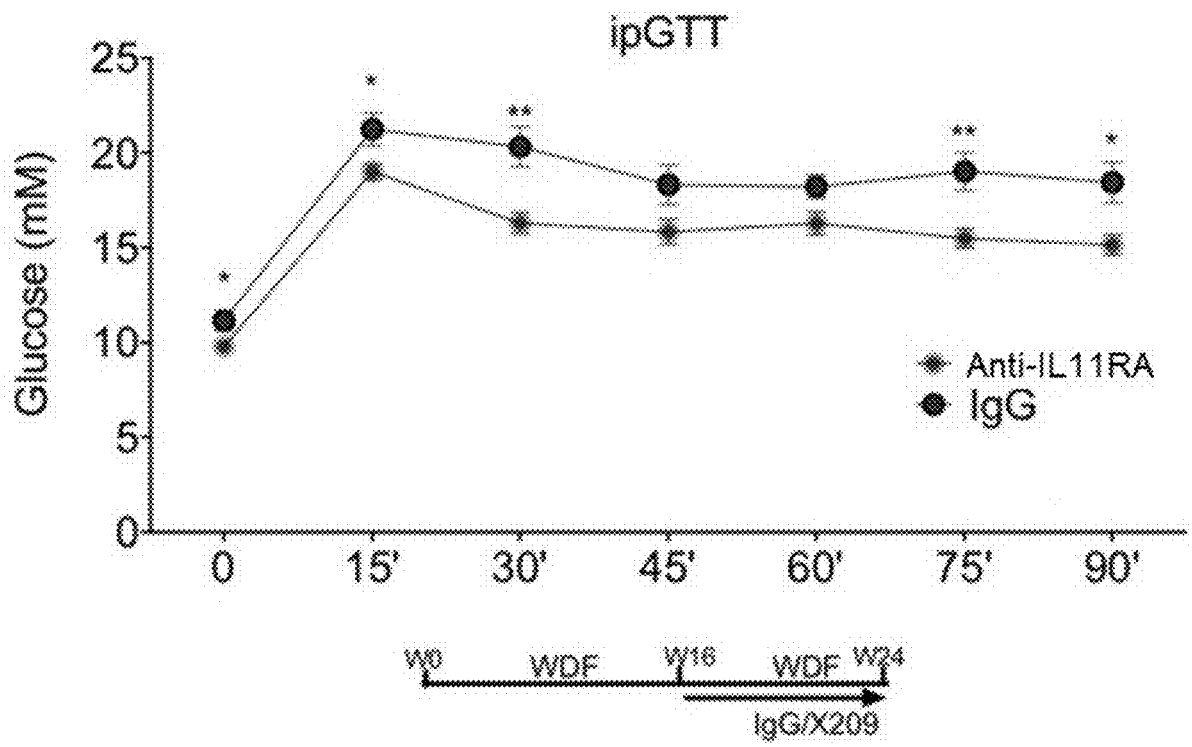
FIGS. 7A and 7B. Graph, schematic and bar chart showing glucose tolerance for mice fed a Western diet with fructose (WDF), and treated with anti-IL-11 RA antibody or IgG control, as determined by intraperitoneal glucose tolerance test (ipGTT). (7A) shows changes in the level glucose (mM) from 1 min timepoint. (7B) shows the area under the curve. *P<0.05, ** P<0.01.
Figure 7B:
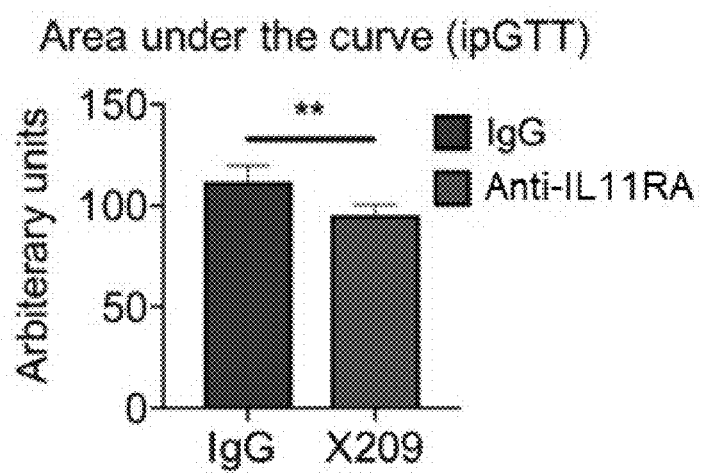

Interestingly, an increase in lean mass was also observed in mice treated with anti-IL-11 RA antibody compared to IgG control-treated mice, suggesting that inhibition of IL-11 signalling during WDF-induced metabolic pathogenesis recovered muscle mass. Furthermore, intraperitoneal glucose tolerance test (ipGTT) results showed, along with fasting glucose, significant improvement in glucose tolerance in mice treated with anti-IL-11 RA antibody (FIGS. 7A and 7B).

Figure 8:
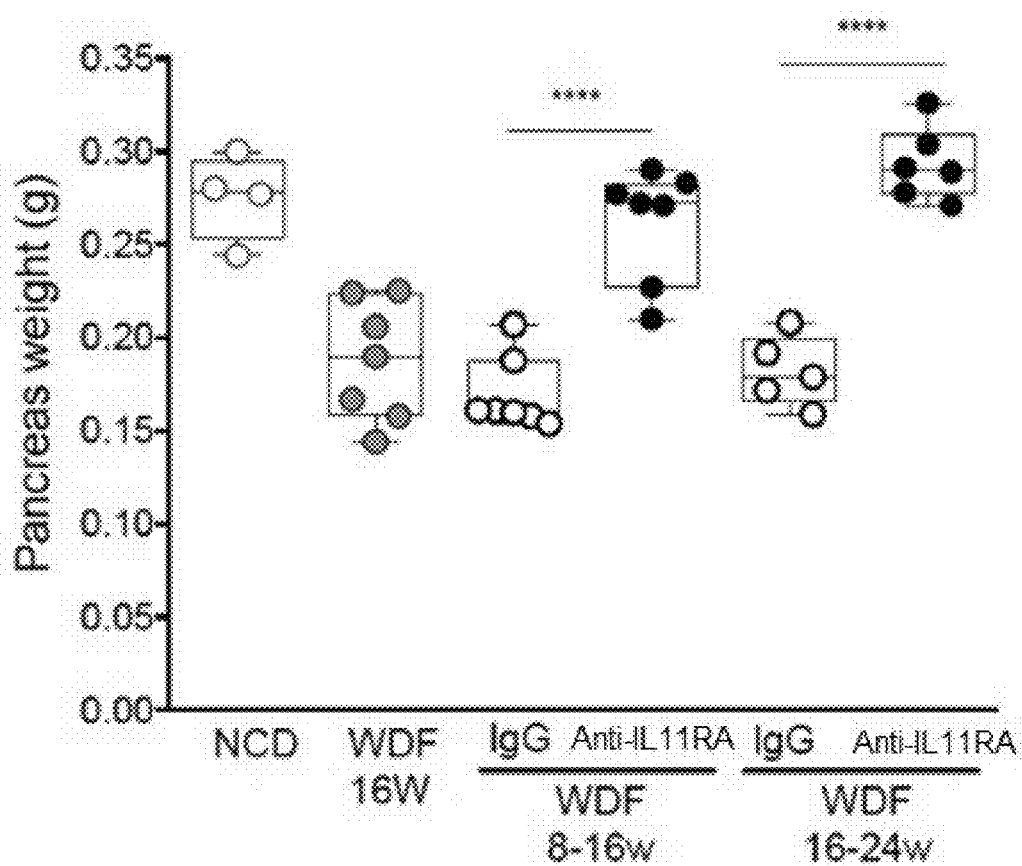
FIG. 8. Box plot showing pancreas weight for mice fed normal chow (NCD) or a Western diet with fructose (WDF), and treated from different time points with anti-IL-11 RA antibody or IgG control. ****P<0.0001.

The analysis was extended to the effects on the pancreas. Anti-IL-11 RA antibody-treated mice fed on WDF were unexpectedly found to display remarkable protection against WDF-induced loss of pancreas (FIG. 8) whether treated from 8 to 16 weeks (for protecting against effects associated with metabolic disease) or treated from 16 to 24 week (for reversing effects associated with metabolic disease) when compared to IgG control-treated mice.

Figure 9A:
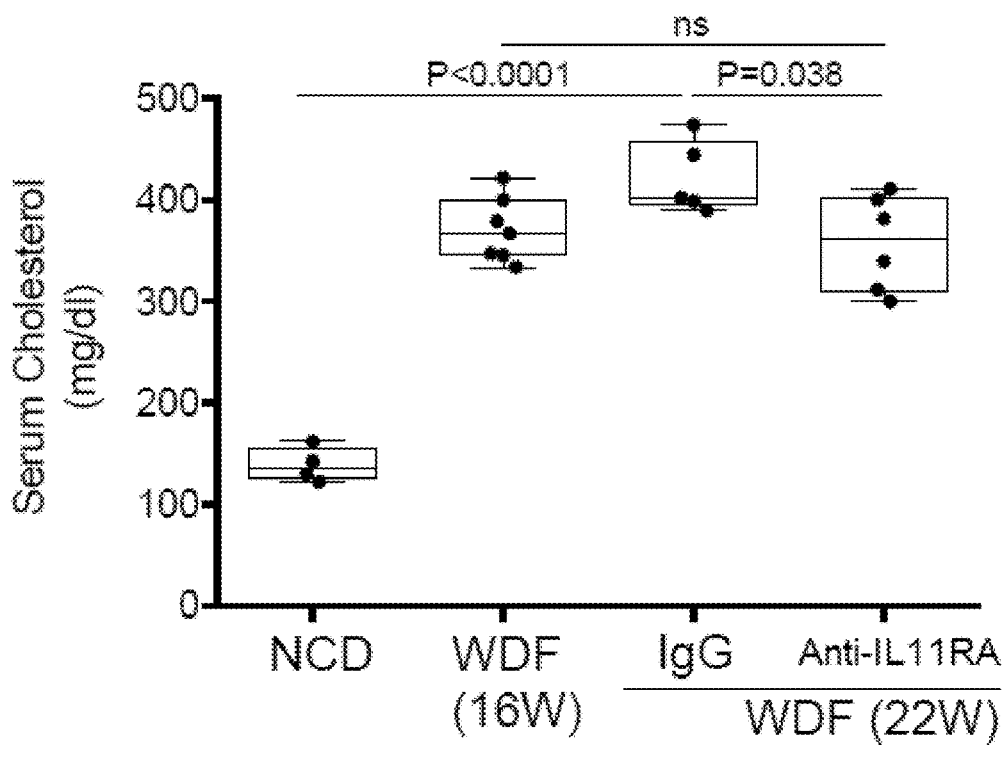
FIGS. 9A to 9C. Box plots showing (9A) serum cholesterol levels (mg/dl), (9B) serum triglyceride levels (mg/g) and (9C) fasting blood glucose levels (mM) for mice fed normal chow (NCD) or a Western diet with fructose (WDF), and treated anti-IL-11 RA antibody or IgG control, at the indicated time points.
Figure 9B:
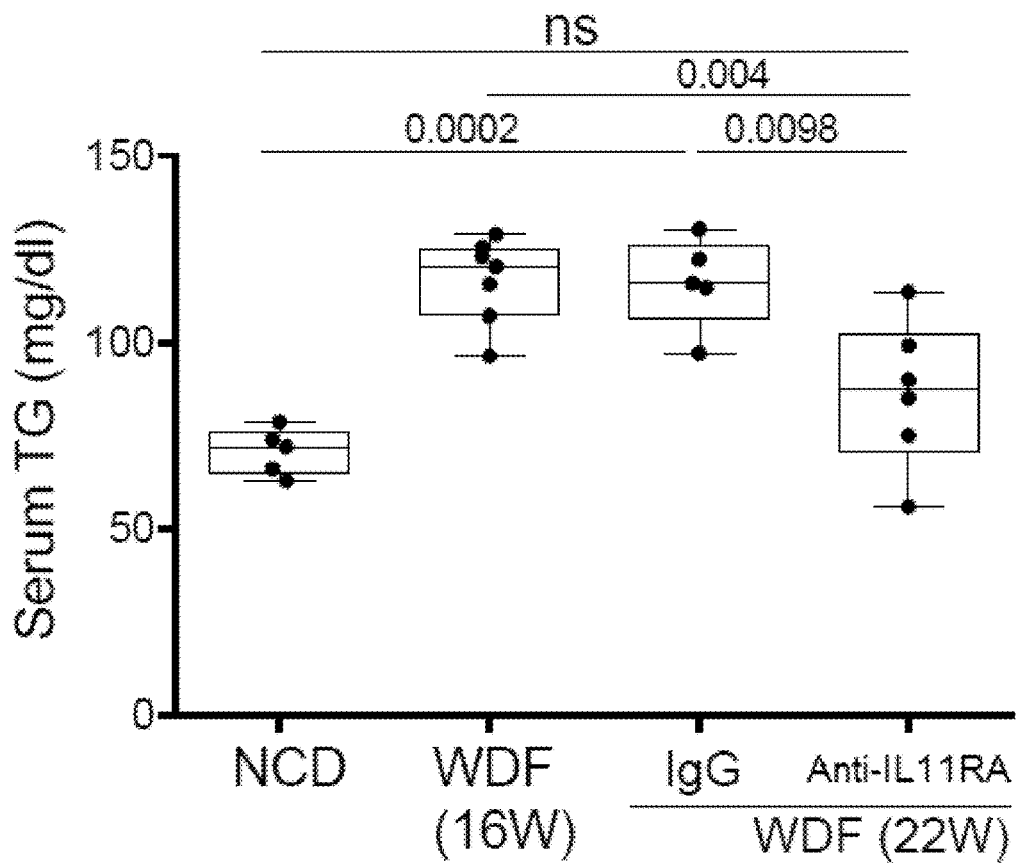
Figure 9C:
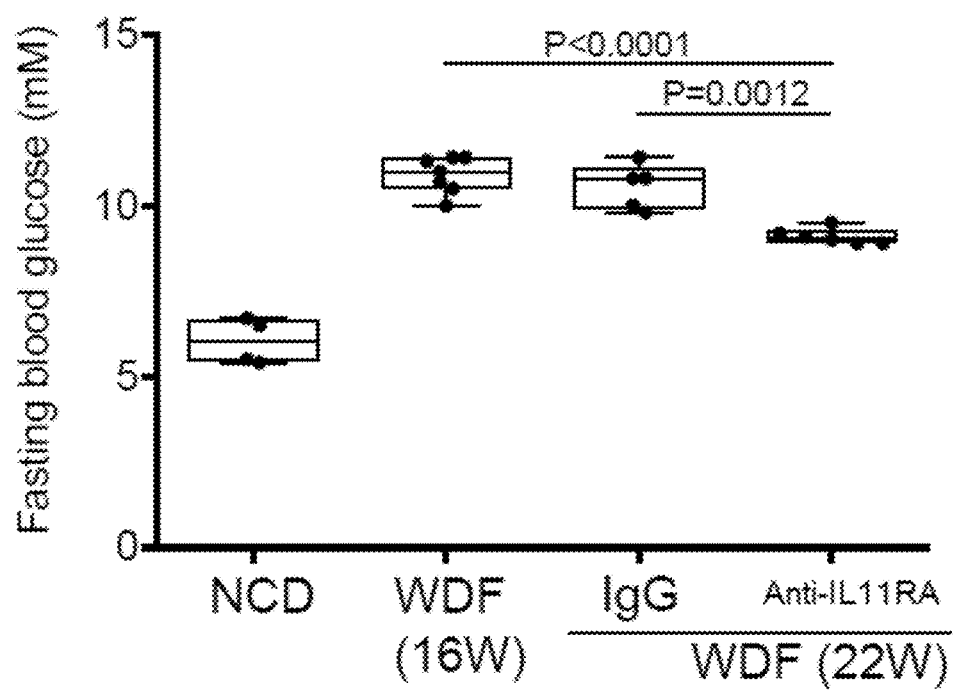

FIG. 9A shows that anti-IL-11 RA antibody-treated mice fed on WDF had significantly lower serum cholesterol levels compared to control IgG anybody-treated mice fed on WDF, and FIG. 9B shows that anti-IL-11 RA antibody-treated mice fed on WDF had significantly lower serum triglyceride levels compared to control IgG anybody-treated mice fed on WDF. FIG. 9C shows that anti-IL-11 RA antibody-treated mice fed on WDF had significantly lower fasting blood glucose levels compared to control IgG anybody-treated mice fed on WDF.

Figure 10A:
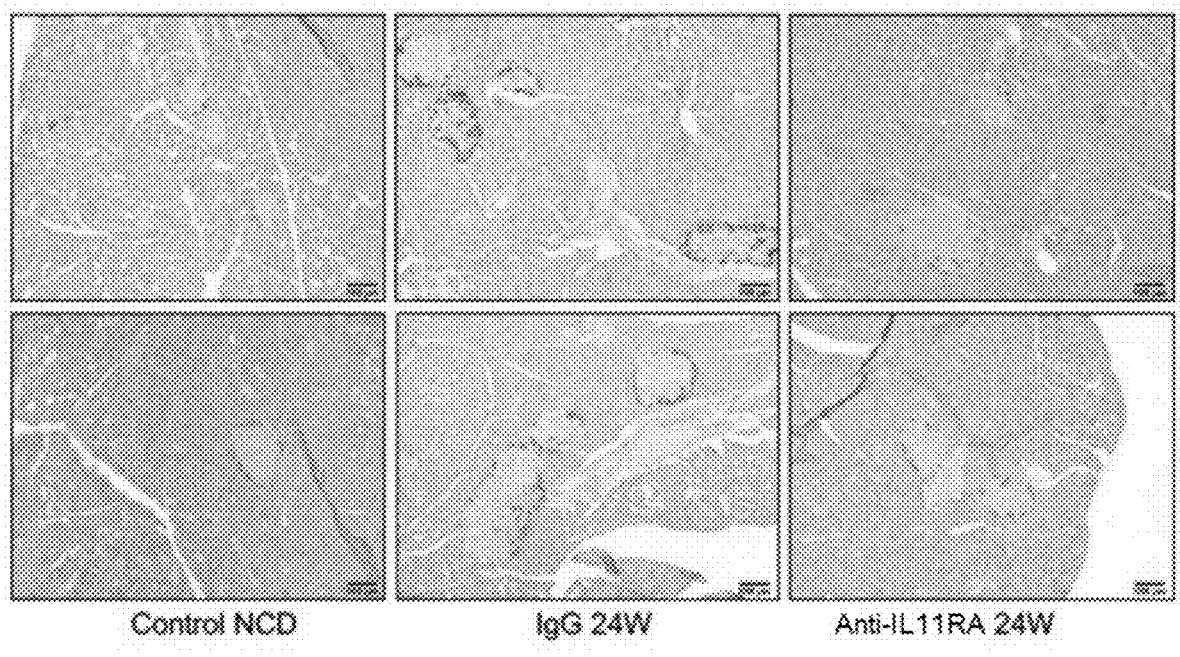
FIGS. 10A and 10B. Images showing the results of immunohistochemical analysis of (10A) glucagon content and (10B) insulin content of sections of pancreatic tissue obtained at week 24 from mice fed normal chow (NCD), or mice fed a Western diet with fructose (WDF) and treated with anti-IL-11 RA antibody or IgG control from 16 weeks.
Figure 10B:
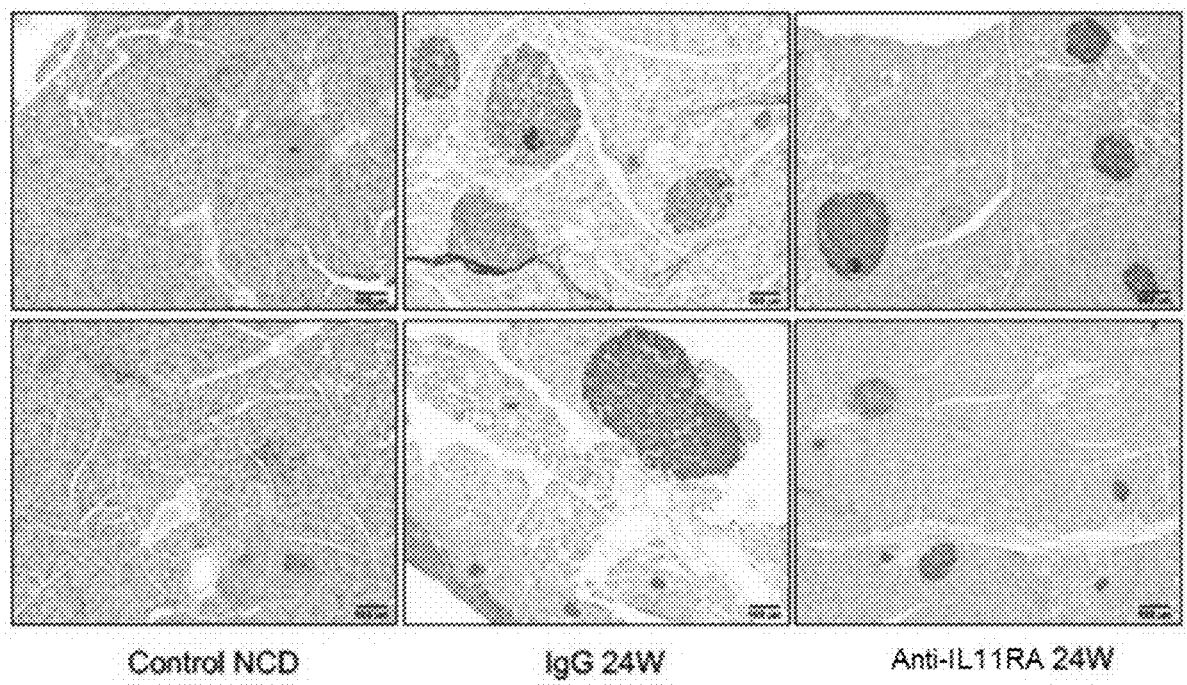

Moreover, immune-histology of pancreas also revealed increase in glucagon and insulin staining in pancreatic islets along with islet hyperplasia in IgG treated WDF fed mice (FIGS. 10A and 10B), which are classical features of T2D (Bonner-Weir and O'Brien Diabetes (2008) 57:2899-2904). Anti-IL-11 RA antibody treatment in WDF fed mice from 16 to 24 weeks remarkably reduced islet hyperplasia and glucagon staining as well improved insulin expression in the islets of mice fed on WDF (FIGS. 10A and 10B), suggesting that antagonism of IL-11 mediated signalling is useful to improve and reverse metabolic diseases caused by a Western-type diet.

Example 3: Antagonism of IL-11-Mediated Signalling and Cachexia

Anti-IL-11 therapies were assessed for their effects on a mouse model of cachexia.

Feeding mice with a methionine-choline deficient (MCD) diet causes severe non-alcoholic steatohepatitis (NASH), hepatic inflammation and fibrosis, and results in severe and sustained weight loss (up to 30% of body weight after 3 weeks of MCD diet). While mice on an MCD diet have 36% higher metabolic rates than those on normal chow diet (NCD) and have a strong appetite-stimulating milieu (low leptin, low glucose, low TGs/cholesterol, low insulin), they do not increase their food consumption (Rizki et al. J. Lipid Res. (2006) 47:2280-2290). As such, the MCD diet is a well-recognised model of cachexia and has many features in common with cancer-associated cachexia. Steatohepatitis is frequently documented in experimental and human cancer cachexia and plays an important but poorly understood role in wasting syndromes.

Five-week old male mice were fed a methionine- and choline-deficient (MCD) diet with 60 kcal % fat (A06071301B, Research Diets), designated a high fat MCD (HFMCD) diet, which causes more severe NASH than an MCD diet alone. Control mice were fed with normal chow (NC; Specialty Feeds). Mice were intraperitoneally injected twice per week with 10 mg/kg of anti-IL-11 antibody or anti-IL-11 RA antibody, or identical concentration of IgG isotype control one week after they had received HFMCD for the same treatment duration. Body weight was measured weekly.

Figure 11A:
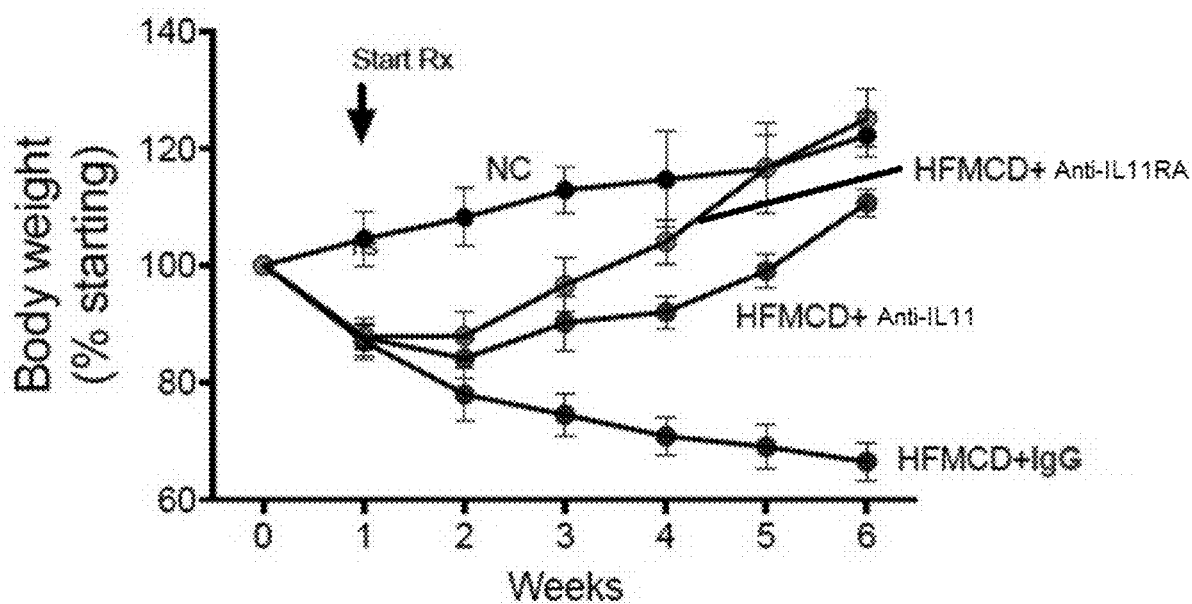
FIGS. 11A and 11B. Graph and images showing the effects of anti-IL-11/anti-IL-11Rα antibody treatment on cachexia-related weight loss. (11A) Mice fed a cachexia-inducing high fat methionine-choline deficient (HFMCD) diet returned to normal or near-normal weight when treated 2×/week with anti-IL-11 or anti-IL-11Rα antibody. Control mice were either fed with normal chow (NC), or fed on a HFMCD diet and treated with IgG isotype control. (11B) Example comparison of body size of mice fed on HFMCD diet and treated with either IgG or anti-IL-11 antibody or anti-IL-11Rα antibody.
Figure 11B:
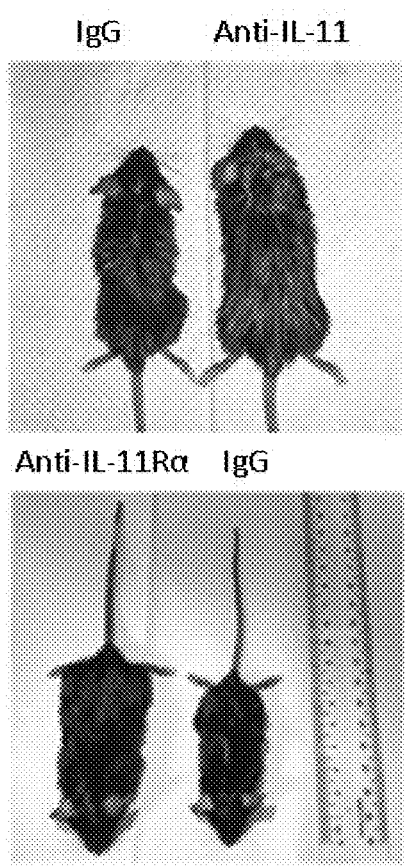

The results are shown in FIGS. 11A and 11B. Anti-IL-11 therapy was found to have a profound positive effect on body weight, indicating that inhibition of IL-11-mediated signalling is able to ameliorate cachexia-associated weight loss. While all HFMCD treatment groups (n≥5 mice/group) lost ~15% of body weight after the first week on the steatohepatitis-inducing HFMCD diet, those receiving anti-IL-11 or anti-IL-11 RA therapy quickly regained weight and returned to normal, or near-normal, weight by 5 weeks later (FIG. 11A). Mice fed with an NC diet steadily gained weight, whilst mice fed on the HFMCD diet and treated with IgG control lost >30% of body weight over the course of the treatment. Example comparison of mouse size is shown in FIG. 11B. Hence inhibition of IL-11-mediated signalling was found to reverse cachexia in vivo in a mouse an model of anorexia/cachexia.

To investigate further the effect of inhibition of IL-11-mediated signalling with respect to cachexia, a range of doses of anti-IL-11 therapy were studied in the MCD model. Five-week old male mice were fed on the HFMCD or NC diet as before for one week to induce cachexia, resulting in a ~15% loss in body weight in MCD mice. After the initial week, mice were intraperitoneally injected twice per week with 0.5, 1, 5 or 10 mg/kg of anti-IL-11 or anti-IL-11 RA antibody. Three antibodies were studied: two anti-IL-11 ((1) and (2)), and one anti-IL-11 RA. 10 mg/kg of IgG isotype antibody was used as a control.

Body weight and food consumption were measured weekly. For food consumption, average food intake was measured (g/mouse/week) in food hoppers from cages (n=3 mice per cage).

Figure 12A:
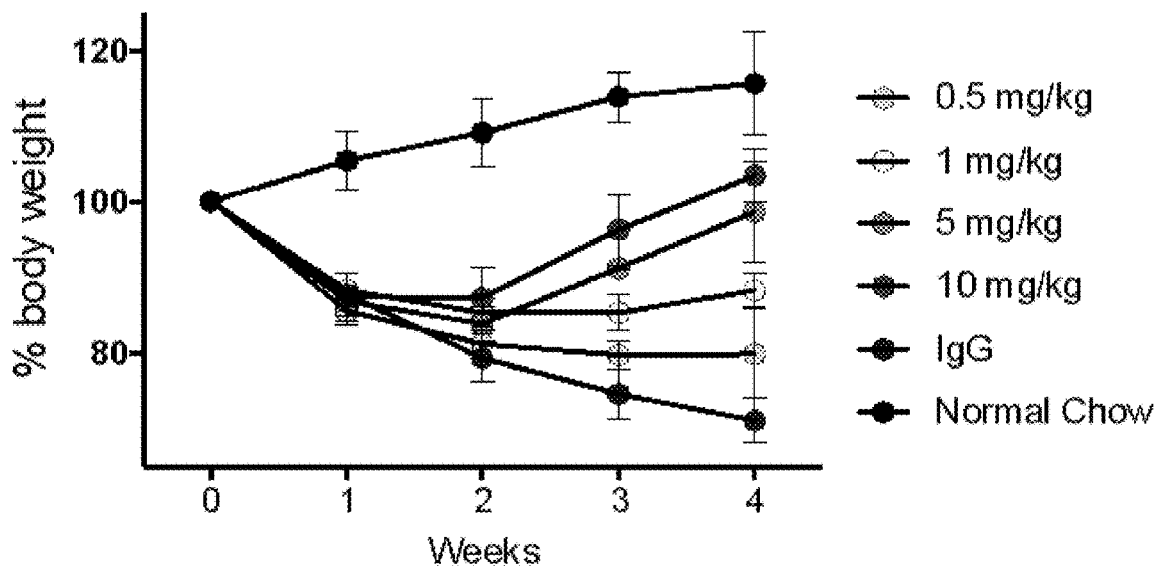
FIGS. 12A to 12C. Graphs showing the effects of anti-IL-11/anti-IL-11Rα antibody treatment on body weight in a model of cachexia-related weight loss. Mice fed a HFMCD diet were treated 2×/week with 0.5, 1, 5 or 10 mg/kg anti-IL-11Rα antibody (12A) or one of two anti-IL-11 antibodies (12B and 12C). Control mice were either fed with normal chow (NC), or fed on a HFMCD diet and treated with IgG isotype control.
Figure 12B:
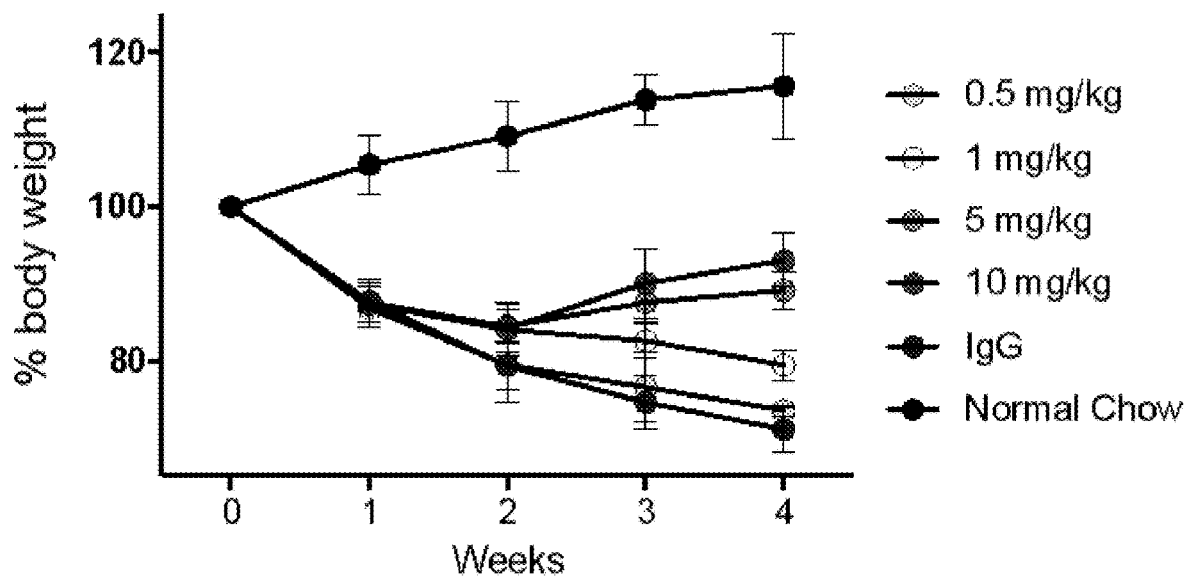
Figure 12C:
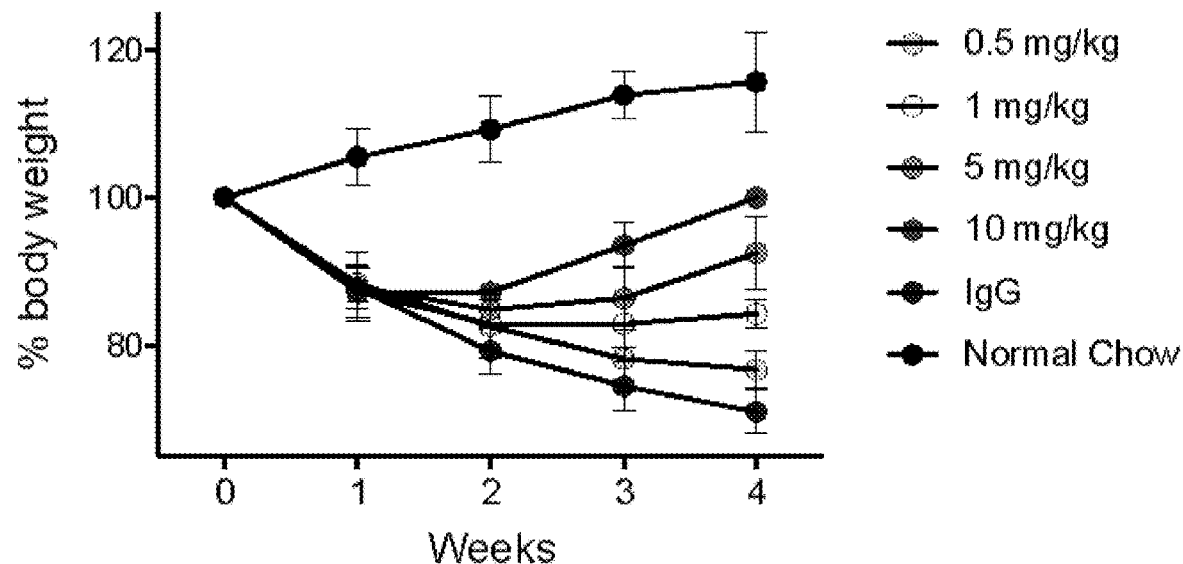

The body weight results are shown in FIGS. 12A to 12C. All three anti-IL-11 therapies were found to provide a dose-dependent gain in body weight, indicating reversal of cachexia. The highest doses show the greatest cachexia-reversing effect. Mice fed with an NC diet steadily gained weight, whilst mice fed on the HFMCD diet and treated with IgG control lost ~30% of body weight over the course of the treatment.

Figure 13A:
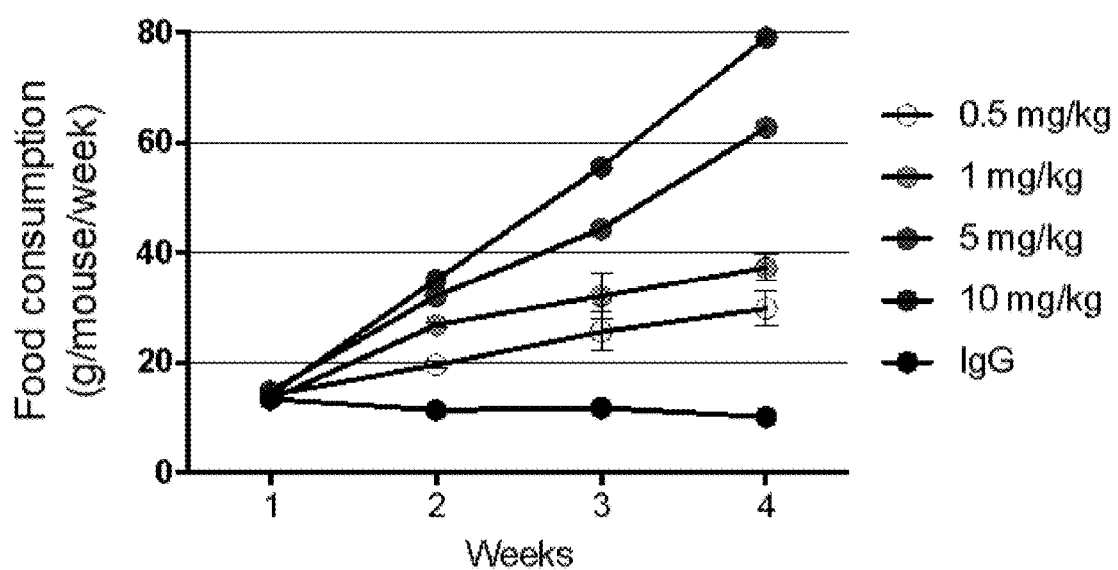
FIGS. 13A to 13C. Graphs showing the effects of anti-IL-11/anti-IL-11Rα antibody treatment on food consumption in a model of cachexia-related weight loss. Mice fed a HFMCD diet were treated 2×/week with 0.5, 1, 5 or 10 mg/kg anti-IL-11Rα antibody (13A) or one of two anti-IL-11 antibodies (13B and 13C). Control mice were either fed with normal chow (NC), or fed on a HFMCD diet and treated with IgG isotype control.
Figure 13B:
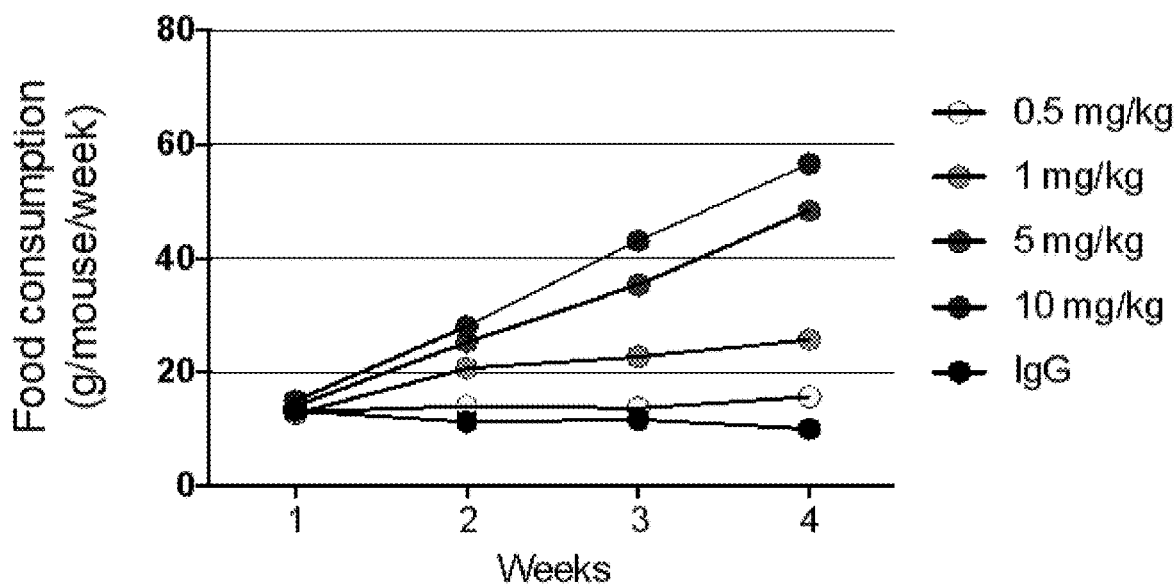
Figure 13C:
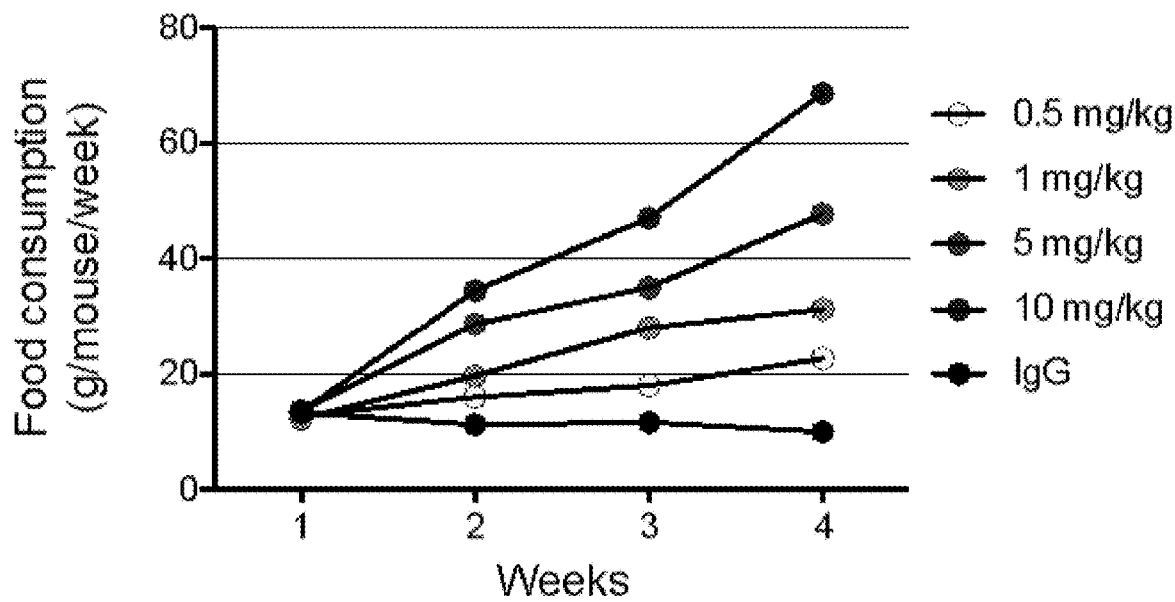

The food consumption results are shown in FIGS. 13A to 13C. All three anti-IL-11 therapies were found to provide a dose-dependent increase in food consumption. The highest doses had the greatest effect on food consumption, whereas mice treated with IgG control showed a slight reduction in food consumption. Anti-IL-11 RA antibody treatment was found to be most effective in reversing weight loss, and was associated with the greatest increase in food intake.

Acute disease, e.g. trauma or sepsis, can also be associated with anorexia and cachexia, and so the inventors next investigated the effects of antagonism of IL-11-mediated signalling on anorexia and cachexia in mouse models of acute kidney injury.

Kidney injury was induced by IP injection of folic acid (180 mg/kg) in vehicle (0.3M NaHCO$_3$) to 10-week old male mice; control mice were administered vehicle alone. Animals were sacrificed 28 days post-injection. Mice were intraperitoneally injected every 3 days with 20 mg/kg of anti-IL-11 antibody, anti-IL-11 RA antibody or identical concentration of IgG isotype control starting from 1 hour before folic acid administration until the mice were sacrificed.

Figure 14A:
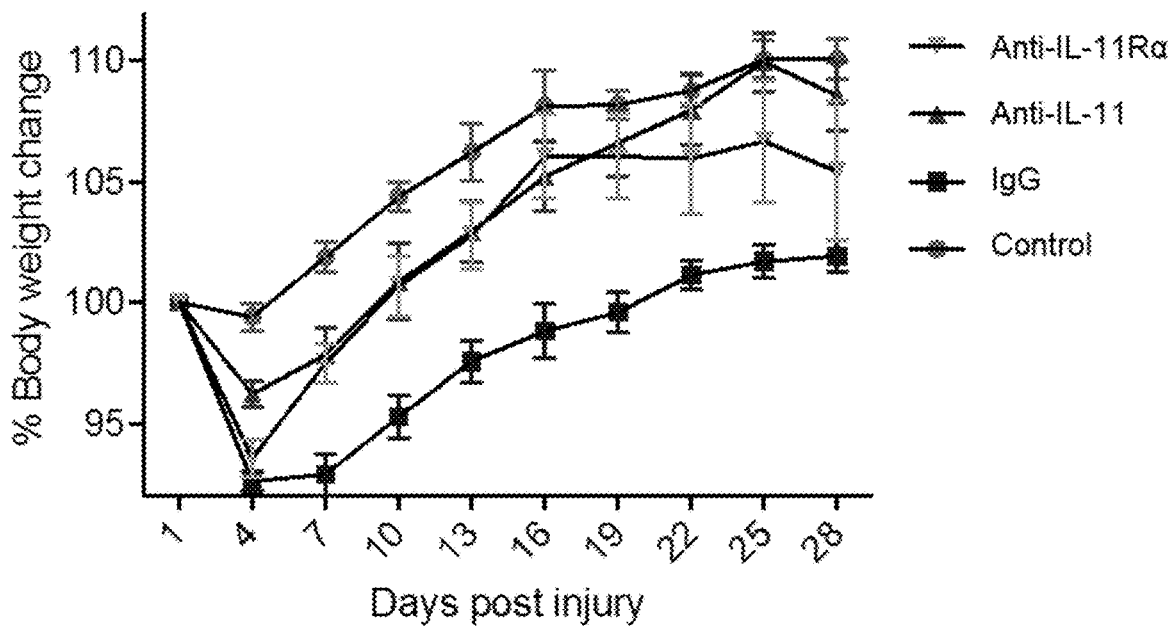
FIGS. 14A and 14B. Graphs showing the effects of anti-IL-11/anti-IL-11Rα antibody treatment on body weight in cachexia-associated weight loss following folate-induced acute kidney injury. (14A) Mice with folate-induced kidney injury were treated with anti-IL-11Rα antibody, anti-IL-11 antibody, or IgG control from 1 hour before injury to 28 days after injury. 'Control' mice were administered vehicle alone. (14B) Mice with folate-induced kidney injury were treated with anti-IL-11 antibody or IgG control from 21 days after injury. FA=folic acid.

The results are shown in FIG. 14A. Folate-induced kidney injury resulted in rapid anorexia/cachexia-associated weight loss associated with the acute phase of severe and bilateral kidney injury. Mice (n=7/group) receiving anti-IL-11Rα or anti-IL-11 therapy at the time of injury, and for the duration of the injury, regained weight more quickly compared to the IgG control and returned to normal, or near normal, weight by 3 weeks later.

In a second experiment kidney injury was induced as before by IP injection of folic acid. Mice were only treated with anti-IL-11 antibody or IgG control from 21 days after kidney injury. Animal weight was assessed before and after antibody treatment. Healthy mice that did not receive folic acid were used as a control.

Figure 14B:
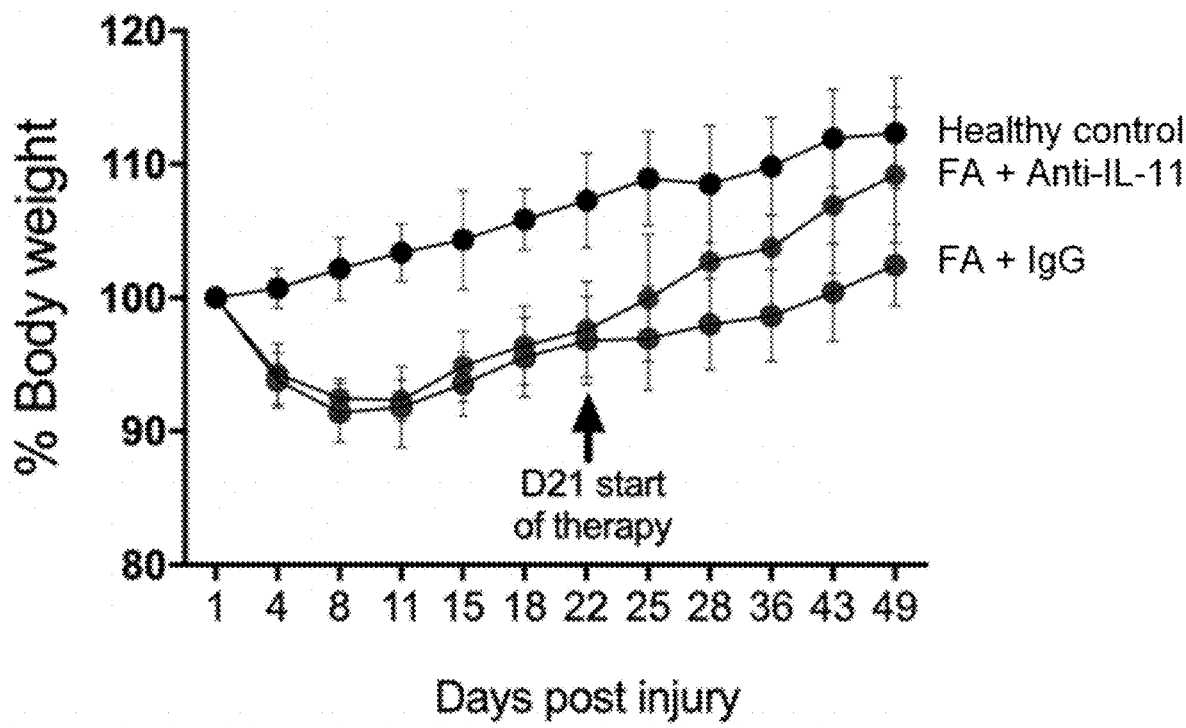

The results are shown in FIG. 14B. Animals treated with anti-IL-11 antibody started to regain weight upon initiation of treatment showing that wasting-associated weight loss can be improved in late-stage disease.

In further experiments, mice were subjected to unilateral ureter obstruction (UUO)-induced acute kidney injury. UUO surgeries were carried out on 12-week old mice. Briefly, mice were anesthetized by IP injection of ketamine (100 mg/kg)/xylazine (10 mg/kg) and full depth of anaesthesia was accessed with the pedal reflex. Mice were then shaved on the left side of the abdomen. A vertical incision was made through the skin with a scalpel, a second incision was made through the peritoneum to reveal the kidney. Using forceps, the kidney was brought to the surface and the ureter was tied with surgical silk, twice, below the kidney. The ligated kidney was placed gently back into its correct anatomical position and sterile saline was added to replenish loss of fluid. The incisions were then sutured. Animals were postoperatively treated with antibiotic enrofloxacin (15 mg/kg, SC) and analgesic buprenorphine (0.1 mg/kg, SC) for three consecutive days. Mice were sacrificed 10 days post-ligation. Mice were intraperitoneally injected with 20 mg/kg (2×/week) of anti-IL-11 antibody or identical concentration of IgG isotype control from day 4 post-surgery until the mice were sacrificed.

Figure 15:
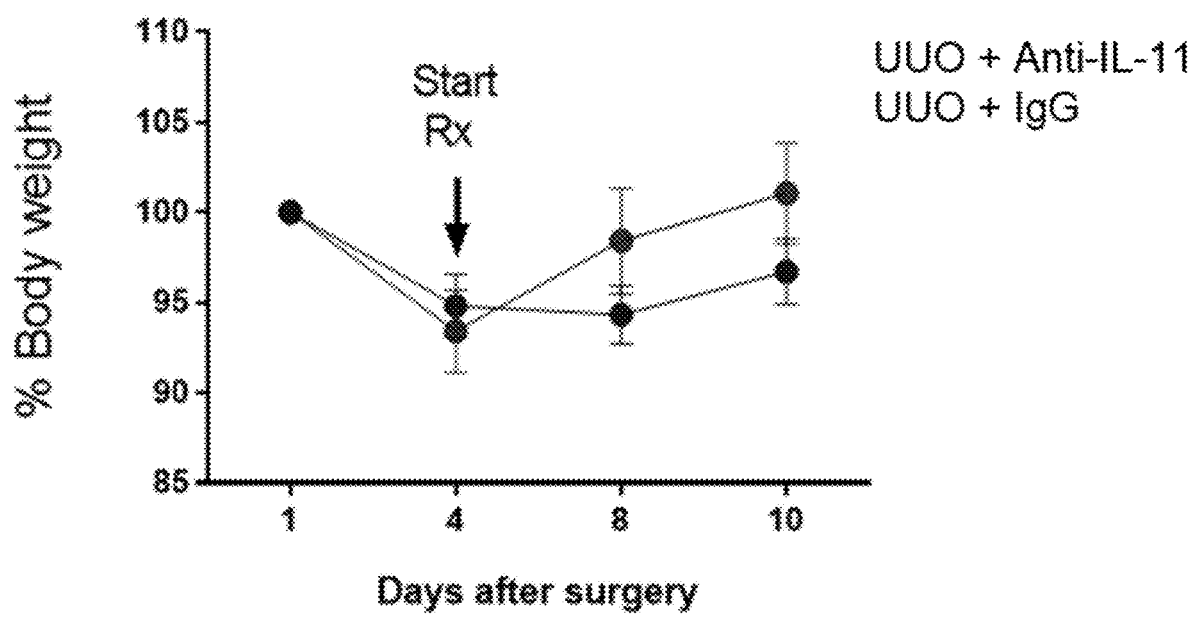
FIG. 15. Graph showing the effects of anti-IL-11 antibody treatment on body weight in cachexia-associated weight loss following unilateral ureter obstruction (UUO)-induced acute kidney injury. Mice with UUO-induced kidney injury were treated with anti-IL-11 antibody or IgG control for 10 days after injury.

The results are shown in FIG. 15. Animals from both groups initially lost similar amount of weight (~6%) due to surgical trauma-associated anorexia. Animals receiving anti-IL-11 therapy (20 mg/kg 2×/week from day 4 post-UUO until the mice were sacrificed) regained their body weight more quickly than those receiving IgG control, and returned to normal weight within 4 days.

Thus antagonism of IL-11 mediated signalling is associated with therapeutic recovery of body weight in models of acute disease.

The inventors next investigated the effects of IL-11 overexpression on mouse body weight, via injection of recombinant mouse IL-11 or induction of IL-11 transgene expression.

Recombinant mouse IL-11 (rmIL11) was reconstituted to a concentration of 50 μg ml$^{-1}$ in saline. Ten-week-old male wild-type C57BL/6J mice received daily subcutaneous injection of either 100 μg kg$^{-1}$ of rmIL11 in saline (n=19) or an identical volume of saline (n=15) for 21 days.

Figure 16A:
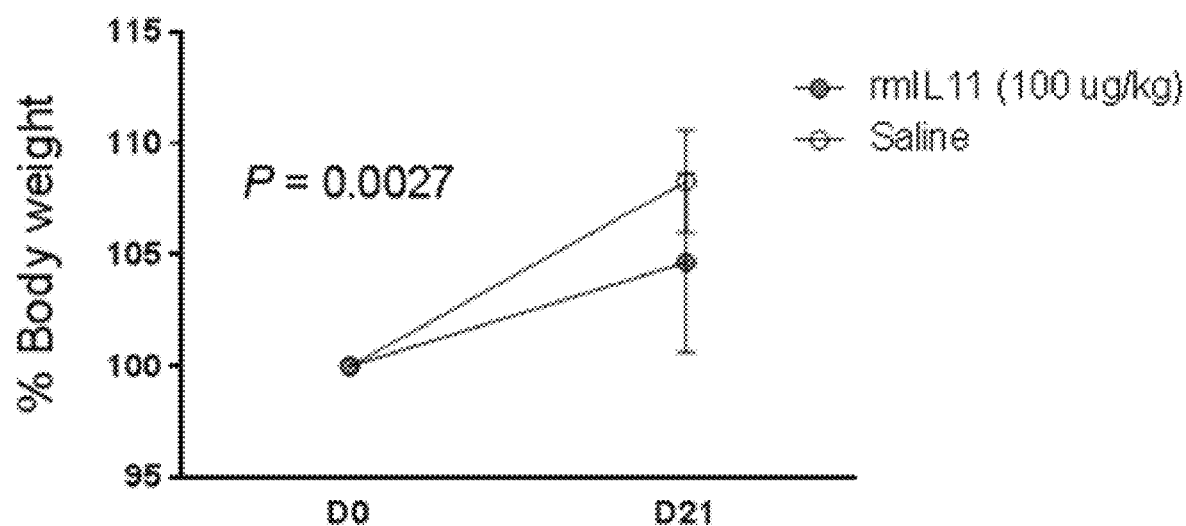
FIGS. 16A and 16B. Graphs showing the effects of IL-11 overexpression on weight gain. (16A) Administration of recombinant mouse IL-11 (rmIL11) slowed normal mouse weight gain progression. (16B) Induction of IL-11 transgene (IL-11 Tg) in mice resulted in loss of body weight over time.

The results are shown in FIG. 16A. Administration of rmIL11 was found to slow down the normal weight gain progression. Mice that received a daily injection of rmIL11 for 21 days gained less weight during the course of treatment, as compared to those receiving saline alone.

IL-11 transgenic (IL-11-Tg) mice were created. Heterozygous Rosa26-IL11 mice were crossed with Col1a2-CreER mice to create double heterozygous Col1a2-CreER:Rosa26-IL11 progenies (IL-11-Tg mice) with IL-11 transgene expression in fibroblasts. For Cre-mediated IL-11 transgene induction, IL-11-Tg mice were injected with 50 mg kg$^{-1}$ Tamoxifen (Sigma-Aldrich) intraperitoneally at 6 weeks of age for 10 consecutive days and the animals were sacrificed on day 21 (n=14). Rosa26:1111 mice (without Col1a2-CreER allele) were injected with an equivalent dose of tamoxifen for 10 consecutive days as controls (n=10).

Figure 16B:
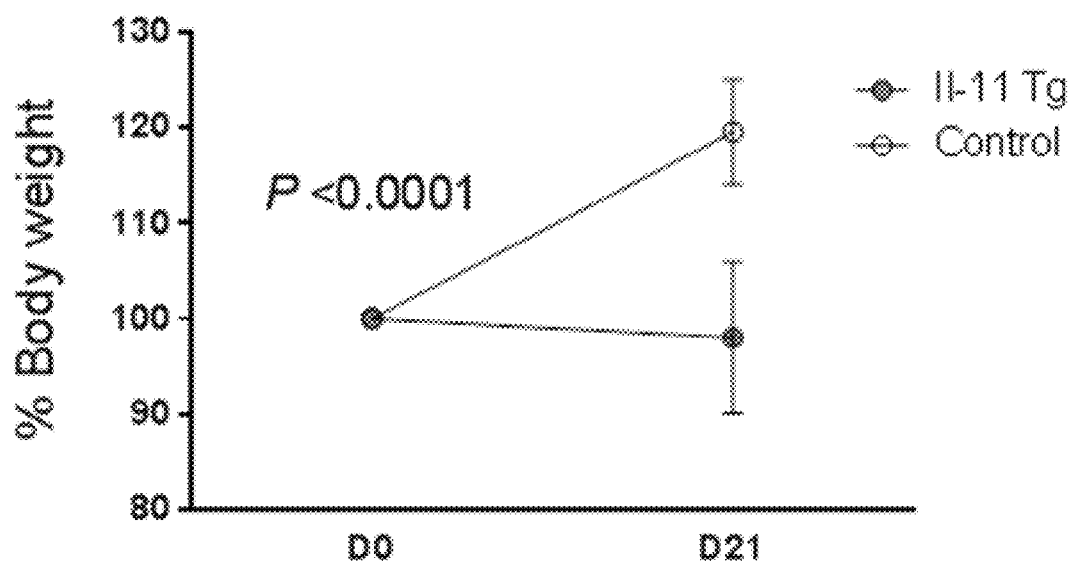

The results are shown in FIG. 16B. IL-11-Tg mice showed early signs of cachexia, stopped gaining weight and experienced loss of body weight over time. Thus, IL-11-mediated signalling was found to contribute to wasting-associated weight loss.

Example 4: Antagonism of IL-11-Mediated Signalling in Mouse Models of Non-Alcoholic Steatohepatitis (NASH)

The inventors investigated the role of IL-11 signalling in the pathogenesis of nonalcoholic steatohepatitis (NASH).

4.1 Methods

Hepatic stellate cells (HSCs) or hepatocytes were stimulated with IL-11 and effects assessed using cellular and high content imaging, immunoblotting, ELISA and invasion assays. Genetic and pharmacological IL-11 gain- or loss-of-function experiments were performed in vitro and in vivo. IL-11 signalling was studied using ERK inhibitors. The effects of anti-IL-11 or anti-IL11RA therapy were assessed in three preclinical NASH models using methionine/choline deficient diets or a Western diet with liquid fructose. Phenotyping was performed using hydroxyproline assay, qPCR, RNA-seq, Western blotting, histology, CyTOF, lipid and metabolic biomarkers.

Animal Experiments

All animal procedures were approved and conducted in accordance with the SingHealth Institutional Animal Care and Use Committee (IACUC). All mice were provided food and water ad libitum.

Mouse Models of NASH

High fat methionine and choline-deficient (HFMCD) diet fed wild-type mice Five week old male C57BL/6N mice were fed with Methionine and Choline deficient diet supplemented with 60 kcal % fat (A060713011316, Research Diets); control mice were fed with normal chow (NC, Specialty Feeds). Durations of diet and antibody therapies are described.

Methionine and Choline-Deficient (MCD) Diet Fed Db/Db Mice

Male BKS.Cg-Dock7m+/+LeprdbJ (db/db) mice on C57BL/6J genetic background were 12 weeks of age and at the hepatic steatosis stage when they were fed methionine- and choline-deficient diet (MCD, A02082002BRi, Research Diets) for 8 weeks; control mice were of the same genotype. Durations of diet and antibody therapies are described.

Western Diet Supplemented with Fructose (WDF) Fed Wild-Type Mice

Ten week old male C57Bl/6J mice were fed Western diet (D12079B, Research Diets), supplemented with 15% weight/volume fructose in drinking water to mimic NAFLD/NASH like humans 17,18, whereas control mice received normal chow and tap water. Durations of diet and antibody therapies are described.

Il11ra-Deleted Mice

Mice lacking functional alleles for Il11ra (Il11ra−/−) were on C57Bl/6J genetic background (66.12951-Il11ratm1Wehi/J, Jackson's Laboratory). Both Il11ra−/− mice and their wild-type littermates (Il11ra+/+) were fed with (1) HFMCD for 10 weeks from 5 weeks of age and (2) WDF for 16 weeks from 12 weeks of age to develop NASH; control mice were fed with NC for the same duration.

In Vivo Administration of Il-11

Ten week old male Col1a1-GFP reporter mice 19 and wild-type C57BL/6J mice received daily subcutaneous injection of either 100 μg/kg of recombinant mouse Il-11 (rmIl-11) or identical volume of saline for 21 days.

In Vivo Administration of Anti-IL-11 or Anti-IL11RA Monoclonal Antibodies

Mice were injected intraperitoneally with either antagonist anti-IL-11 antibody, antagonist anti-IL11RA antibody or an identical amount of IgG isotype control for the treatment durations outlined in the figures.

Fasting Blood Glucose Measurement

Mice were fasted for 6 h prior to blood collection (via tail snip) and Accu-Chek blood glucose meter was used to take fasting glucose measurements.

Cell Culture

Cells (atrial fibroblasts, HSCs and hepatocytes) were grown and maintained at 37° C. and 5% CO2. The growth medium was renewed every 2-3 days and cells were passaged at 80-90% confluence using standard trypsinization techniques. All the experiments were carried out at low cell passage (P1-P2). Cells were serum-starved for 16 h prior to stimulations. Stimulated cells were compared to unstimulated cells that have been grown for the same duration under the same conditions (serum-free media), but without the stimuli.

Primary Human Atrial Fibroblasts

Human atrial fibroblasts were prepared and cultured as described previously 11.

Primary Human Hepatic Stellate Cells (HSCs)

HSCs (5300, ScienCell) were cultured in stellate cells complete media (5301, ScienCell) on poly-L-lysine-coated plates (2 μg/cm2, 0403, ScienCell).

Primary Human Hepatocyte

Human hepatocytes (5200, ScienCell) were grown and maintained in hepatocyte media (5201, ScienCell) supplemented with 2% fetal bovine serum (FBS) and 1% Penicillin-streptomycin.

THP-1

THP-1 (ATCC) were cultured in RPMI 1640 (A1049101, Thermo Fisher) supplemented with 10% FBS and 0.05 mM β-mercaptoethanol. THP-1 cells were differentiated with 10 ng/ml of phorbol 12-myristate 13-acetate (PMA, P1585, Sigma) in RPMI 1640 for 48 h.

Operetta High Throughput Phenotyping Assay

The Operetta assay was performed mostly as described previously 11 with minor modifications described here: HSCs or hepatocytes were seeded in 96-well black CellCarrier plates (PerkinElmer) at a density of $5 \times 10^3$ cells per well. Following experimental conditions, cells were fixed in 4% paraformaldehyde (PFA, 28908, Thermo Fisher), permeabilized with 0.1% Triton X-100 (Sigma) and non-specific sites were blocked with 0.5% BSA and 0.1% Tween-20 in PBS. Cells were incubated overnight (4° C.) with primary antibodies (1:500), followed by incubation with the appropriate AlexaFluor 488 secondary antibodies (1:1000). Rhodamine Phalloidin staining (1:1000, R415, Thermo Fisher) was performed by overnight incubation (4° C.). Cells were counterstained with 1 μg/ml DAPI (D1306, Thermo Fisher in blocking solution. Each condition was imaged from duplicated wells and a minimum of 7 fields/well using Operetta high-content imaging system 1483 (PerkinElmer). Cells expressing ACTA2 were quantified using Harmony v3.5.2 (PerkinElmer) and the percentage of activated fibroblasts/total cell number (ACTA2+ve) was determined for each field. The measurement of fluorescence intensity per area (normalized to the number of cells) of Collagen I was performed with Columbus 2.7.1 (PerkinElmer).

Immunofluorescence

Human HSCs and hepatocytes were seeded on 8-well chamber slides ($1.5 \times 10^4$ cells/well) 24 h before the staining. Cells were fixed in 4% PFA for 20 min, washed with PBS, and non-specific sites were blocked with 5% BSA in PBS for 2 h. Cells were incubated with anti IL11RA or anti IL6R antibody overnight (4° C.), followed by incubation with the appropriate Alexa Fluor 488 secondary antibody for 1 h. Chamber slides were dried in the dark and 5 drops of mounting medium with DAPI were added to the slides for 15 min prior to imaging by fluorescence microscope (Leica).

Mass Cytometry by Time of Flight (CyTOF)

Immune cells were isolated from liver as described previously 20. Liver tissues were minced and digested with 100 μg/ml Collagenase IV and 20 U/ml DNase I, at 37° C. for 1 h. Following digestion, cells were passed through strainer to obtain single cell suspension and subjected to percoll gradient centrifugation for isolation of immune cells. CyTOF staining was performed as previously described 21. Cells were thawed and stained with cisplatin (Fluidigm) to identify live cells, followed by staining with metal-conjugated CD45 antibody, for barcoding purpose. After barcoding, cells were stained with metal-conjugated cell surface antibody (Ly6C). Cells were then fixed with 1.6% PFA, permeabilized with 100% methanol, and subjected to intracellular antibody staining (TGFβ1). Cells were labeled with DNA intercalator before acquisition on Helios mass cytometer (Fluidigm). For analysis, first live single cells were identified, followed by debarcoding to identify individual samples. Manual gating was performed using Flowjo software (Flowjo).

Statistical Analysis

Statistical analyses were performed using GraphPad Prism software (version 6.07). P values were corrected for multiple testing according to Dunnett's (when several experimental groups were compared to one condition), Tukey (when several conditions were compared to each other within one experiment), Sidak (when several conditions from 2 different genotypes were compared to each other). Analysis for two parameters (antibody efficacy across time) for comparison of two different groups were performed by two-way ANOVA. The criterion for statistical significance was $P<0.05$.

Data Availability

High-throughput sequencing data generated for this study can be downloaded from GSE128940. All other data are in the manuscript or in the supplementary methods.

4.2 Results

Overview

When stimulated with NASH factors HSCs secrete IL-11, which drives an autocrine, ERK-dependent signalling loop required for the HSC-to-myofibroblast transformation. IL-11 is upregulated in human and murine NASH, Il-11 injection causes liver damage, inflammation and fibrosis in mice and Il11ra1 deleted mice are protected from NASH in two preclinical models. Therapeutic antibodies against IL11RA or IL-11 consistently inhibit and reverse fibrosis and steatosis in three murine NASH models. Unexpectedly, IL-11 causes hepatocyte damage and promotes stromal-mediated inflammation and anti-IL-11 therapies reverse NASH-associated hepatotoxicity and hepatitis. Genetic or pharmacologic inhibition of IL-11 signalling in NASH is associated with lower serum triglyceride, cholesterol and glucose.

IL-11 Activates HSCs and Drives Liver Fibrosis

Figure 17A:
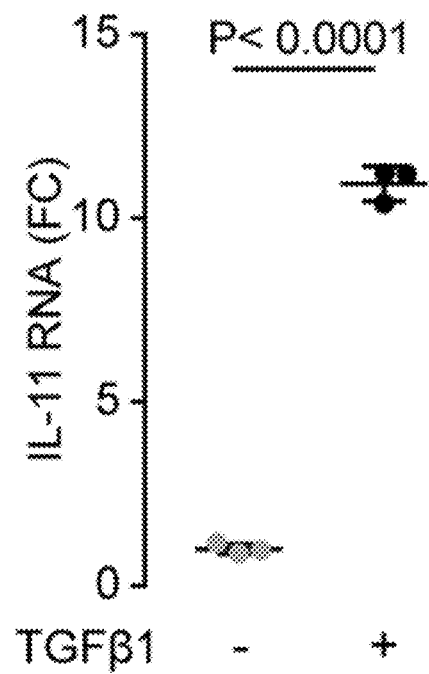
FIGS. 17A to 17N. IL-11 induces HSC activation and liver fibrosis. (A) IL-11 RNA is upregulated in HSCs stimulated with TGFβ1. (B) IL-11 protein is secreted from HSCs stimulated with TGFβ1. (C) Human precision cut liver slices were stimulated with TGFβ1 and IL-11 protein was measured in supernatant. (D) Immunofluorescence images of IL6R and IL11RA expression in HSCs and activated THP-1 cells (scale bars, 100 μm). (E) Immunofluorescence images (scale bars, 100 μm) and (F) Western blots of ACTA2 in HSCs following incubation without stimulus (−), with TGFβ1, PDGF, or IL-11. (G) Immunofluorescence images (scale bars, 100 μm) of HSCs for Collagen I staining and (H) collagen secretion in HSC supernatant stimulated with TGFβ1, PDGF, or IL-11. (I) Dose-dependent matrigel invasion of HSCs induced by IL-11. (J) Hyper IL-11 induces IL-11 protein secretion from HSCs (ELISA). (A-C, E-H, J) TGFβ1 (5 ng/ml), Hyper IL-11 (0.2 ng/ml), PDGF (20 ng/ml), IL-11 (5 ng/ml); 24 h; (I) 48 h. (K) Schematic of mice receiving daily injection of either saline (control) or rmIl-11 (100 μg/kg). (L-N) Data for rmIl-11 injection experiments as shown in 1K, (n≥7/group). (L) Relative liver hydroxyproline content, (M) liver mRNA expression of pro-fibrotic and pro-inflammatory markers, and (N) serum ALT levels. (A-B,H-J,L,N) Data are represented as mean±s.d; (C, M) box-and-whisker plots show median (middle line), 25th-75th percentiles (box) and min-max percentiles (whiskers). (A-C, J, L-N) Two-tailed Student's t-test; (H-I) two-tailed Dunnett's test. FC: fold change; I/A: intensity/area.
Figure 17B:
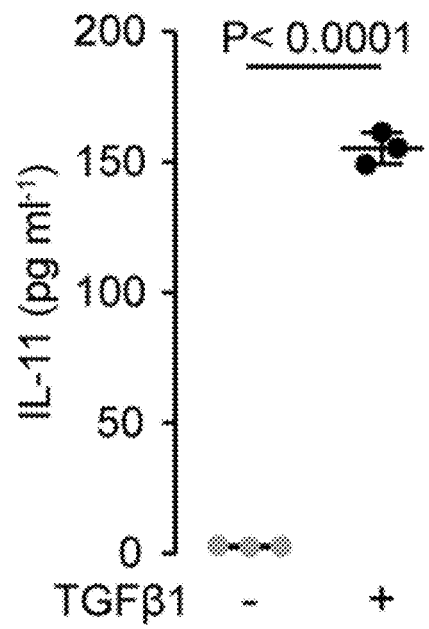
Figure 17C:
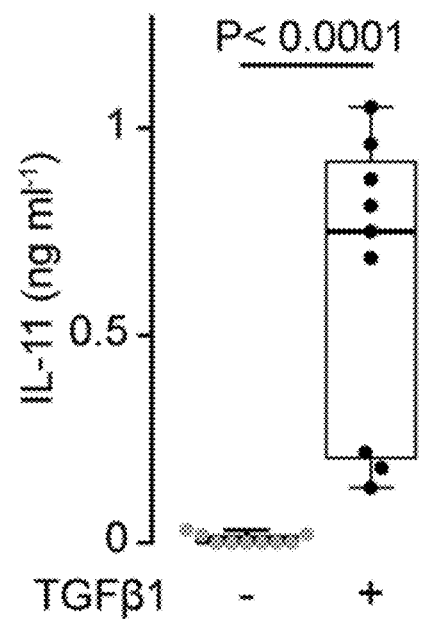
Figure 17D:
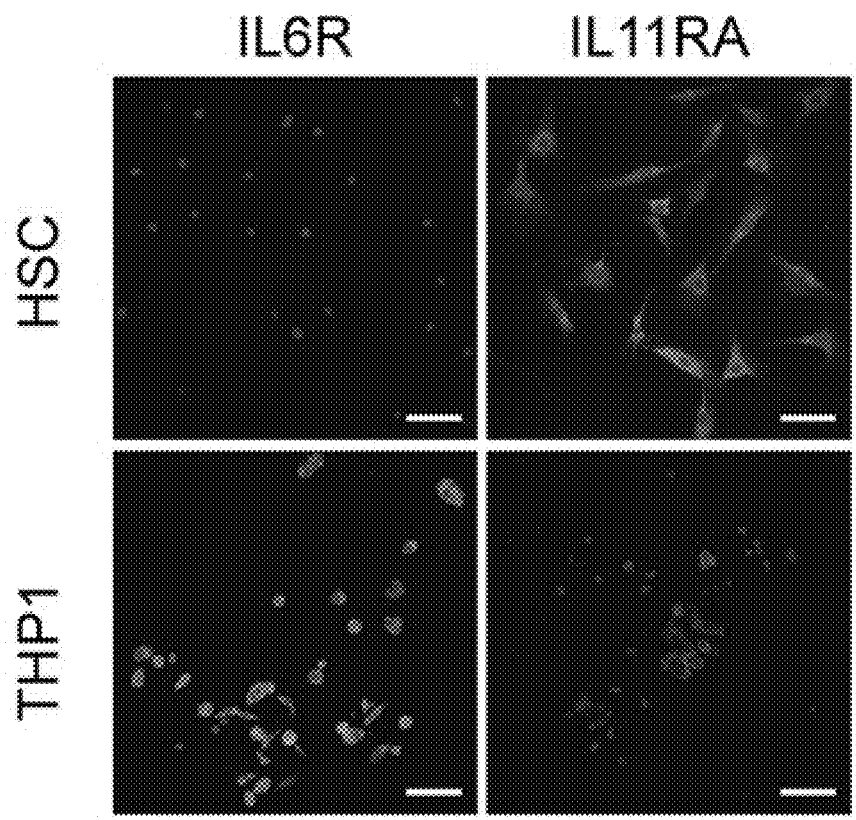
Figure 17E:
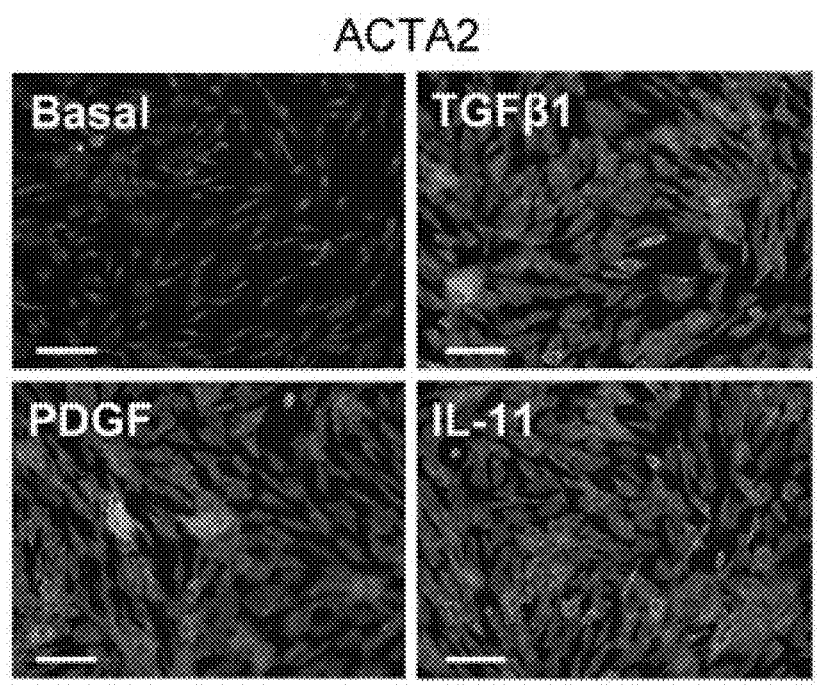
Figure 17F:
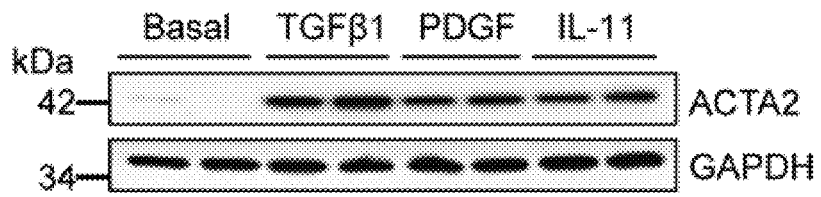
Figure 17G:
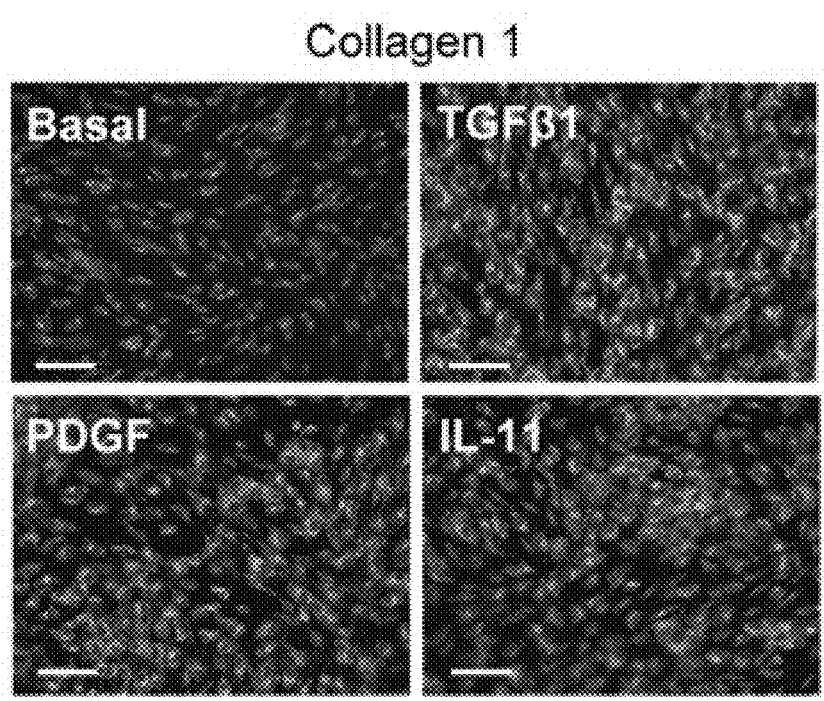
Figure 17H:
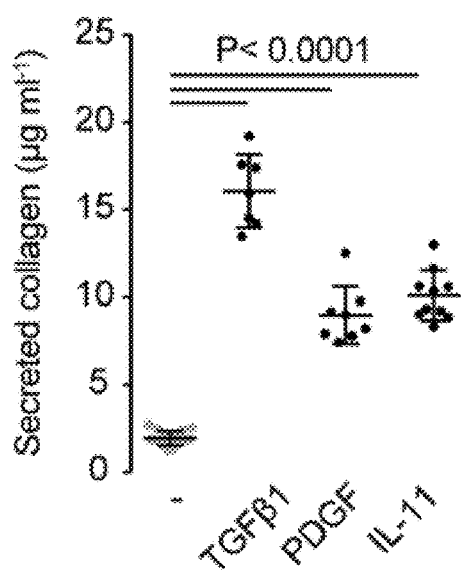
Figure 24A:
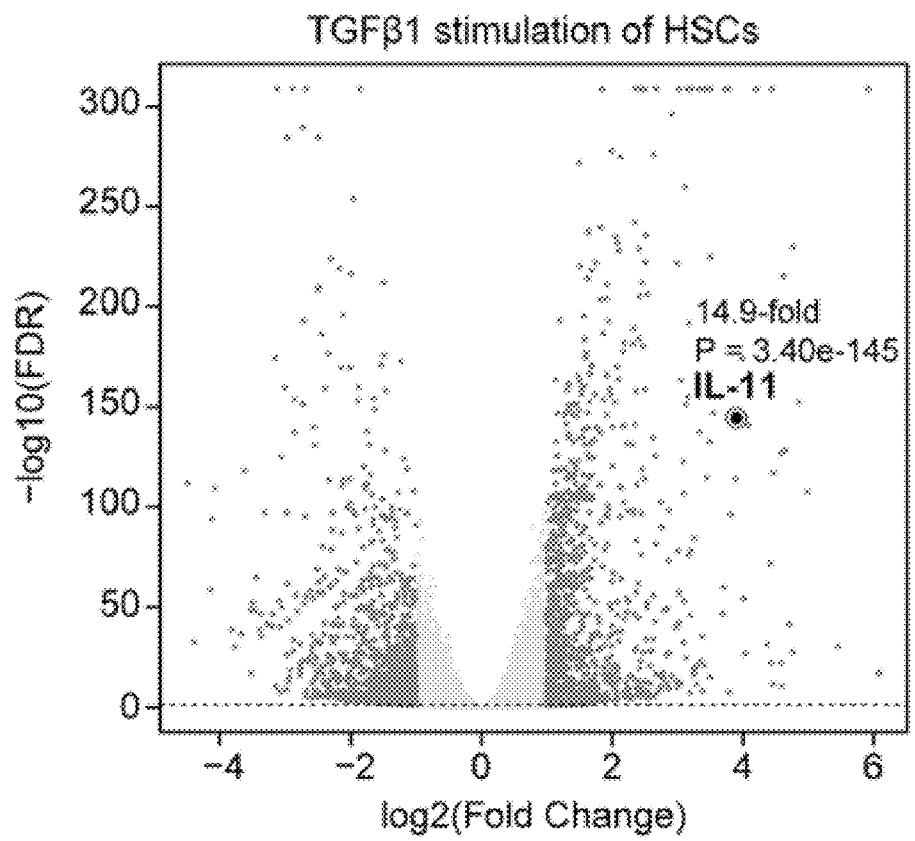
FIGS. 24A to 24K. HSCs secrete and respond to IL-11 and Il-11 injection to mouse causes liver fibrosis. (A) Genome-wide changes in RNA expression in HSCs after TGFβ1 stimulation (n=3, RNAseq). (B) Stiffness-induced RNA upregulation in humans HSCs (RNA-seq[14]), genes are ranked according to fragments per kilobase million (FPKM), IL-11 upregulation is the most highly upregulated gene genome wide. (C) IL11RA transcripts in human cardiac fibroblasts (HCF), human lung fibroblasts (HLF), and human HSC. (D) Western blots and (E) densitometry of IL-11 and GAPDH in human liver samples of healthy individuals and patients suffering from alcoholic liver disease (ALD), primary sclerosing cholangitis (PSC), primary biliary cirrhosis (PBC), and non-alcoholic steatohepatitis (NASH). Automated fluorescence quantification for (F) ACTA2$^{+ve}$ cells and (G) Collagen I immunostaining following incubation without stimulus (−), with TGFβ1, PDGF, or IL-11. (H) MMP-2 concentration in the HSC supernatant without stimulus (−), with TGFβ1 or IL-11 by ELISA. (A,F-H) TGFβ1 and IL-11 (5 ng/ml), PDGF (20 ng/ml); 24 h stimulation. (I) Representative (scale bars, 100 μm) and (J) quantification of Masson's Trichrome staining images of liver sections from mice injected with saline or rmIl-11. (K) Schematic and representative fluorescence images GFP$^{+ve}$ cells of Col1a1-GFP mice injected daily with either rmIl-11 or saline. Sections were immunostained for Acta2 and counterstained with DAPI (scale bars, 200 μm). (C,F-G) Data are shown as box-and-whisker with median (middle line), 25th-75th percentiles (box) and min-max percentiles (whiskers); (E, H, J) data are represented as mean±s.d. (F-H) Two-tailed Dunnett's test; (J) two-tailed Student's t-test. FC: fold change; TPM: Transcript per millions.
Figure 24B:
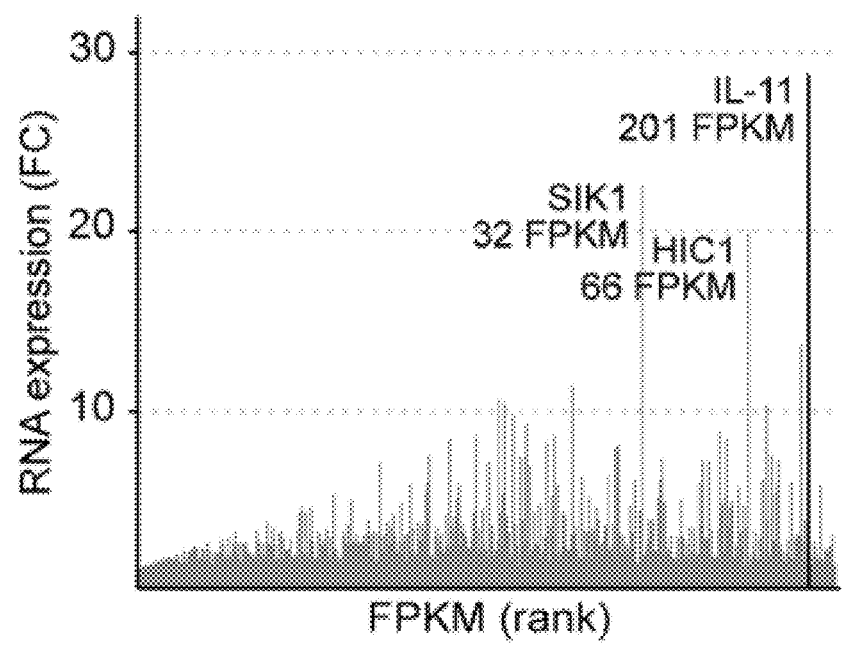
Figure 24C:
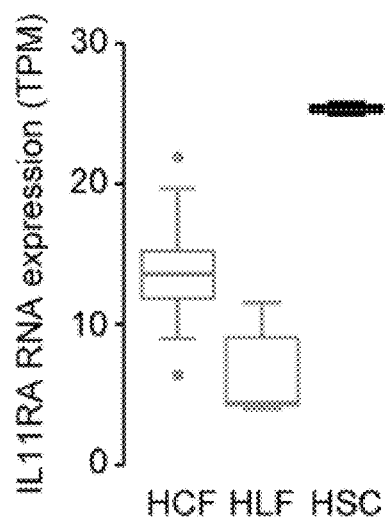
Figure 24D:
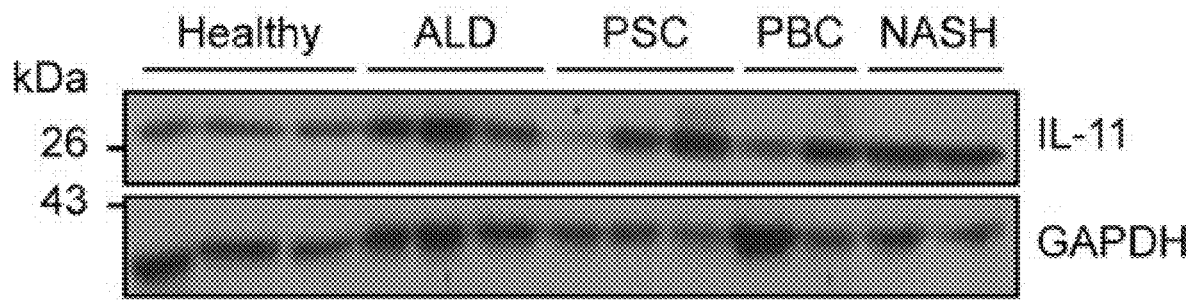
Figure 24E:
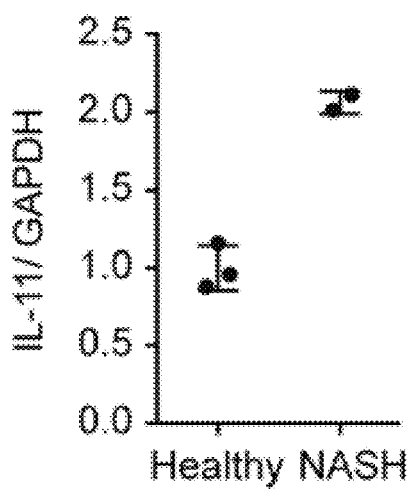
Figure 24F:
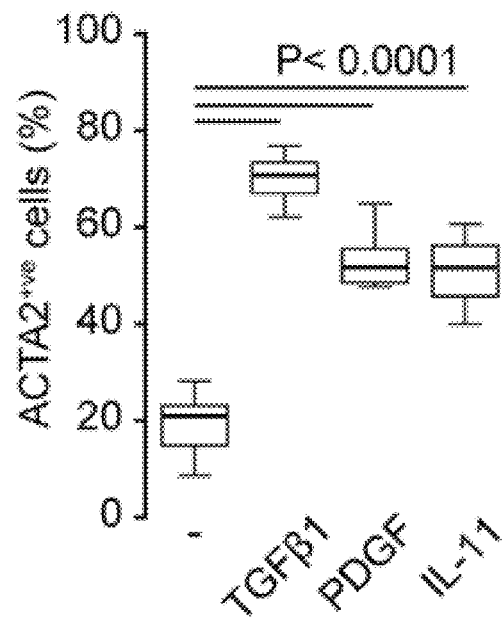
Figure 24G:
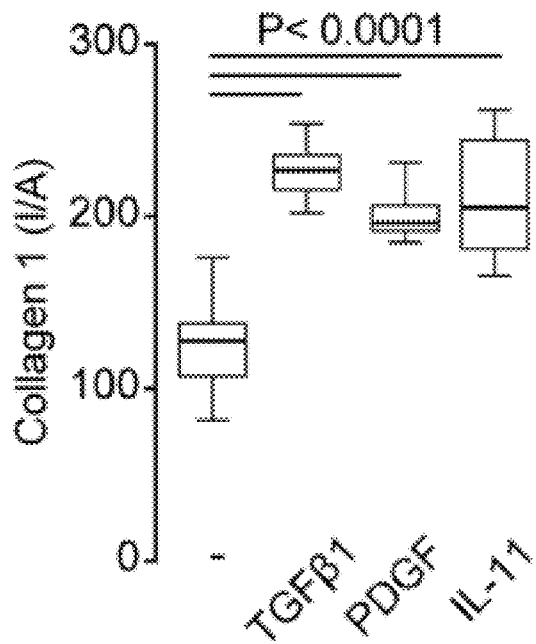
Figure 24H:
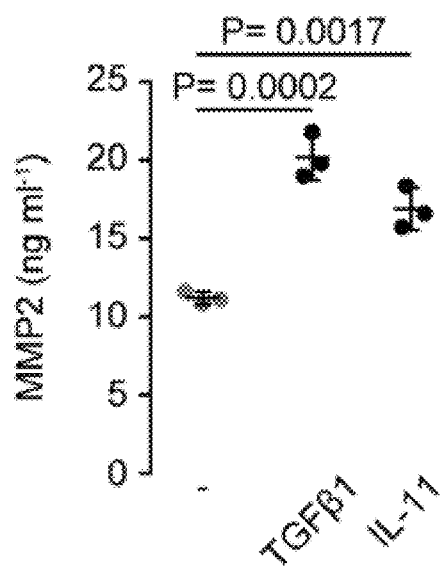
Figure 24I:
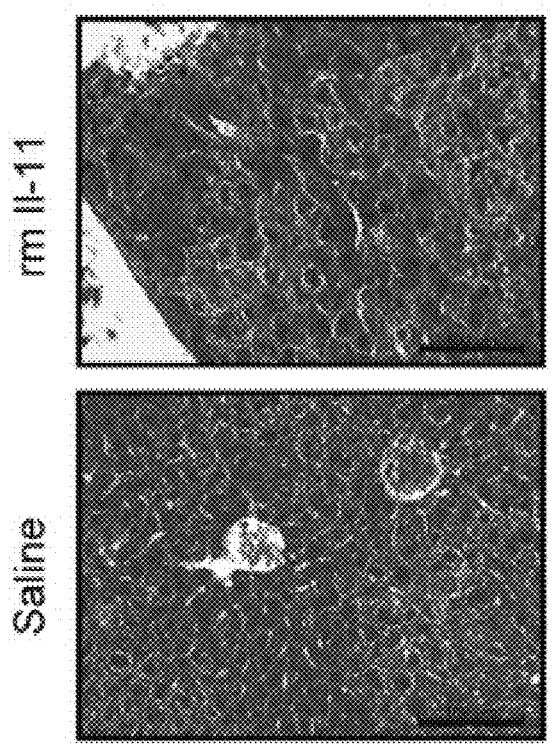
Figure 24J:
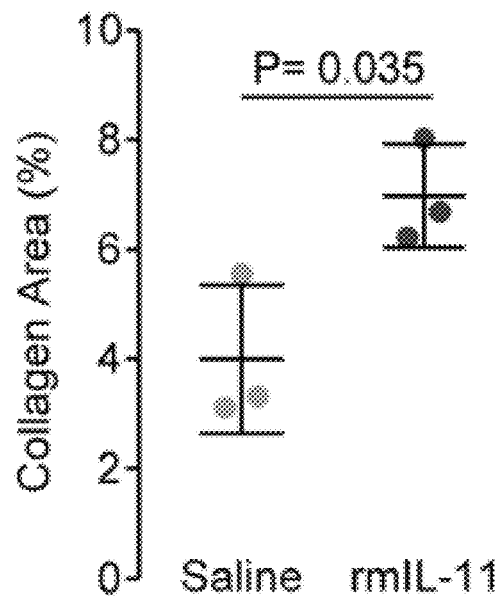
Figure 24K:
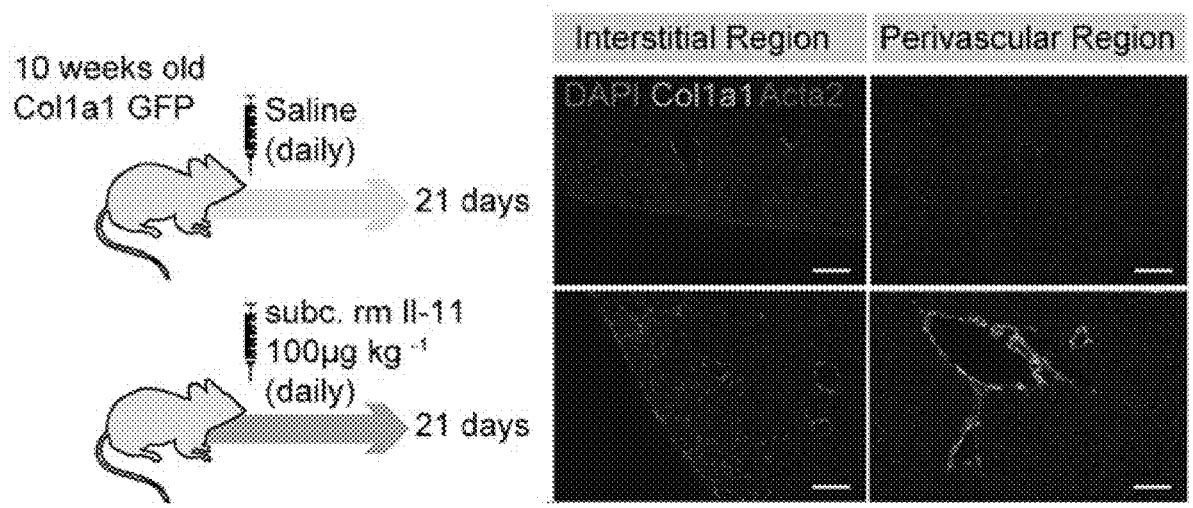

Genome wide RNA-seq analysis revealed that TGFβ1 strongly upregulates IL-11 (14.9-fold, $P=3.40 \times 10^{-145}$) in HSCs, which was verified by qPCR, confirmed at the protein level and replicated in experiments using precision cut human liver slices (FIGS. 17A-17C, FIG. 24A). Independently generated RNA-seq data[22] show that IL-11 is the most upregulated gene in HSCs when grown on a stiff substrate to model cirrhotic liver (FIG. 24B). HSCs express higher levels of the IL-11 receptor subunit alpha (IL11RA) than either cardiac or lung fibroblasts, which are responsive to IL-11 (FIG. 24B). Immunohistochemical analysis confirmed high IL11RA expression and undetectable IL6R expression in HSCs (FIG. 17D). Western blots of human liver samples showed increased IL-11 in patients with fibrotic liver diseases including NASH (FIGS. 24D-24E). These data show that HSCs are both a source and target of IL-11 in the human liver and that IL-11 is elevated in human liver disease.

Figure 17I:
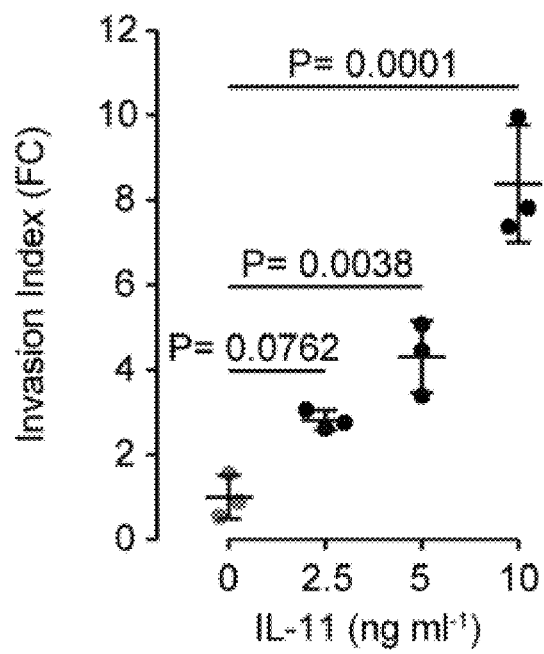
Figure 17J:
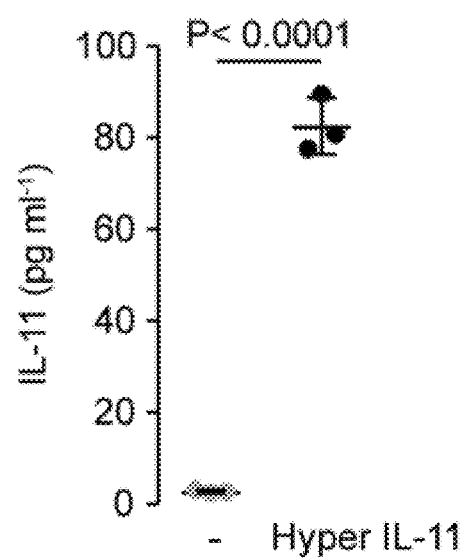
Figure 17K:
Figure 17L:
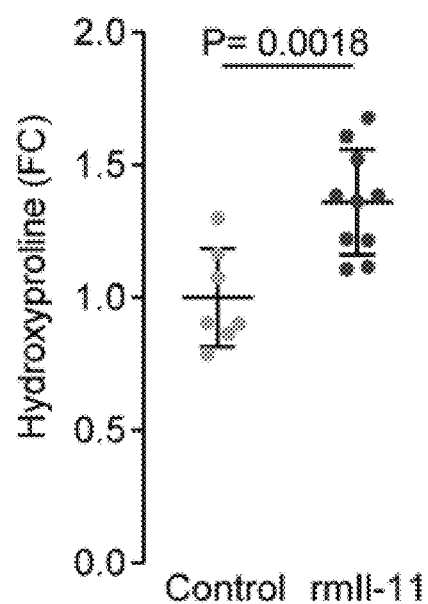
Figure 17M:
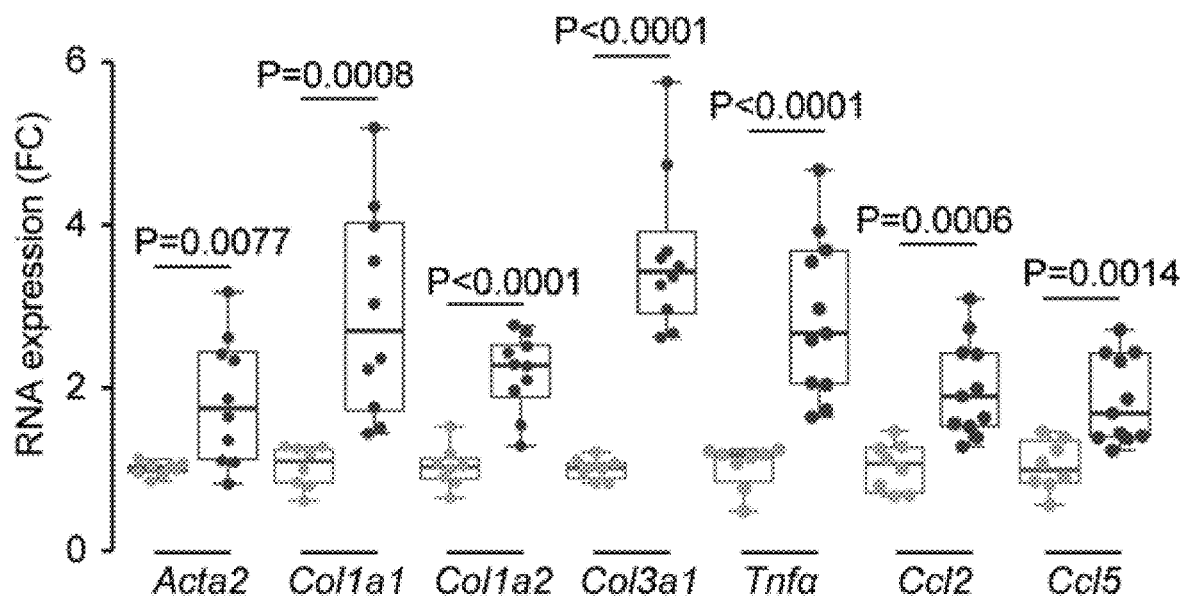
Figure 17N:
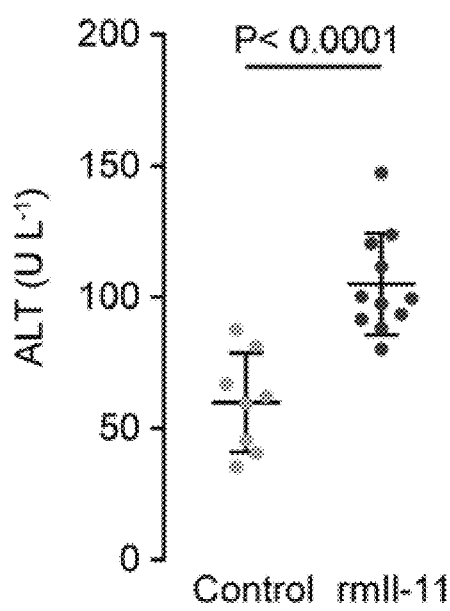

To investigate the effect of IL-11 on HSCs, cells were stimulated with either IL-11, TGFβ1 or PDGF. IL-11 activated HSCs to a similar extent as TGFβ1 or PDGF, transforming quiescent HSCs into ACTA2+ve myofibroblasts that secrete collagen and matrix modifying enzymes (FIGS. 17E-17H, FIGS. 24F-24H). IL-11 also promoted dose-dependent matrix invasion by HSCs, which is an important aspect of HSC pathobiology in NASH[23] (FIG. 17I). HSCs stimulated with hyperIL-11[11] also secreted IL-11, confirming an autocrine feed-forward loop of IL-11 signalling (FIG. 17J).

Col1a1-GFP reporter mice[19] treated with recombinant mouse Il-11 (rmIl-11) accumulated GFP-expressing Col1a1$^{+ve}$ myofibroblasts in the liver, further confirming an effect of Il-11 on HSC-to-myofibroblast transformation in vivo. Subcutaneous administration of rmIl-11 to mice for 21 days also increased hepatic collagen content, expression of key pro-fibrotic and pro-inflammatory genes and serum alanine aminotransferase (ALT) (FIGS. 17K-17N, FIGS. 24I-24K). This implied that rmIl-11 causes hepatocyte damage and inflammation in addition to fibrosis.

Figure 18A:
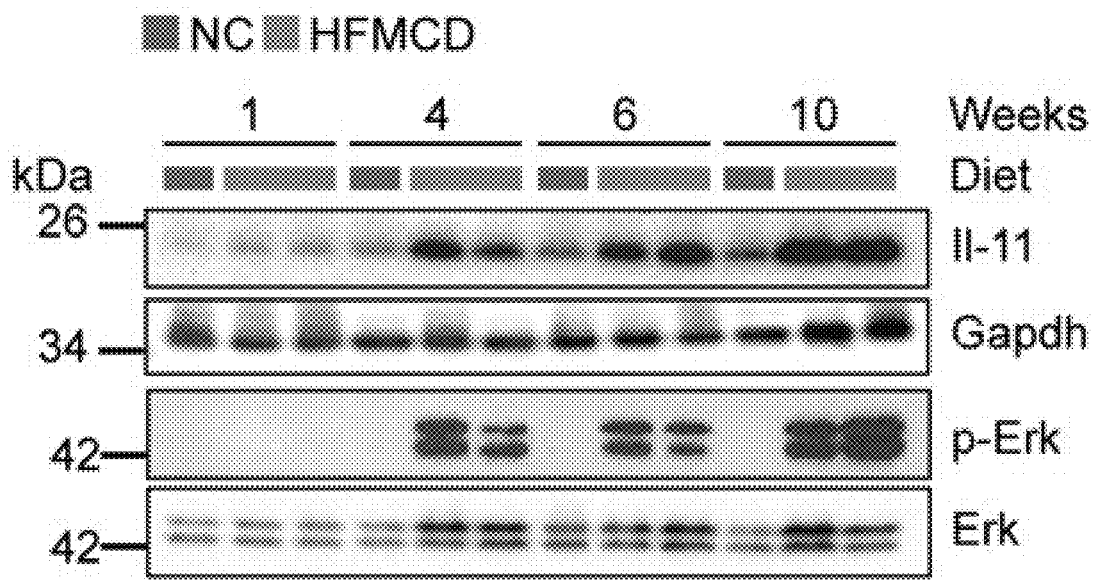
FIGS. 18A to 18N. Mice deleted for Il11ra1 are protected from NASH liver pathologies, hyperlipidaemia and hyperglycaemia. (A) Western blots of hepatic Il-11, Gapdh, p-Erk and Erk in mice on HFMCD diet for 1, 4, 6, and 10 weeks. (B) Representative Masson's Trichrome images of livers (scale bars, 100 μm), the levels of (C) liver triglyceride, (D) serum ALT, and (E) pro-inflammatory mRNA expression in the livers of Il11ra$^{+/+}$ (WT) and Il11ra$^{-/-}$ (KO) mice following 10 weeks of HFMCD diet (n≥5/group). (F-N) Data for WT and KO mice on WDF for 16 weeks. (F) Western blots of hepatic Il-11 and Gapdh. (G) Relative mRNA expression levels of liver pro-inflammatory markers, (H) serum ALT levels, (I) relative liver hydroxyproline content (n≥4/group). (J) Representative Masson's Trichrome images of liver (scale bars, 100 μm). (K) Western blots of hepatic Erk activation status, (L) fasting blood glucose, (M) serum triglyceride and (N) serum cholesterol levels (n≥3/group). (C-E, G-I) Data are shown as box-and-whisker with median (middle line), 25th-75th percentiles (box) and min-max percentiles (whiskers); (L-N) data are represented as mean±s.d., dotted line represents the mean value of WT on NC; Sidak-corrected Student's t-test. FC: fold change; NC: normal chow; HFMCD: high fat methionine- and choline-deficient; WDF: Western diet+15% (w/v) fructose.
Figure 18B:
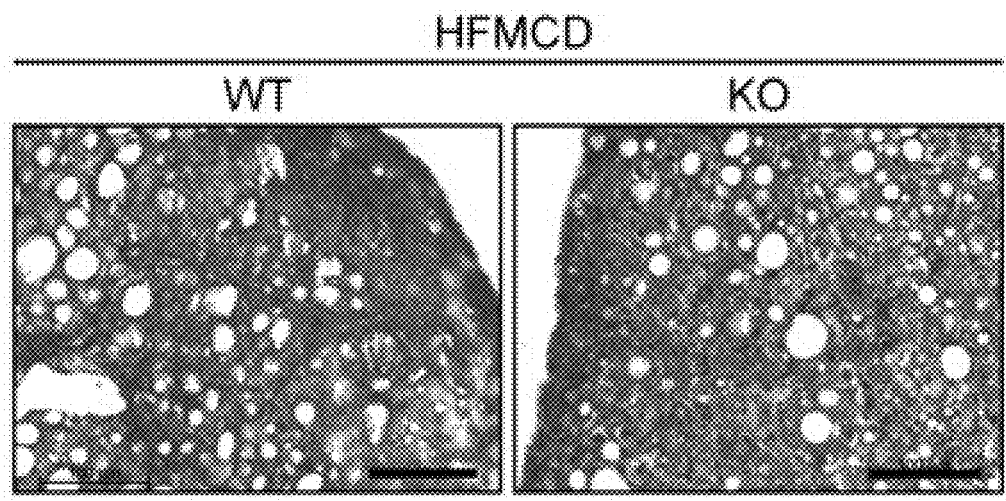
Figure 18C:
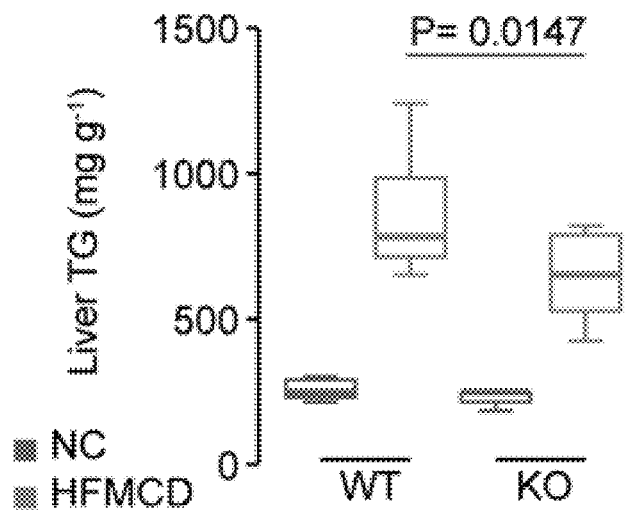
Figure 18D:
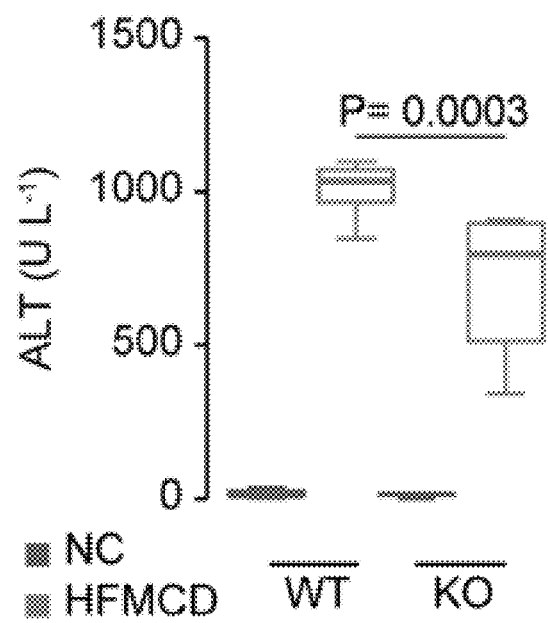
Figure 25A:
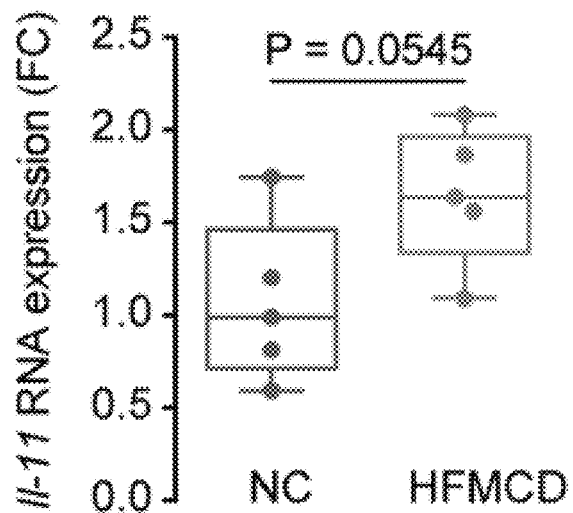
FIGS. 25A to 25I. Genetic inhibition of Il-11 signalling protects mice from HFMCD-induced NASH pathologies. Effects of 16 weeks of HFMCD diet as compared to NC diet on hepatic (A) Il-11 mRNA and (B) Il-11 protein levels. (A-B) RNA and protein were extracted from the same mice (n=5/group). (C) Relative liver hydroxyproline content and (D) serum ALT levels from mice fed with NC or HFMCD diet for 1, 4, 6, or 10 weeks (n≥5/group). (E-I) Data for Il11ra$^{+/+}$ (WT) and Il11ra$^{-/-}$ (KO) mice after 10 weeks of HFMCD diet. (E) Relative liver hydroxyproline content, (F) representative (scale bars, 100 μm) and (G) quantification of Masson's Trichrome staining images of livers. (H) Relative liver mRNA expression level of Acta2, Col1a1, Col1a2, and Col3a1(n≥5/group). (I) Western blots of phosphorylated and total Erk following 10 weeks of NC and HFMCD diet. (A, E, H) Data are shown as box-and-whisker with median (middle line), 25th-75th percentiles (box) and min-max percentiles (whiskers); (C-D, G) data are represented as mean±s.d. (A, G) Two-tailed Student's t-test; (C-D) two-way ANOVA; (E, H), Sidak-corrected Student's t-test. (C) The values of NC and HFMCD 6 weeks are the same as those used in FIG. 20C; the values of NC and HFMCD 1 week are the same as those used in FIG. 22F. (D) The values of HFMCD 6 weeks are the same as those used in FIG. 20D; the values of NC and HFMCD 1 week are the same as those used in FIG. 22G. FC: fold change; NC: normal chow; HFMCD: high fat methionine- and choline-deficient.
Figure 25B:
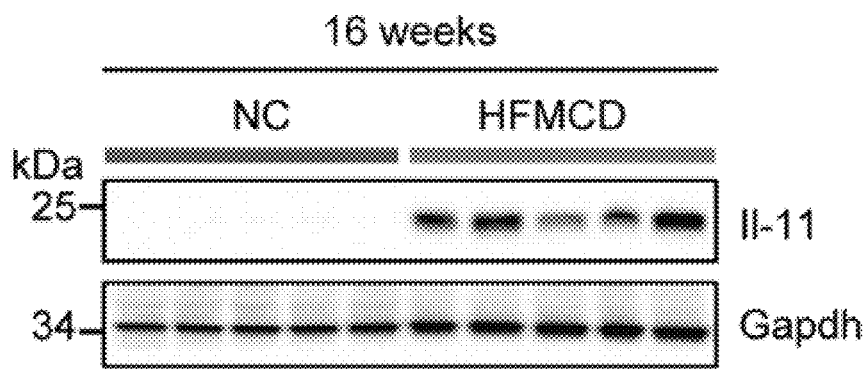
Figure 25C:
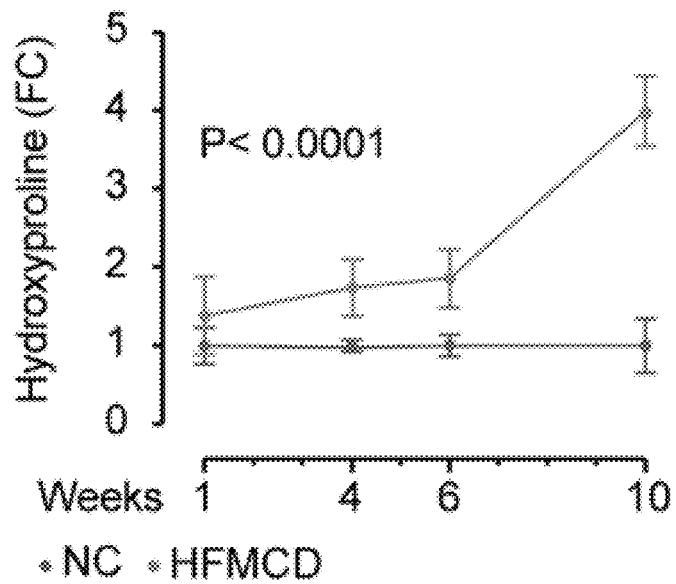
Figure 25D:
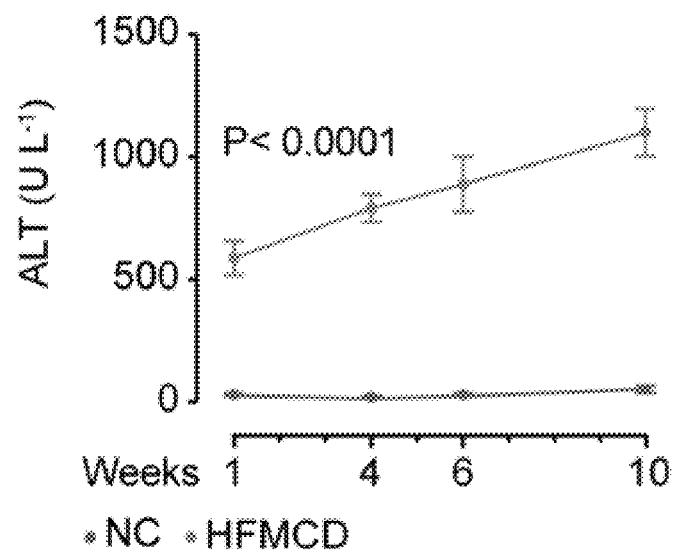
Figure 25E:
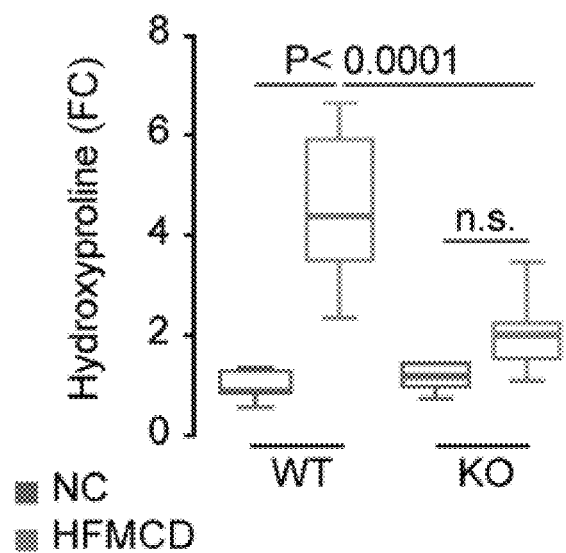
Figure 25F:
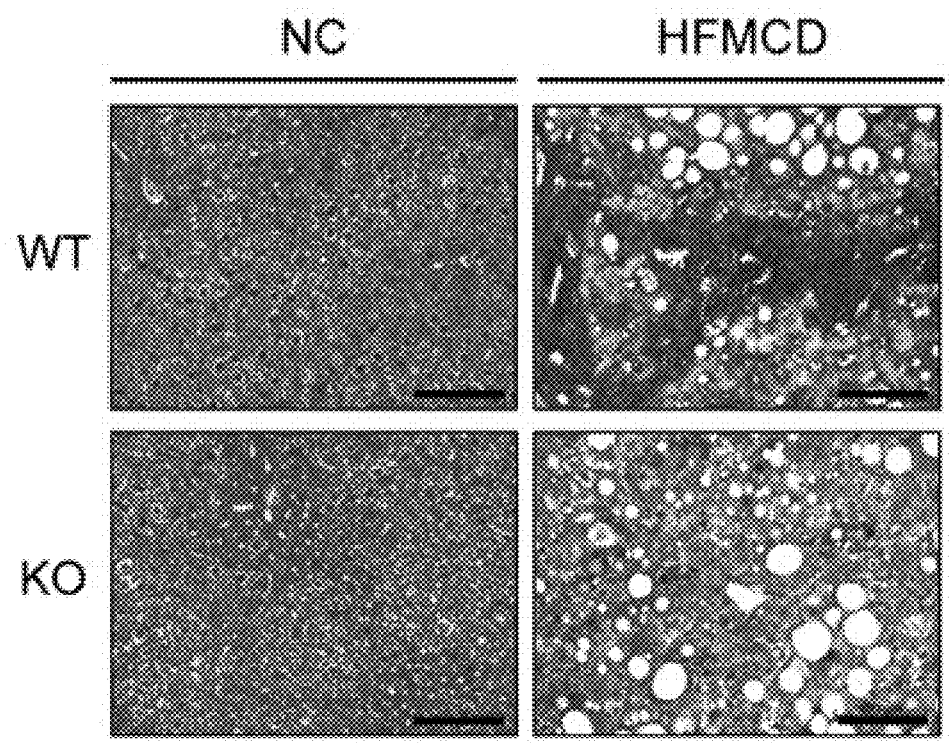
Figure 25G:
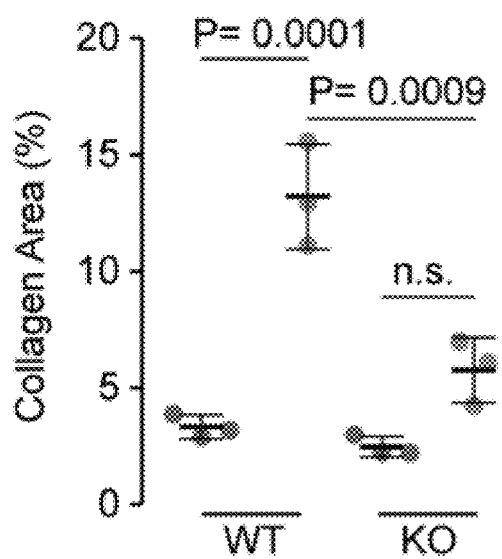
Figure 25H:
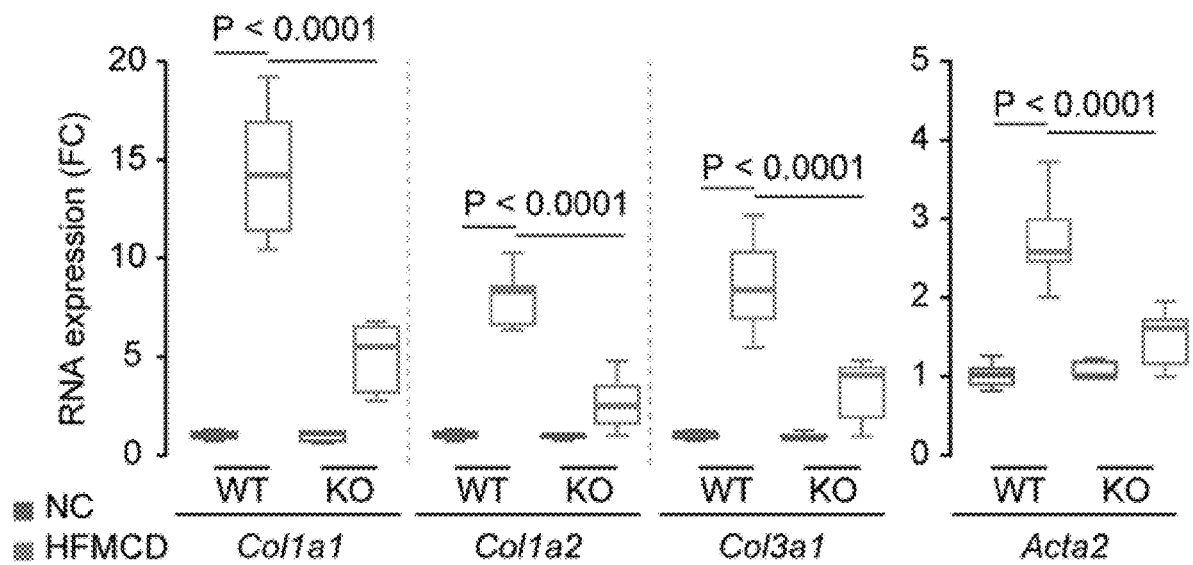

Deletion of Il11ra1 Protects Mice from NASH-Associated Inflammation, Hepatotoxicity and Fibrosis and Lowers Serum Lipids and Glucose Studies were performed in a preclinical model of severe NASH using the high fat methionine- and choline-deficient (HFMCD) diet[16]. In this model, Il-11 mRNA was mildly elevated whereas protein levels were highly upregulated, suggesting post-transcriptional regulation of Il-11 expression in the liver (FIGS. 25A-25B). Progressive induction of Il-11 protein during NASH was mirrored by Erk activation, which may be important in NASH pathogenesis[24], increased collagen and elevated serum ALT levels (FIG. 18A, FIGS. 25C-25D).

Figure 18E:
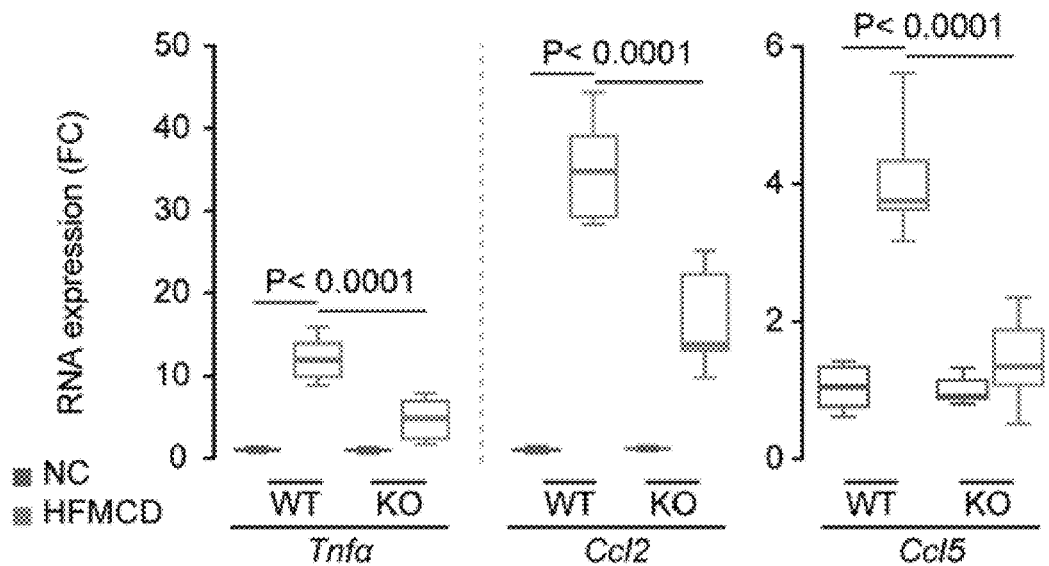

To evaluate the pathophysiological relevance of increased Il-11 levels in NASH, the inventors used a genetic loss-of-function model: the Il-11 receptor subunit alpha deleted mouse (Il11ra1$^{-/-}$)[25]. Il11ra1$^{-/-}$ mice on the HFMCD diet were strongly protected from fibrosis and had lesser steatosis and liver damage as compared to controls (FIGS. 18B-18D, FIGS. 25E-25H). Furthermore, markedly less liver inflammation was observed in Il11ra1$^{-/-}$ mice (FIG. 18E), suggesting that Il-11 plays an important role across multiple NASH pathologies.

Figure 18F:
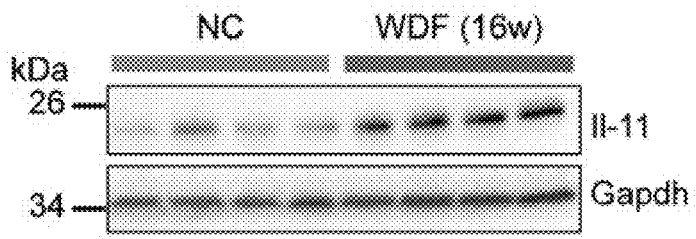
Figure 18G:
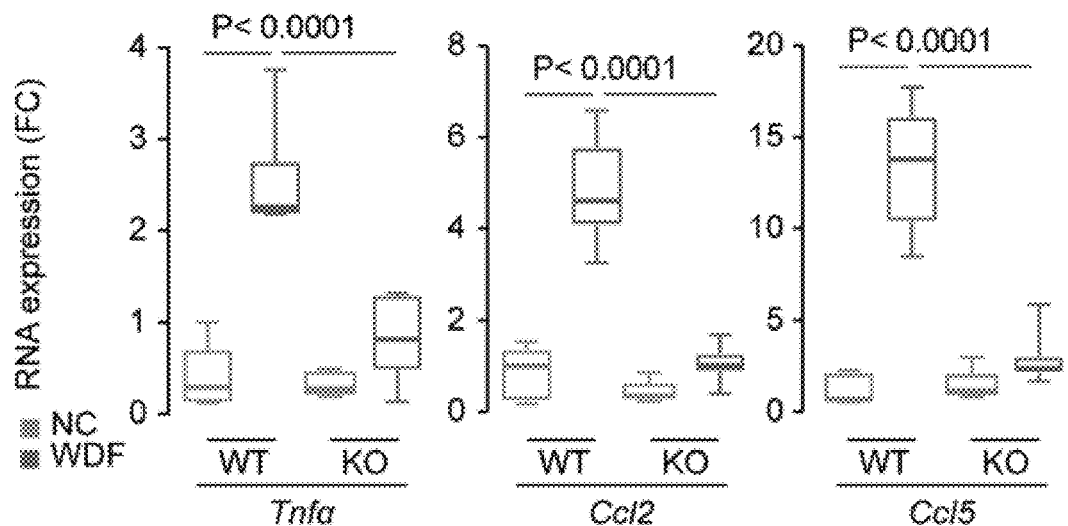
Figure 18H:
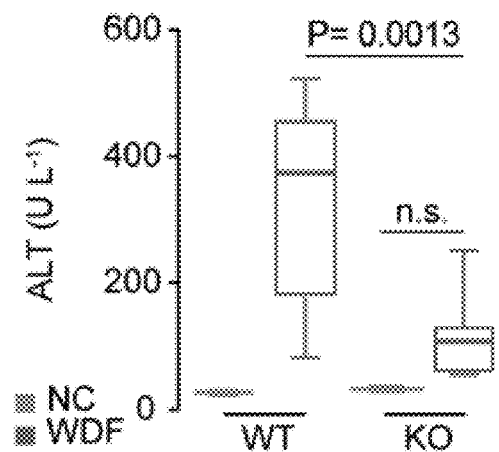
Figure 18I:
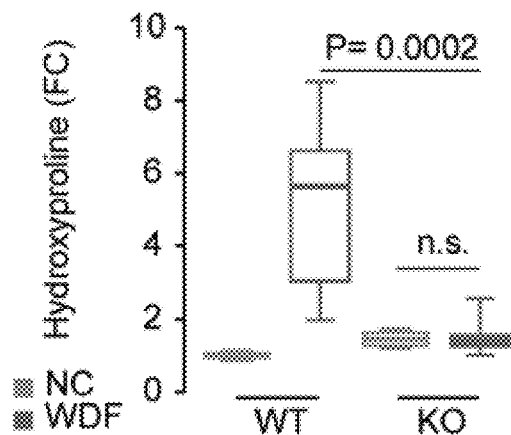
Figure 18J:
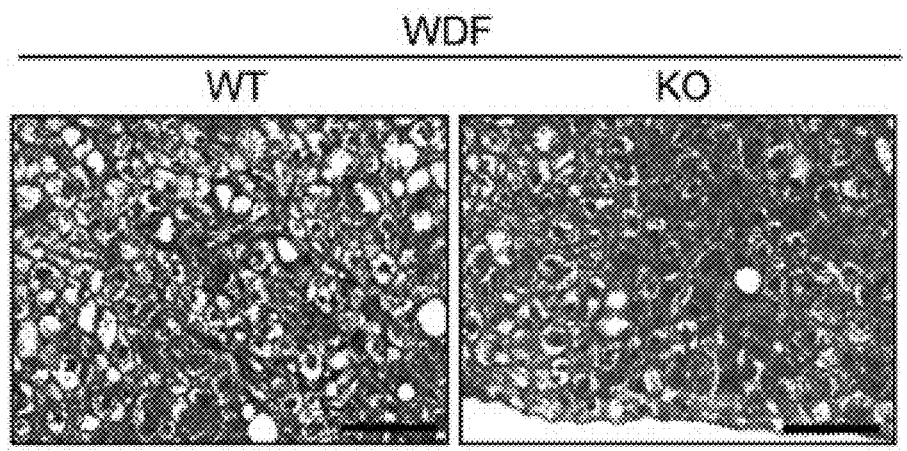
Figure 18K:
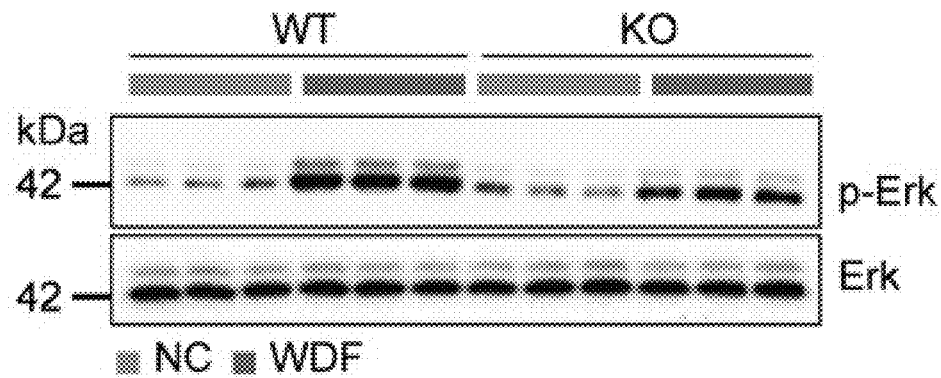
Figure 25I:
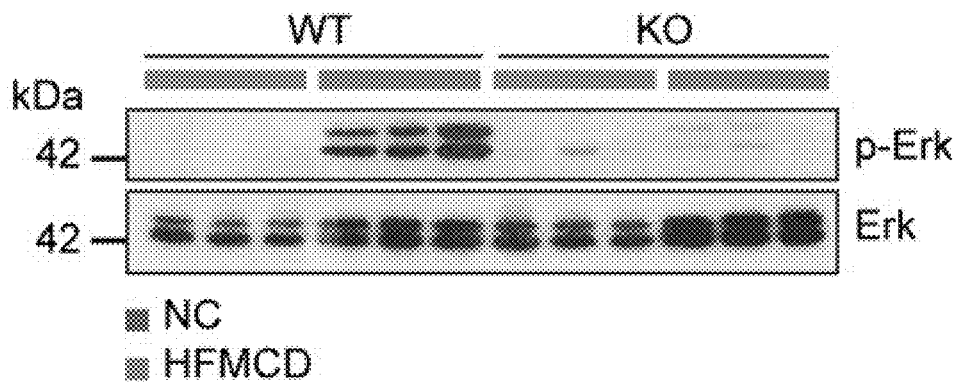
Figure 26A:
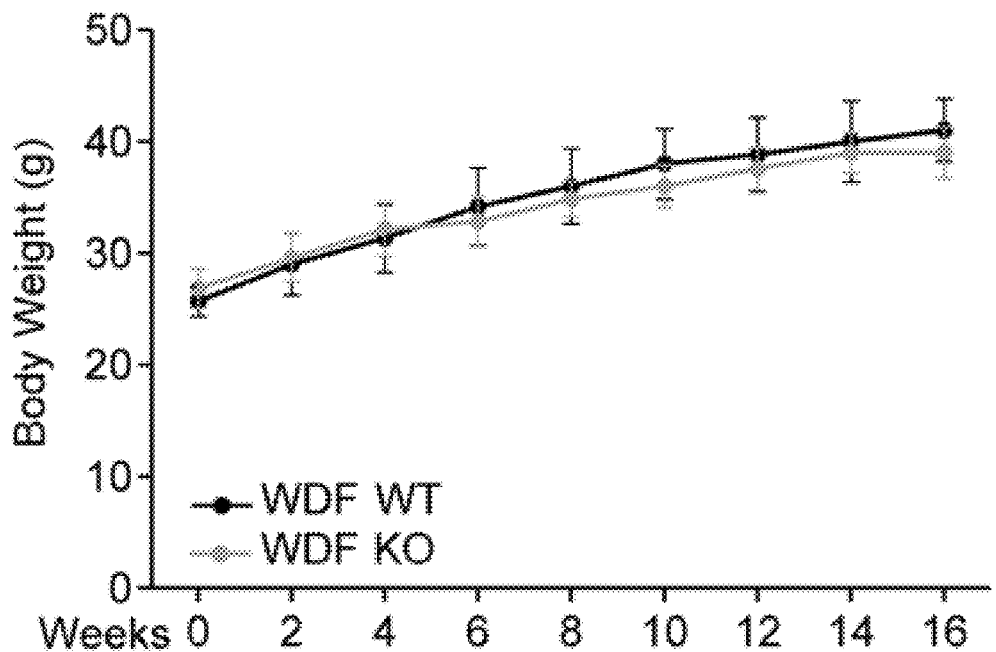
FIGS. 26A to 26E. Genetic inhibition of Il-11 signalling protects mice from WDF-induced NASH pathologies. Effect of 16 weeks of WDF on (A) body weight (n≥6/group) of Il11ra$^{+/+}$ (WT) and Il11ra$^{-/-}$ (KO) mice. (B) Liver triglyceride levels, (C) representative (scale bars, 100 μm) and (D) quantification of Masson's Trichrome staining images of livers, (E) relative liver mRNA expression levels for pro-fibrosis genes (n≥5/group) of WT and KO mice following 16 weeks of NC and WDF. (A, D) Data are shown as mean±s.d, two-tailed Student's t-test; (B, E) data are shown as box-and-whisker with median (middle line), 25th-75th percentiles (box) and min-max percentiles (whiskers), Sidak-corrected Student's t-test. FC: fold change; NC: normal chow; WDF: Western diet+15% (w/v) fructose.
Figure 26B:
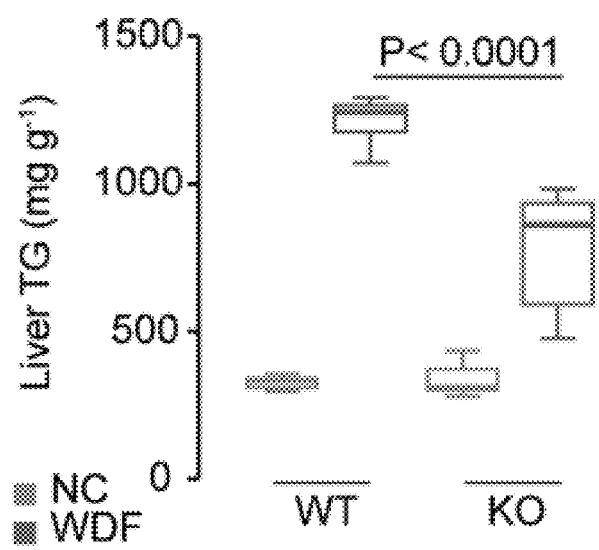
Figure 26C:
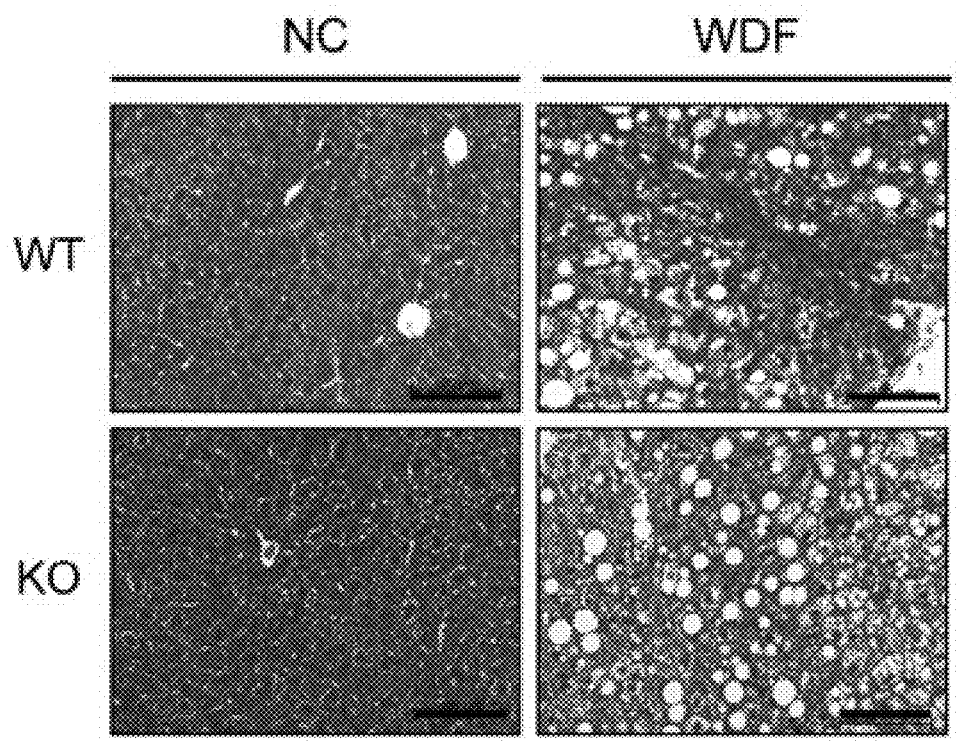
Figure 26D:
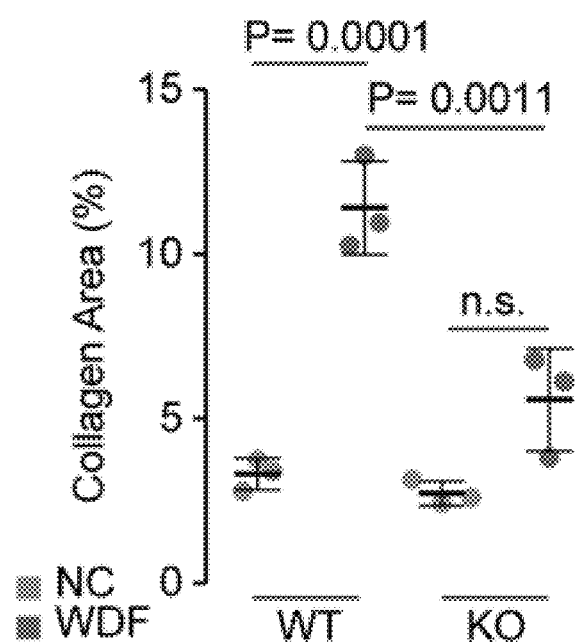
Figure 26E:
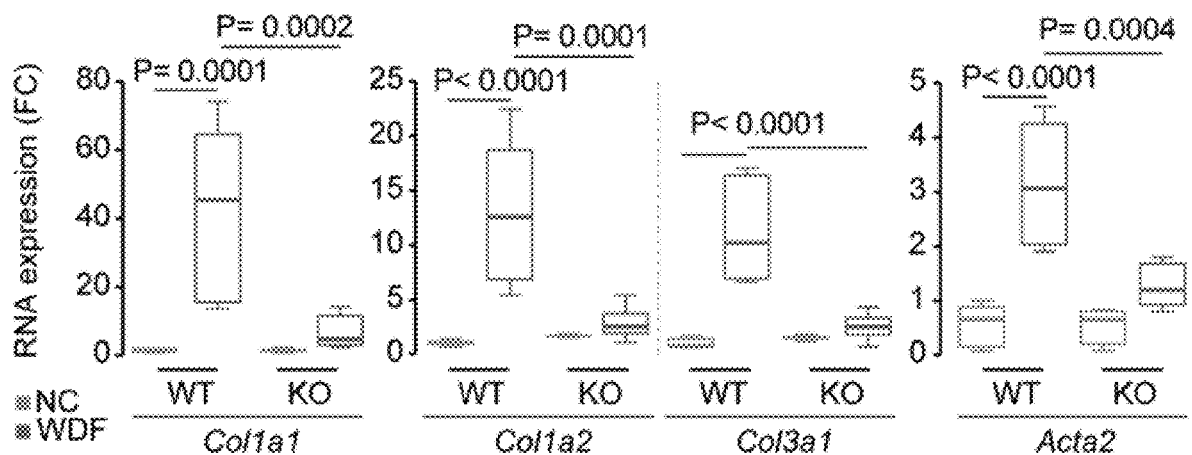

The HFMCD model has early onset steatotic hepatitis followed by fibrosis. However, this model is not obese or insulin resistant. Another NASH model was established, using a Western Diet supplemented with liquid Fructose (WDF)[26] that is obese, insulin resistant and hyperglycaemic, mirroring human NASH[18]. After 16 weeks of WDF feeding, NASH was established and Il-11 protein was upregulated in the liver (FIG. 18F). Il11ra1$^{-/-}$ mice on WDF had similar weight gain as compared to control mice but were protected from liver steatosis, inflammation, hepatocyte damage, and fibrosis (FIGS. 18G-18J, FIG. 26). Erk activation in Il11ra1$^{-/-}$ mice was diminished in both the HFMCD and WDF model, implying Il-11-driven Erk activation is important for NASH (FIG. 18K, FIG. 25I).

Figure 18L:
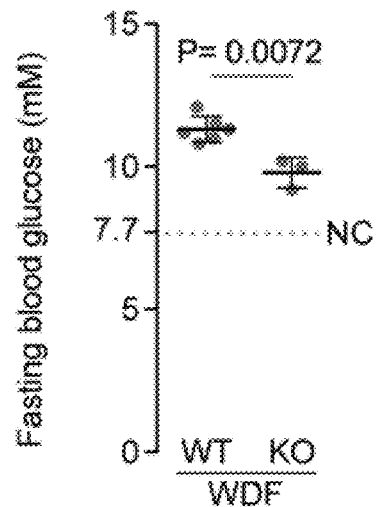
Figure 18M:
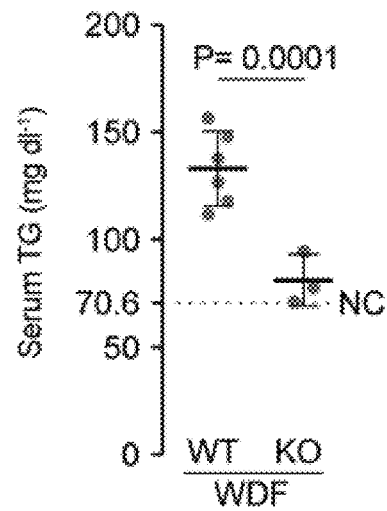
Figure 18N:
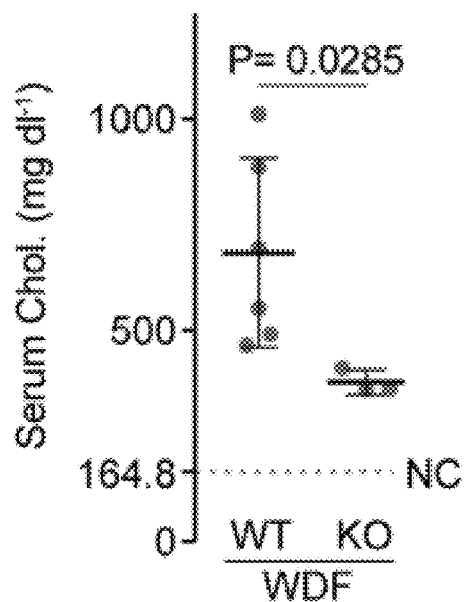

The primary causes of mortality in NASH are cardiovascular: myocardial infarction, renal failure and stroke[27,28]. Biomarkers of cardiovascular risk were measured in Il11ra1$^{-/-}$ mice after 16 weeks on the WDF diet. As compared to littermate controls, Il11ra1$^{-/-}$ mice on WDF had lower levels of fasting blood glucose, serum cholesterol and triglycerides (FIGS. 18L-18N).

Neutralising Anti-IL-11 or Anti-IL11RA Antibodies Block HSC Activation

Mice were genetically immunised with IL11RA to generate neutralising anti-IL11RA antibodies. Clones that blocked fibroblast transformation[11] were identified and clone X209 (IgG1$_\kappa$, K$_D$=6 nM) was prioritised. X209 blocked MMP2 secretion from HSCs with an IC$_{50}$ of 5.8 pM and has an in vivo half-life of approximately 18 days with good liver uptake (FIG. 19A, FIG. 27A-27D). To ensure therapeutic specificity for IL-11 signalling, the neutralising anti-IL-11 antibody X203[12] (IgG1$_\kappa$, IC$_{50}$=40.1 pM for HSC activation) was developed and used in experiments.

Figure 19A:
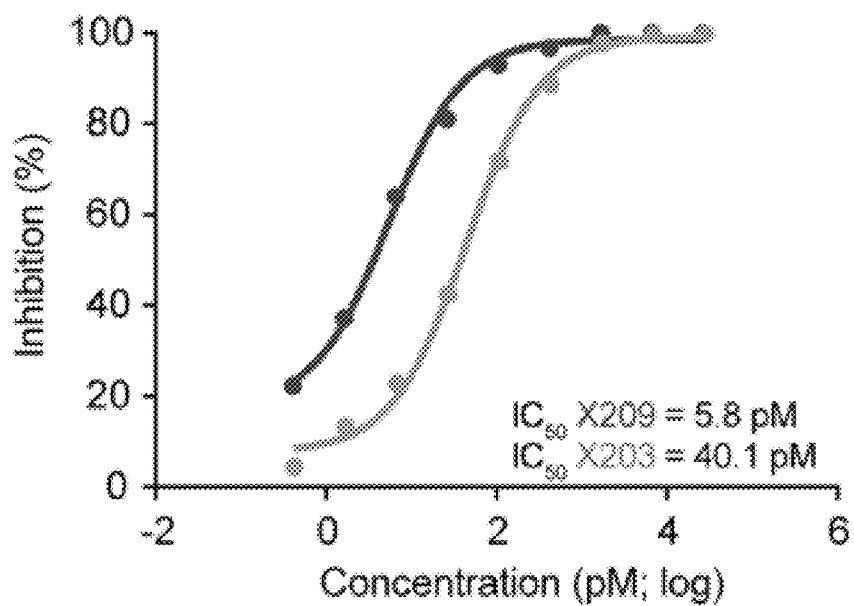
FIGS. 19A to 19J. Anti-IL-11 therapies inhibit HSC-to-myofibroblasts transformation in an ERK dependent manner and have a favourable metabolic safety profile. (A) Dose-response curve and IC$_{50}$ value of X203 and X209 and (61 μg/ml to 4 μg/ml; 4-fold dilution) in inhibiting MMP2 secretion by TGFβ1-stimulated HSCs. (B) ELISA of IL-11 secretion from HSCs stimulated with various NASH factors (n≥5/group). (C) Representative fluorescence images and quantification of ACTA2$^{+ve}$ cells from HSCs treated with TGFβ1 and other NASH factors in the presence of IgG, X203, or X209 (scale bars, 100 μm and dotted line represents the median value of baseline). (D) Effects of X203 and X209 on PDGF- or CCL2-induced HSC invasion. (E) Western blots of p-ERK and ERK in HSC lysates stimulated IL-11 (upper panel) or with various NASH factors in the presence of IgG or X209 (bottom panel). (F) Representative fluorescence images and quantification of ACTA2$^{+ve}$ cells in HSCs treated with IL-11 and important NASH factors in the presence of ERK/MEK inhibitors U0126 or PD98059 (scale bars, 100 μm and dotted line represents the median value of baseline). (A-F) TGFβ1 (5 ng/ml), IL-11 (5 ng/ml), PDGF (20 ng/ml), AngII (100 nM), bFGF (10 ng/ml), CM (5 ng/ml), H$_2$O$_2$ (0.2 mM), IgG, X203 and X209 (2 μg/ml), U0126 or PD98059 (10 μM); (A,C,E-F) 24 h; (B,D) 48 h. (G) Peripheral platelet counts, (H) serum ALT levels, (I), serum triglycerides levels, and (J) serum cholesterol levels from mice injected biweekly with 10 mg/kg of X203 and X209 for 5 months (n≥5/group). (B,D) Data are shown as mean±s.d; (C,F,G-J) data are shown as box-and-whisker with median (middle line), 25th-75th percentiles (box) and min-max percentiles (whiskers). (B,D,G-J) Two-tailed Dunnett's test; (C, F) two-tailed, Tukey-corrected Student's t-test. FC: fold change.
Figure 19B:
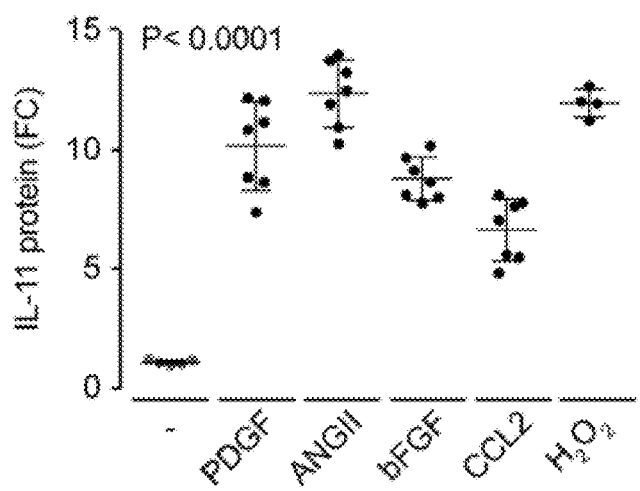
Figure 19C:
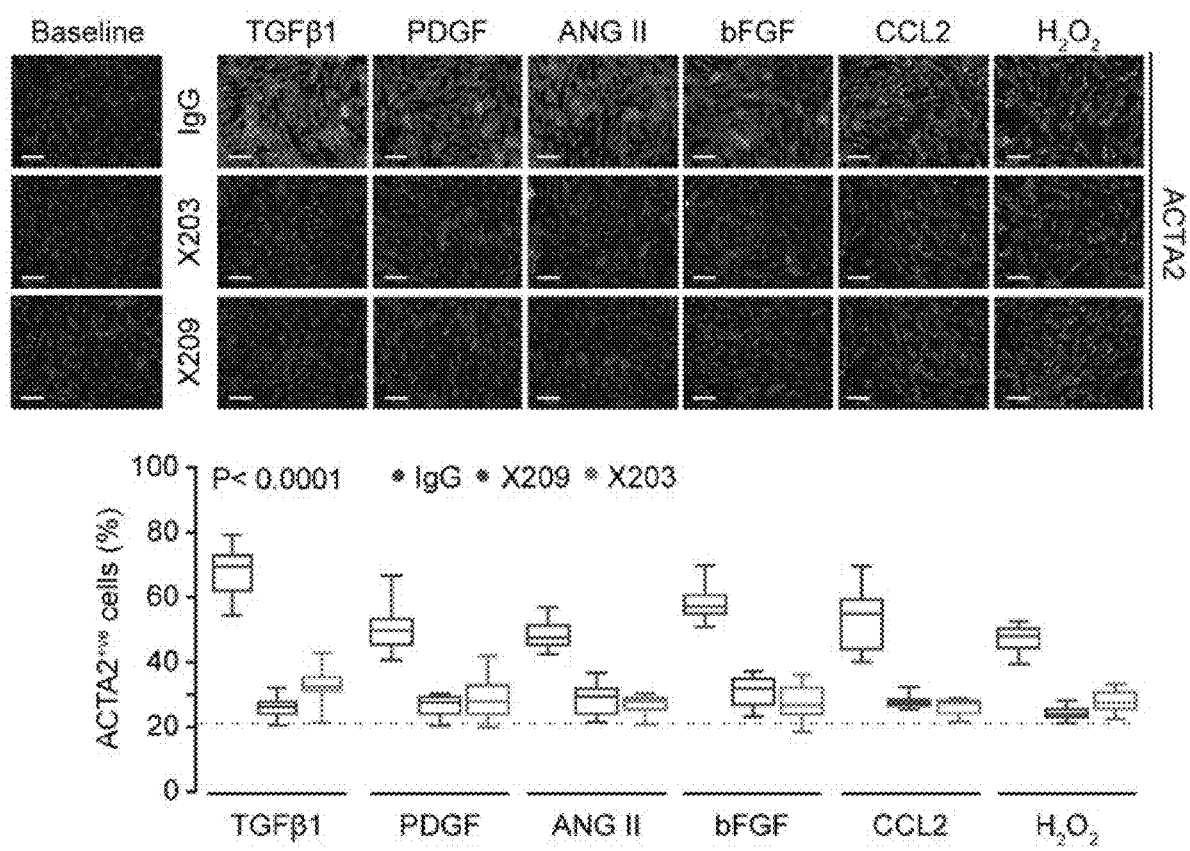
Figure 19D:
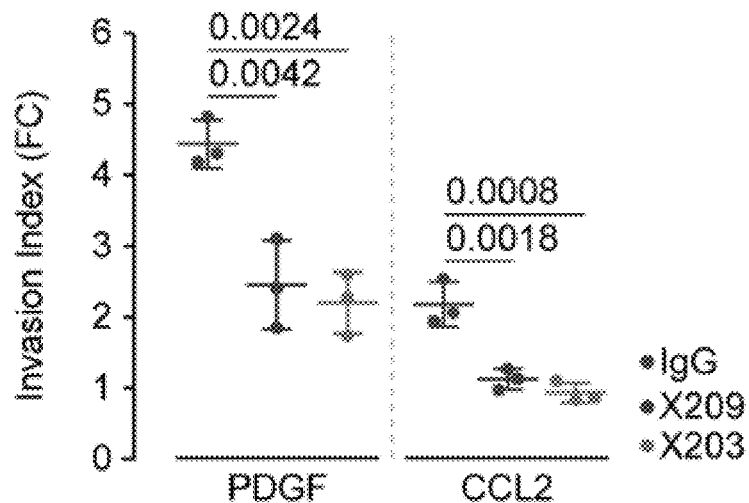
Figure 27A:
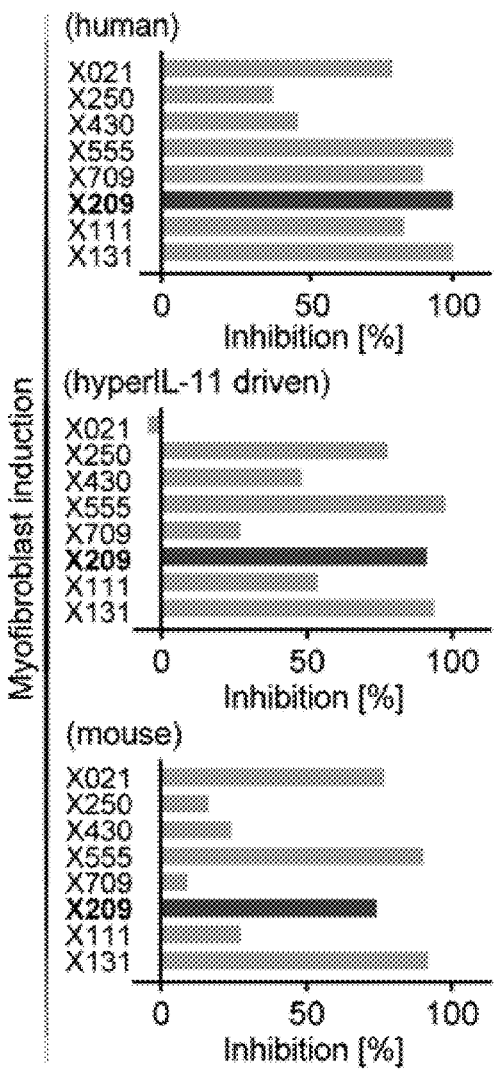
FIGS. 27A to 27F. Development of a neutralizing anti-IL-11 RA monoclonal antibody. (A) Inhibition of ACTA2$^{+ve}$ cell transformation of TGFβ1-(upper), hyperIL-11-(middle) stimulated human atrial fibroblasts and TGFβ1—(bottom) stimulated mouse atrial fibroblasts with purified mouse monoclonal anti-IL11RA candidates (6 μg ml$^{-1}$). (B) X209 interactions with IL11RA as determined by SPR (1:1 Langmuir). (C) Blood pharmacokinetics of $^{125}$I-X209 in mice (n=5). Result was fitted (R$^2$=0.92) to a two-phase exponential decay model. (D) Percentage of $^{125}$I-X209 uptake by liver (n=5) at the indicated time points, following retro-orbital injection. (E-F) Representative fluorescence images (scale bars, 100 μm) and quantification of Collagen 1 immunostaining of HSCs treated with various NASH factors in the presence of (E) IgG control, X203, or X209 or in the presence of (F) MEK/ERK inhibitors (U0126 or PD98059). (A, E-F) TGFβ1 (5 ng/ml), IL-11 (5 ng/ml), PDGF (20 ng/ml), AngII (100 nM), bFGF (10 ng/ml). CM (5 ng/ml), H$_2$O$_2$ (0.2 mM), IgG, X203 and X209 (2 μg/ml), U0126 or PD98059 (10 μM); 24 h stimulation. (C-D) Data are represented as mean+s.d; (E-F) data are shown as box-and-whisker with median (middle line), 25th-75th percentiles (box) and min-max percentiles (whiskers), dotted line represents the mean of baseline values, Tukey-corrected Student's t-test. FC: fold change; I/A: intensity/area.
Figure 27B:
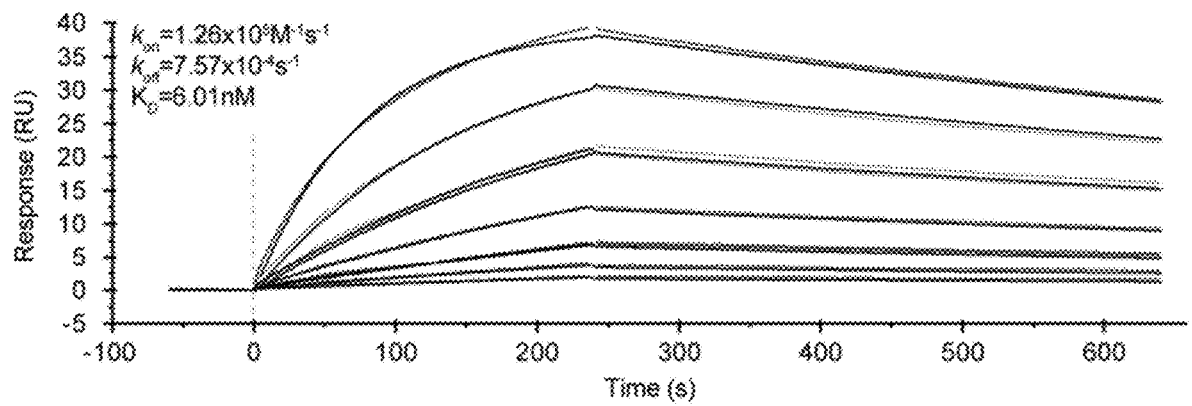
Figure 27C:
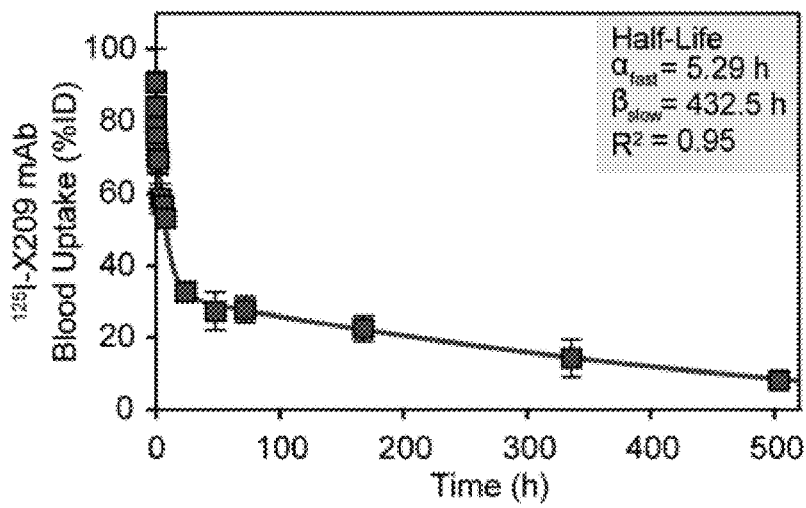
Figure 27D:
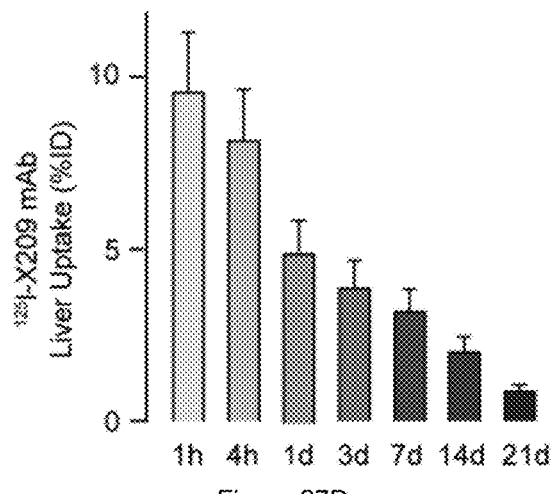
Figure 27E:
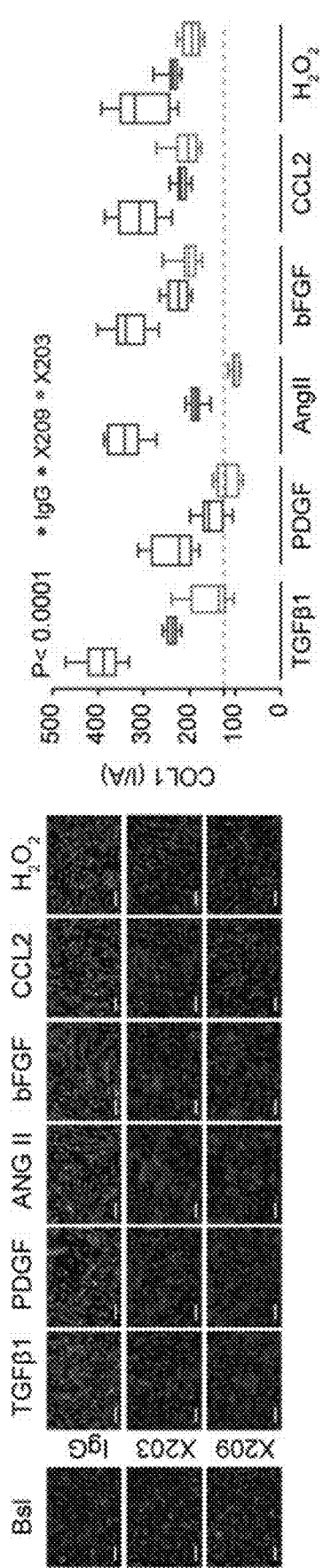

The inventors found that, in addition to TGFβ1 (FIGS. 17A-17C), other key NASH stimuli such as PDGF, CCL2, angiotensin II, bFGF or oxidative stress induce IL-11 secretion from HSCs (FIG. 19B). This suggested IL-11 has a role in HSC activation downstream of multiple factors. To test this, HSCs were stimulated with various NASH factors and found all stimuli to depend on intact IL-11 signalling to induce ACTA2 or collagen expression (FIG. 19C, FIG. 27E). In separate assays, the pro-invasive effects of PDGF or CCL2 on HSCs were also shown to be IL-11-dependent (FIG. 19D).

Figure 19E:
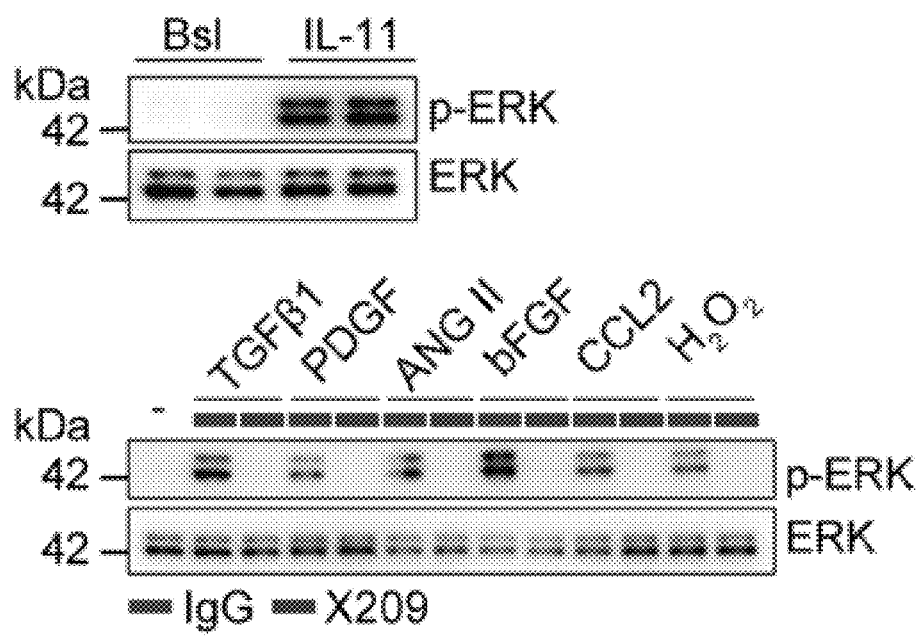
Figure 19F:
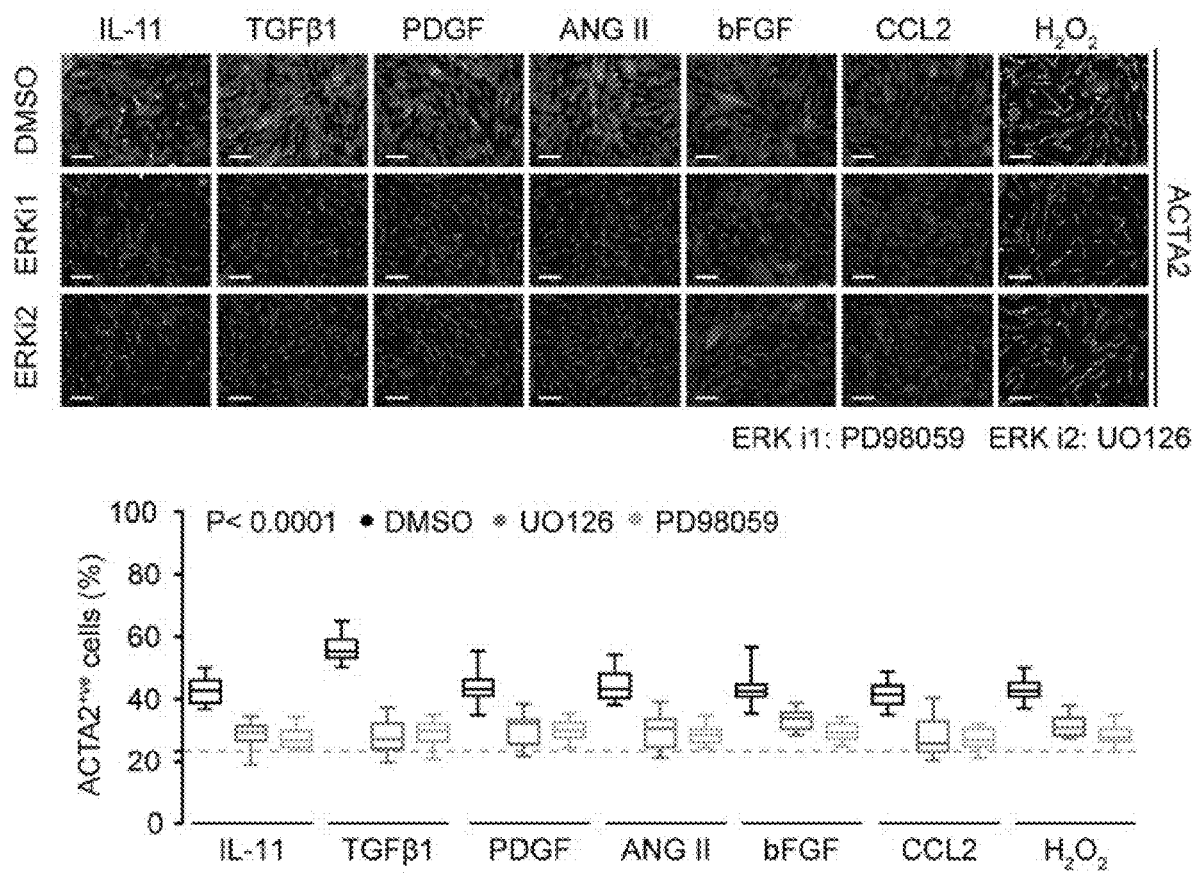
Figure 27F:
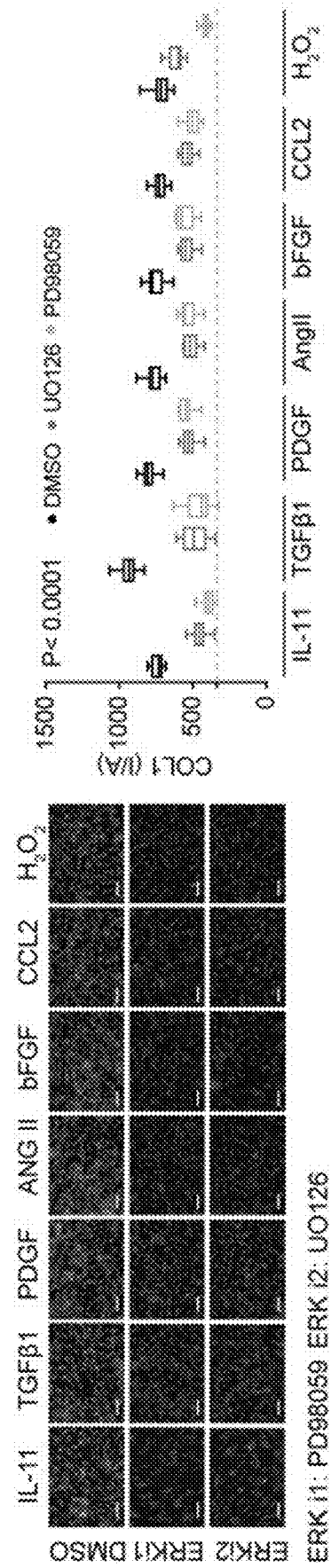

In the Il11ra1$^{-/-}$ mouse, liver protection on either HFMCD or WDF diets was associated with reduced Erk activation. The inventors found that IL-11 directly activates ERK in HSCs and that all stimuli that induce IL-11 secretion from HSCs also induce ERK activation. X209 abolished ERK phosphorylation and HSC transformation downstream of all factors, including IL-11 itself. ERK inhibitors blocked the IL-11 effect and HSC activation downstream of all NASH triggers, suggesting IL-11 driven ERK phosphorylation is of central importance for HSC transformation (FIGS. 19E-19F, FIG. 27F).

Figure 19G:
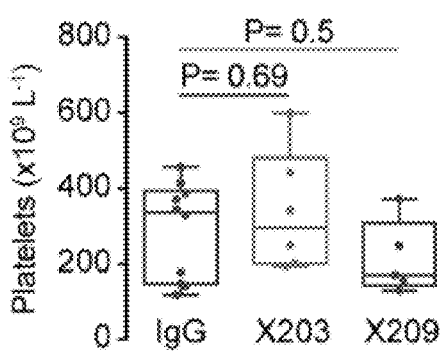
Figure 19H:
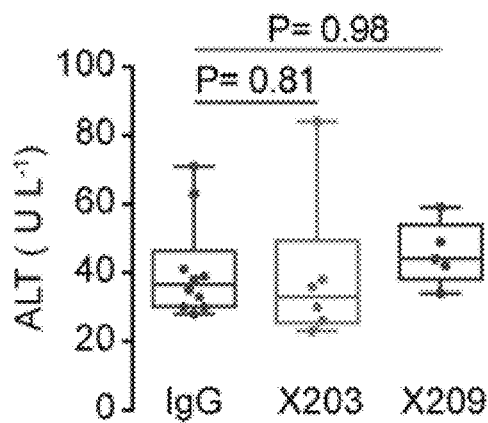
Figure 19I:
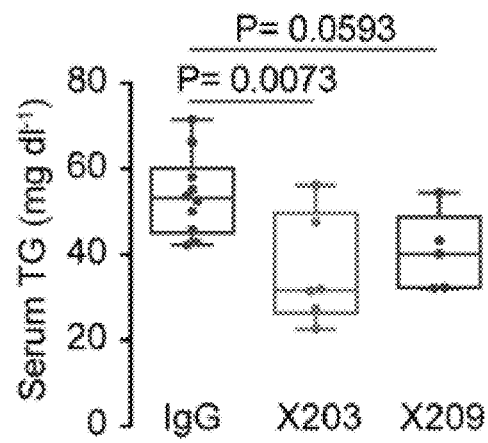
Figure 19J:
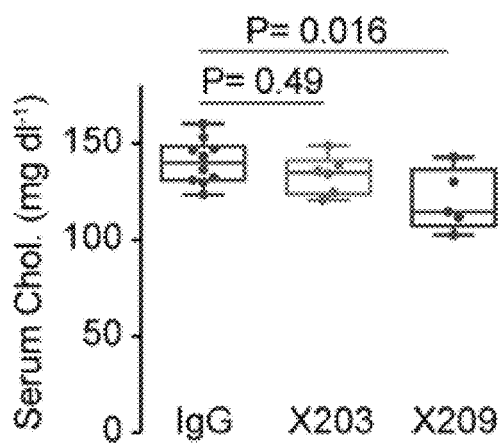

The published literature on IL-11 in the liver is limited but injection of high dose recombinant human IL-11 into rodents has been associated with protective effects[13,14] and there is confusion as to a role for IL-11 in platelets biology[25]. To exclude safety issues, the inventors performed long-term (5 months) high dose (10 mg/kg×2/week) preclinical toxicology studies of X209 and X203 and observed no effect on serum ALT levels or platelets (FIG. 19G-19H). Consistent with the data in the Il11ra$^{-/-}$ mice, anti-IL-11 therapies lowered, or trended towards lowering, serum lipid levels during this treatment period (FIGS. 19I-19J).

Figure 20A:
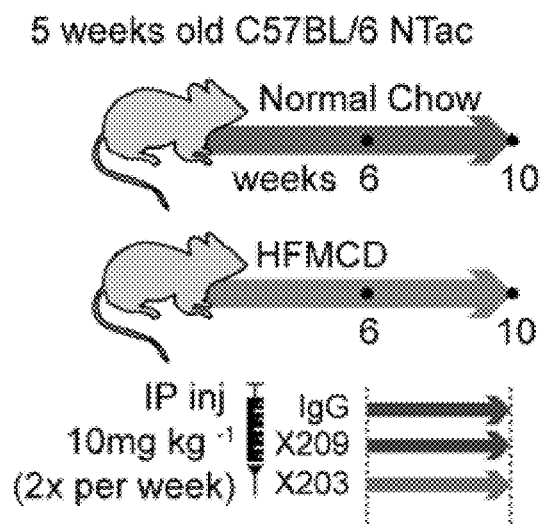
FIGS. 20A to 20N. Therapeutic targeting of Il-11 inhibits and reverses NASH pathologies in preclinical models. (A) Schematic showing therapeutic use of X203 and X209 (10 mg/kg, biweekly) in HFMCD-fed mice for experiments shown in (B-E). X203, X209 or IgG isotype control were administered from week 6 to 10 of HFMCD diet. (B) Representative liver histological images (Masson's Trichrome staining; scale bars, 100 μm), (C) relative liver hydroxyproline content, (D) relative liver pro-inflammatory mRNA expression levels (n≥6/group) and (E) serum ALT levels. (F) Western blots of hepatic Erk activation status. (G) Schematic of X203 or IgG administration to MCD-fed db/db mice for experiments shown in H-N. Western blots of hepatic (H) Il-11 and Gapdh, (I) p-Erk and Erk. (J) Representative Masson's Trichrome images of liver from X203 or IgG-treated MCD-fed db/db mice (scale bars, 100 μm). The levels of (K) hepatic triglyceride, (L) relative liver hydroxyproline, (M) serum ALT, and (N) mRNA expression of liver pro-inflammatory markers (n≥5/group). (C-E,K-N) Data are shown as box-and-whisker with median (middle line), 25th-75th percentiles (box) and min-max percentiles (whiskers); two-tailed, Tukey-corrected Student's t-test. FC: fold change; NC: normal chow; HFMCD: high fat methionine- and choline-deficient; MCD: methionine- and choline-deficient.
Figure 20B:
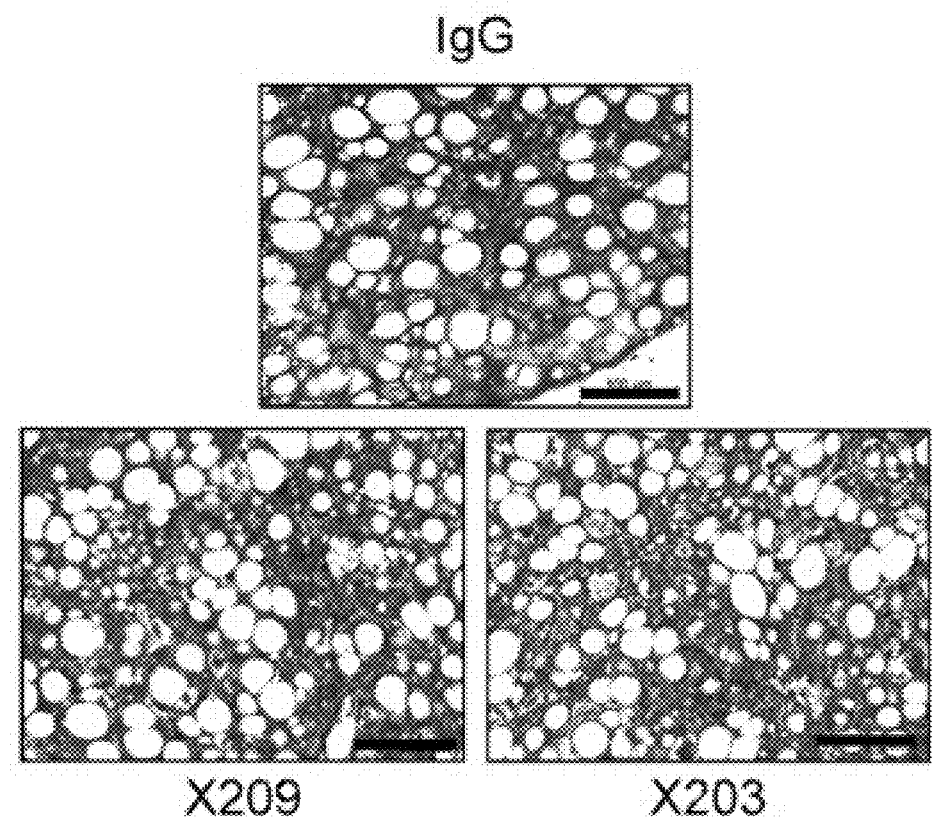
Figure 20C:
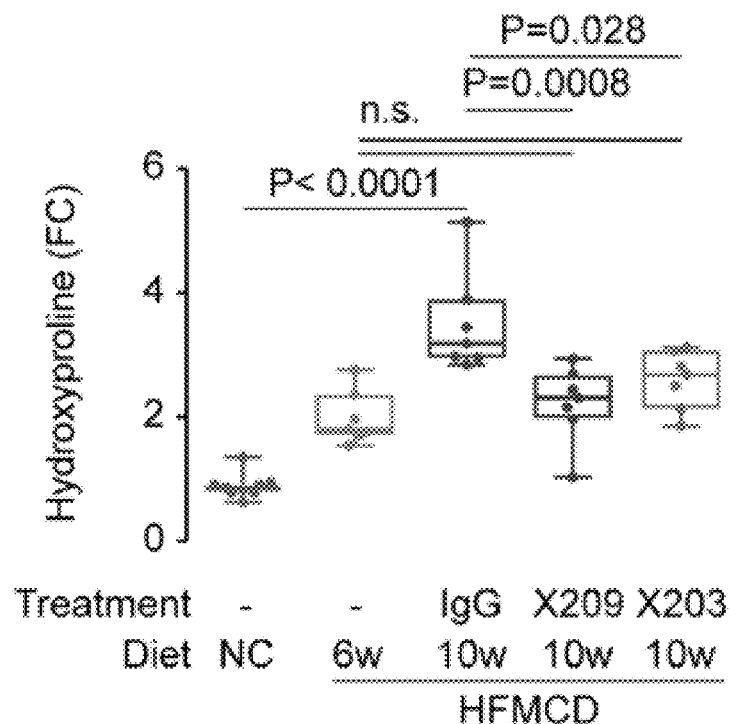
Figure 20D:
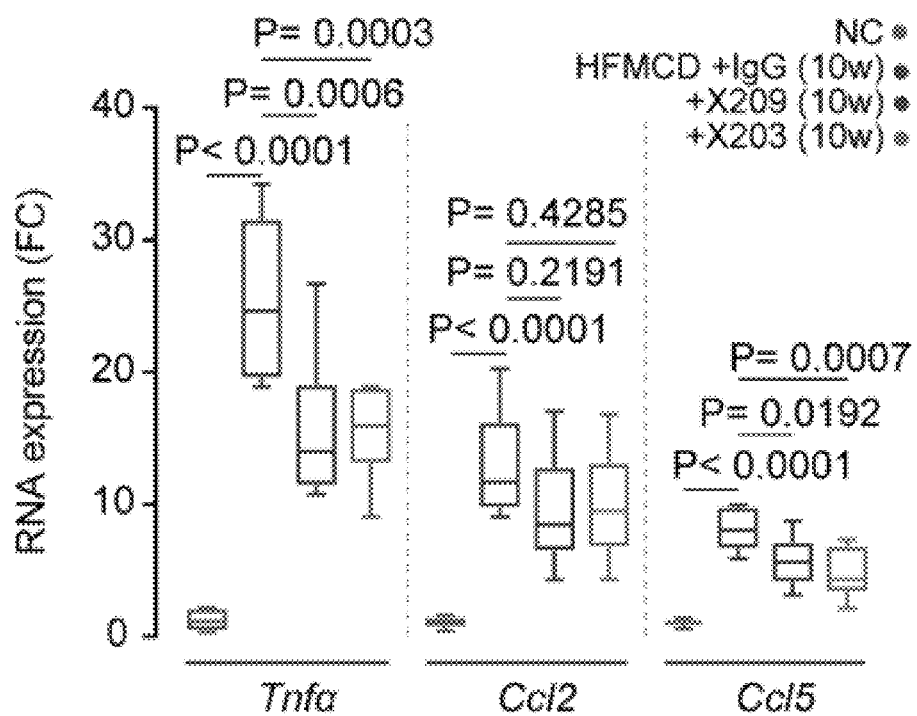
Figure 20E:
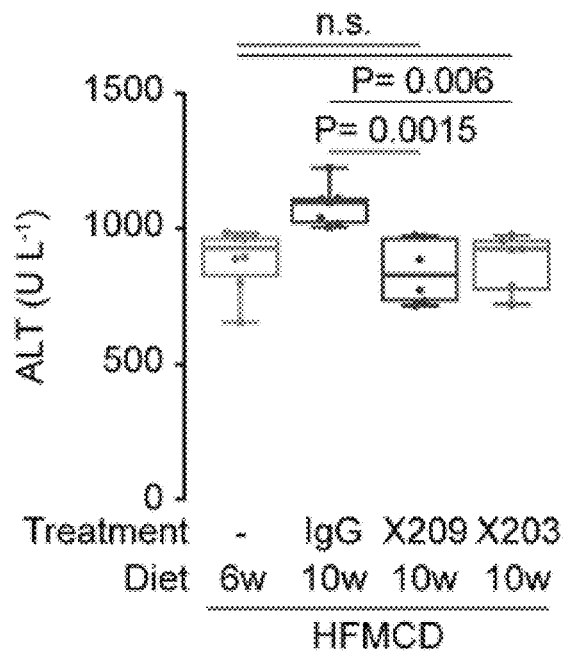
Figure 20F:
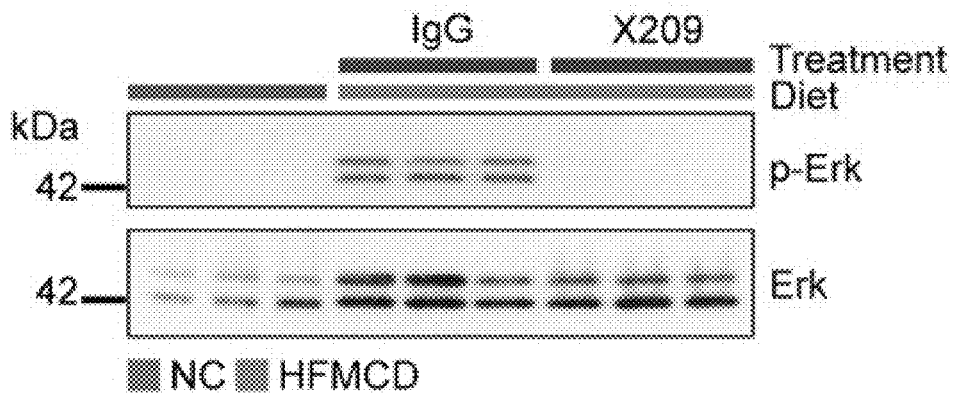
Figure 28A:
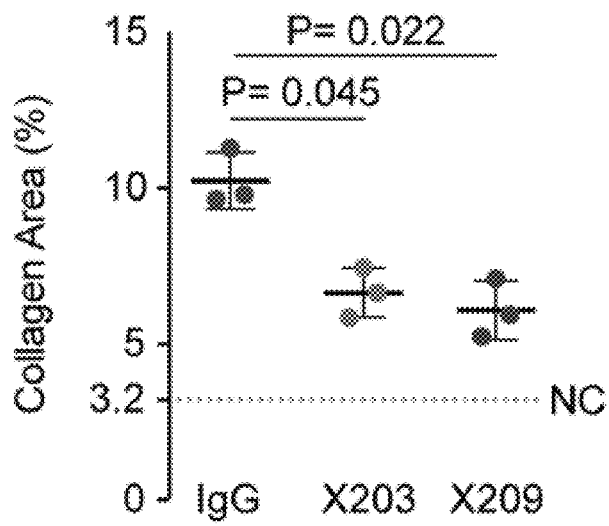
FIGS. 28A to 28F. Neutralizing anti-IL-11 and anti-IL11RA antibodies inhibit HFMCD- and WDF-induced NASH pathologies. (A-D) Data for therapeutic use of X203 and X209 in HFMCD-fed mice as shown in FIG. 20A. (A) Quantification of Masson's Trichrome staining of liver sections (dotted line represents the mean NC value). (B) Relative liver mRNA expression levels of fibrosis genes and (C) liver triglyceride content (n≥5/group). (D) Western blots of liver ERK activation from NC, IgG- and X203-treated mice (10 mg/kg, biweekly) on HFMCD diet. (E) Quantification of Masson's Trichrome staining of liver sections, dotted line represents the mean value of steatotic livers from 12 week old db/db (see FIG. 20G) and (F) relative pro-fibrotic mRNA expression levels in the livers of steatotic and MCD-fed db/db mice injected with either IgG or X203 as shown in schematic (FIG. 20G, n≥5/group). (A, E) Data are represented as mean+s.d.; (8-C, F) data are shown as box-and-whisker with median (middle line), 25th-75th percentiles (box) and min-max percentiles (whiskers). (A-C, E-F) Two-tailed, Tukey-corrected Student's t-test. FC: fold change; NC: normal chow; HFMCD: high fat methionine- and choline-deficient; MCD: methionine- and choline-deficient.
Figure 28B:
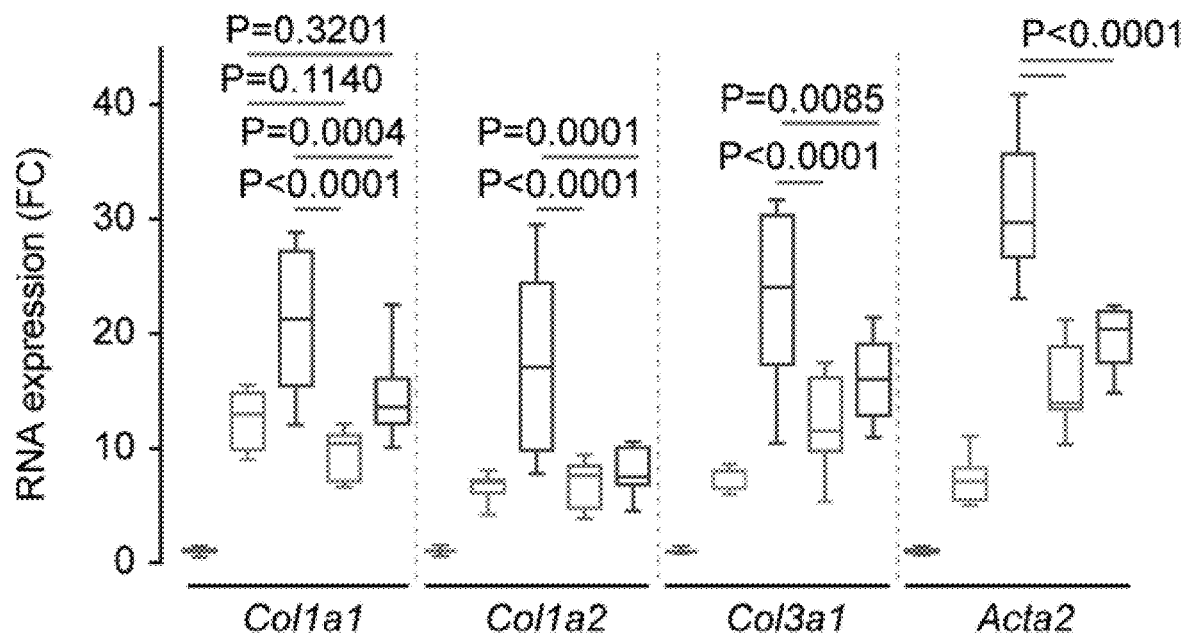
Figure 28C:
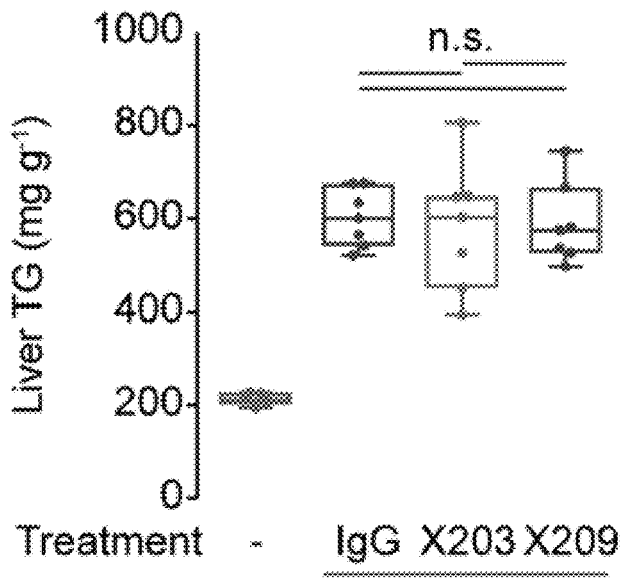
Figure 28D:
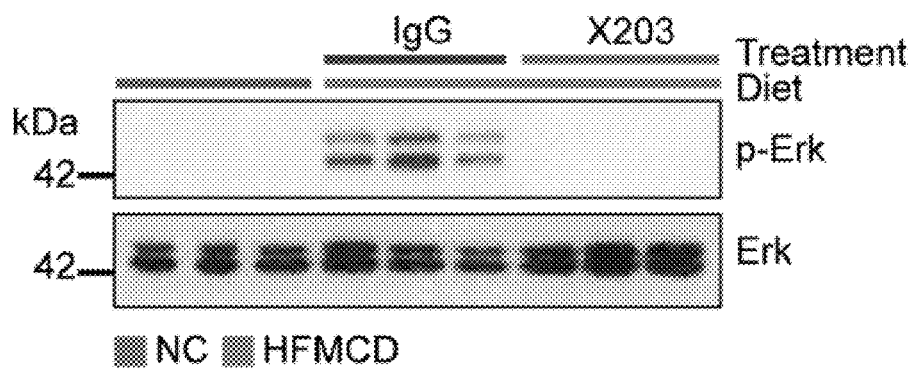
Figure 28E:
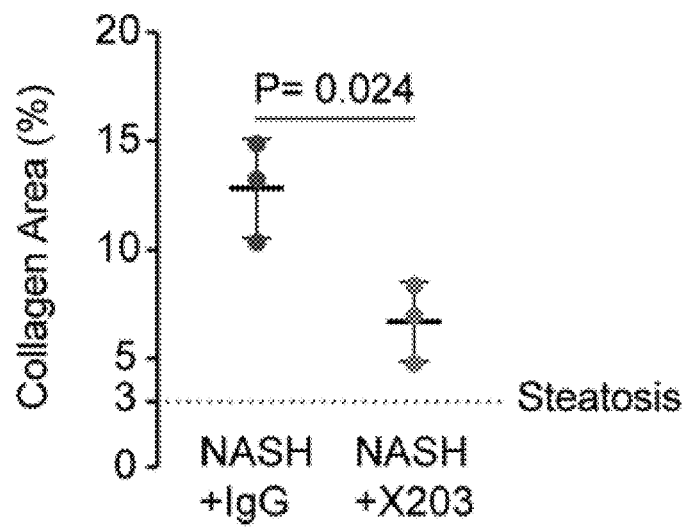
Figure 28F:
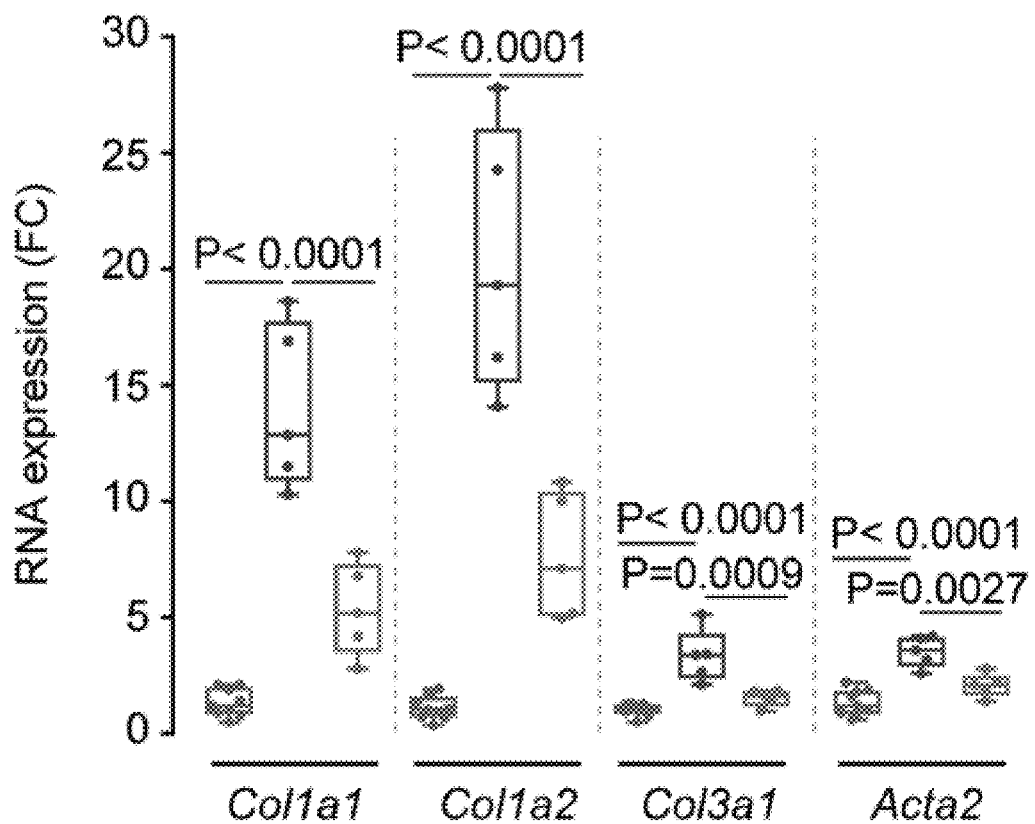

Therapeutic Targeting of IL-11 or IL11RA is Effective in Three Preclinical NASH Models The inventors then tested X209 and X203 therapy in vivo and started antibody administration after six weeks of HFMCD diet when IL-11 is strongly upregulated, collagen has accumulated and steatohepatitis is established (FIGS. 18A, 20A, and FIGS. 25C-25D). After four weeks of therapy both antibodies had inhibited or reversed liver fibrosis, inflammation and damage, while steatosis was unchanged (FIGS. 20B-20E, FIGS. 28A-28C). Furthermore, both antibodies abolished Erk activation indicating target engagement and coverage (FIG. 20F, FIG. 28D).

Figure 20G:
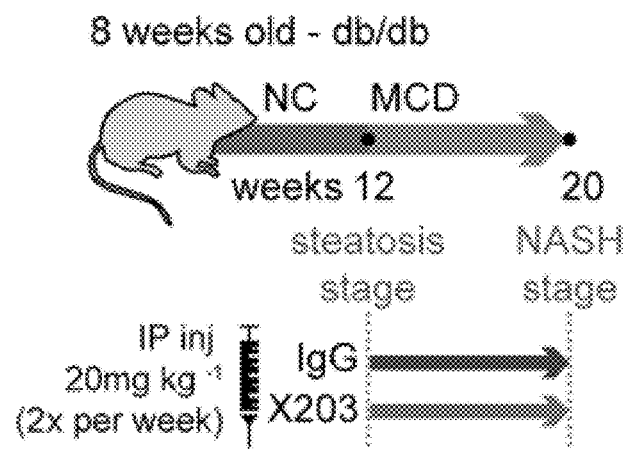
Figure 20H:
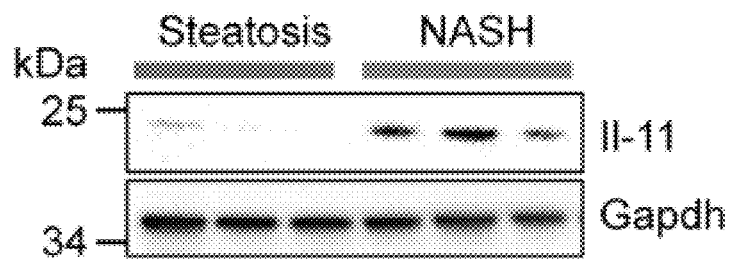
Figure 20I:
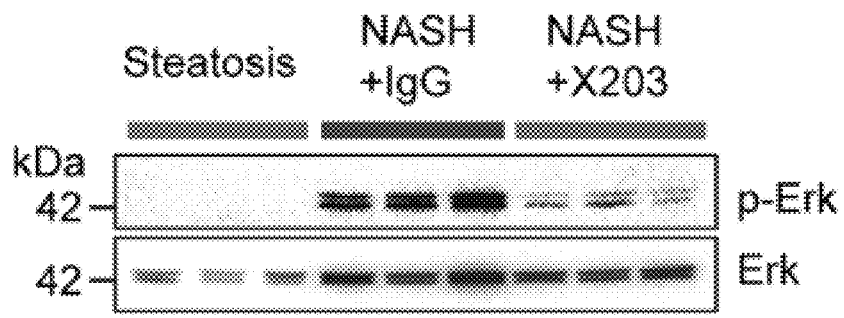
Figure 20J:
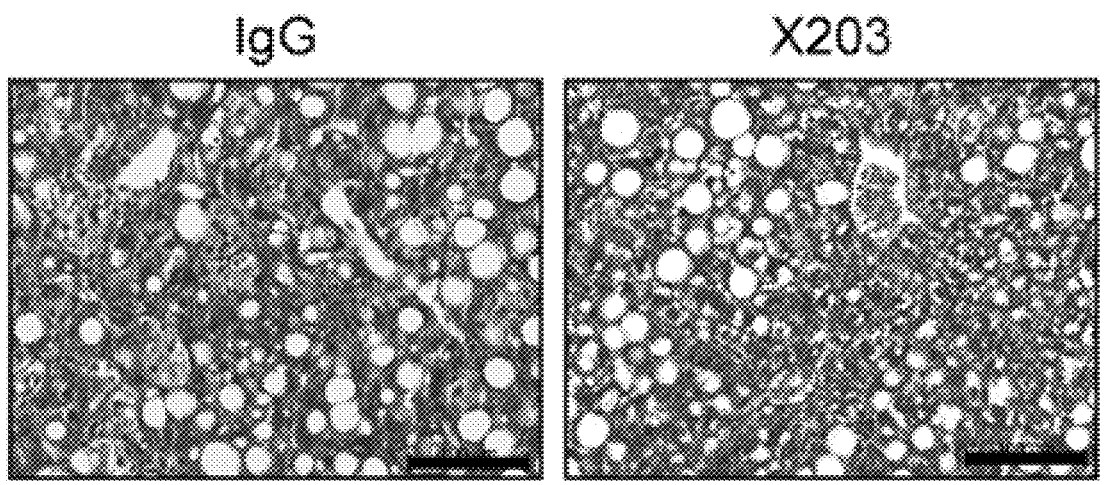
Figure 20K:
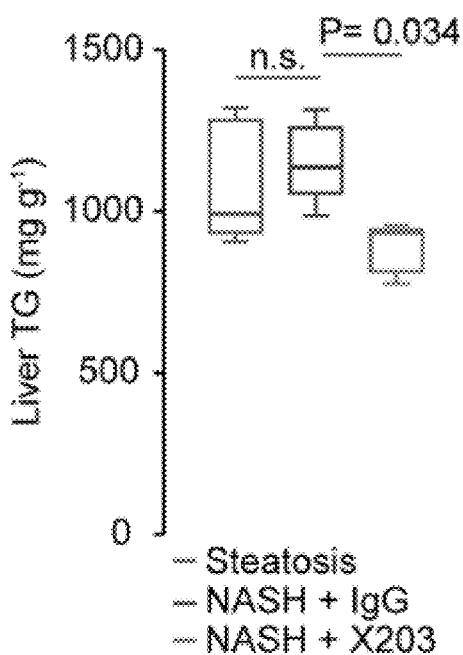
Figure 20L:
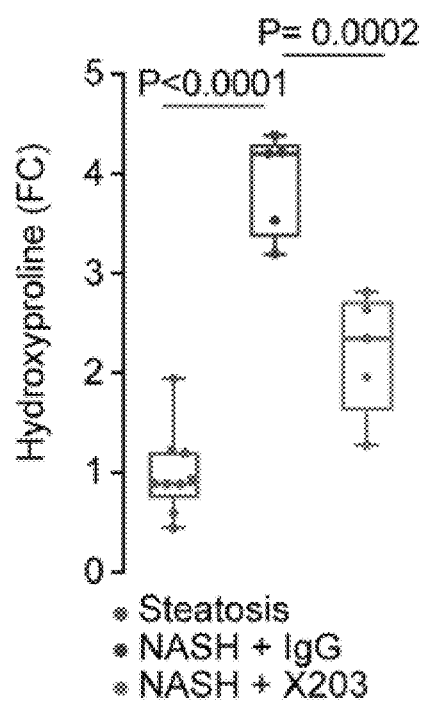
Figure 20M:
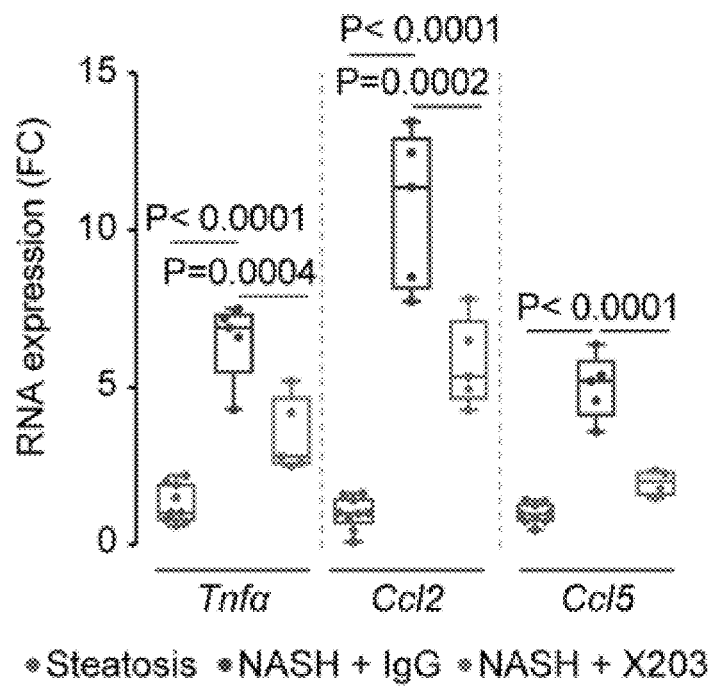
Figure 20N:
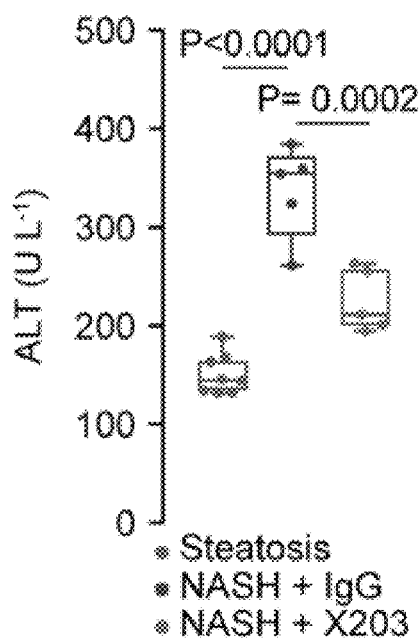

The inventors also tested anti-IL-11 therapy in twenty week old db/db mice that are obese, diabetic and have steatotic livers when put onto a NASH-inducing methionine-choline-deficient (MCD) diet for eight weeks (FIG. 20G)[29-31]. Consistent with our other models, IL-11 expression and Erk activation were increased in livers of MCD-fed db/db mice and Erk activation was inhibited by therapy (FIGS. 20H-20I). In this model, anti-IL-11 therapy reduced hepatic steatosis, fibrosis, and inflammation while lowering ALT levels (FIGS. 20J-20N, FIGS. 28E-28F).

Figure 21A:
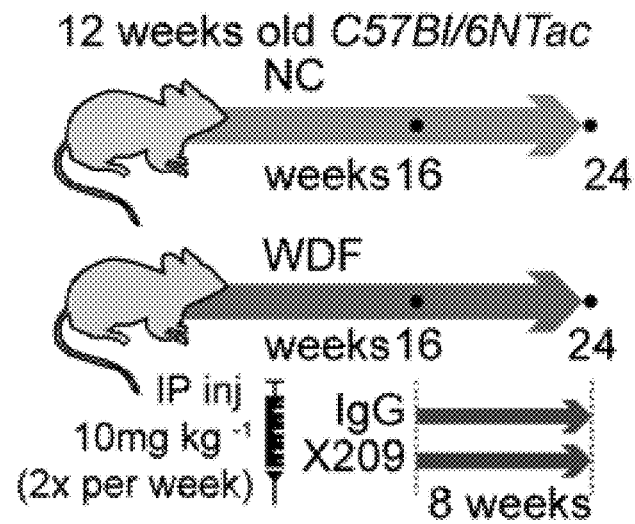
FIGS. 21A to 21L. Inhibition of Il-11 signalling reverses NASH pathologies in preclinical models and HSC-to-myofibroblast transformation. (A) Schematic showing therapeutic dosing regime in NASH reversal experiment for data shown in (B-G). Mice were fed with WDF for 16 weeks to induce NASH and then treated with (10 mg/kg) X209 or IgG for 8 weeks while they were on continuous WDF feeding. (B) Total liver hydroxyproline content, the levels of (C) liver triglycerides, (D) serum ALT, (E) fasting blood glucose, (F) serum triglycerides, and (G) serum cholesterol in mice on NC and IgG- and X209-treated WDF (n≥5/group). (H) Schematic showing reversal experiment in which fibrosis was established by feeding mice HFMCD for 10 weeks and then replacing this with NC and initiating antibody (X203 and X209) therapy. Mice were euthanized at the indicated time points. (I) Total liver hydroxyproline content (dotted line represents the mean value of NC=0.93) and (J) relative mRNA expression of Mmp2/Timp1 at 1-, 3-, 6-weeks after concurrent metabolic intervention (diet switch) and X203, X209, or IgG treatment (n≥3/group). Quantification of ACTA2$^{+ve}$ immunostaining (scale bars, 200 μm) following incubation (K) with TGFβ1 or (L) with PDGF, either prior to or after the addition of X203, X209, or IgG (n=5/group). (K-L) TGFβ1 (5 ng/ml), PDGF (20 ng/ml), IgG, X203 and, X209 (2 μg/ml). (B-G, K-L) Data are shown as box-and-whisker with median (middle line), 25th-75th percentiles (box) and min-max percentiles (whiskers); (I) data are shown as mean±s.d; (J) data are represented as line chart (mean) and transparencies indicate s.d. (B) Two-tailed Student's t-test; (C-G,K-L) two-tailed, Tukey-corrected Student's t-test; (I-J) two-way ANOVA. FC: fold change; NC: normal chow; WDF: Western diet+15% (w/v) fructose; HFMCD: high fat methionine- and choline-deficient.
Figure 21B:
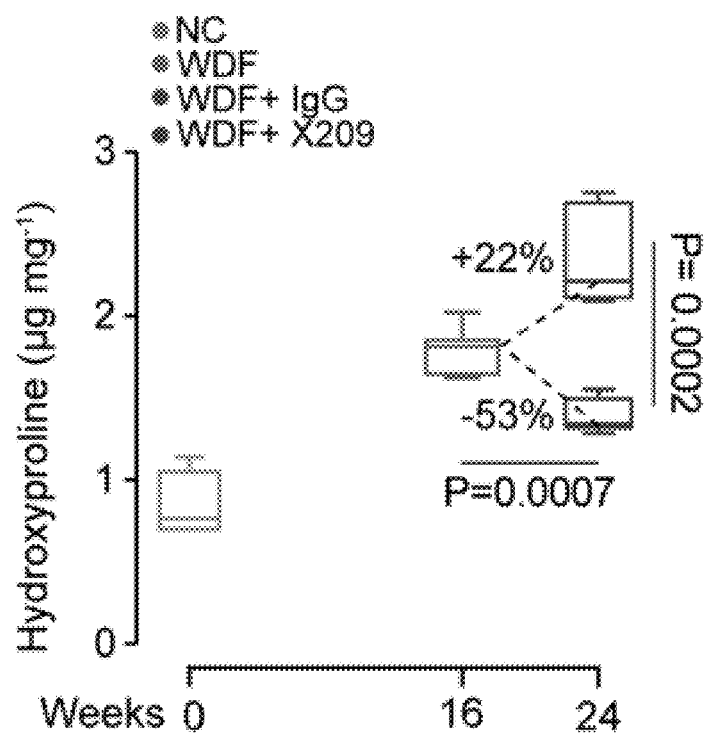
Figure 21C:
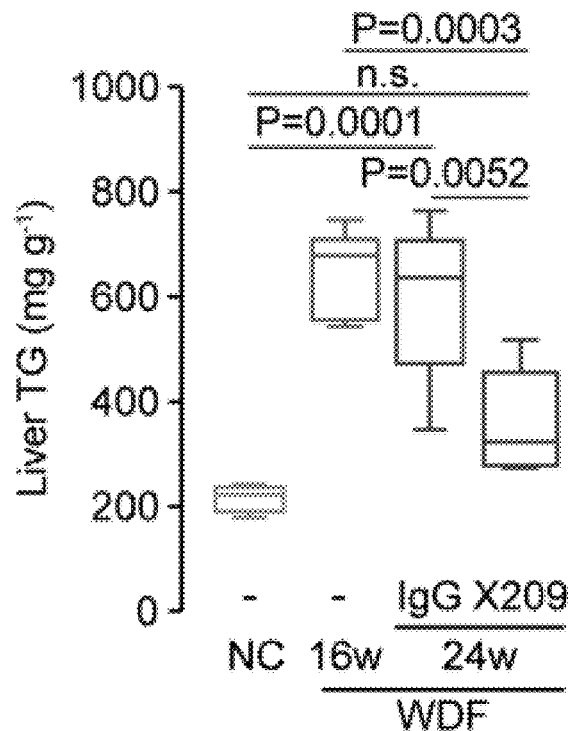
Figure 21D:
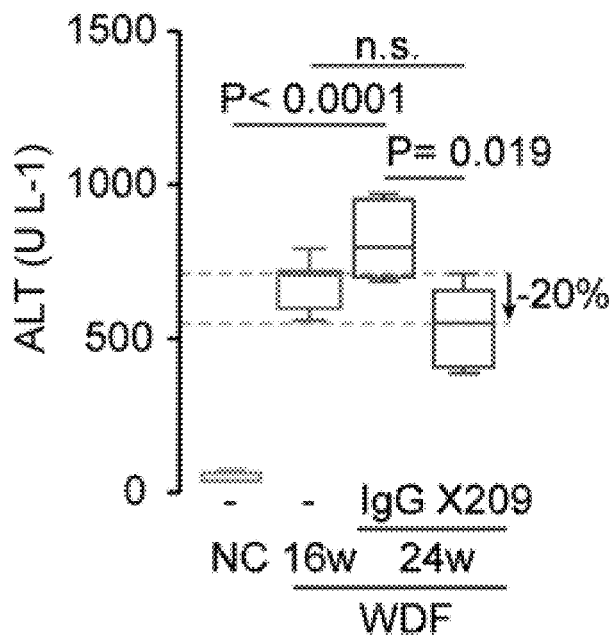
Figure 21E:
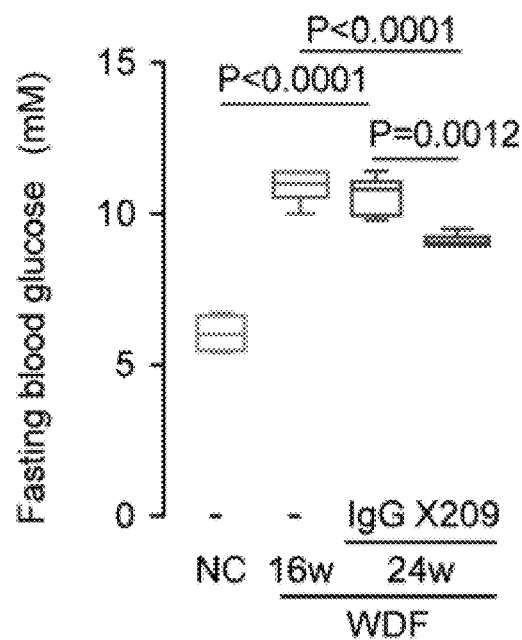
Figure 21F:
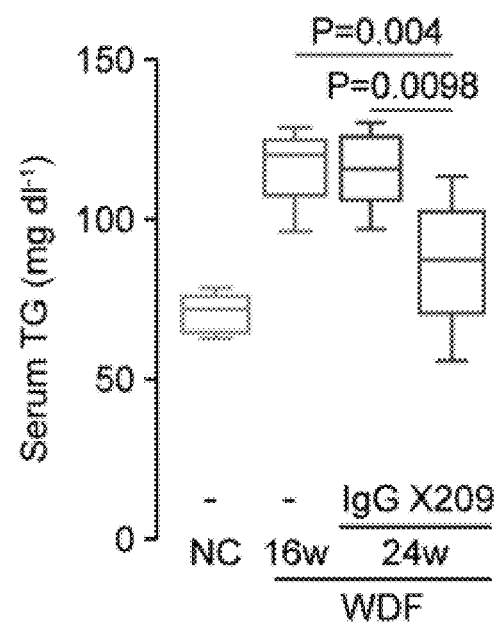
Figure 21G:
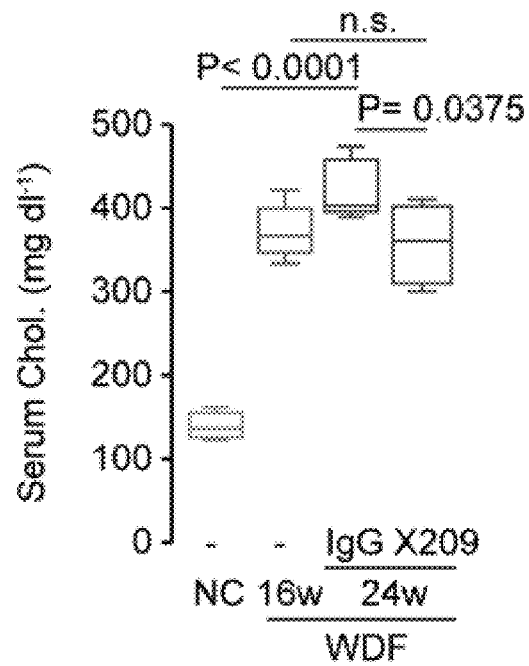
Figure 29A:
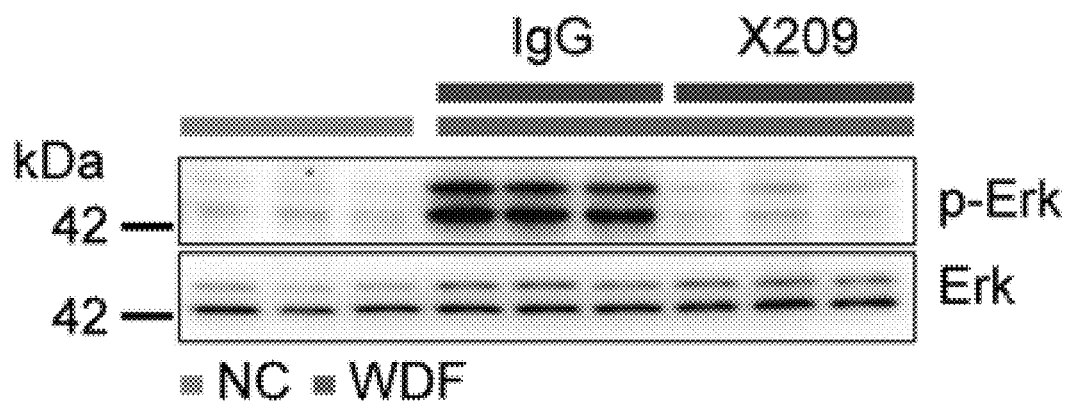
FIGS. 29A to 29E. Neutralizing anti-IL11RA therapy reverses WDF-induced NASH pathologies. (A-E) Data for anti-IL-11 RA therapeutic intervention study in mice on WDF diet as shown in schematic (FIG. 21A). Mice on WDF received biweekly IgG or X209 (10 mg/kg) treatment for 8 weeks starting from week 16 until the time of sacrifice (week 24). (A) Western blots of p-Erk and Erk in the livers from mice on NC or WDF for 24 weeks. (B) Bimonthly body weight measurement (n≥4/group). (C) Representative (scale bars, 100 μm) and (D) quantification of Masson's Trichrome staining images of livers from mice on WDF for 16 weeks (left), for 24 weeks with IgG injection from week 16-24 (middle), and for 24 weeks with X209 treatment from week 16-24 (right), dotted line represents mean value of NC. (E) Relative liver mRNA expression levels of pro-inflammation genes (n≥5/group). (B, D) Data are shown as mean±s.d; (E) data are shown as box-and-whisker with median (middle line), 25th-75th percentiles (box) and min-max percentiles (whiskers). (D, E) Two-tailed, Tukey-corrected Student's t-test.
Figure 29B:
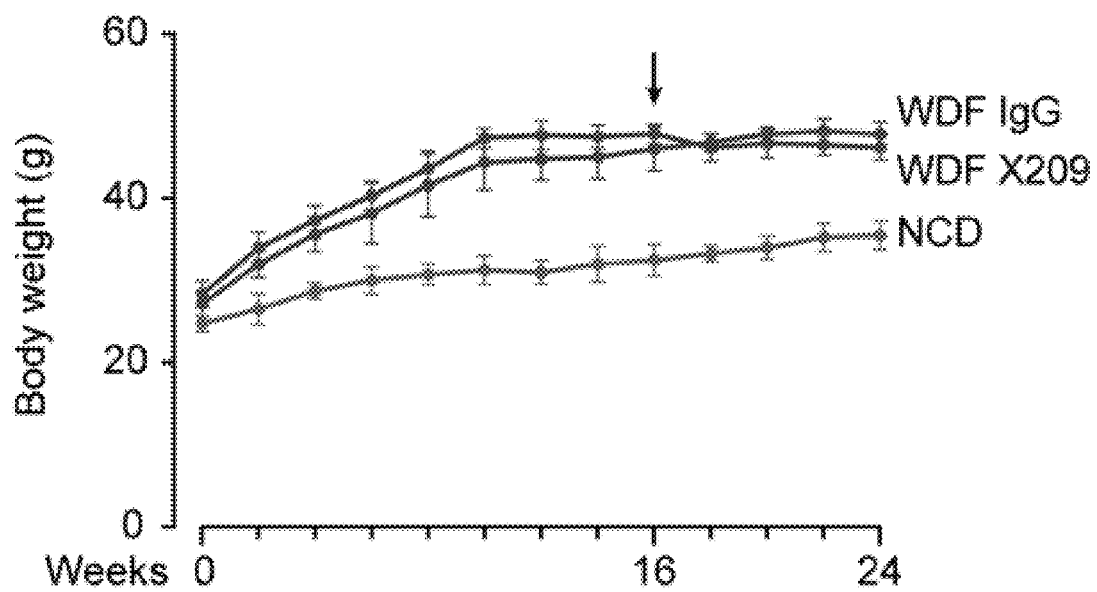
Figure 29C:
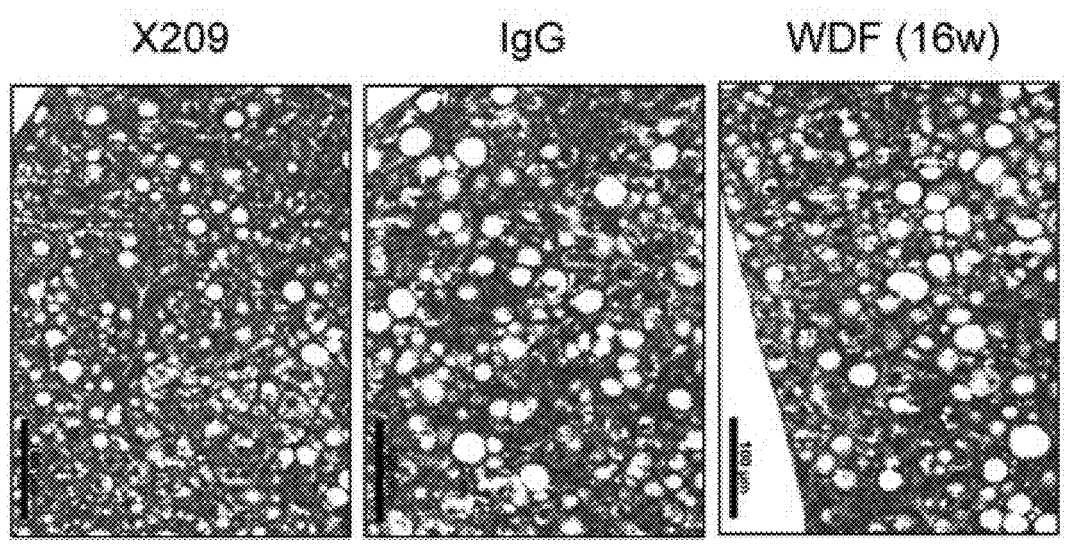
Figure 29D:
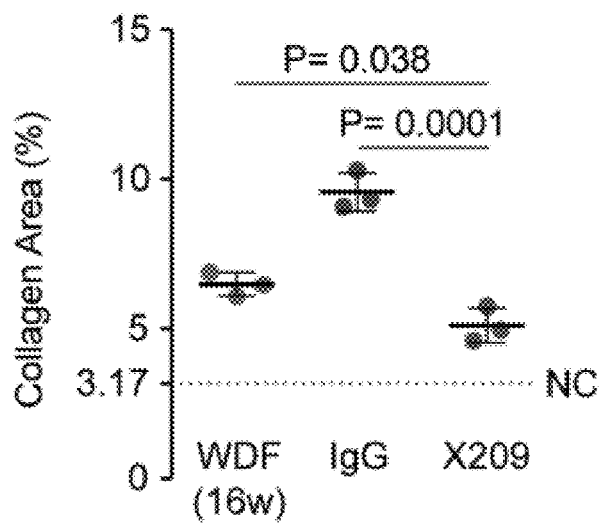
Figure 29E:
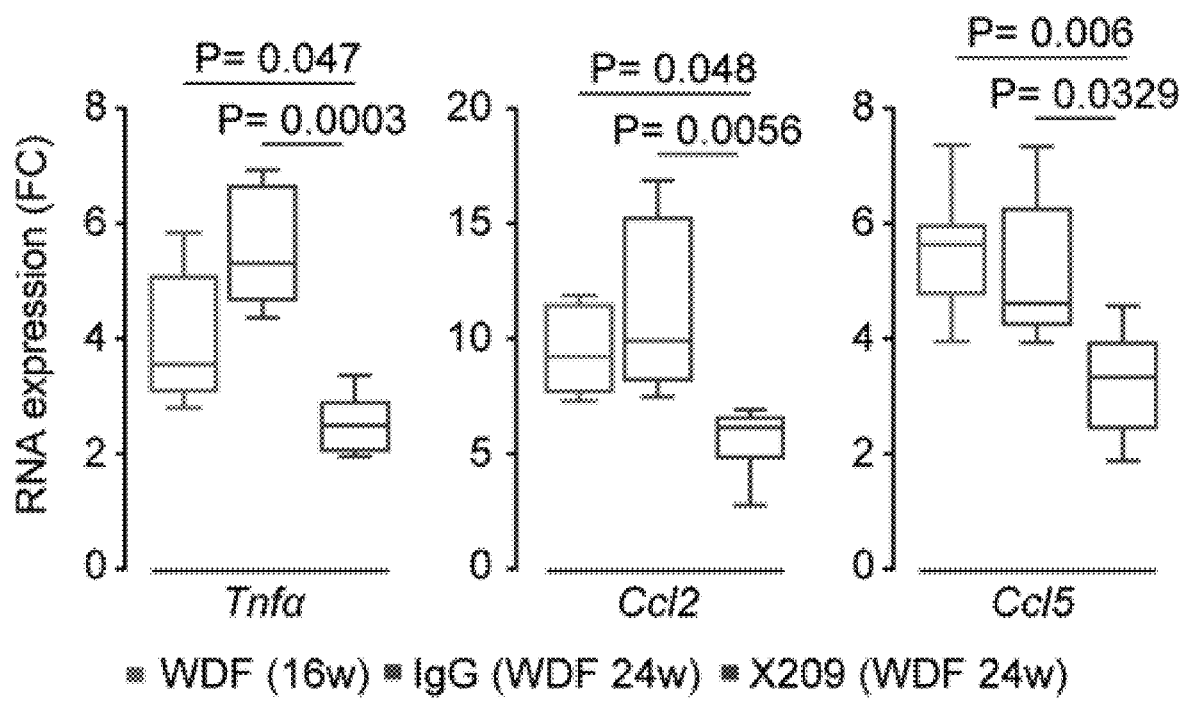

A third model of WDF-induced NASH was used to test effects of anti-IL-11 therapy in the context of obesity, insulin resistance and diabetes[18]. Mice were fed WDF for 16 weeks by which time they were obese and insulin resistant with liver steatosis, inflammation and fibrosis. Treatment with anti-IL11RA (X209) therapy was then initiated (FIG. 21A). Hepatic Erk activation was inhibited in NASH livers when IL-11 signalling was targeted (FIG. 29A). Despite similar weight gain, reversal of liver fibrosis, steatosis, inflammation, and reduction in serum ALT levels in mice on anti-IL11RA therapy was observed. This was accompanied by a reduction in serum glucose, triglycerides and cholesterol levels (FIG. 21B-21G and FIG. 29B-29E).

Effects of Combined Metabolic and Anti-IL-11 Interventions on Hepatic Fibrosis

Figure 21H:
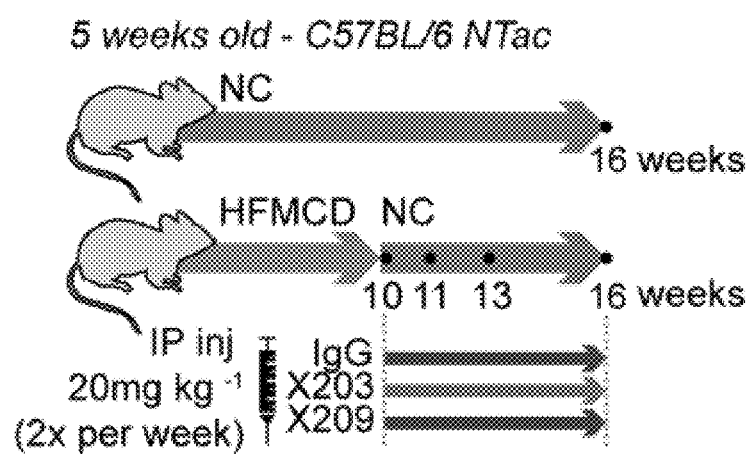

Our data showed that anti-IL-11 therapy reversed fibrosis but did not assess whether this effect was sustained or progressive. Furthermore, combination therapies may be beneficial for reversing fibrosis in NASH'. To address these points, severe liver fibrosis was established using HFMCD for 10 weeks, then converted mice to normal chow, mimicking a robust metabolic intervention, and initiated anti-IL-11 treatments in parallel (FIG. 21H).

Figure 21I:
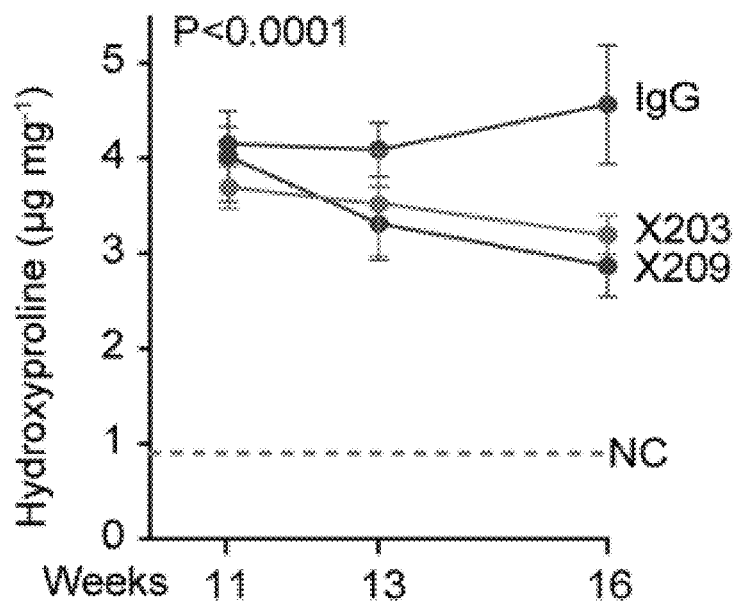
Figure 30A:
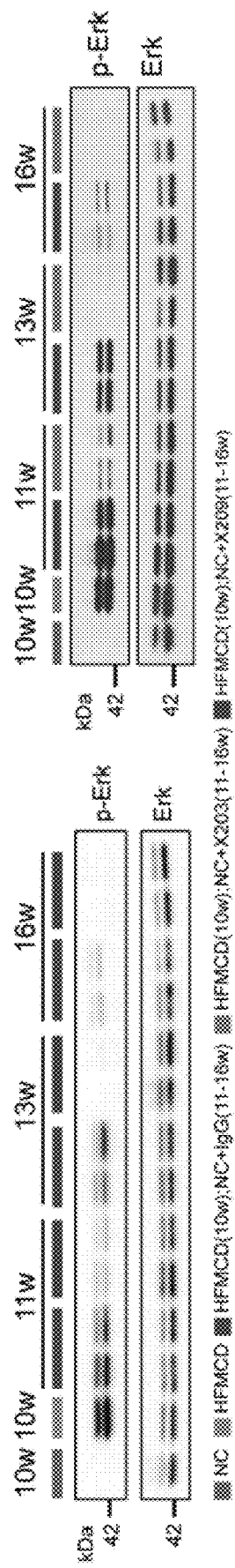
FIGS. 30A to 30G. Neutralizing anti IL-11 or anti-IL11RA antibodies reverse HFMCD-induced hepatic fibrosis and HSC-to-myofibroblast transformation. (A-D) Data from mice treated with IgG, X203, or X209 for 1, 3, or 6 weeks as shown in 5G (HFMCD reversal experiment) (A) Western blots of hepatic ERK activation status. (B) Representative (scale bars, 100 μm) and (C) quantification Masson's Trichrome staining of livers from mice treated with IgG, X203, or X209 for 6 weeks. (D-G) Data from reversal of HSC transformation experiments as shown in FIGS. 21K-21L; TGFβ1 (5 ng/ml), PDGF (20 ng/ml), IgG, X203, and X209 (2 μg/ml). (D) Representative fluorescence images (scale bars, 200 μm) of ACTA2+ve immunostaining following incubation with TGFβ1 or with PDGF either prior to or after addition of X203, X209, or IgG. The amount of collagen secreted by HSCs stimulated with (E) TGFβ1 or (F) PDGF either prior to or after the addition of IgG, X203, or X209 (n=5/group). (G) Western blots of ERK activation status after X203 and X209 treatment in TGFβ1-treated HSC. (C) Data are shown as mean±s.d.; (E-F) data are shown as box-and-whisker with median (middle line), 25th-75th percentiles (box) and min-max percentiles (whiskers). (C, E-F) Two-tailed, Tukey-corrected Student's t-test. FC: fold change; NC: normal chow; HFMCD: high fat methionine- and choline-deficient.
Figure 30B:
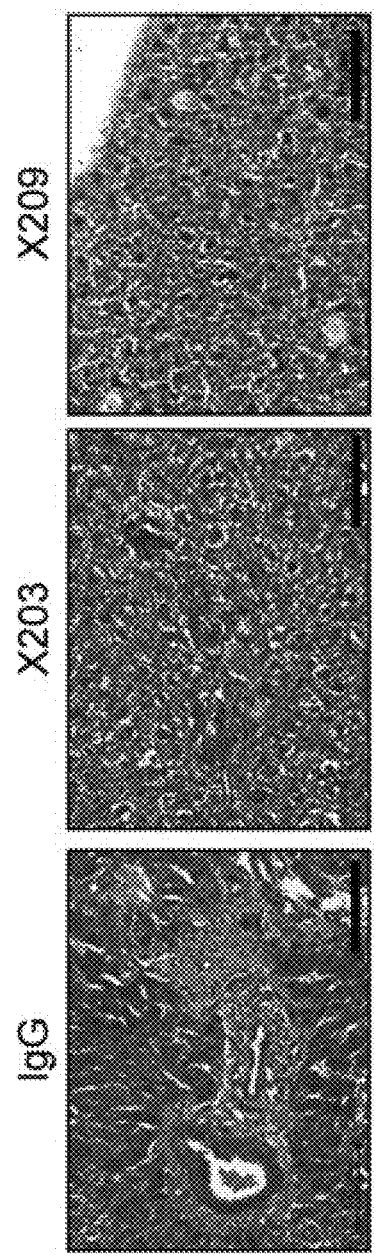
Figure 30C:
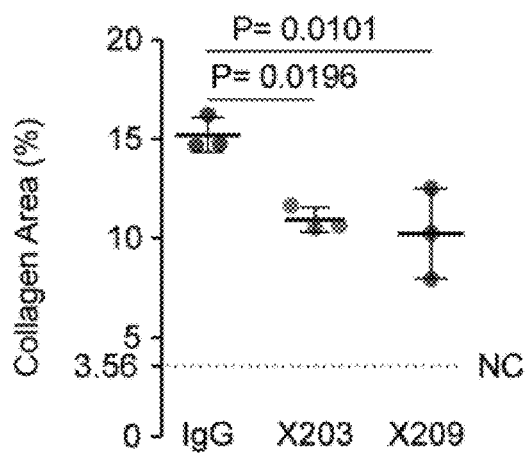
Figure 30D:
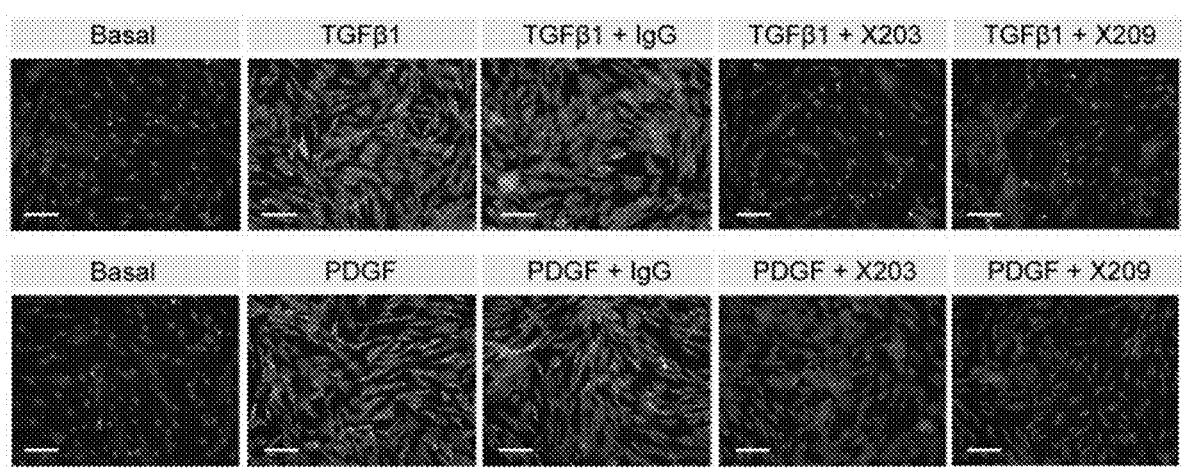
Figure 30E:
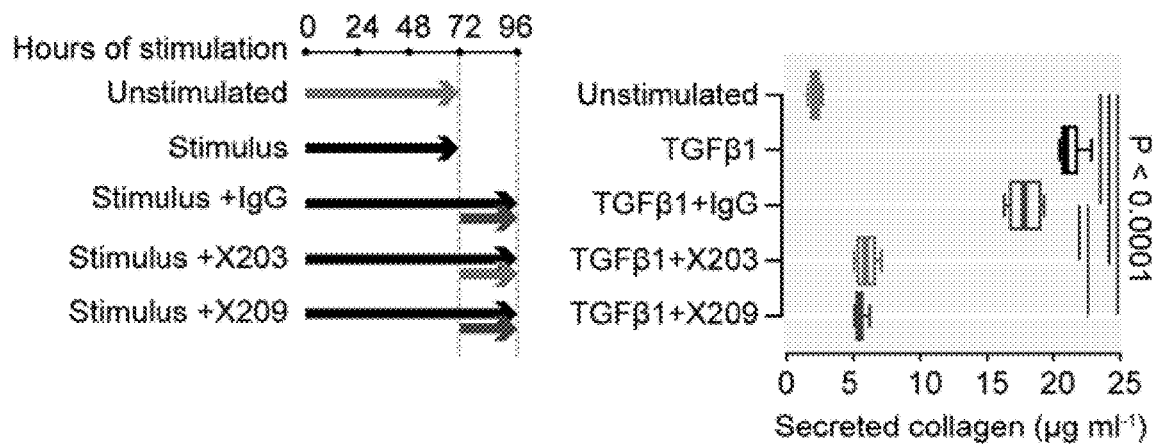
Figure 30F:
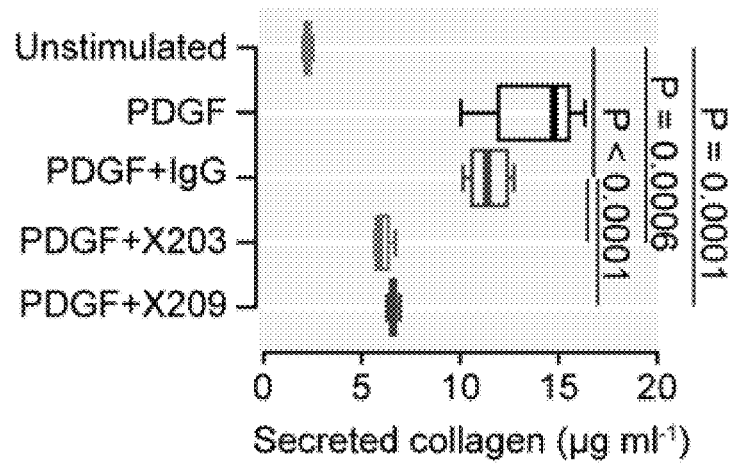
Figure 30G:
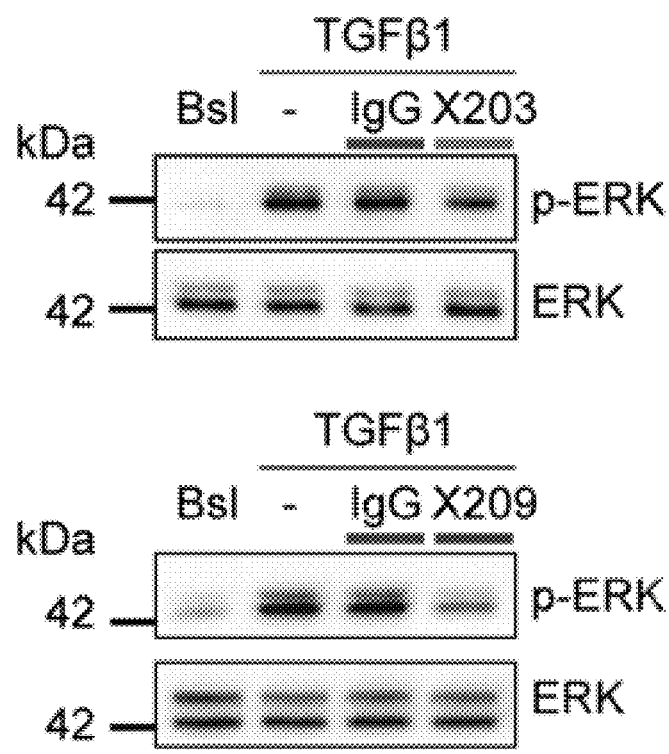

Upon removal of the metabolic stimulus, Erk activation slowly regressed, which was accelerated by X203 or X209-treatment (FIG. 30A). Fibrosis was unchanged in IgG treated animals for the duration of the experiment, suggesting complete metabolic correction alone does not reverse fibrosis, or very slowly reverses fibrosis. In contrast, hepatic collagen content was significantly reversed after three weeks of antibody treatment (reversal: 18%, X203; 24%, X209) with further reversal at six weeks (reversal: 37%, X203; 46%, X209), showing a progressive and sustained effect (FIG. 21I, FIGS. 30B-30C).

Figure 21J:
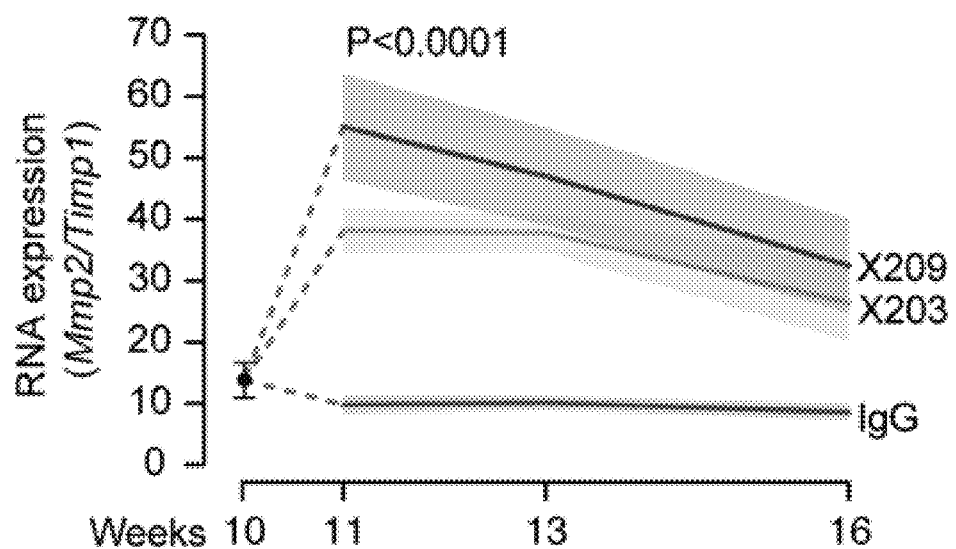
Figure 21K:
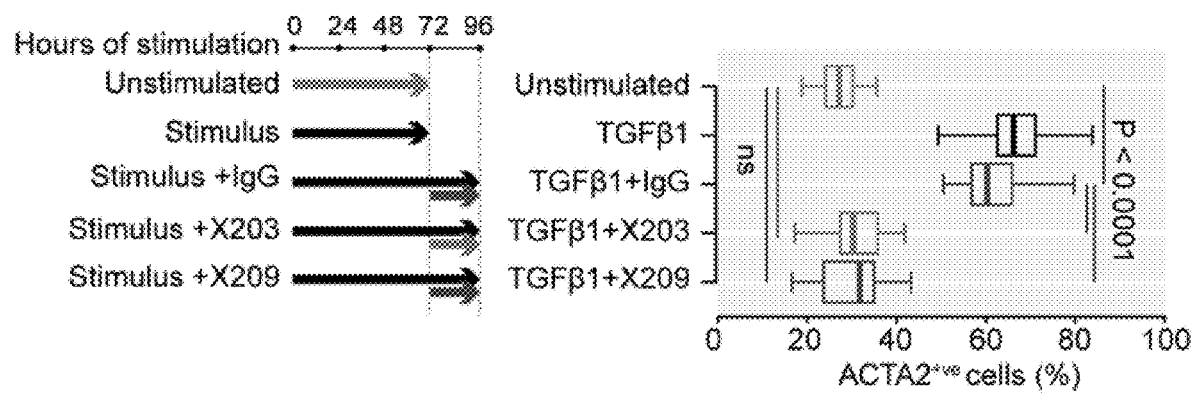
Figure 21L:
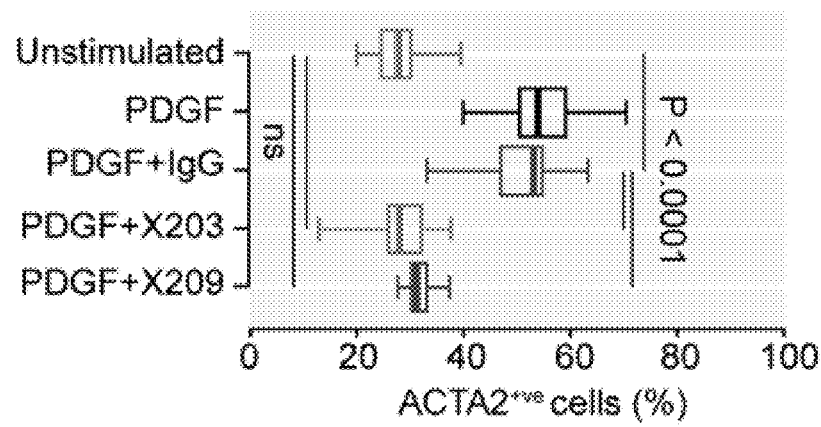

Regression of fibrosis is associated with lower TIMP and higher MMP levels, which promotes favorable matrix remodelling[3,32]. Consistent with this, X203 or X209 treated mice with severe fibrosis rapidly upregulated Mmp2 and downregulated Timp1 (FIG. 21J). Reversal of hepatic fibrosis is favoured when transformed HSCs undergo apoptosis[33], senescence[34,36] and/or revert to an inactive ACTA2$^{-ve}$ state[36]. To check if IL-11 is required to maintain HSCs in a transformed state, HSCs were stimulated with TGFβ1 or PDGF followed by inhibition of IL-11 signalling. Within 24 h of IL-11 inhibition, the percentage of ACTA2$^{+ve}$ cells and the amount of secreted collagen were reversed to near baseline levels, and ERK activity was largely diminished despite ongoing TGFβ1/PDGF stimulation (FIGS. 21K-21L, FIG. 30D-30G).

Figure 31A:
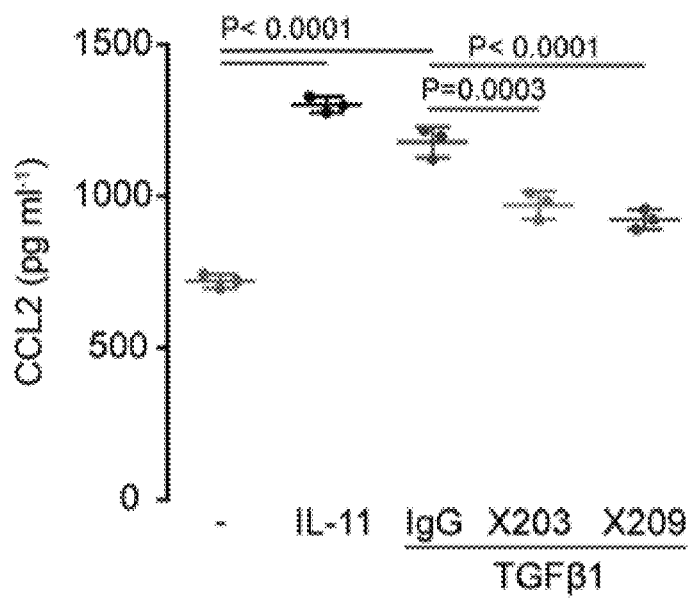
FIG. 31A to 31H. Neutralizing anti-IL-11 and anti-IL11 RA antibodies protect HFMCD-fed mice from hepatic fibrosis and inflammation. (A) CCL2 in the supernatants of HSCs (n=4/group) without stimulus (−), with IL-11, or with TGFβ1 in the presence of IgG, X203, or X209 by ELISA; IL-11 (5 ng ml$^{-1}$), TGFβ1 (5 ng ml$^{-1}$), IgG, X203, and X209 (2 μg ml$^{-1}$). (B-I) Data for therapeutic dosing experiments as shown in FIG. 22B. (B) Representative gross liver images, (C) Western blots of hepatic ERK activation status, (D) representative (scale bars, 100 μm) and (E) quantification of Masson's Trichrome stained images of livers after 5 weeks of early X203 and X209 treatments. (F) Liver hydroxyproline content (the values of NC and HFMCD 1 week diets are the same as those used in FIG. 25C, the values of IgG 3 and 6 weeks are the same as those used in FIG. 22F, n≥5/group), (G) relative RNA expression levels of fibrosis markers in the livers after 5 weeks treatment of X203 and X209 by qPCR, which confirms data from RNA-seq (the values of NC 6 week for Col1a1, Col1a2, Col3a1, and Acta2 are the same as those shown in FIG. 28D, n≥5/group), and (H) serum ALT levels (the values of NC and HFMCD 1 week are the same as those used in FIG. 25D, the values of IgG 3 and 6 weeks (2 weeks and 5 weeks treatment, respectively) are the same as those used in FIG. 22G, n≥5/group). (A, E-F, H) Data are represented as mean±s.d.; (G) data are shown as box-and-whisker with median (middle line), 25th-75th percentiles (box) and min-max percentiles (whiskers). (A, E, G) Two-tailed, Tukey-corrected Student's t-test; (F, H) two-way ANOVA. FC: fold change; NC: normal chow; HFMCD: high fat methionine- and choline-deficient.
Figure 31B:
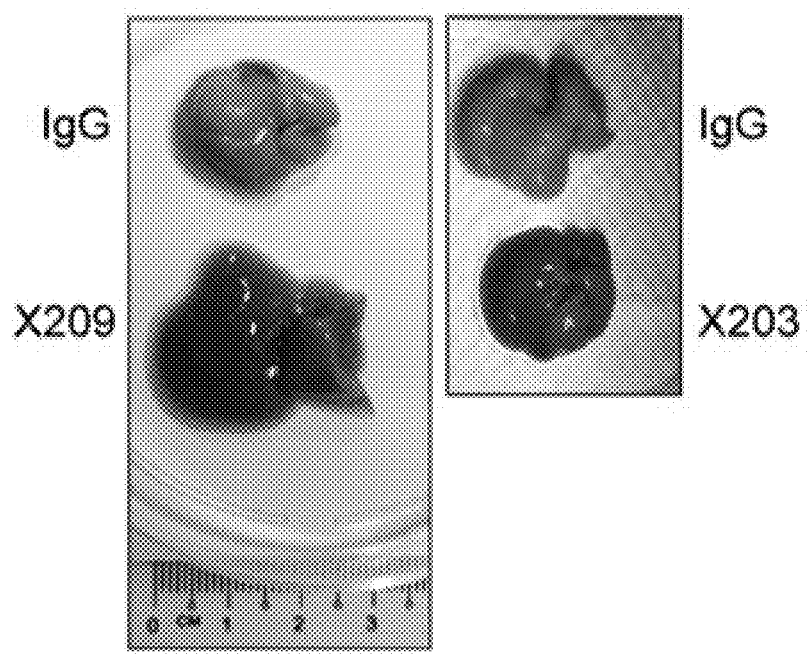
Figure 31C:
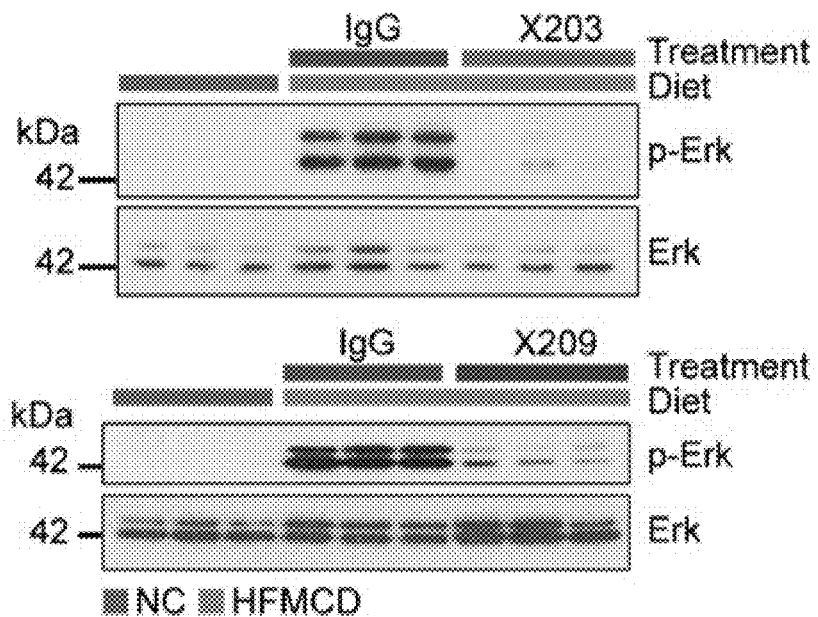
Figure 31D:
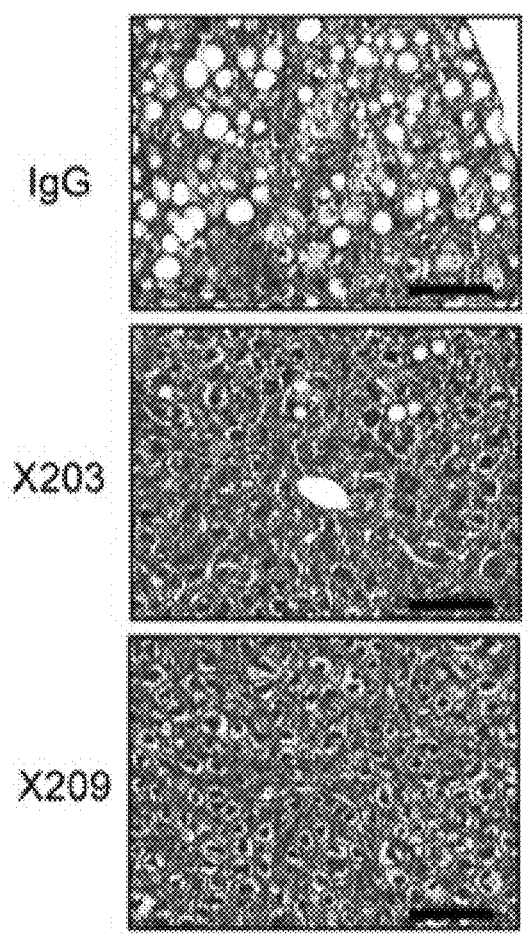
Figure 31E:
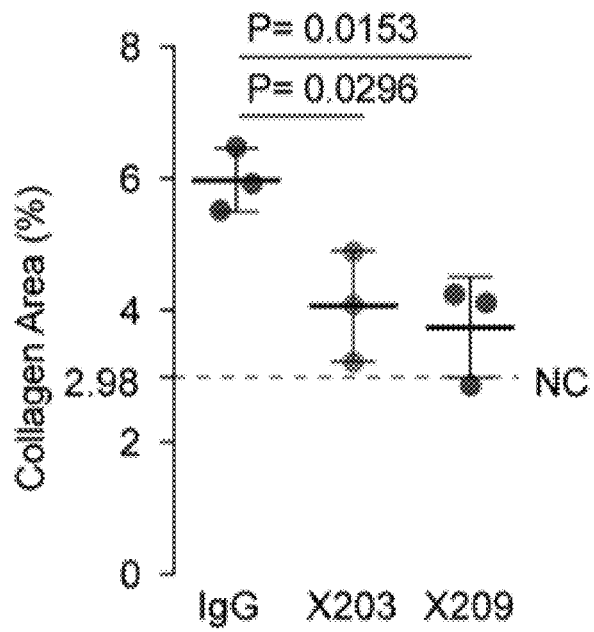
Figure 31F:
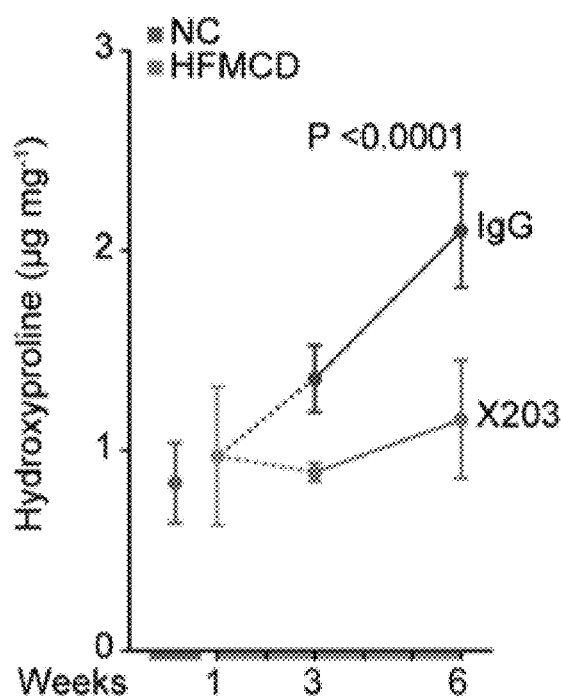
Figure 31G:
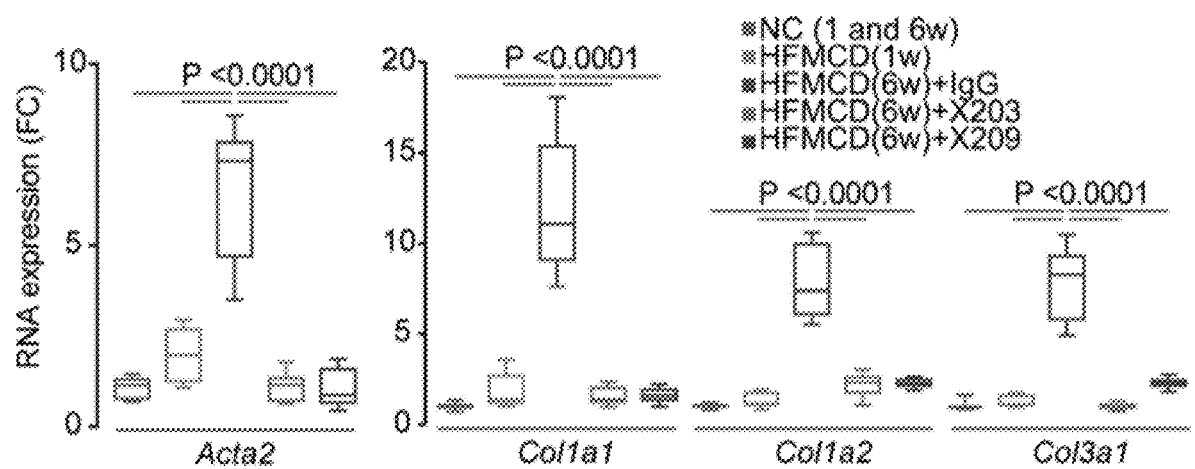

Effects of anti-IL-11 therapy on liver health during acute necroinflammation in early-stage NASH The transition from NAFLD to NASH is characterised the development of steatotic hepatitis, inflammation and cell death (necroinflammation). HSCs have a central role in this process through the secretion of pro-inflammatory factors[3,8,37,38]. The inventors investigated whether IL-11 affected HSC-driven inflammatory pathways, and found that IL-11 stimulated HSC production of CCL2 whereas IL-11 inhibition blocked CCL2 secretion (FIG. 31A). This shows an unappreciated pro-inflammatory role for IL-11 in stromal immunity in keeping with the consistently low levels of inflammation observed in livers from Il11ra1$^{-/-}$, X203- or X209- treated mice across NASH diets.

Figure 22A:
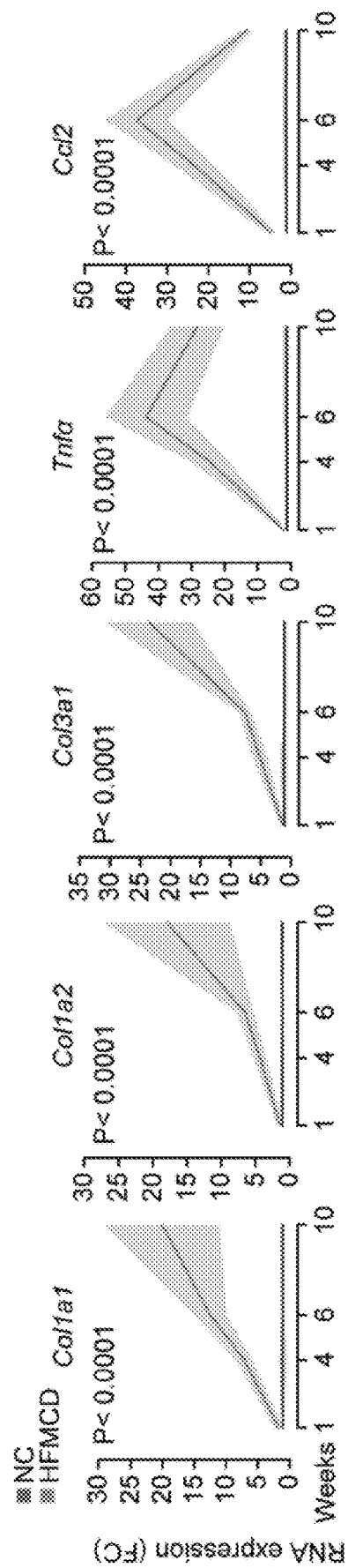
FIGS. 22A to 22K. Neutralisation of Il-11 signalling reverses liver damage in early stage NASH. (A) Relative liver mRNA expression of fibrosis and inflammation markers from mice fed with NC or HFMCD diets for the indicated time points. (B) Schematic of the anti-IL-11 therapy experiment early on in the HFMCD diet NASH model. Antibody treatments were started 1 week after the start of NASH diet when X209, X203, or IgG (10 mg/kg, biweekly) were administered intraperitoneally for 5 weeks. (C-G) Data for experiments as shown in FIG. 21B. (C) Representative gross liver images and (D) Masson's Trichrome stained images of livers (scale bars, 100 μm) after 5 weeks of IgG or X209 treatments. (E) Hepatic triglyceride levels (n≥5/group), (F) liver hydroxyproline content of X209- and IgG-treated mice (n≥5/group), (G) serum ALT levels (n≥5/group). (H) Immunofluorescence images of IL6R and IL11RA expression in hepatocytes (scale bars, 100 μm). Dose-dependent effect of (I) IL-11 on ALT in hepatocyte supernatant and (J) stress fibers formation (rhodamine-phalloidin staining) in hepatocyte (scale bars, 200 μm). (K) IL-11 protein is secreted from primary human hepatocytes stimulated with TGFβ1 (5 ng/ml); 24 h. (E) Data are shown as box-and-whisker with median (middle line), 25th-75th percentiles (box) and min-max percentiles (whiskers); (F-G, I,K) data are shown as mean±s.d. (E) Tukey-corrected Student's t-test; (F,G) two-way ANOVA; (I,K) two-tailed Dunnett's test. FC: fold change; NC: normal chow; HFMCD: high fat methionine- and choline-deficient.
Figure 22B:
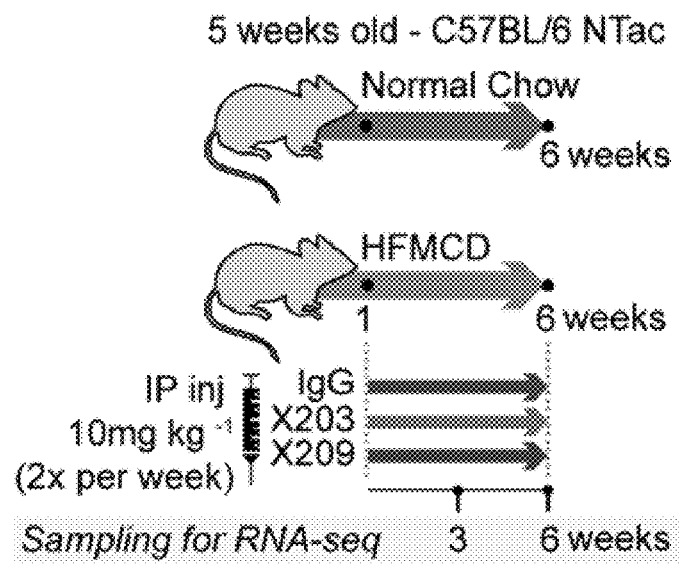
Figure 22C:
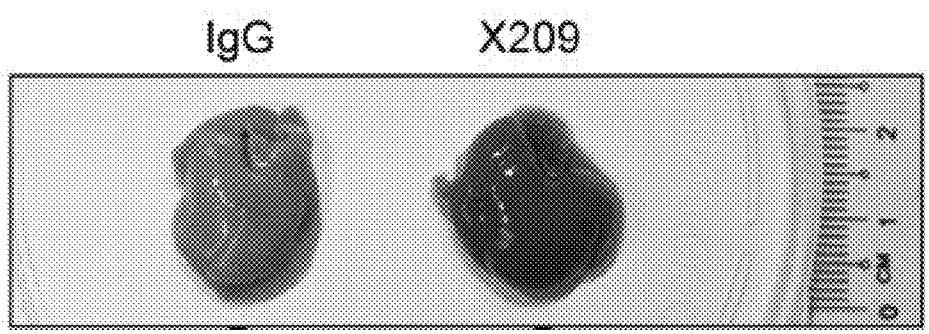
Figure 22D:
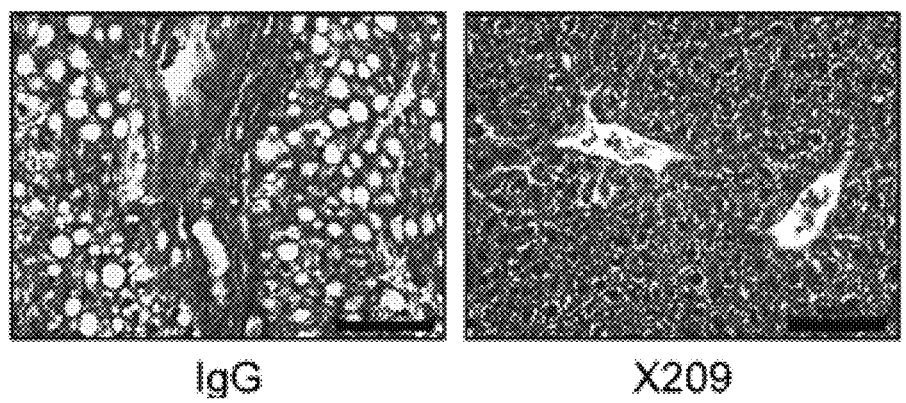
Figure 22E:
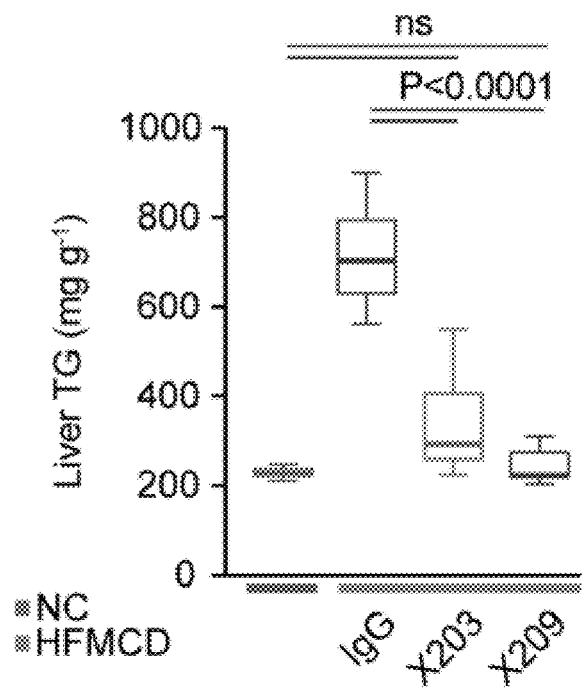
Figure 22F:
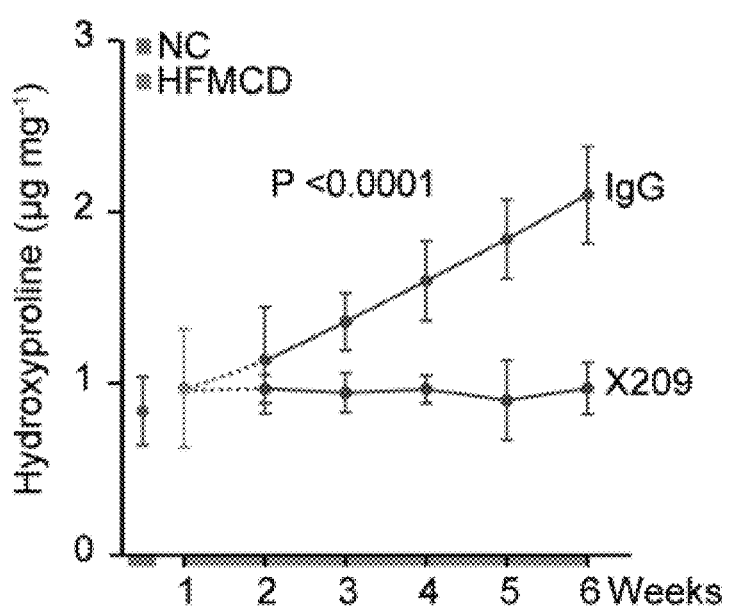
Figure 22G:
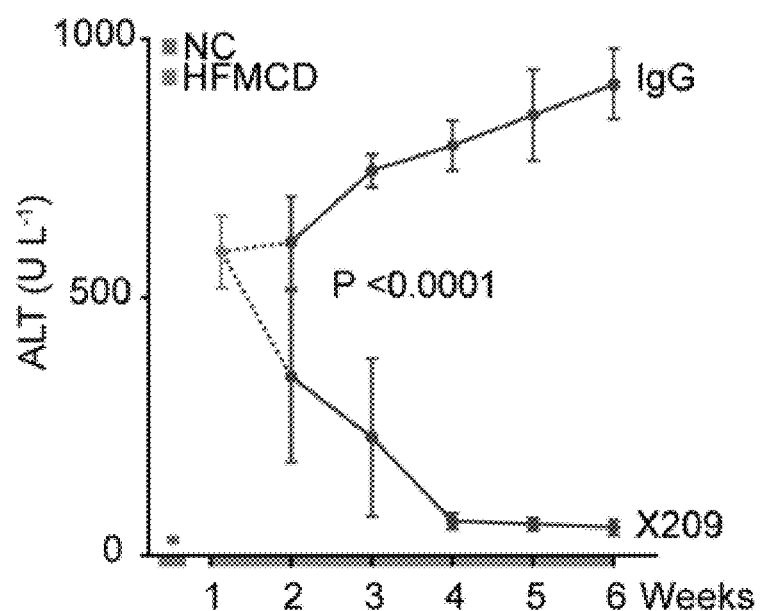
Figure 31H:
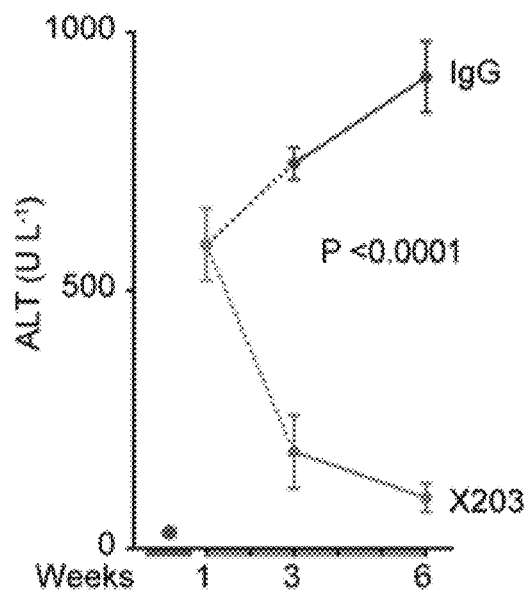

In the HFMCD model of NASH, early inflammation is followed by a fibrotic phase (FIG. 22A). Therapeutic targeting of IL-11 during early steatohepatitis strikingly reduced hepatic steatosis, which was accompanied by lesser Erk activation (FIGS. 22B-22E, FIGS. 31B-31C). Lipid droplets were not seen in livers of mice receiving either X203- and X209, nor did these mice develop fibrosis (FIGS. 22D, 22F and FIGS. 31D-31G). The HFMCD diet also induces acute and severe necroinflammation (>20-fold increase in ALT by 1 week), substantial reversal of liver damage with anti-IL-11 therapy was unexpectedly observed, over a three week period (FIG. 22G, FIG. 31H). These rapid therapeutic benefits precede the fibrotic stage of disease and suggest, together with consistently lower ALT levels in Il11ra1$^{-/-}$, X203 or X209-treated mice in previous preclinical models, a damaging effect of IL-11 directly on hepatocytes.

Figure 22H:
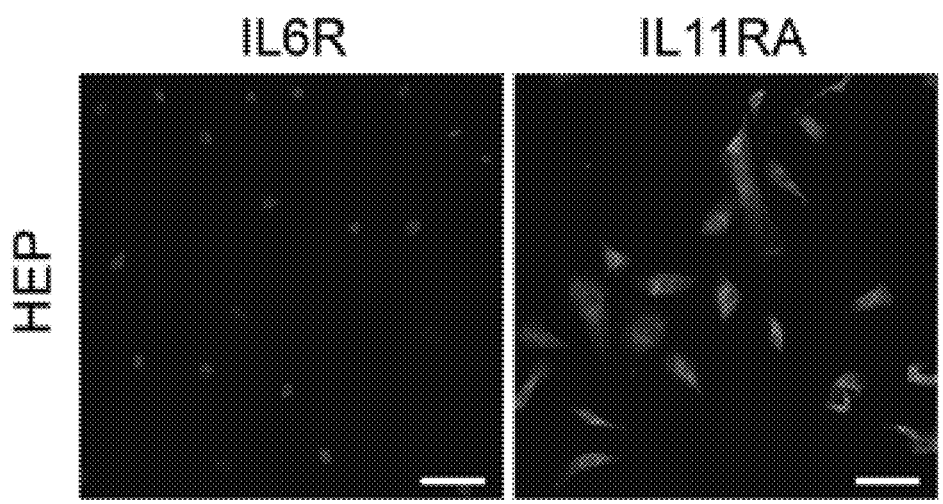
Figure 22I:
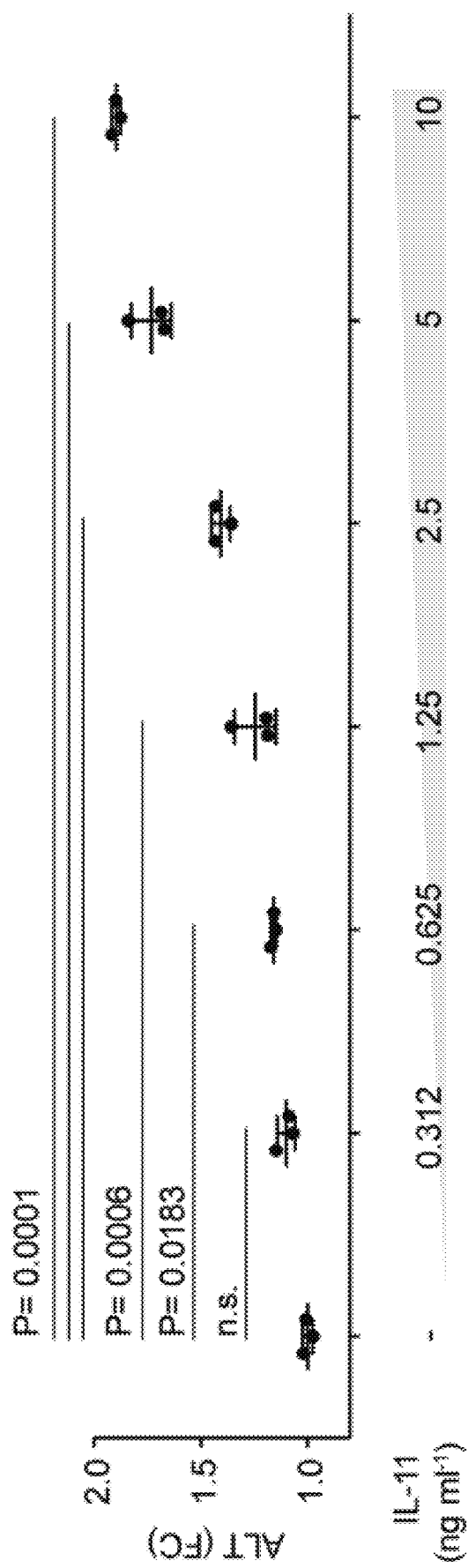
Figure 22J:
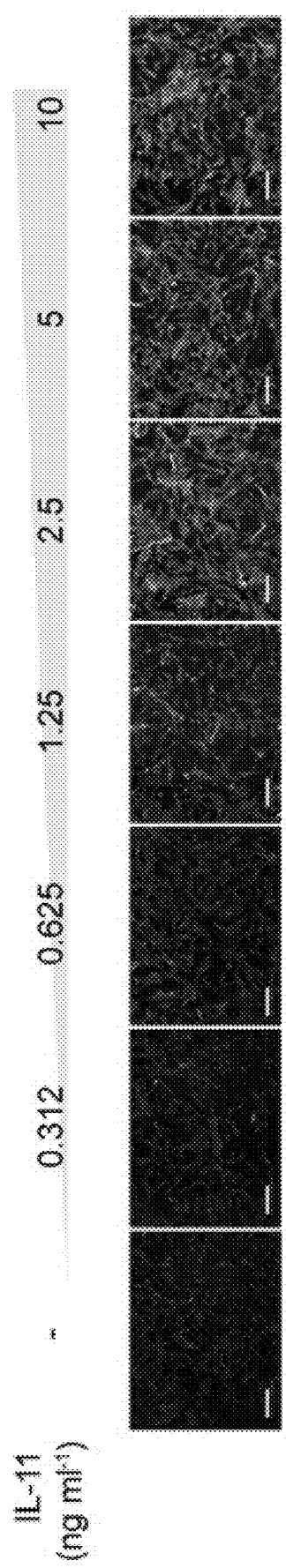
Figure 22K:
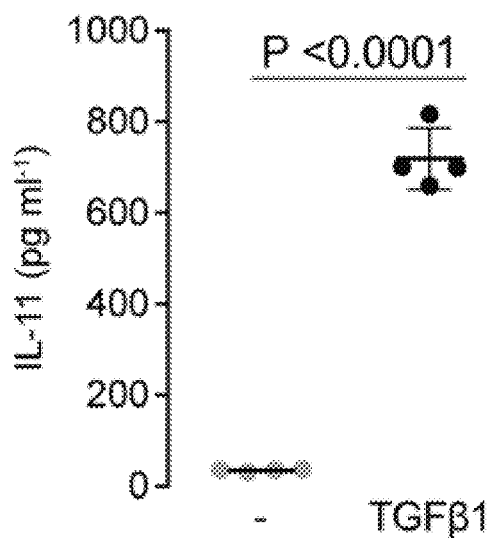

Primary human hepatocytes were found to express IL11RA but not IL6R (FIG. 22H). When hepatocytes were stimulated with physiological levels of IL-11 there is a dose-dependent release of ALT. This was coincident with a progressive increase in expression of stress fibres in hepatocytes (FIGS. 22I-22J). Intriguingly, hepatocytes also robustly secreted IL-11 when stimulated with TGFβ1, suggesting maladaptive autocrine activity of IL-11 in hepatocytes (FIG. 22K). Thus IL-11 signalling directly impairs hepatocyte function.

Figure 23A:
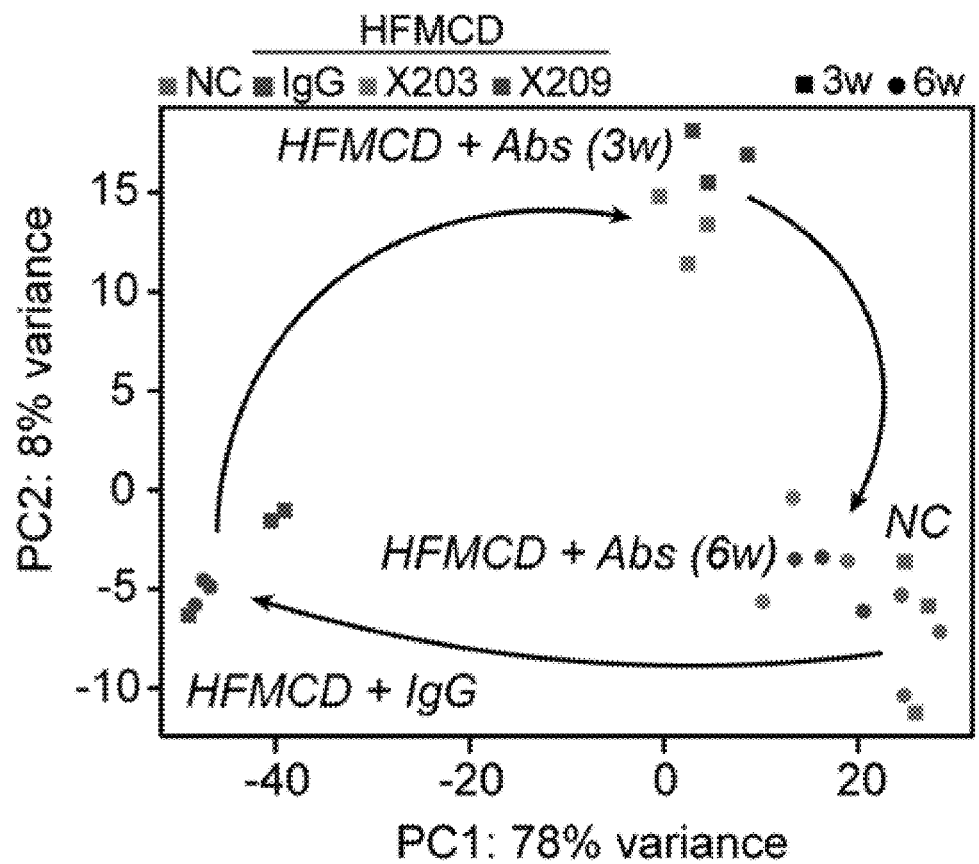
FIGS. 23A to 23G. Anti-IL11RA therapy reverses the molecular signature of NASH towards a normal liver profile while inhibiting immune cell activation. (A-G) Data for experiments as shown in FIG. 22B. (A) Principal component analysis (PCA) plot of liver gene expression in mice on NC or HFMCD in the presence of IgG, X203 or X209 antibodies for the times shown in 68. Arrows depict the transitions from normal gene expression (NC) to most perturbed gene expression in NASH (HFMCD+IgG), to intermediately restored gene expression (HFMCD+Abs (3w)), to normalised gene expression (HFMCD+Abs(6w)). (B) Pro-fibrotic and pro-inflammatory genes expression heatmap (scaled Transcripts Per Million, TPM). (C)Tnfα, Ccl2, and Ccl5 mRNA expression by qPCR (n≥5/group). (D) Liver CD45$^{+ve}$ immune cell numbers, (E) Ly6C$^{+ve}$ TGFβ1$^{+ve}$ cells in the total CD45$^{+ve}$ populations, (F) representative pseudo-color plots illustrating the gating strategy used to detect Ly6C$^{+ve}$ TGFβ1$^{+ve}$ cells (n≥4/group). (G) Serum TGFβ levels (n≥5/group). (C-E,G) Data are shown as box-and-whisker with median (middle line), 25th-75th percentiles (box) and min-max percentiles (whiskers). (C, G) two-tailed, Tukey-corrected Student's t-test; (D-E) two-tailed Student's t-test. FC: fold change; NC: normal chow; HFMCD: high fat methionine- and choline-deficient.
Figure 23B:
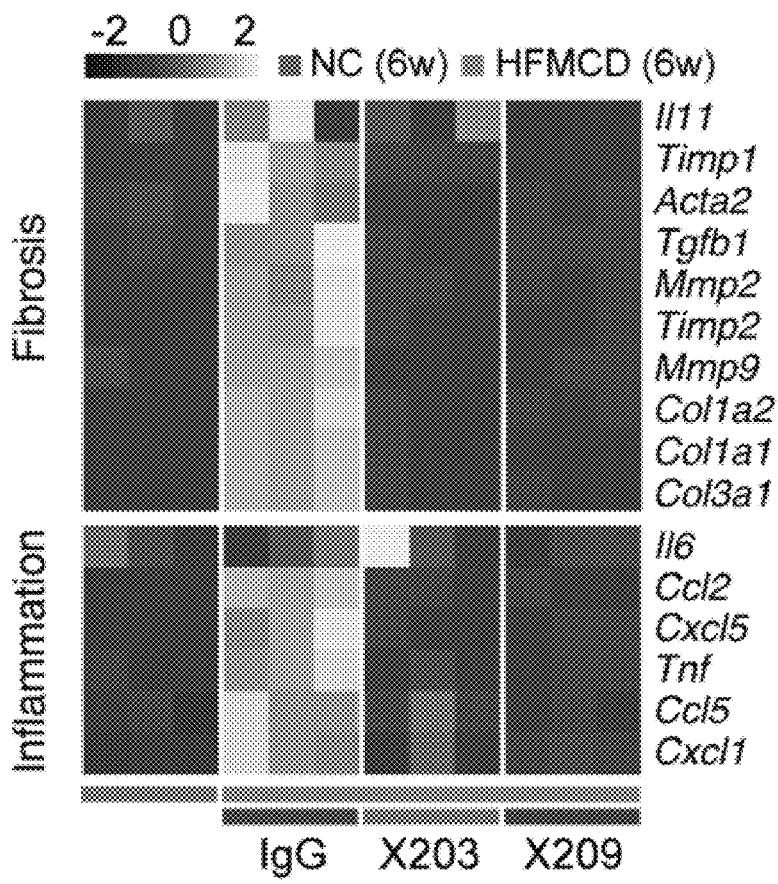
Figure 23C:
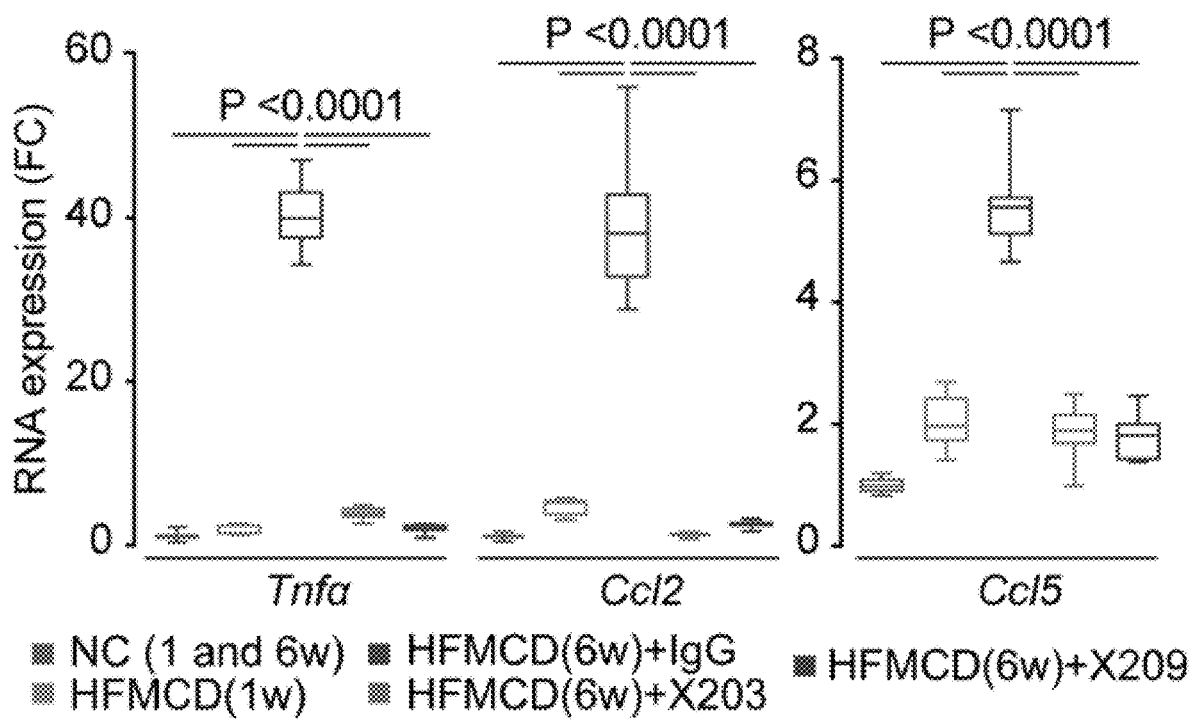
Figure 32A:
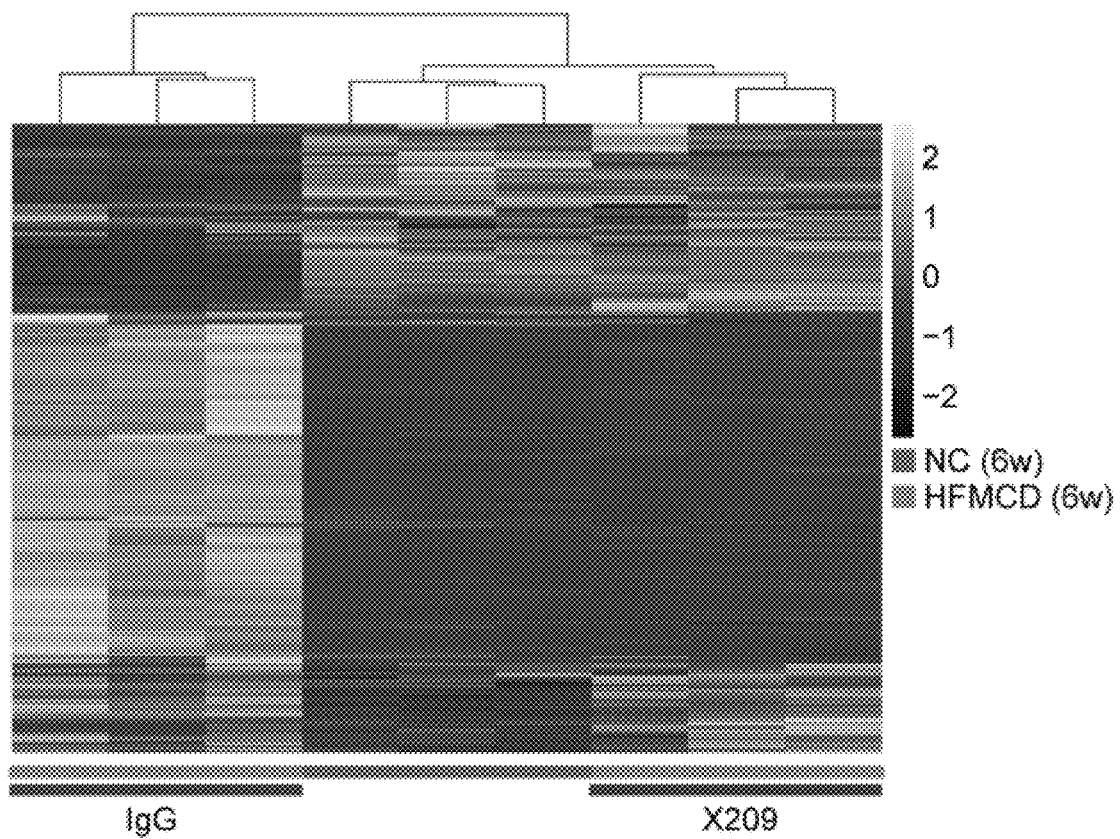
FIGS. 32A to 32D. Neutralizing anti-IL-11 or anti-IL11RA antibodies reverse the molecular signature of NASH towards a normal liver profile. (A-D) Data for RNA-seq and gene set enrichment analysis for early therapeutic dosing experiments as shown in FIG. 22A (n=3/group). (A-B) Heatmaps showing gene expression levels (scaled Transcripts Per Million mapped reads, TPM) across samples for all genes statistically differentially expressed between IgG and (A) X209 or (B) X203 treatments. The expression profile for the anti-IL-11 treatments clusters together with the profiles in NC, suggesting an almost complete reversal of the transcriptional effect of HFMCD diet. (C) Lipogenesis and β-oxidation genes expression heatmap showing that X209, more so than X203, improved hepatic lipid metabolism as compared to IgG. (D) Bubblemap showing results of the gene set enrichment analysis (GSEA) for differentially expressed genes after 6-weeks of NC or HFMCD diet and antibody therapy. Each dot represents the normalized enrichment score (NES) for the gene set and its FDR-corrected significance level, summarized by colour and size respectively. Gene sets for the enrichment test were selected from the "H—Hallmark" collection in MSigDB. FC: fold change; NC: normal chow; HFMCD: high fat methionine- and choline-deficient.
Figure 32B:
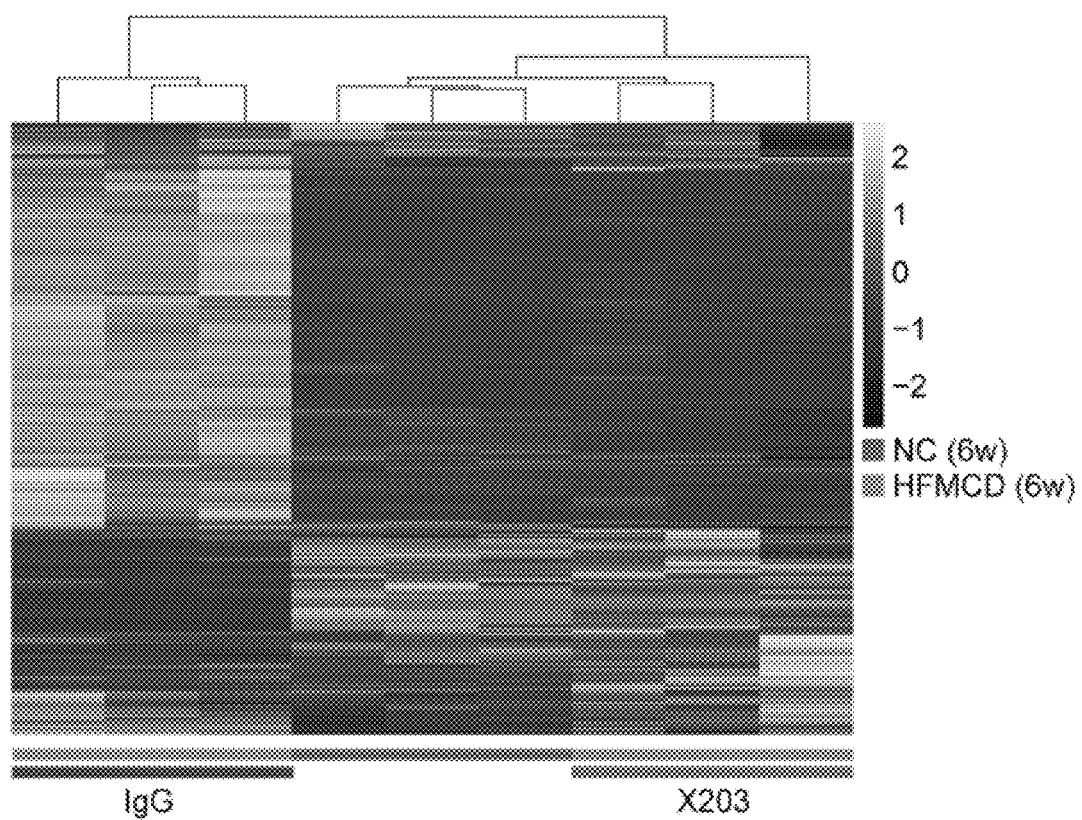
Figure 32C:
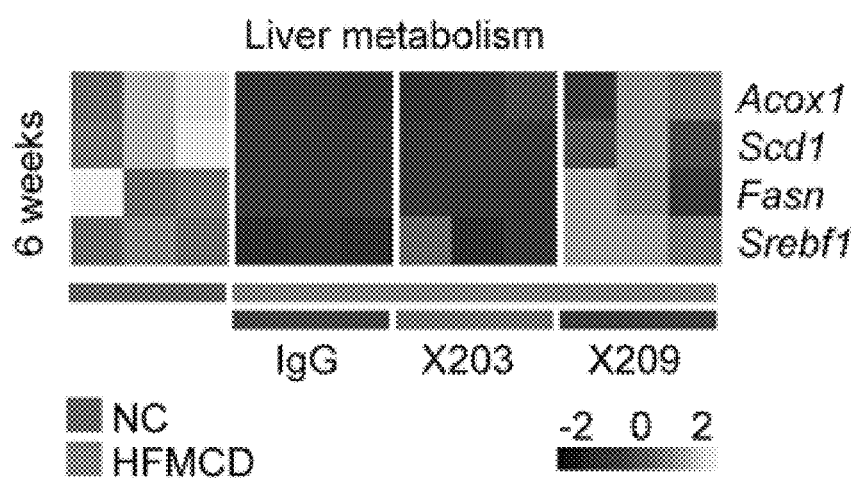
Figure 32D:
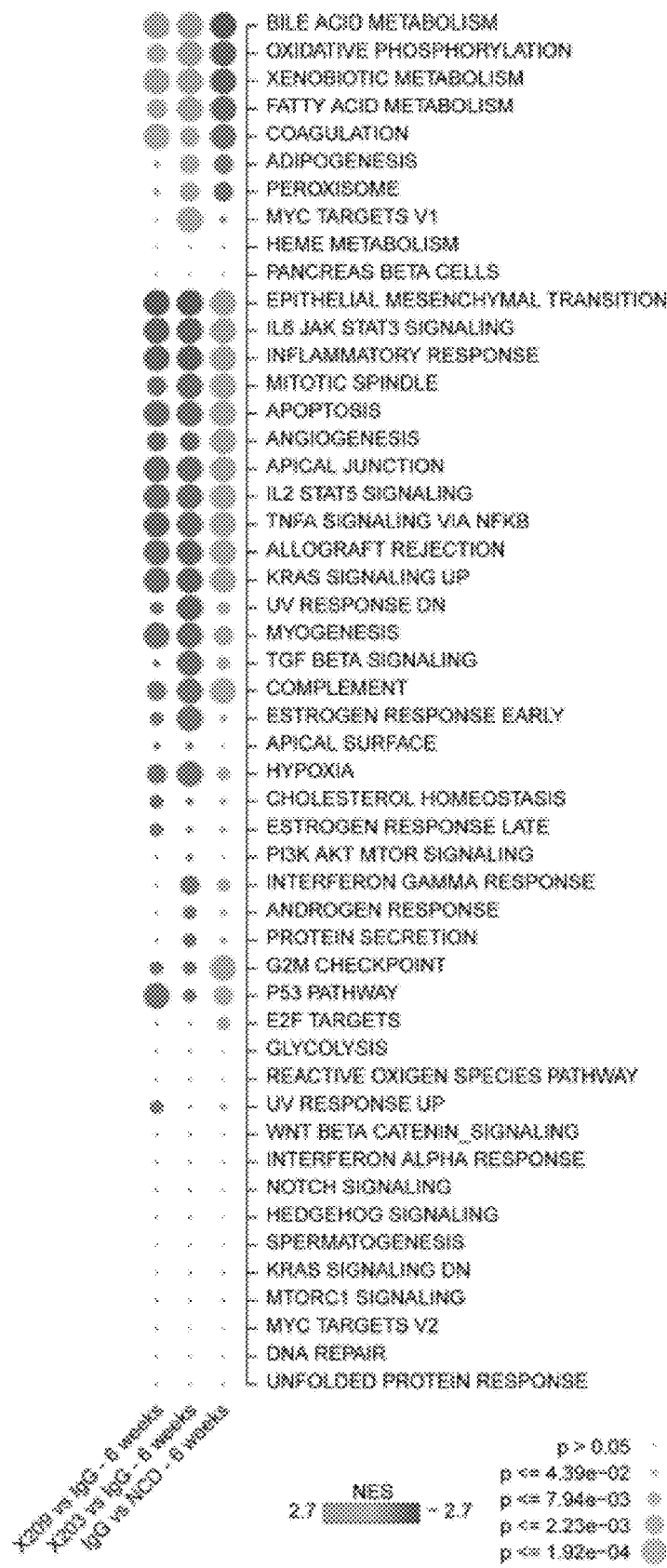

RNA-seq analysis was performed to profile the effects of IL-11 therapy during the acute inflammatory phase of HFMCD-induced NASH. Unsupervised analyses showed that antibody treatment almost completely reverses the pathological RNA expression signature induced by the HFMCD diet (FIG. 23A, FIGS. 32A-32B). Upregulation of pro-fibrotic and pro-inflammatory genes was abolished and lipid metabolism gene expression was re-established (FIGS. 23B-23C, FIG. 32C). Unbiased Gene Set Enrichment studies confirmed restoration of near-normal fatty acid, bile acid, oxidative stress, fibrosis and inflammatory transcriptional signatures (FIG. 32D).

Figure 23D:
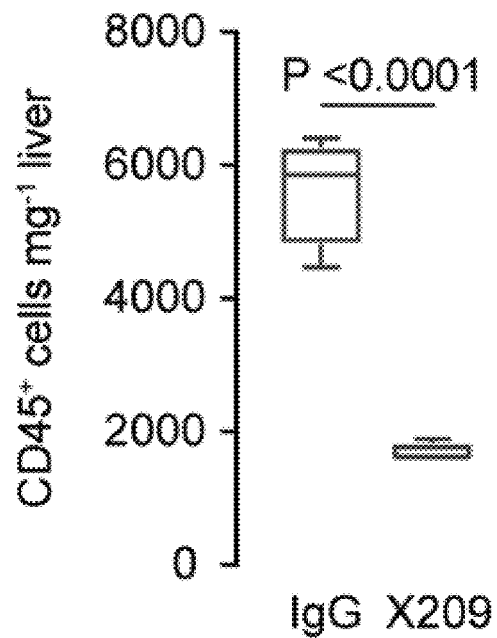
Figure 23E:
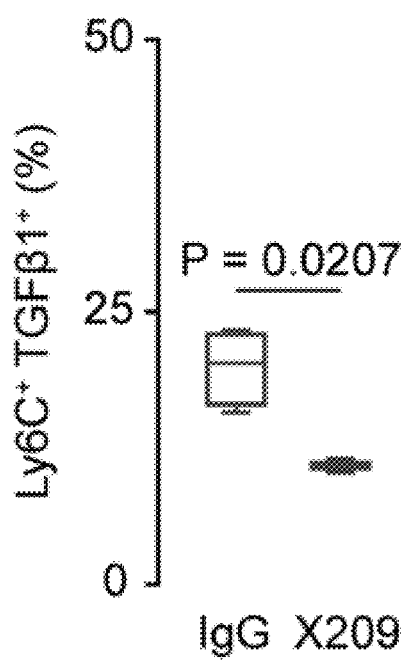
Figure 23F:
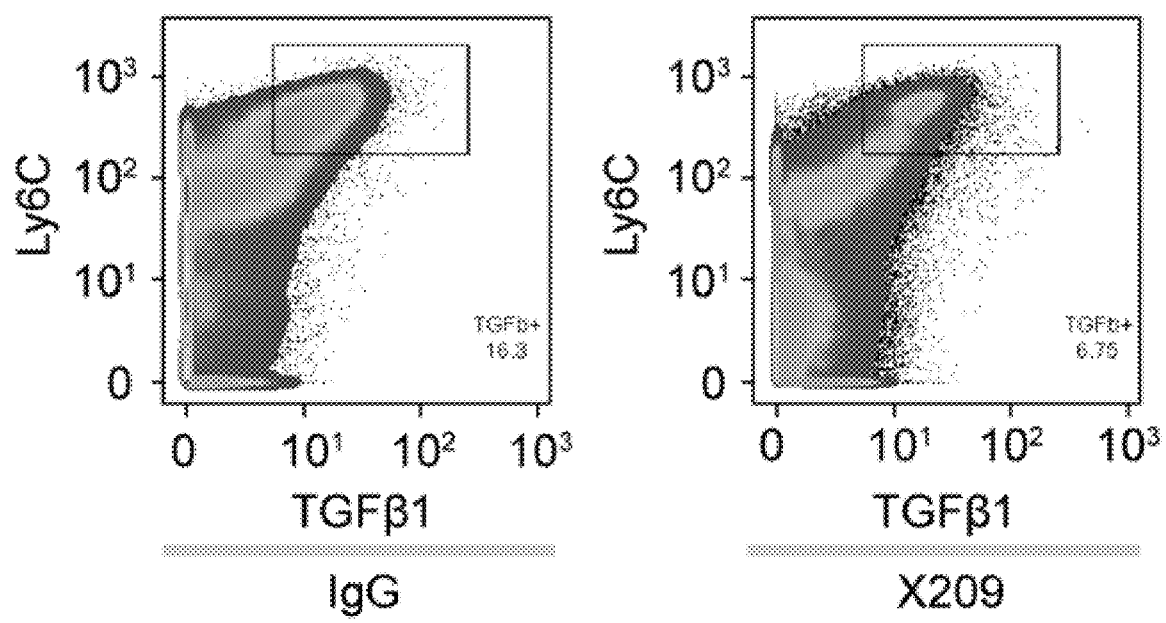
Figure 23G:
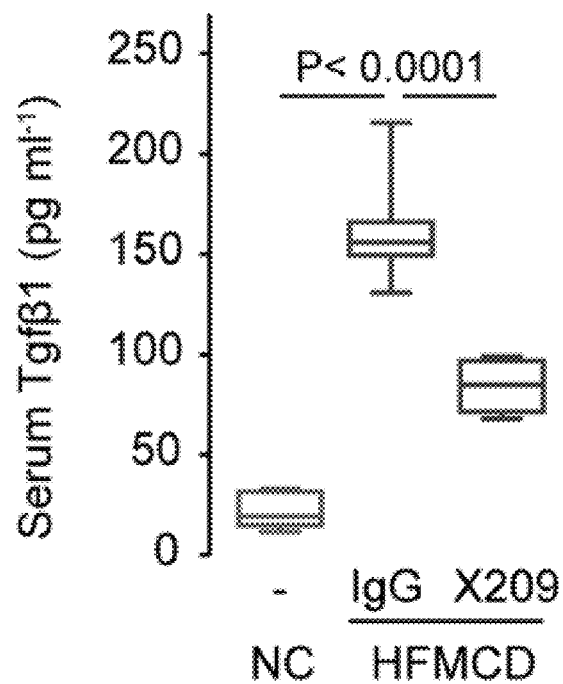

Resident macrophages and infiltrating monocytes are important for NASH pathogenesis and a major source of TGFβ1[39]. Inflammatory cell populations were examined in the liver during steatohepatitis and observed fewer immune cells in general in X209-treated livers and a specific reduction in Ly6C$^{+ve}$TGFβ1$^{+ve}$ cells (FIGS. 23D-23F). Circulating TGFβ1 levels were elevated by HFMCD diet but reduced by X209 therapy, which shows that anti-IL11 RA therapy is disease-modifying (FIG. 23G).

4.3 Discussion

HSCs are the major source of pro-inflammatory myofibroblasts in the liver[2] and inhibiting and reversing their transformation is a target for NASH therapies. Non-redundant, ERK-dependent IL-11 signalling is shown to be required for HSC transformation, similar to its role for fibroblast activation in heart, kidney and lung[11,12]. As such, targeting IL-11 to reverse liver fibrosis may have benefits when compared to therapies against other immune, metabolic or fibrosis factors that often exhibit some level of redundancy. Interestingly, potent metabolic intervention alone had no effect on fibrosis in our experiments and metabolic therapies may have limited effects on reversing fibrosis in NASH.

The inventors discovered an unexpected pro-inflammatory role for IL-11 in the liver and show that HSCs express high levels of IL11 RA whereas immune cells express IL6R instead. The data suggests an indirect effect of IL-11 on immune cells that is mediated via the stroma. Irrespective of using genetic or pharmacologic loss-of-function approaches inhibition of IL-11 mediated signalling was consistently and robustly demonstrated to prevent/reverse inflammation across multiple NASH models. While earlier publications suggest Il-11 may have a protective role in the liver, these studies used extremely high-doses of foreign recombinant human IL-11 in rodents[13,14] that does not stimulate murine Il11ra1[11]. The true biological effect of IL-11 at physiological levels is shown to be pro-inflammatory and stromal driven.

Hepatocytes also express IL11 RA and strongly secrete IL-11 upon stimulation with TGFβ1 and IL-11 signalling in hepatocytes induced stress fibre formation and cytotoxicity. The effects of IL-11 on hepatocytes during acute necroinflammation in NASH are profound and therapeutic targeting of IL-11 signalling reversed ALT levels from approximately 700 U/L to normal within three weeks. At later time points in NASH, genetic or therapeutic inhibition of IL-11 also prevents or reverses hepatocyte damage, which requires further study.

Human[40] and mouse[25] knockouts for IL11RA can have a mild skull deformity and exhibit joint laxity but are otherwise healthy and IL-11 appears redundant in adult mammals. This provides compelling genetic safety data for IL-11 as a drug target. On top of this target safety data, the present studies show that there are no adverse effects when IL-11 signalling is neutralized for an extended period of time using high doses of therapeutic antibodies. Furthermore, genetic or pharmacologic inhibition is associated with lower serum triglycerides, cholesterol and fasting glucose. This aspect of IL-11 inhibition is a desirable feature for a potential NASH therapy, as patients with NASH often suffer from cardiovascular diseases.

The inventors have identified an unappreciated and central role for IL-11 in liver pathobiology. Targeting IL-11 signalling with neutralizing antibodies reverses fibrosis, steatosis, hepatocyte death and inflammation across the spectrum of NASH. This novel therapeutic approach is associated with a favorable cardiometabolic profile.

4.4 References to Example 4

1. Friedman S L, Neuschwander-Tetri B A, Rinella M, et al. Mechanisms of NAFLD development and therapeutic strategies. Nat Med 2018. Available at: http://dx.doi.org/10.1038/s41591-018-0104-9.
2. Mederacke I, Hsu C C, Troeger J S, et al. Fate tracing reveals hepatic stellate cells as dominant contributors to liver fibrosis independent of its aetiology. Nat Commun 2013; 4:2823.
3. Friedman S L. Hepatic stellate cells: protean, multifunctional, and enigmatic cells of the liver. Physiol Rev 2008; 88:125-172.
4. Friedman S L. Molecular Regulation of Hepatic Fibrosis, an Integrated Cellular Response to Tissue Injury. J Biol Chem 2000; 275:2247-2250.
5. Higashi T, Friedman S L, Hoshida Y. Hepatic stellate cells as key target in liver fibrosis. Adv Drug Deliv Rev 2017; 121:27-42.
6. Hellerbrand C, Stefanovic B, Giordano F, et al. The role of TGFβ1 in initiating hepatic stellate cell activation in vivo. J Hepatol 1999; 30:77-87.
7. Tsuchida T, Friedman S L. Mechanisms of hepatic stellate cell activation. Nat Rev Gastroenterol Hepatol 2017; 14:397-411.
8. Kim B-M, Abdelfattah A M, Vasan R, et al. Hepatic stellate cells secrete Ccl5 to induce hepatocyte steatosis. Sci Rep 2018; 8:7499.
9. Banini B A, Sanyal A J. Current and future pharmacologic treatment of nonalcoholic steatohepatitis. Curr Opin Gastroenterol 2017; 33:134-141.
10. Iwaisako K, Jiang C, Zhang M, et al. Origin of myofibroblasts in the fibrotic liver in mice. Proc Natl Acad Sci USA 2014; 111:E3297-305.
11. Schafer S, Viswanathan S, Widjaja A A, et al. IL-11 is a crucial determinant of cardiovascular fibrosis. Nature 2017; 552:110-115.
12. Cook S, Ng B, Dong J, et al. IL-11 is a therapeutic target in idiopathic pulmonary fibrosis. 2018. Available at: http://dx.doi.org/10.1101/336537.
13. Zhu M, Lu B, Cao Q, et al. IL-11 Attenuates Liver Ischemia/Reperfusion Injury (IRI) through STAT3 Signalling Pathway in Mice. PLoS One 2015; 10:e0126296.
14. Yu J, Feng Z, Tan L, et al. Interleukin-11 protects mouse liver from warm ischemia/reperfusion (WI/Rp) injury. Clin Res Hepatol Gastroenterol 2016; 40:562-570.
15. Lawitz E J, Hepburn M J, Casey T J. A pilot study of interleukin-11 in subjects with chronic hepatitis C and advanced liver disease nonresponsive to antiviral therapy. Am J Gastroenterol 2004; 99:2359-2364.
16. Gomes A L, Teijeiro A, Buren S, et al. Metabolic Inflammation-Associated IL-17A Causes Non-alcoholic Steatohepatitis and Hepatocellular Carcinoma. Cancer Cell 2016; 30:161-175.
17. Baena M, Sangüesa G, Flutter N, et al. Liquid fructose in Western-diet-fed mice impairs liver insulin signalling and causes cholesterol and triglyceride loading without changing calorie intake and body weight. J Nutr Biochem 2017; 40:105-115.
18. Machado M V, Michelotti G A, Xie G, et al. Mouse models of diet-induced nonalcoholic steatohepatitis reproduce the heterogeneity of the human disease. PLoS One 2015; 10:e0127991.
19. Yata Y. DNase I-hypersensitive sites enhance a1 (I) collagen gene expression in hepatic stellate cells. Hepatology 2003; 37:267-276.
20. Sheng J, Ruedl C, Karjalainen K. Most Tissue-Resident Macrophages Except Microglia Are Derived from Fetal Hematopoietic Stem Cells. Immunity 2015; 43:382-393.
21. Chew V, Lai L, Pan L, et al. Delineation of an immunosuppressive gradient in hepatocellular carcinoma using high-dimensional proteomic and transcriptomic analyses. Proc Natl Acad Sci USA 2017; 114:E5900-E5909.
22. Dou C, Liu Z, Tu K, et al. P300 Acetyltransferase Mediates Stiffness-Induced Activation of Hepatic Stellate Cells Into Tumor-Promoting Myofibroblasts. Gastroenterology 2018; 154:2209-2221.e14.
23. Yang C, Zeisberg M, Mosterman B, et al. Liver fibrosis: insights into migration of hepatic stellate cells in response to extracellular matrix and growth factors. Gastroenterology 2003; 124:147-159.
24. Lawan A, Bennett A M. Mitogen-Activated Protein Kinase Regulation in Hepatic Metabolism. Trends Endocrinol Metab 2017; 28:868-878.
25. Nandurkar H H, Robb L, Tarlinton D, et al. Adult mice with targeted mutation of the interleukin-11 receptor (IL11Rα) display normal hematopoiesis. Blood 1997; 90:2148-2159.
26. Stephenson K, Kennedy L, Hargrove L, et al. Updates on Dietary Models of Nonalcoholic Fatty Liver Disease: Current Studies and Insights. Gene Expr 2018; 18:5-17.
27. Simon T G, Bamira D G, Chung R T, et al. Nonalcoholic Steatohepatitis is Associated with Cardiac Remodeling and Dysfunction. Obesity 2017; 25:1313-1316.
28. Yasui K, Sumida Y, Mori Y, et al. Nonalcoholic steatohepatitis and increased risk of chronic kidney disease. Metabolism 2011; 60:735-739.
29. Lau J K C, Zhang X, Yu J. Animal models of nonalcoholic fatty liver disease: current perspectives and recent advances. J Pathol 2017; 241:36-44.
30. Rinella M E, Elias M S, Smolak R R, et al. Mechanisms of hepatic steatosis in mice fed a lipogenic methionine choline-deficient diet. J Lipid Res 2008; 49:1068-1076.

31. Wortham M, He L, Gyamfi M, et al. The Transition from Fatty Liver to NASH Associates with SAMe Depletion in db/db Mice Fed a Methionine Choline-Deficient Diet. Dig Dis Sci 2008; 53:2761-2774.
32. Hemmann S, Graf J, Roderfeld M, et al. Expression of MMPs and TIMPs in liver fibrosis—a systematic review with special emphasis on anti-fibrotic strategies. J Hepatol 2007; 46:955-975.
33. Elsharkawy A M, Oakley F, Mann D A. The role and regulation of hepatic stellate cell apoptosis in reversal of liver fibrosis. Apoptosis 2005; 10:927-939.
34. Krizhanovsky V, Yon M, Dickins R A, et al. Senescence of activated stellate cells limits liver fibrosis. Cell 2008; 134:657-667.
35. Schnabl B, Purbeck C H, Choi Y H, et al. Replicative senescence of activated human hepatic stellate cells is accompanied by a pronounced inflammatory but less fibrogenic phenotype. Hepatology 2003; 37:653-664.
36. Kisseleva T, Cong M, Paik Y, et al. Myofibroblasts revert to an inactive phenotype during regression of liver fibrosis. Proc Natl Acad Sci USA 2012; 109:9448-9453.
37. Seki E, De Minicis S, Osterreicher C H, et al. TLR4 enhances TGF-6 signalling and hepatic fibrosis. Nat Med 2007; 13:1324-1332.
38. Marra F, Valente A J, Pinzani M, et al. Cultured human liver fat-storing cells produce monocyte chemotactic protein-1. Regulation by proinflammatory cytokines. J Clin Invest 1993; 92:1674-1680.
39. Koyama Y, Brenner D A. Liver inflammation and fibrosis. J Clin Invest 2017; 127:55-64.
40. Brischoux-Boucher E, Trimouille A, Baujat G, et al. IL11RA-related Crouzon-like autosomal recessive craniosynostosis in ten new patients: resemblances and differences. Clin Genet 2018. Available at: http://dx.doi.org/10.1111/cge.13409.

4.5 Supplementary Materials

Antibodies

ACTA2 (ab7817, Abcam; IF), ACTA2 (19245, CST; WB), CD45 (103102, Biolegend), Collagen I (ab34710, Abcam), p-ERK1/2 (4370, CST), ERK1/2 (4695, CST), GAPDH (2118, CST), IgG (Aldevron), neutralizing anti-IL-11 (X203, Aldevron), neutralizing anti-IL11RA (X209, Aldevron; in vivo study), IL11RA (ab1250515, Abcam; IF), Ly6C (128039, Biolegend), TGFβ1 (141402, Biolegend), anti-rabbit HRP (7074, CST), anti-mouse HRP (7076, CST), anti-rabbit Alexa Fluor 488 (ab150077, Abcam), anti-mouse Alexa Fluor 488 (ab150113, Abcam).

Recombinant Proteins

Commercial recombinant proteins: Human angiotensin H (A9525, Sigma-Aldrich), human CCL2 (279-MC-050/CF, R&D Systems), human bFGF (233-FB-025, R&D Systems), human (PHC0115, Life Technologies), human PDGF (220-BB-010, R&D Systems), human TGFβ1 (PHP143B, Bio-Rad), and mouse TGFβ1 (7666-MB-005, R&D Systems).

Custom recombinant proteins: Mouse Il-11 (UniProtKB: P47873) were synthesized without the signal peptide. HyperIL-11 (IL11 RA:IL-11 fusion protein), which mimics the trans-signalling complex, was constructed using a fragment of IL11 RA (amino acid residues 1-317; UniProtKB: Q14626) and IL-11 (amino acid residues 22-199, UniProtKB: P20809) with a 20 amino acid linker ((SEQ ID NO: 60) GPAGQSGGGGGSGGGSGGGSV)[1]. All custom recombinant proteins were synthesized by GenScript using a mammalian expression system.

Chemicals

Hydrogen Peroxide ($H_2O_2$, 31642, Sigma), PD98059 (9900, CST), U0126 (9930, CST).

Generation of Mouse Monoclonal Antibodies Against IL11RA

Genetic Immunisation and Screening for Specific Binding

A cDNA encoding amino acids 23-422 of human IL11RA was cloned into expression plasmids (Aldevron). Mice were immunised by intradermal application of DNA-coated gold-particles using a hand-held device for particle-bombardment. Cell surface expression on transiently transfected HEK cells was confirmed with anti-tag antibodies recognising a tag added to the N-terminus of the IL11RA protein. Sera were collected after 24 days and a series of immunisations and tested in flow cytometry on HEK293 cells transiently transfected with the aforementioned expression plasmids. The secondary antibody was goat anti-mouse IgG R-phycoerythrin-conjugated antibody (Southern Biotech, #1030-09) at a final concentration of 10 μg ml$^{-1}$. Sera were diluted in PBS containing 3% FBS. Interaction of the serum was compared to HEK293 cells transfected with an irrelevant cDNA. Specific reactivity was confirmed in 2 animals and antibody-producing cells were isolated from these animals and fused with mouse myeloma cells (Ag8) according to standard procedures. Supernatant of hybridoma cultures were incubated with HEK cells expressing an IL11RA-flag construct and hybridomas producing antibodies specific for IL11RA were identified by flow cytometry.

Identification of Neutralizing Anti-IL11RA Antibodies

Antibodies that bound to IL11RA-flag cells but not to the negative control were considered specific binders and subsequently tested for anti-fibrotic activity on human and mice atrial fibroblasts as described by Schafer et al[2]. Briefly, primary human or mouse fibroblasts were stimulated with human or mouse TGFβ1, respectively (5 ng ml$^{-1}$; 24 h) in the presence of the antibody candidates (6 μg ml$^{-1}$). TGFβ1 stimulation results in an upregulation of endogenous IL-11, which if neutralized, blocks the pro-fibrotic effect of TGFβ1. The fraction of activated myofibroblasts (ACTA2$^{+ve}$ cells) was measured on the Operetta platform as described above to estimate the neutralization potential of the antibody candidates. In order to block potential trans-signalling effects, antibodies were also screened in the context of hyperIL-11 stimulation of human fibroblasts (200 μg ml$^{-1}$). Three specific and neutralizing anti-IL11RA antibodies were detected, of which X209 was taken forward for in vivo studies. The same procedures were performed to obtain a neutralizing antibody that binds to the ligand IL-11[3].

Bindings Kinetics of X209 to IL11RA

Binding of X209 to human IL11RA was measured on Biacore T200 (GE Healthcare). X209 was immobilized onto an anti-mouse capture chip. Interaction assays were performed with HEPES-buffered saline pH 7.4 containing 0.005% P20 and 0.5% BSA. A concentration range (1.56 nM to 100 nM) of the analyte (human IL11 RA) was injected over X209 and reference surfaces at a flow rate of 40 μl min$^{-1}$. Binding to mouse Il11ra1 was confirmed on Octet system (ForteBio) using a similar strategy. All sensograms were aligned and double-referenced[4]. Affinity and kinetic constants were determined by fitting the corrected sensorgrams with 1:1 Langmuir model. The equilibrium binding constant $K_D$ was determined by the ratio of $k_d/k_a$.

X209 IC$_{50}$ Measurement.

HSCs were stimulated with TGFβ1(5 ng ml$^{-1}$, 24 h) in the presence of IgG (4 μg ml$^{-1}$) and varying concentrations of X209 (4 μg ml$^{-1}$ to 61 pg ml$^{-1}$; 4-fold dilutions). Supernatants were collected and assayed for the amount of secreted MMP2. Dose-response curves were generated by plotting the logarithm of X209 tested concentration (pM) versus corresponding percent inhibition values using least squares (ordinary) fit. The $IC_{50}$ value was calculated using log(inhibitor) versus normalized response-variable slope equation.

Blood Pharmacokinetics and Biodistribution

C57BL/6J mice (10-12-weeks old) were retro-orbitally injected (left eye) with 100 µl of freshly radiolabeled $^{125}$I-X209 (5 µCi, 2.5 µg) in PBS. Mice were anesthetized with 2% isoflurane and blood were collected at several time points (2, 5, 10, 15, 30 m, 1, 2, 4, 6, 8 h, 1, 2, 3, 7, 14 and 21 days) post injection via submandibular bleeding. For biodistribution studies, blood was collected via cardiac puncture and tissues were harvested at the following time points: 1, 4 h, 1, 3, 7, 14, 21 days post injection. The radioactivity contents were measured using a gamma counter (2480 Wizard2, Perkin Elmer) with decay-corrections (100× dilution of 100 µl dose). The measured radioactivity was normalized to % injected dose/g tissue.

RNA-Seq

Generation of RNA-Seq Libraries

Total RNA was quantified using Qubit RNA high sensitivity assay kit (Thermo Fisher Scientific) and RNA integrity number (RIN) was assessed using the LabChip GX RNA Assay Reagent Kit (Perkin Elmer). TruSeq Stranded mRNA Library Preparation Kit (Illumina) was used to prepare the transcript library according to the manufacturer's protocol. All final libraries were quantified using KAPA library quantification kits (KAPA Biosystems). The quality and average fragment size of the final libraries were determined using LabChip GX DNA High Sensitivity Reagent Kit (Perkin Elmer). Libraries were pooled and sequenced on a NextSeq 500 benchtop sequencer (Illumina) using NextSeq 500 High Output v2 kit and paired-end 75-bp sequencing chemistry.

RNA-Seq Analysis

Stiffness-induced RNA regulation in hepatic stellate cells: Normalized gene expression values were downloaded from Dou et al[5]. Lowly expressed genes (FPKM at baseline 2) were removed from the analysis and fold changes were calculated as average FPKM in HSCs on stiff surface divided by average FPKM in HSCs on soft surface. The fold change of RNA expression for upregulated genes (f.c.>1) was plotted and genes were ranked according to their average FPKM value.

TGFβ1 stimulation of human hepatic stellate cells and antibody treatment in HFMCD: Sequenced libraries were demultiplexed using bcl2fastq v2.19.0.316 with the-no-lane-splitting option. Adapter sequences were then trimmed using trimmomatic[6] v0.36 in paired end mode with the options MAXINFO:35:0.5 MINLEN:35. Trimmed reads were aligned to the Homo sapiens GRCh38 using STAR' v. 2.2.1 with the options—outFilterType BySJout-outFilterMultimapNmax 20-alignSJoverhangMin 8-alignSJDBoverhangMin 1-outFilterMismatchNmax 999-alignIntronMin 20-alignIntronMax 1000000-alignMatesGapMax 1000000 in paired end, single pass mode. Only unique alignments were retained for counting. Counts were calculated at the gene level using the FeatureCounts module from subread[8]v. 1.5.1, with the options -O-s 2-J-T 8-p-R-G. The Ensembl release 86 hg38 GTF was used as annotation to prepare STAR indexes and for FeatureCounts.

For the antibody treatment experiments in mouse, libraries were treated as for the human samples, only using mm10 Ensembl release 86 genome and annotation.

Differential expression analyses were performed in R 3.4.1 using the Bioconductor package DESeq2[9] 1.18.1, using the Wald test for comparisons and including the variance shrinkage step setting a significance threshold of 0.05.

Gene set enrichment analysis (GSEA) were performed in R 3.4.1 using the fgsea package and the MSigDB Hallmark genesets[10,11], performing 100000 iterations. The "stat" column of the DESeq2 results output was used as ranked input for each enrichment, taking only mouse genes with one-to-one human orthologs.

Enzyme-Linked Immunosorbent Assay (ELISA) and Colorimetric Assays

The levels of IL-11 and MMP-2 in equal volumes of cell culture media were quantified using Human IL-11 Quantikine ELISA kit (D1100, R&D Systems) and Total MMP-2 Quantikine ELISA kit (MMP200, R&D Systems), respectively. Total secreted collagen in the cell culture supernatant was quantified using Sirius red collagen detection kit (9062, Chondrex). Total hydroxyproline content in the livers was measured using Quickzyme Total Collagen assay kit (Quickzyme Biosciences). Mouse serum levels of alanine aminotransferease (ALT), cholesterol, and triglycerides were measured using Alanine Transaminase Activity Assay Kit (ab105134, abcam), Cholesterol Assay Kit (ab65390, abcam), and Triglyceride Assay Kit (ab65336, abcam), respectively. Liver Triglycerides (TG) measurements were performed using triglyceride colorimetric assay kit (Ser. No. 10/010,303, Cayman). All ELISA and colorimetric assays were performed according to the manufacturer's protocol.

Matrigel Invasion Assay

The invasive behavior of human HSCs was assayed using 24-well Boyden chamber invasion assays (Cell Biolabs Inc.). Equal numbers of HSCs in serum-free HSC media were seeded in triplicates onto the ECM-coated matrigel and were allowed to invade towards HSC media containing 0.2% FBS. After 48 h of incubation with stimuli, media was aspirated and non-invasive cells were removed using cotton swabs. The cells that invaded towards the bottom chamber were stained with cell staining solution (Cell Biolabs Inc.) and invasive cells from 5 non-overlapping fields/membrane were imaged and counted under 40× magnification. For antibody inhibition experiments, HSCs were pretreated with X203, X209, or IgG control antibodies for 15 m prior to addition of stimuli.

Precision Cut Liver Slices (PCLS) and Western Blotting of NASH Patient Liver

Briefly, human PCLS were cut and incubated with TGFβ1 for 24 h. ELISA from the supernatant was performed using Human IL-11 DuoSet (DY218, R&D Systems). This CRO also collected liver biopsies from patients undergoing liver resections for cancers where adjacent, non-cancerous tissue was collected for molecular studies. Patients had either no documented intrinsic liver disease (controls) or previously documented alcoholic liver disease, primary biliary cirrhosis, primary sclerosing cholangitis or NASH. For confidentiality reasons no further information was provided for these samples.

Quantitative Polymerase Chain Reaction (qPCR)

Total RNA was extracted from either the snap-frozen liver tissues or HSCs lysate using Trizol (Invitrogen) followed by RNeasy column (Qiagen) purification. The cDNAs were synthesized with iScript™ cDNA synthesis kit (Bio-Rad) according to manufacturer's instructions. Gene expression analysis was performed on duplicate samples with either TaqMan (Applied Biosystems) or fast SYBR green (Qiagen) technology using StepOnePlus™ (Applied Biosystem) over 40 cycles. Expression data were normalized to GAPDH mRNA expression and fold change was calculated using $2^{-\Delta\Delta Ct}$ method. The sequences of specific TaqMan probes and SYBR green primers are available upon request.

Immunoblotting

Western blots were carried out on total protein extracts from HSCs and liver tissues. Both cells and frozen tissues were homogenized in radioimmunoprecipitation assay (RIPA) buffer containing protease and phosphatase inhibitors (Thermo Scientifics), followed by centrifugation to clear the lysate. Protein concentrations were determined by Bradford assay (Bio-Rad). Equal amount of protein lysates were separated by SDS-PAGE, transferred to PVDF membrane, and subjected to immunoblot analysis for the indicated primary antibodies. Proteins were visualized using the ECL detection system (Pierce) with the appropriate secondary antibodies.

Histology Liver tissues were fixed for 48 h at RT in 10% neutral-buffered formalin (NBF), dehydrated, embedded in paraffin blocks and sectioned at 7 μm. Sections stained with Masson's Trichrome were examined by light microscopy. Each histology experiment was repeated independently with similar results from n=3/group Images of the sections were captured and blue-stained fibrotic areas were semi-quantitatively determined with Image-J software (color deconvolution-Masson Trichrome) from 4 sections/liver. Treatment and genotypes were not disclosed to investigators performing the histology and generating semi-quantitative readouts.

REFERENCES TO SUPPLEMENTARY MATERIALS

1. Dams-Kozlowska H, Gryska K, Kwiatkowska-Borowczyk E, et al. A designer hyper interleukin 11 (H11) is a biologically active cytokine. BMC Biotechnol 2012; 12:8.
2. Schafer S, Viswanathan S, Widjaja A A, et al. IL-11 is a crucial determinant of cardiovascular fibrosis. Nature 2017; 552:110-115.
3. Cook S, Ng B, Dong J, et al. IL-11 is a therapeutic target in idiopathic pulmonary fibrosis. 2018. Available at: http://dx.doi.org/10.1101/336537.
4. Myszka D G. Improving biosensor analysis. J Mol Recognit 1999; 12:279-284.
5. Dou C, Liu Z, Tu K, et al. P300 Acetyltransferase Mediates Stiffness-Induced Activation of Hepatic Stellate Cells Into Tumor-Promoting Myofibroblasts. Gastroenterology 2018; 154:2209-2221.e14.
6. Bolger A M, Lohse M, Usadel B. Trimmomatic: a flexible trimmer for Illumina sequence data. Bioinformatics 2014; 30:2114-2120.
7. Dobin A, Davis C A, Schlesinger F, et al. STAR: ultrafast universal RNA-seq aligner. Bioinformatics 2013; 29:15-21.
8. Liao Y, Smyth G K, Shi W. The Subread aligner: fast, accurate and scalable read mapping by seed-and-vote. Nucleic Acids Res 2013; 41:e108.
9. Love M I, Huber W, Anders S. Moderated estimation of fold change and dispersion for RNA-seq data with DESeq2. Genome Biol 2014; 15:550.
10. Liberzon A, Subramanian A, Pinchback R, et al. Molecular signatures database (MSigDB) 3.0. Bioinformatics 2011; 27:1739-1740.
11. Subramanian A, Tamayo P, Mootha V K, et al. Gene set enrichment analysis: a knowledge-based approach for interpreting genome-wide expression profiles. Proc Natl Acad Sci USA 2005; 102:15545-15550.

Example 5: Autocrine IL11 Cis-Signaling in Hepatocytes is an Initiating Nexus Between Lipotoxicity and Non-Alcoholic Steatohepatitis (NASH)

5.1 Overview

IL11 signaling is important in non-alcoholic steatohepatitis (NASH). In the present Example, the inventors show that lipid-laden hepatocytes secrete IL11, which acts through an autocrine cis-signaling loop to cause lipoapoptosis. While IL6 protects hepatocytes, IL11 causes hepatocyte death through activation of non-canonical signaling pathways and upregulation of NOX4 and reactive oxygen species. In two preclinical models, hepatocyte-specific deletion of Il11ra1 protected mice from all aspects of NASH. In addition, restoration of IL11 cis-signaling in hepatocytes only in global Il11ra1 knock out mice reconstituted steatosis and inflammation. No evidence was found to support the existence of IL6 or IL11 trans-signaling. The inventors conclude that hepatocyte lipotoxicity stimulates IL11 secretion leading to hepatocyte death that is followed by fibrosis and inflammation. These data outline a new, hepatocyte-specific mechanism for the transition from non-alcoholic fatty liver disease to NASH.

5.2 Introduction

Interleukin 11 (IL11) is a key fibrogenic factor (Ng et al., 2019; Schafer et al., 2017) that is elevated in fibrotic precision-cut liver slices across species (Bigaeva et al., 2019). IL11 has been shown to have negative effects on hepatocyte function after toxic liver insult (Widjaja et al.) and, directly or indirectly, contributes to nonalcoholic steatohepatitis (NASH) pathologies (Widjaja et al., 2019). At the other end of the spectrum, a number of earlier publications suggested that IL11 is protective in mouse models of ischemic-, infective- or toxin-induced liver damage (Bozza et al., 1999; Maeshima et al., 2004; Nishina et al., 2012; Trepicchio et al., 2001; Yu et al., 2016; Zhu et al., 2015). However, it is now apparent that the recombinant human IL11 (rhIL11) reagent used in earlier studies is ineffective in the mouse (Widjaja et al.).

IL11 is a member of the interleukin 6 (IL6) cytokine family and, like IL6, binds to its membrane-bound alpha receptor (IL11 RA) and glycoprotein 130 (gp130) to signal in cis. IL6 itself has been linked to liver function and publications suggest an overall beneficial effect (Klein et al., 2005; Kroy et al., 2010; Matthews et al., 2010; Schmidt-Arras and Rose-John, 2016; Wuestefeld et al., 2003). However, it is also thought that IL6 can bind to soluble IL6 receptor (sIL6R) and signal in trans, which is considered maladaptive (Schmidt-Arras and Rose-John, 2016). It is possible that IL11, like IL6, signals in a pathogenic mode in trans but experiments to date have found no evidence for this in tumors or reproductive tissues (Agthe et al., 2017; Balic et al., 2017).

The factors underlying the transition from non-alcoholic fatty liver disease (NAFLD) to NASH are multifactorial but lipid loading of hepatocytes is centrally important (Friedman et al., 2018). Certain lipid species are toxic for hepatocytes and this lipotoxicity stimulates cytokine release causing hepatocyte death and paracrine activation of hepatic stellate cells (HSCs) and immune cells (Farrell et al., 2018; Friedman et al., 2018). Lipotoxicity, such as that due to palmitate (Kakisaka et al., 2012), is an early event in NASH and represents a linkage between diet, NAFLD and NASH.

While genetic or pharmacological inhibition of IL6 cis-signaling worsens steatosis phenotypes (Kroy et al., 2010; Matthews et al., 2010; Yamaguchi et al., 2010), a role for IL11 in hepatic lipotoxicity has not been described.

In the present Example, a range of in vitro and in vivo approaches were used to address key questions regarding IL11 in hepatocyte biology, NAFLD and NASH: (1) Defining the true role of IL11 cis- and trans-signaling in human hepatocytes, (2) examining whether lipotoxicity is related to IL11 activity in hepatocytes, (3) establishing whether IL11 or IL6 trans-signaling contributes to NASH, (4) dissecting the inter-relationship between IL11 cis-signaling in hepatocytes and the development of steatosis, hepatocyte death, inflammation, and fibrosis. These studies reveal unexpected aspects of IL6 and IL11 biology and demonstrate an unambiguous pathogenic effect of lipotoxicity-activated, autocrine IL11 cis-signaling in hepatocytes that initiates the transition from NAFLD to NASH.

5.3 Results

5.3.1 Synthetic IL11 Trans-Signaling Constructs Cause Hepatocyte Death

Figure 33A:
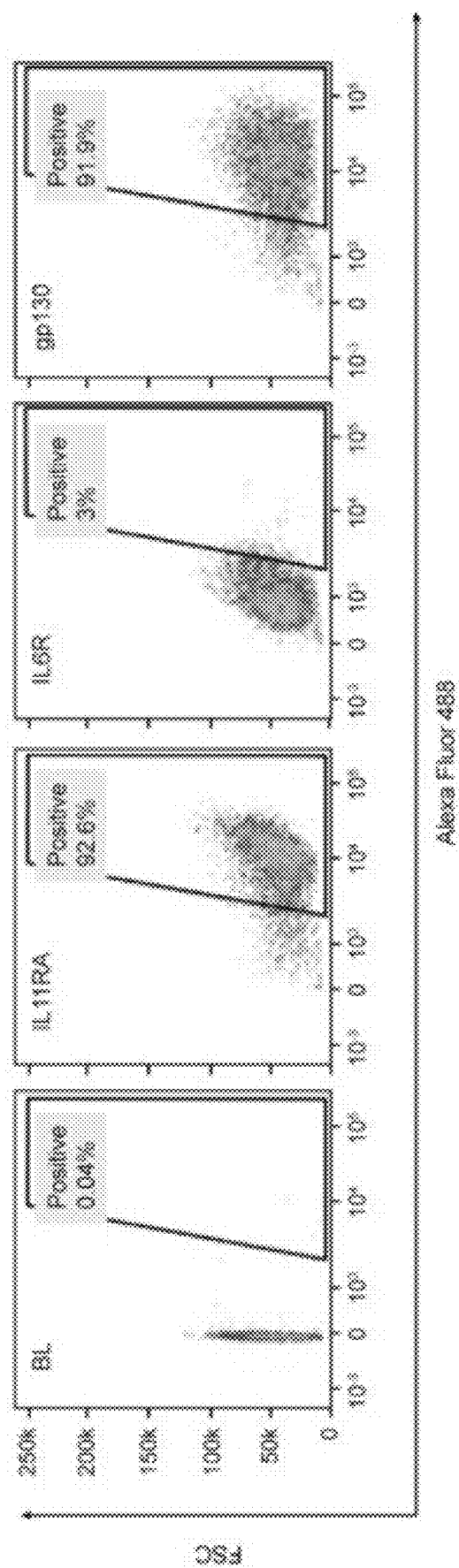
FIGS. 33A to 33K. Scatterplots, box plots, histograms and images relating to the expression of receptors for IL-11 and IL-6 and the effects of IL-11 and IL-6 signalling in primary human hepatocytes. (A) Representative flow cytometry forward scatter (FSC) and fluorescence intensity plots of IL11 RA, IL6R and gp130 staining on hepatocytes. (B) Abundance of IL11RA1 and IL6R reads in hepatocytes at basal based on RNA-seq (left) and Ribo-seq (right) (Transcripts per million, TPM). (C and D) Read coverage of (C) IL11RA1 and (D) IL6R transcripts based on RNA-seq and Ribo-seq of human hepatocytes (n=3). (E and F) (E) Western blots showing ERK, JNK and STAT3 activation status and (F) ALT secretion by hepatocytes following stimulation of either hyperIL11 or hyperIL6 over a dose range. (G) ALT levels in the supernatants of hepatocytes stimulated with hyperIL11 alone or in the presence of increasing amounts of soluble gp130 (sgp130). (H and I) Western blots of hepatocyte lysates showing (H) phosphorylated ERK and JNK and their respective total expression in response to hyperIL11 stimulation alone or with sgp130 and (I) phosphorylated STAT3 and total STAT3 in response to hyperIL6 stimulation with and without sgp130. (J) Representative FSC plots of propidium Iodide (PI) staining of IL11-stimulated hepatocytes in the presence of sgp130 or soluble IL11 RA (sIL11RA). (K) Western blots showing p-ERK, p-JNK and their respective total expression in hepatocytes in response to IL11 stimulation alone or in the presence of sgp130 or sIL11RA. (A-K) primary human hepatocytes; (E-K) 24 h stimulation; (E-K) hyperIL11, hyperIL6, IL11 (20 ng/ml), sgp130, sIL11RA (1 µg/ml). (B, F-G) Data are shown as box-and-whisker with median (middle line), 25th-75th percentiles (box) and min-max values (whiskers).
Figure 33B:
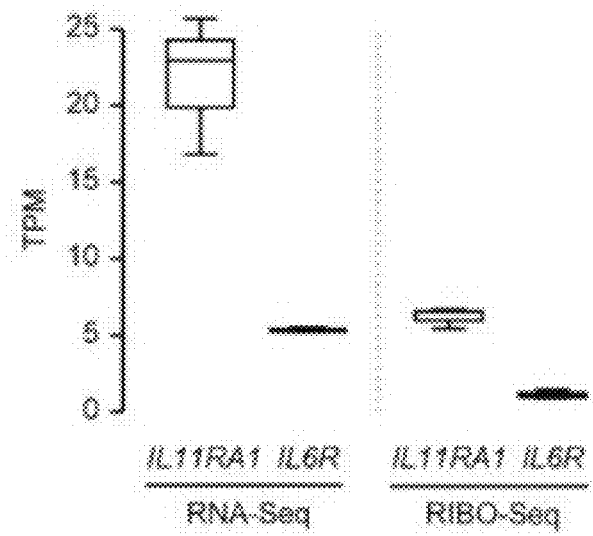
Figure 33C:
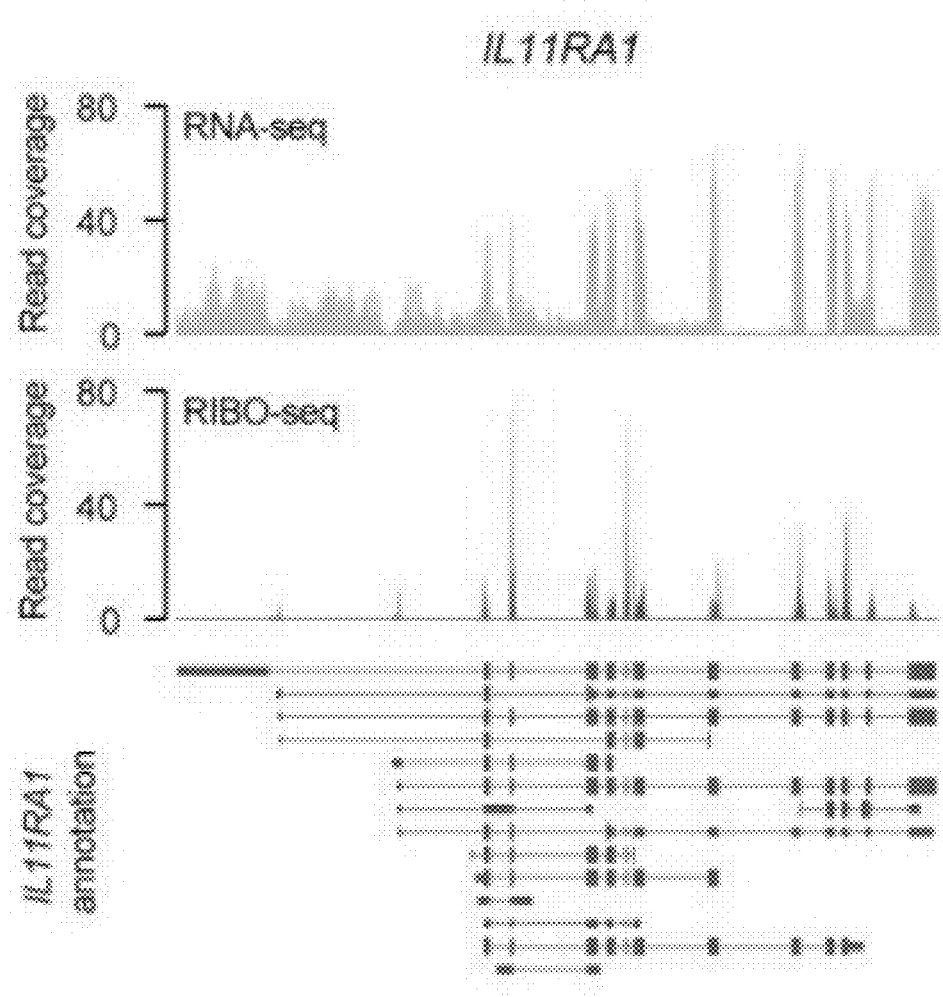
Figure 33D:
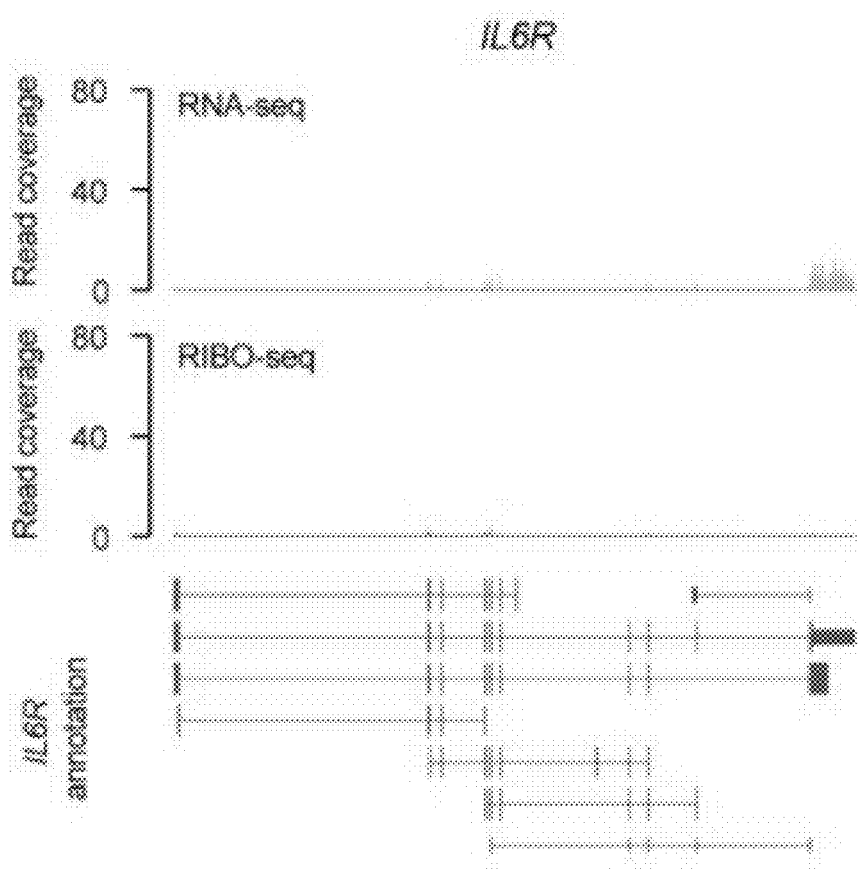
Figure 40A:
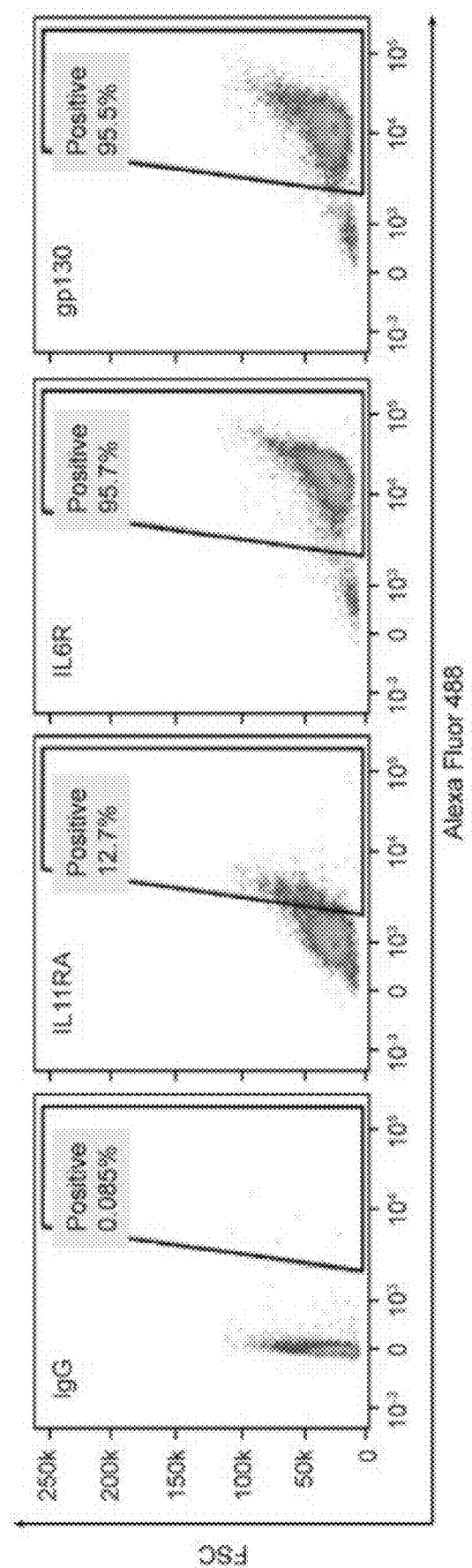
FIGS. 40A to 40I. Scatterplots, box plots histograms, images and graphs relating to the expression of receptors for IL-11 and IL-6 and the effects of IL-11 and IL-6 signalling in primary human hepatocytes. (A) Representative FSC plots of IL11 RA, IL6R, and gp130 staining on activated THP-1 cells. (B) gp130 transcripts in primary human hepatocytes based on RNA-seq and Ribo-seq (Transcripts per million, TPM). (C) Read coverage of gp130 transcripts based on RNA-seq and Ribo-seq of primary human hepatocytes (n=3). (D) Immunofluorescence images (scale bars, 100 μm) of IL11 RA, IL6R, gp130, and Albumin expression in primary human hepatocytes and activated THP-1 cells. (E) Basal levels of soluble IL6R in the hepatocyte media. (F) Quantification of PI staining on IL11-stimulated primary human hepatocytes (PI+ve cells) in the presence of sgp130 or sIL11RA. (G) Dose-dependent effect of increasing concentration of IL11 in the presence of 1 μg/ml of sgp130 or sIL11 RA on ALT levels secreted by primary human hepatocytes. (H) Dose-dependent effect of increasing concentration of either sgp130 or sIL11 RA on IL11-induced ALT secretion. (I) Hepatocyte triglyceride levels following palmitate stimulation in the presence of IgG (2 μg/ml), anti-IL11 RA (X209, 2 μg/ml), or sgp130 (1 μg/ml). (B, G-H) Data are shown as box-and-whisker with median (middle line), 25th-75th percentiles (box) and min-max values (whiskers); (E-F, I) data are shown as mean±SEM; (F-I) Tukey-corrected Student's t-test. (G) for each concentration of IL11, from left to right, conditions shown are: BL, sgp130, sIL11 RA. (H) for each concentration of IL11+ sgp130/IL11RA, from left to right, conditions shown are: sgp130, sIL11 RA.
Figure 40B:
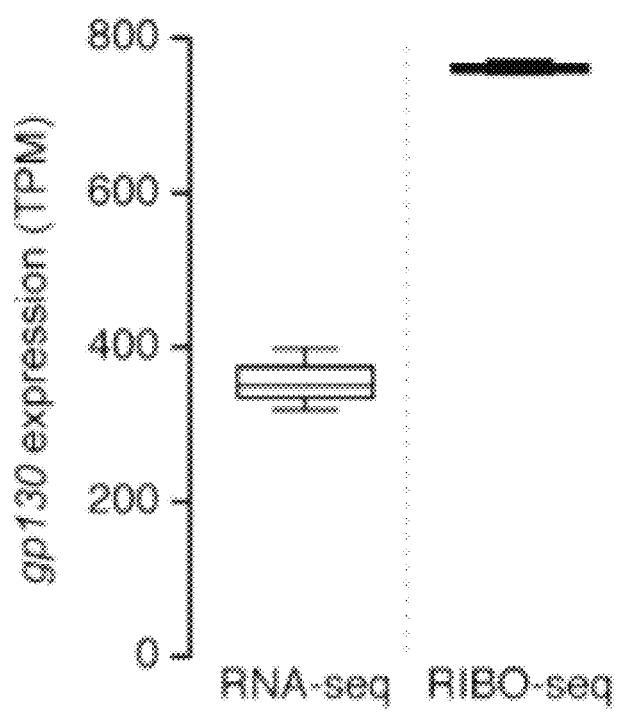
Figure 40C:
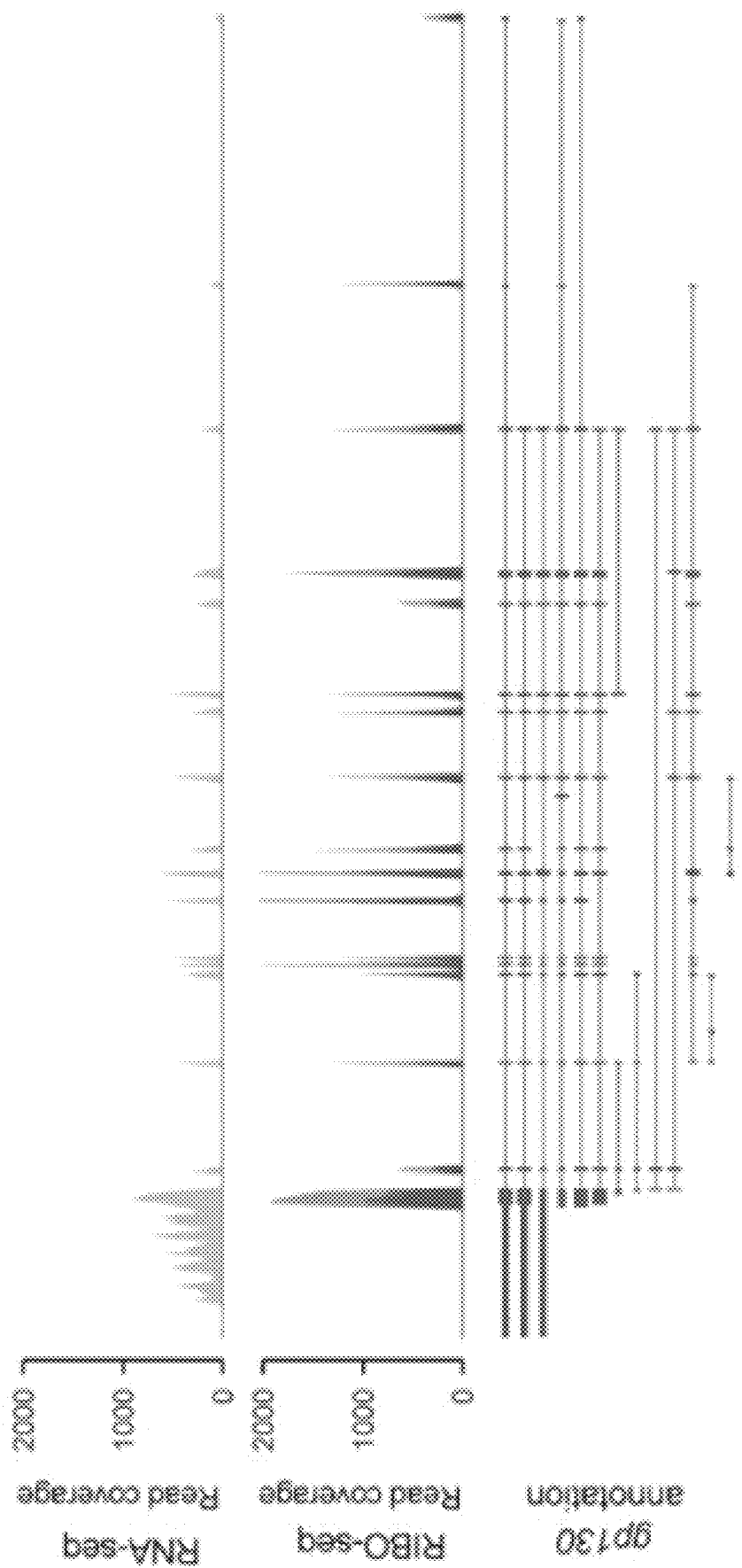
Figure 40D:
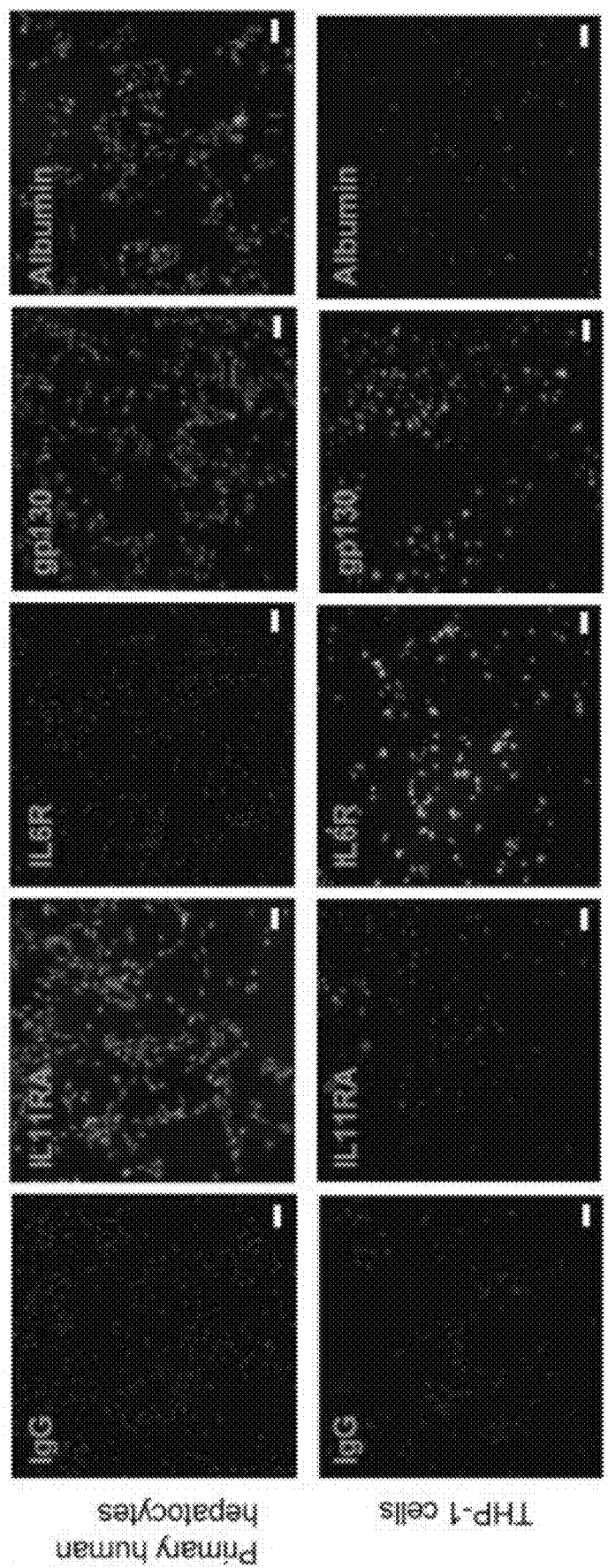
Figure 40E:
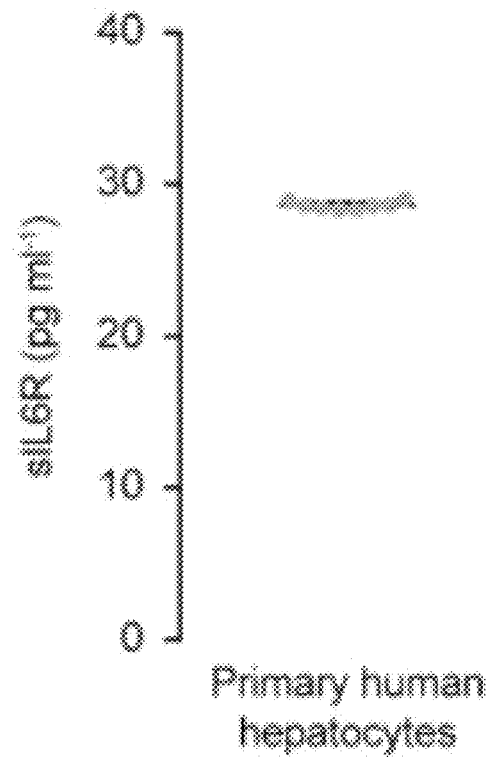

The inventors first assessed the expression levels of IL6R, IL11 RA and gp130 in primary human hepatocytes by flow cytometry. Robust expression of IL11 RA and gp130 was observed in the large majority of cells (92.6% and 91.9%, respectively) but only few hepatocytes (3.0%) expressed IL6R, and at low levels (FIGS. 33A and 40A). In accordance with this result, RNA-seq and Ribo-seq studies found IL11 RA and gp130 transcripts to be highly expressed and actively translated in hepatocytes. By contrast, few IL6R transcripts were observed, and there was almost no detectable IL6R translation (FIGS. 33B-33D, 40B, and 40C). Immunofluorescence staining of hepatocytes corroborated the results of the Ribo-seq data: high IL11 RA expression but no detectable IL6R expression (FIG. 40D). The inventors also did not detect significant levels of IL6R into culture media (levels were just above the lower limit of detection), and so they excluded the possibility that IL6R was being shed (FIG. 40E). Taken together these data show that IL6R is expressed at very low levels in primary human hepatocytes, implying a limited role for IL6 cis-signaling in these cells. However, these cells display strong co-expression of both IL11 RA and gp130.

Figure 33E:
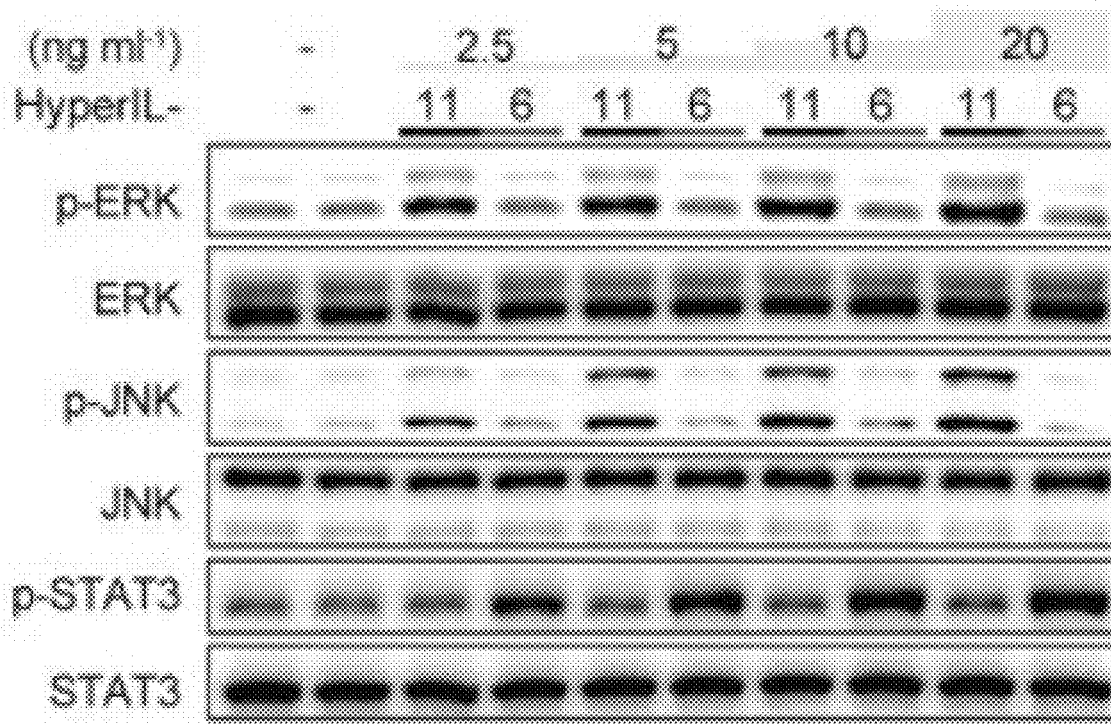

Given the lack of IL6R expression by human hepatocytes the inventors employed a synthetic IL6 trans-signaling construct (hyperIL6) to activate IL6 signaling in these cells and compared this with a synthetic IL11 trans-signaling complex (hyperIL11). HyperIL11, like IL11 itself (Widjaja et al.), activated ERK and JNK in a dose-dependent manner (2.5 ng/ml to 20 ng/ml). By contrast, IL6 trans-signaling did not activate non-canonical signaling pathways but instead dose-dependently induced STAT3 activation (FIG. 33E). Thus, IL11 or IL6 in a pre-formed synthetic complex with their cognate receptors activate different intracellular pathways when bound to gp130 on hepatocytes, which is a novel and intriguing finding.

Figure 33F:
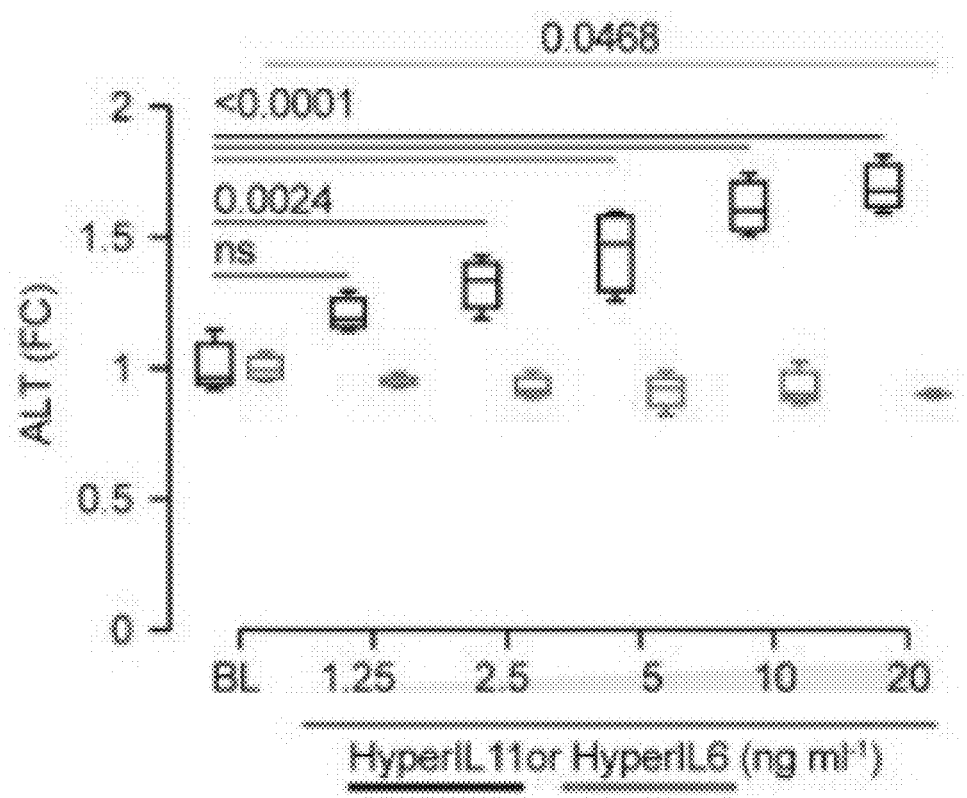
Figure 33G:
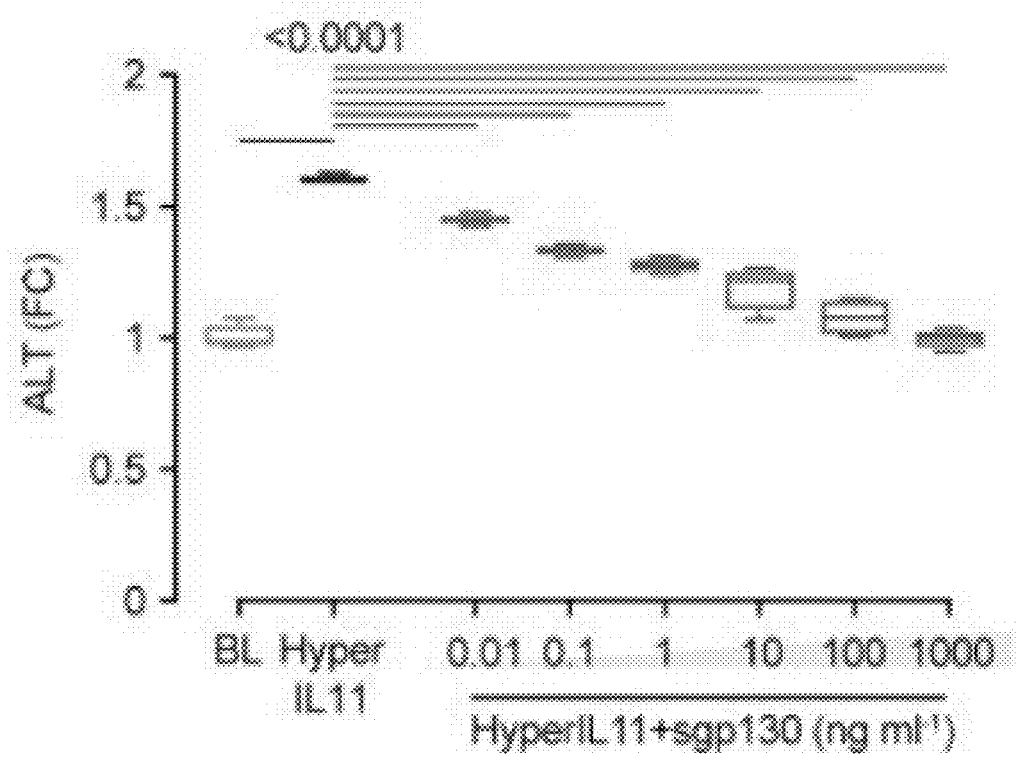
Figure 33H:
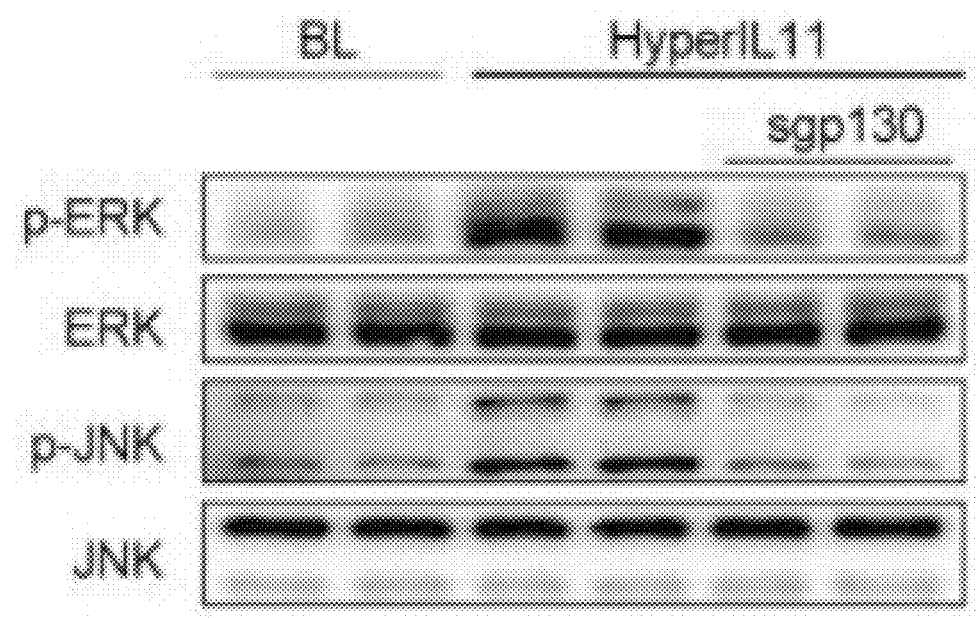
Figure 33I:
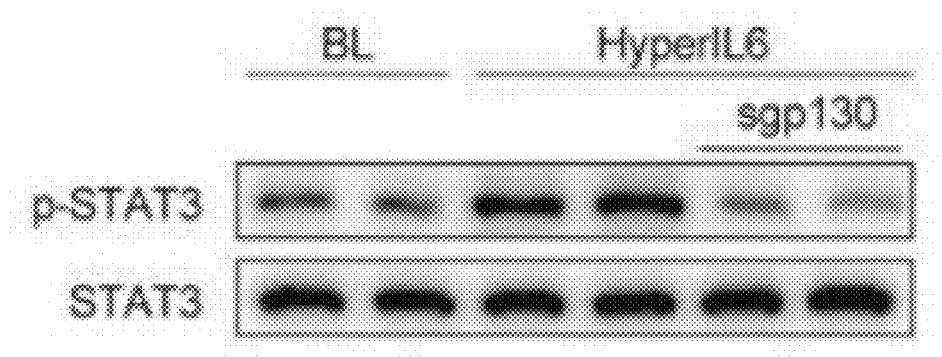

HyperIL11 caused a dose-dependent increase in alanine transaminase (ALT) in the media of primary human hepatocyte cell cultures whereas hyperIL6 (20 ng/ml) was found to have a significant, albeit limited, cytoprotective effect (fold change (FC)=0.9; P=0.0468) (FIG. 33F). Soluble gp130 (sgp130) is an inhibitor of trans-signaling complexes acting through gp130 (Schmidt-Arras and Rose-John, 2016). Consistent with its reported decoy effects, sgp130 blocked the activation of signaling pathways downstream of both hyperIL11 (p-ERK/p-JNK) and hyperIL6 (p-STAT3) and also inhibited the hepatotoxic effects of hyperIL11 (FIGS. 33G-33I).

Figure 33J:
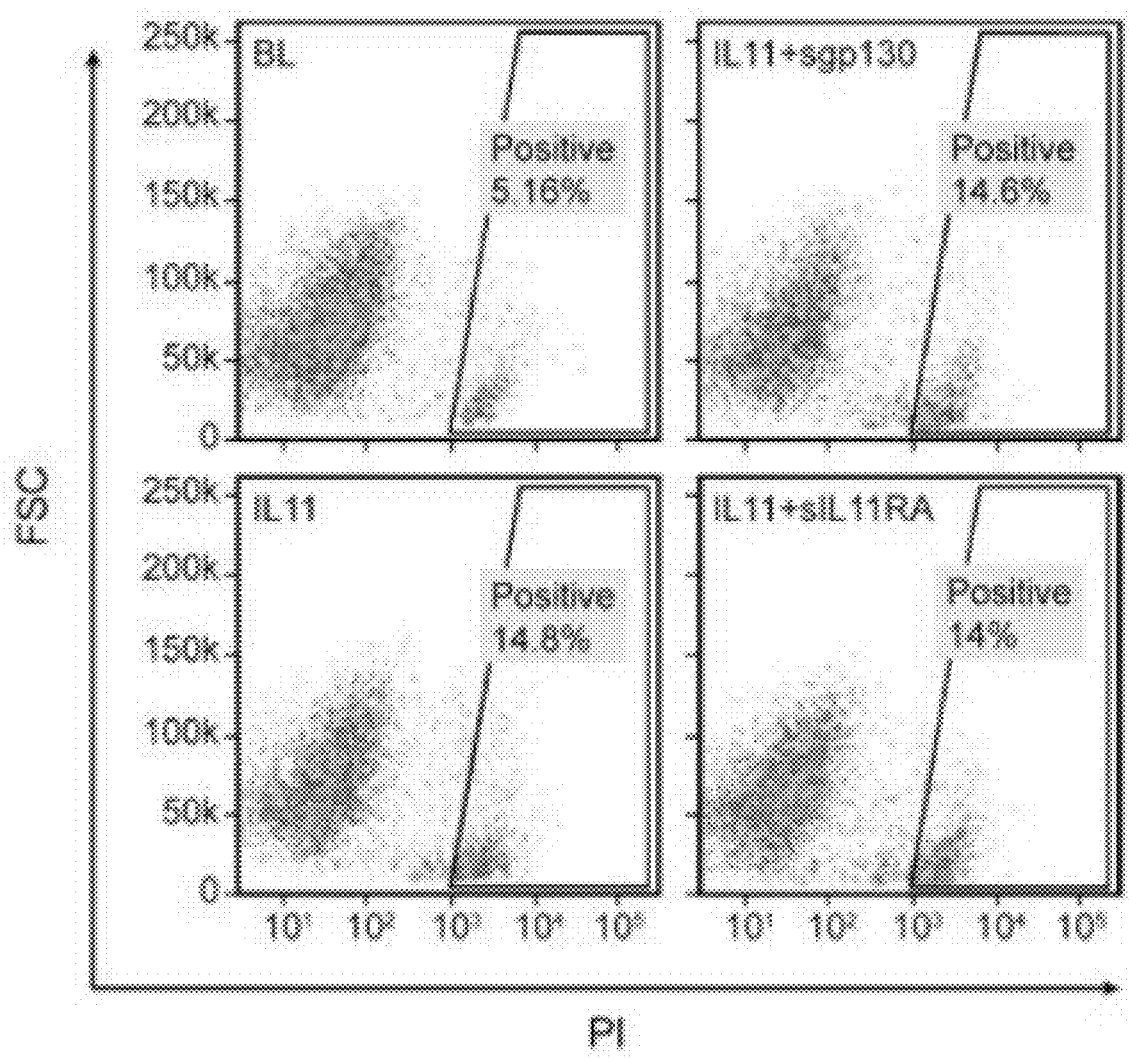
Figure 33K:
Figure 40F:
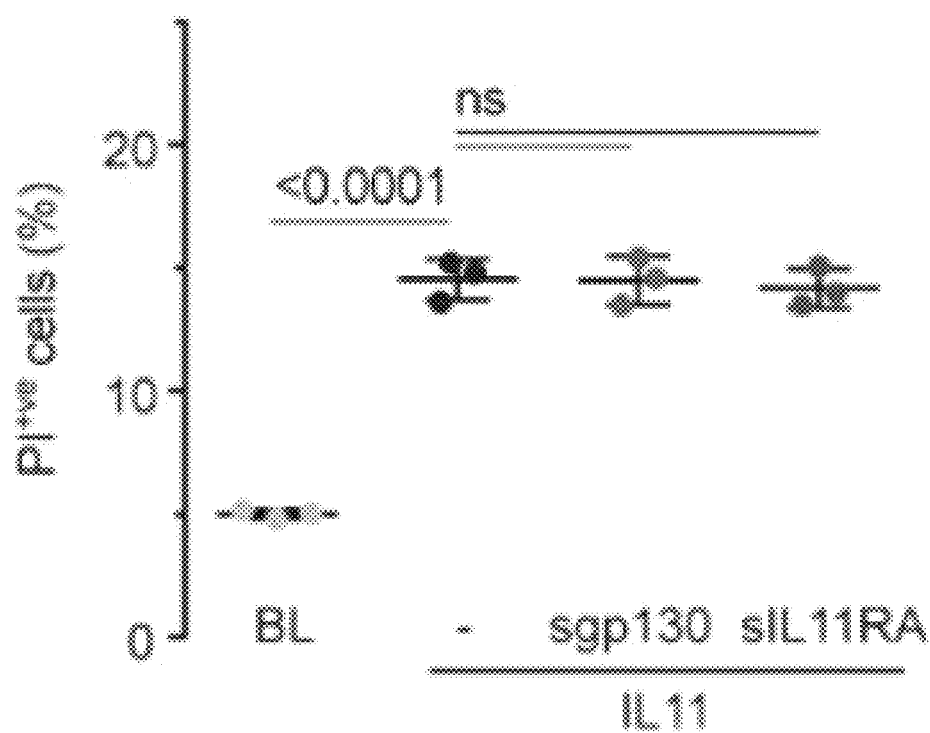
Figure 40G:
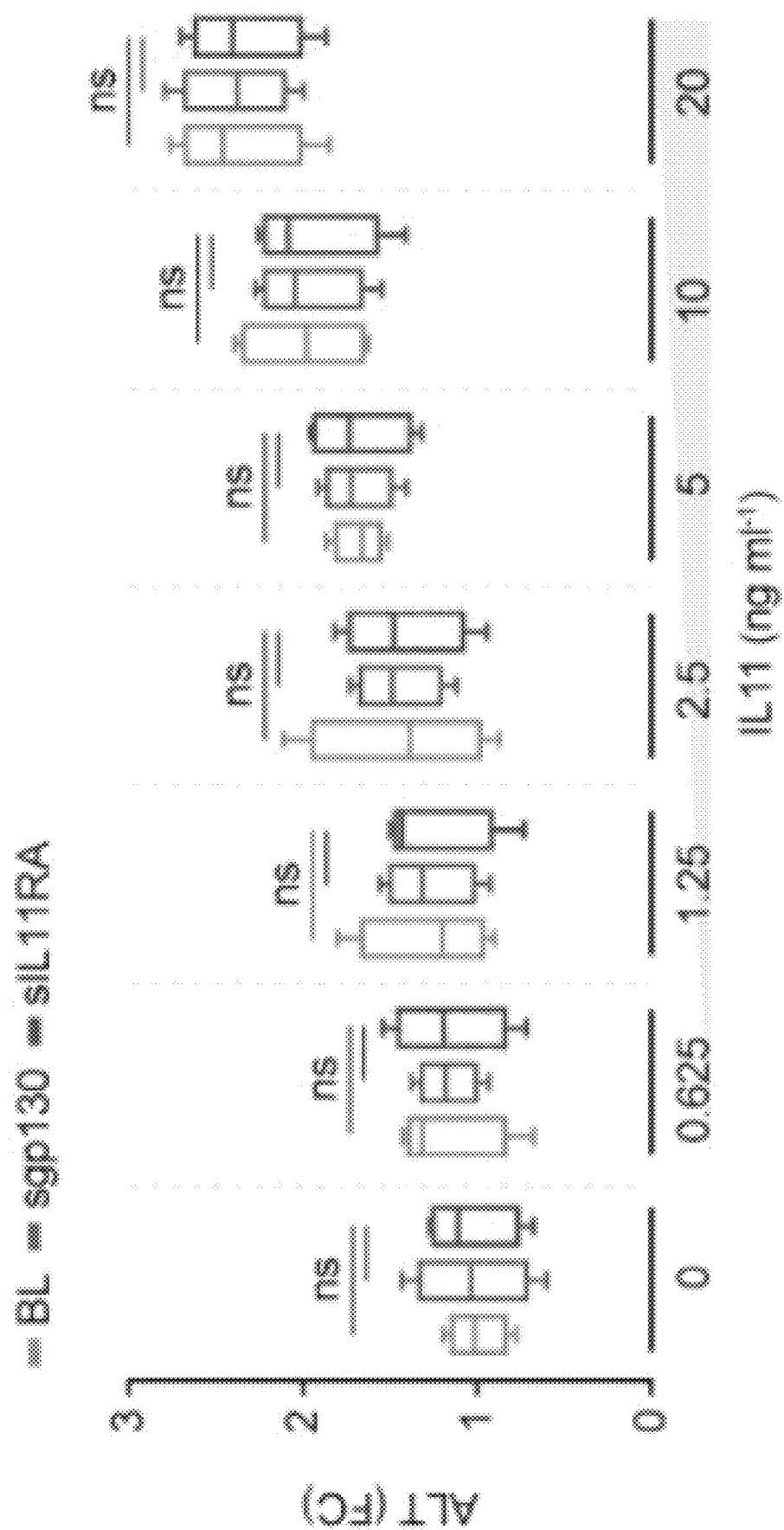
Figure 40H:
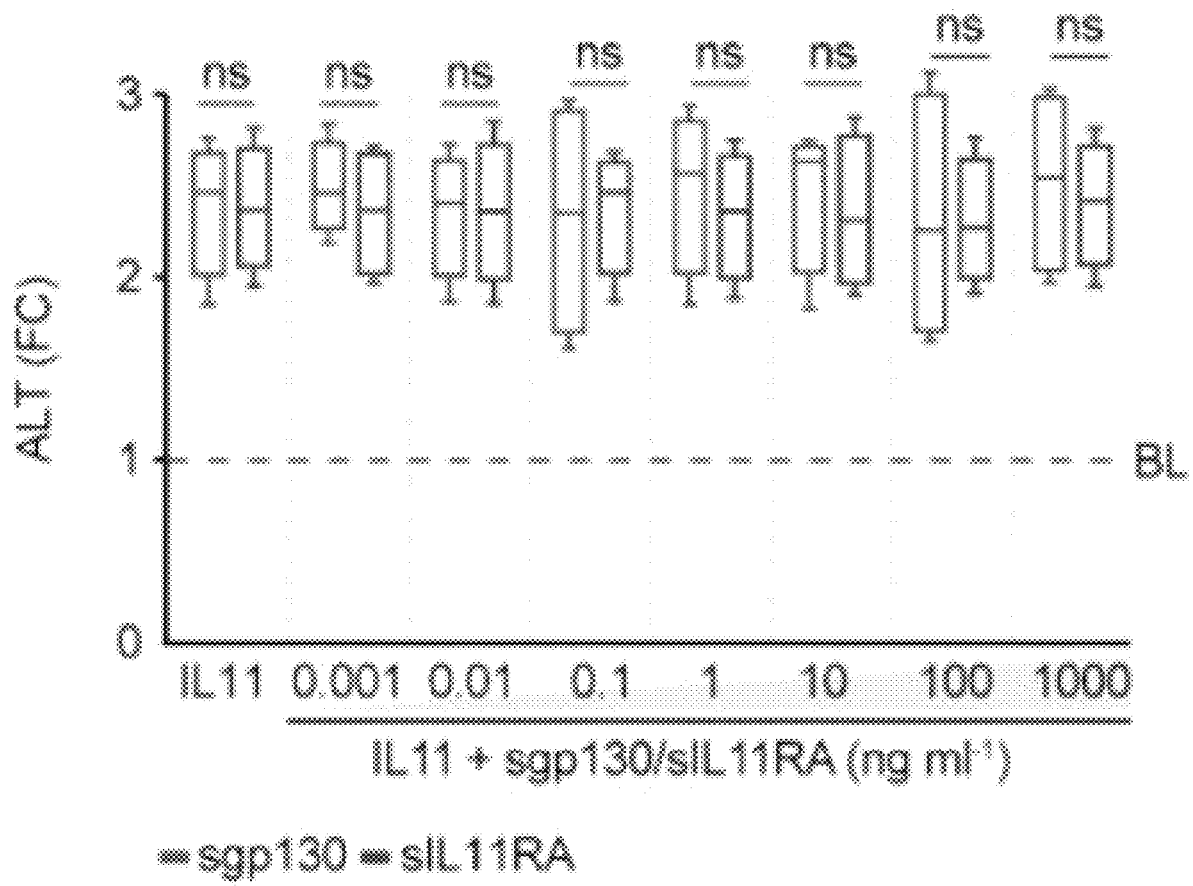

The inventors then performed experiments in order to detect IL11 trans-signaling in the absence of the artificial protein complexes hyperIL6 or hyperIL11. Cells were stimulated with IL11 in the presence of either soluble gp130 (sgp130, to inhibit putative trans-signaling) or soluble IL11 RA (sIL11RA, to potentiate putative trans-signaling). IL11-induced hepatocyte death and signaling were unaffected by sgp130 or sIL11 RA (FIGS. 33J-33K and 40F). Furthermore, IL11 dose-dependently (0.625 ng/ml to 20 ng/ml) caused hepatocyte cell death, which was unaffected by the addition of sgp130 (1 µg/ml) or sIL11RA (1 µg/ml) (FIG. 40G). Reciprocally, increasing doses of sgp130 or sIL11RA had no effect on ALT release from IL11-stimulated hepatocytes (FIG. 40H). These data suggest that IL11 trans-signaling may not exist in the absence of synthetic constructs.

5.3.2 IL11 Cis-Signaling Underlies Lipotoxicity in Hepatocytes

Figure 34A:
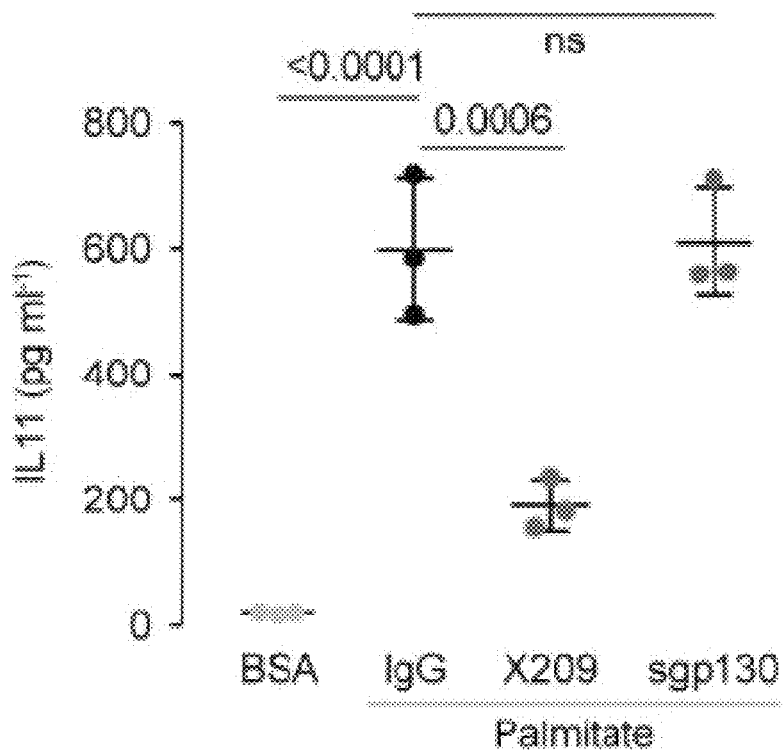
FIGS. 34A to 34K. Graphs, scatterplots, and images showing that lipid laden hepatocytes secrete IL11, which drives multiple lipotoxic phenotypes through autocrine IL11 cis-signaling. (A-K) Data for palmitate loading experiment on primary human hepatocytes in the presence of either IgG (2 µg/ml), anti-IL11RA (X209, 2 µg/ml), or sgp130 (1 µg/ml). (A) IL11, (B) IL6, (C) CCL2, and (D) CCL5 protein secretion levels as measured by ELISA of supernatants. (E and F) (E) Representative FSC plots and (F) quantification of PI+ve hepatocytes stimulated with palmitate. (G) ALT levels in supernatants. (H) Hepatocyte glutathione (GSH) levels. (I) Representative fluorescence images of DCFDA staining (ROS detection; scale bars, 100 µm). (J) Western blots of pERK, ERk, pJNK, JNK, cleaved Caspase3, Caspase3, NOX4, FASN and GAPDH (K) Representative images of Oil Red O staining (scale bars, 100 µm). (A-D, F-H) Mean±SD; Tukey-corrected Student's t-test.
Figure 34B:
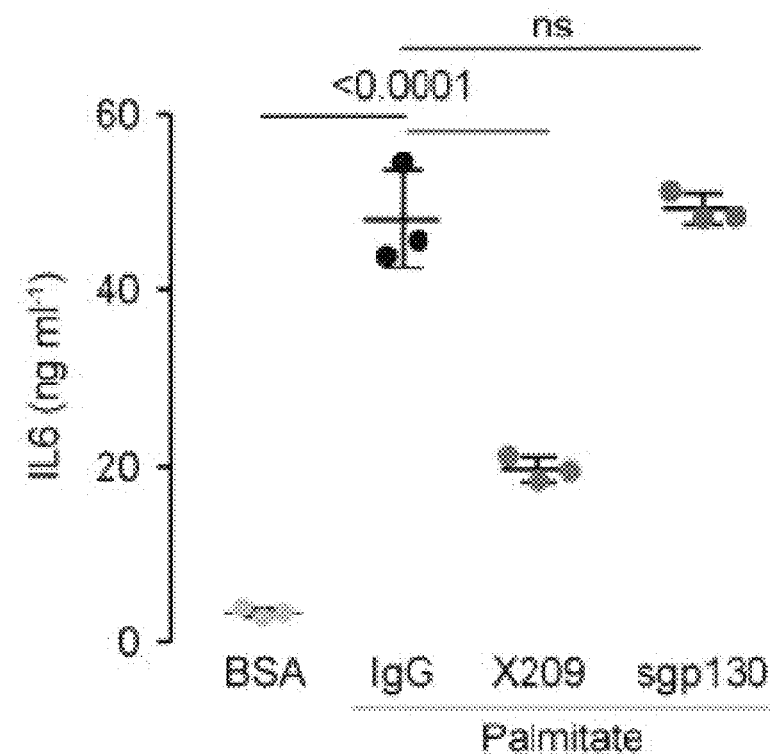
Figure 34C:
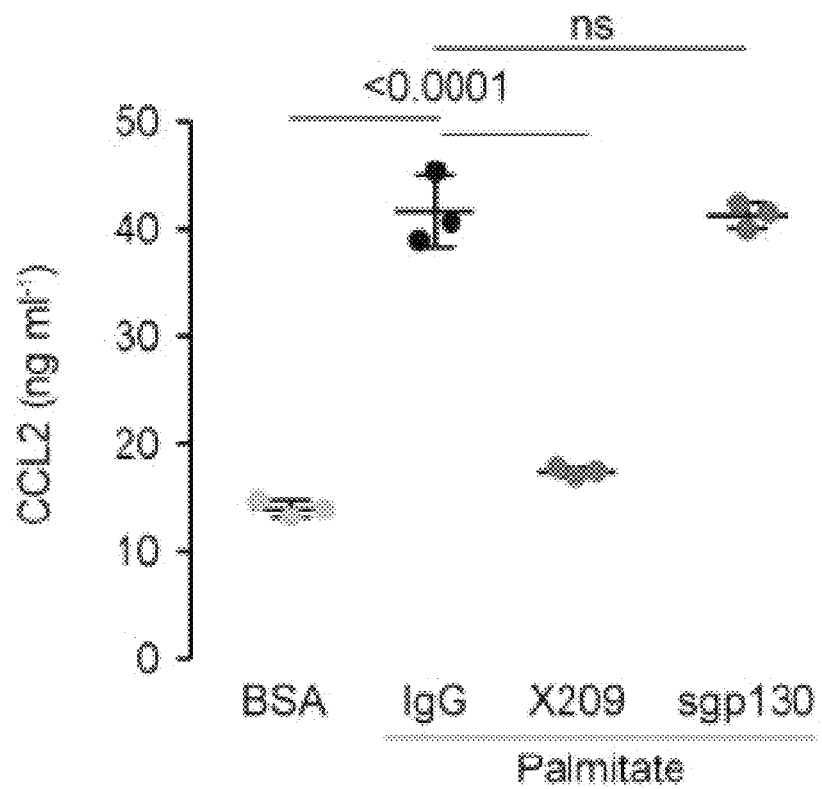
Figure 34D:
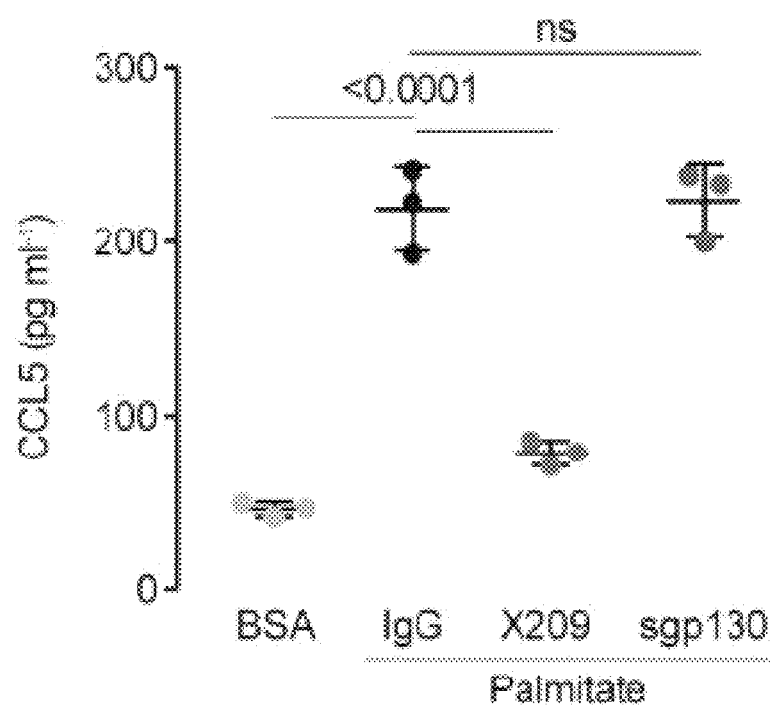
Figure 34E:
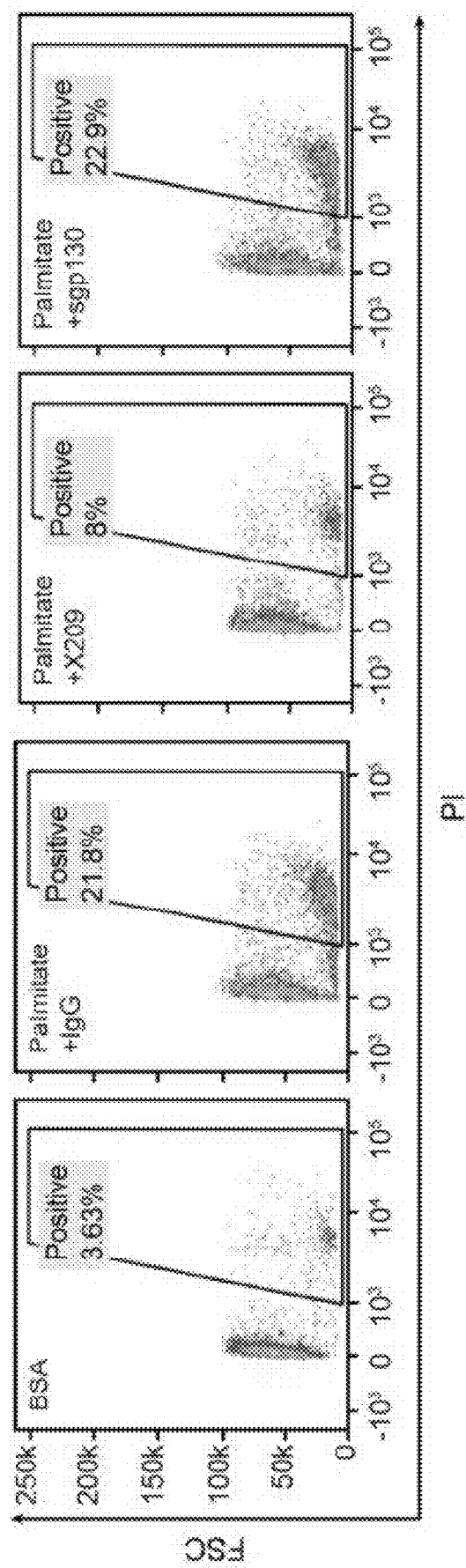
Figure 34F:
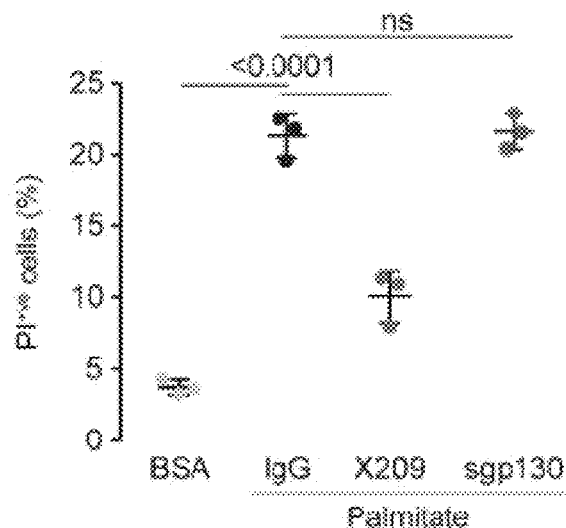
Figure 34G:
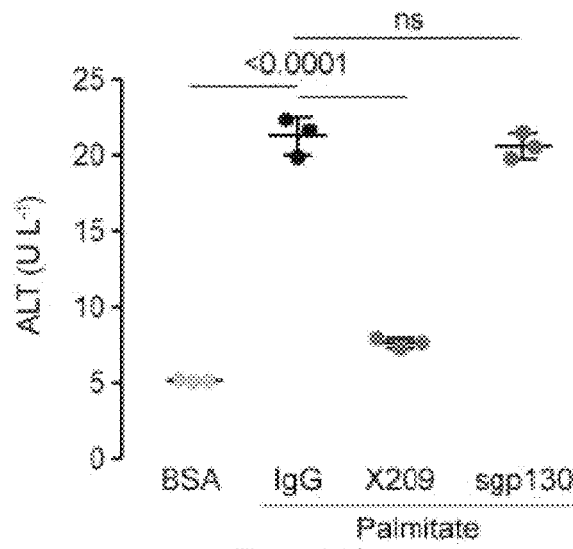

In order to address the role of IL11 in fatty liver disease, the inventors modelled hepatocyte lipotoxicity, viewed as an initiating pathology for NASH and related to cytokine release from damaged hepatocytes (Friedman et al., 2018). Hepatocytes were loaded with palmitate:BSA mixture at a ratio of 6:1 using a concentration of saturated fatty acids (sFSs) seen in the serum of NAFLD patients (Kleinfeld et al., 1996). Compared to control, sFA loaded cells secreted greater amounts of IL11 (FC=28, P<0.0001) and also IL6, CCL2 and CCL5 (FIGS. 34A-34D). Lipid loaded hepatocytes underwent apoptotic cell death by FACS and also necrotic release of ALT (FIGS. 34E-34G).

Figure 34H:
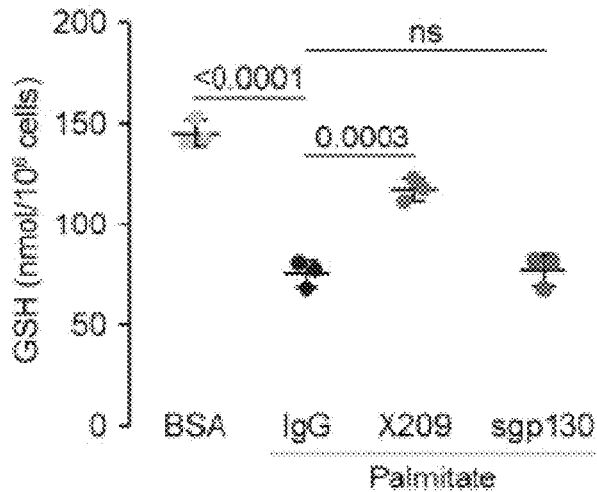
Figure 34I:
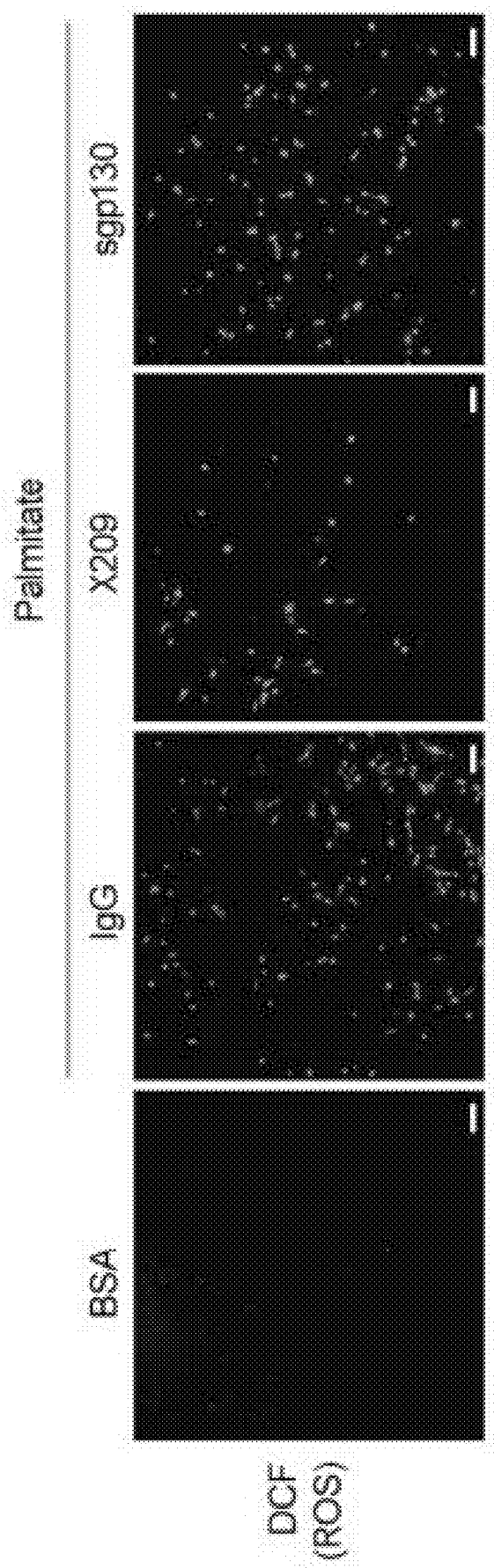

To test if IL11 secretion from lipid loaded hepatocytes was functionally related to lipotoxicity in a cis- or trans-signaling manner, cells were incubated either with anti-IL11 RA antibody (X209) or sgp130. X209 reduced the secretion of all cytokines, including IL11 itself, whereas sgp130 had no effect (FIGS. 34A-34G). This suggests an autocrine loop of IL11 cis-signaling in hepatocyte lipotoxicity. The production of reactive oxygen species (ROS) from damaged mitochondria is important for lipotoxicity (Farrell et al., 2018) and ROS from NOX4 is also pertinent in NASH (Bettaieb et al., 2015). X209 was found to prevent ROS production in sFA-loaded hepatocytes, and that this was accompanied by partial restoration of glutathione (GSH) levels (FIGS. 34H and 34I).

Figure 34J:
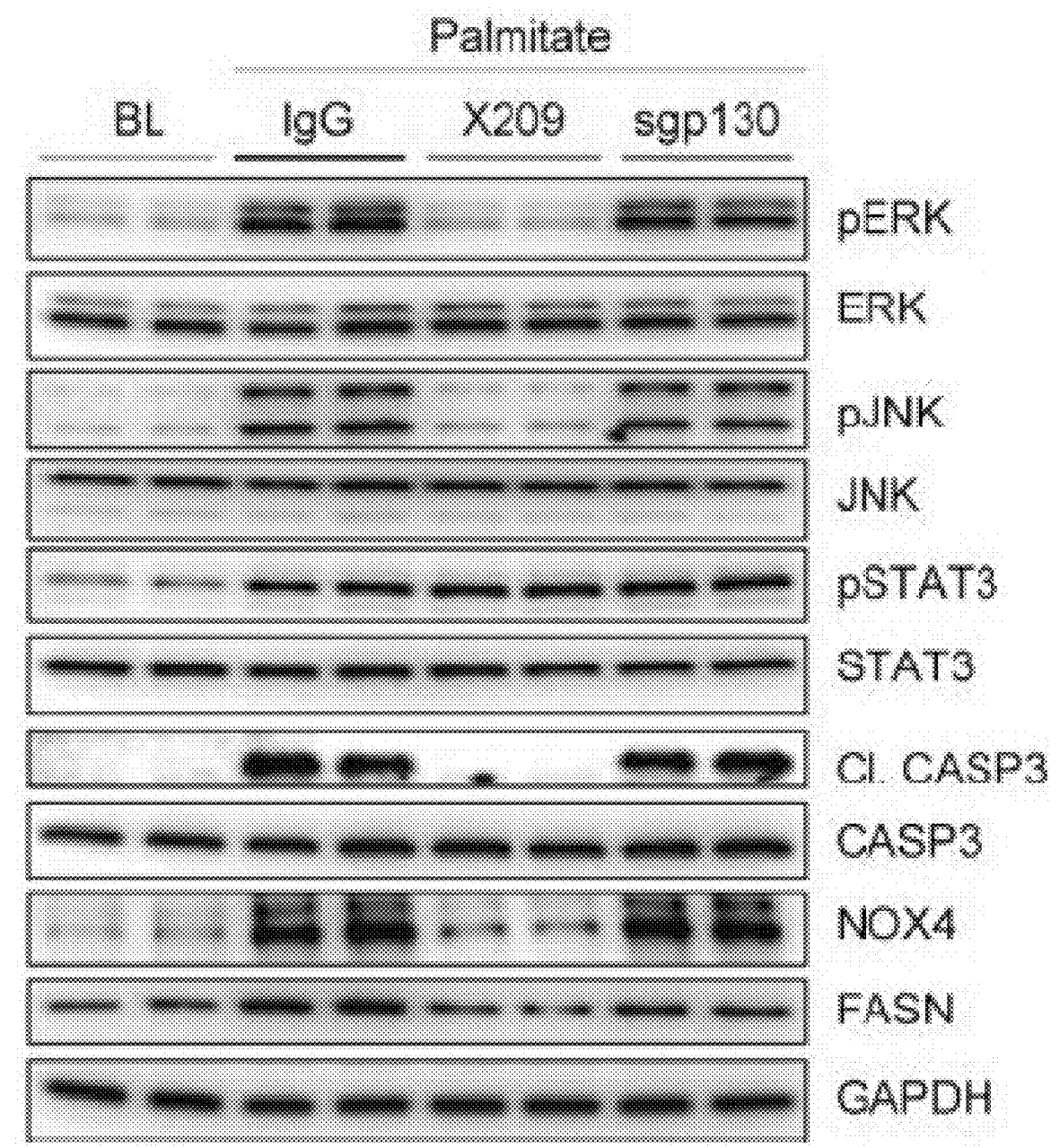
Figure 34K:
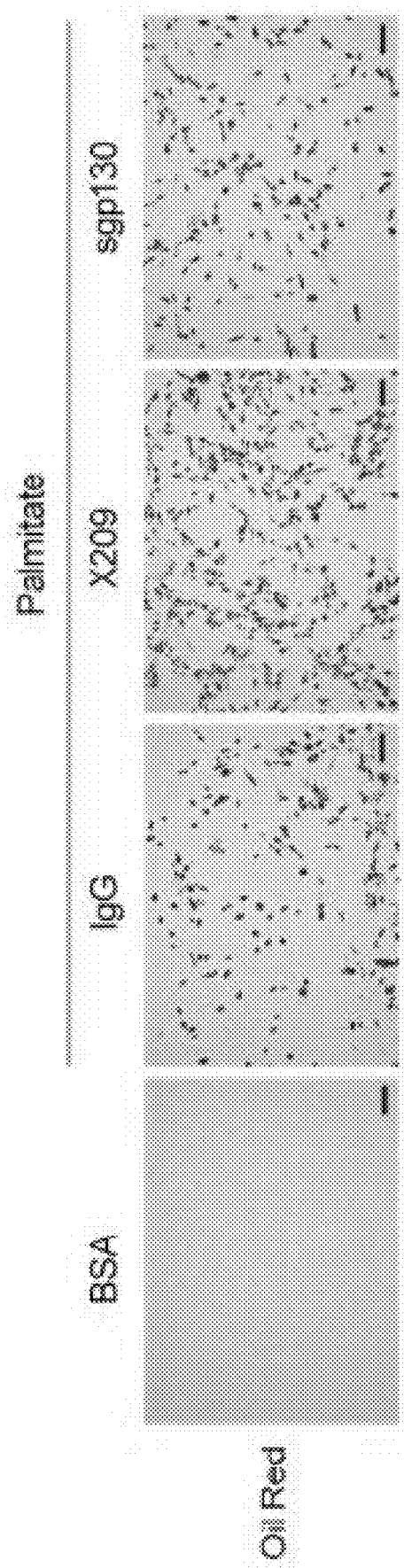
Figure 40I:
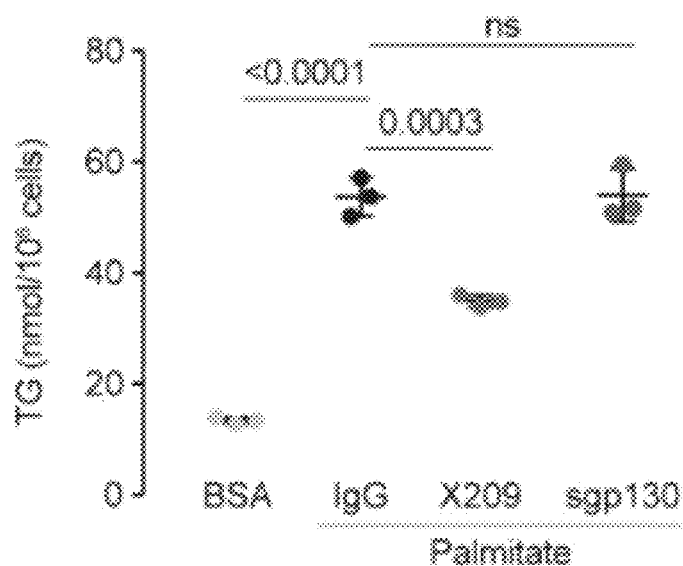

The inventors next examined signaling events. Lipotoxicity is strongly associated with activation of JNK, which drives caspase-3 activation and lipoapoptosis. Accordingly, palmitate loaded hepatocytes displayed JNK activation and caspase-3 cleavage, as well as ERK phosphorylation (FIG. 34J). This pattern was notably similar to the effects seen with IL11 stimulation (FIG. 33E). X209 largely inhibited palmitate-induced signaling events as well as fatty acid synthase (FASN) upregulation, caspase3 activation and triglyceride accumulation despite similar sFA uptake by hepatocytes (FIGS. 34J, 34K, and 40I). NOX4 was upregulated by palmitate and also inhibited by X209 (FIG. 34J). While STAT3 was activated by sFA loading, this effect was found to be independent of IL11 RA-mediated signaling and unrelated to lipoapoptosis (FIG. 34J). Throughout these experiments sgp130 had no effect. Taken together, these data show that palmitate-induced IL11 secretion and autocrine, feed-forward IL11 cis-signaling is important for hepatocyte lipotoxicity.

5.3.3 No Evidence for IL11 or IL6 Trans-Signaling in Two NASH Models

The inventors then investigated whether trans-signaling underlies NASH in vivo using two preclinical mouse NASH models: The Western Diet supplemented with fructose (WDF) model and the methionine- and choline-deficient high fat diet (HFMCD) model. The WDF model is associated with obesity, hyperlipidemia and insulin resistance and seen as translatable to common forms of human NASH, as in diabetic patients. The HFMCD model stimulates rapid onset NASH, specifically driven by hepatocyte lipotoxicity, which is associated with weight loss in the absence of insulin resistance. Lipotoxicity is common to both models whereas obesity and insulin resistance are not.

Figure 35A:
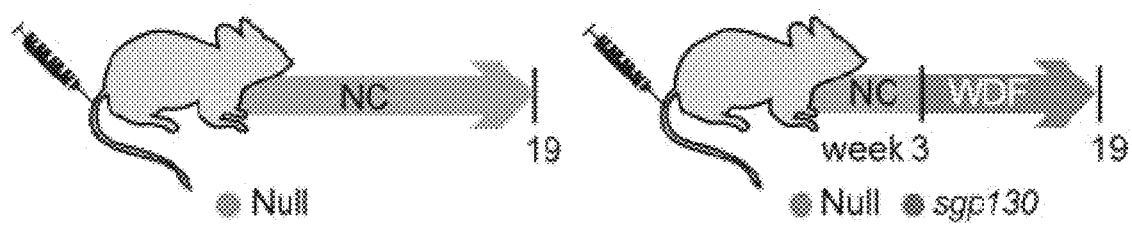
FIGS. 35A to 35P. Schematic, images, and box plots showing that inhibition of IL6 family cytokine trans-signaling has no effect on NASH or metabolic phenotypes in mice on Western Diet supplemented with fructose. (A) Schematic of WDF feeding in mice with hepatocyte-specific expression of sgp130 for data shown in (B-P). Three weeks following AAV8-Alb-Null or AAV8-Alb-sgp130 virus injection, mice were fed WDF for 16 weeks. (B) Western blots showing hepatic levels of sgp130, IL11, IL6, and GAPDH as internal control. (C) Serum IL11 levels. (D) Serum IL6 levels. (E) Representative gross anatomy and H&E stained images of livers. (F) Liver weight. (G) Hepatic triglycerides content. (H) Serum ALT levels. (I) serum AST levels. (J) Hepatic collagen levels. (K) Fasting blood glucose levels. (L) Serum triglycerides levels. (M) Serum cholesterol levels. (N) Hepatic GSH content. (O) Hepatic pro-inflammatory and fibrotic genes expression heat map (values are shown in FIGS. 41D and 41E). (P) Western blots of hepatic p-ERK, ERK, p-JNK, JNK, p-STAT3, and STAT3. (C-N) Data are shown as box-and-whisker with median (middle line), $25^{th}$-$75^{th}$ percentiles (box) and min-max values (whiskers), Tukey-corrected Student's t-test; from left to right, conditions shown are: NC Null, WDF Null, WDF sgp130.
Figure 41A:
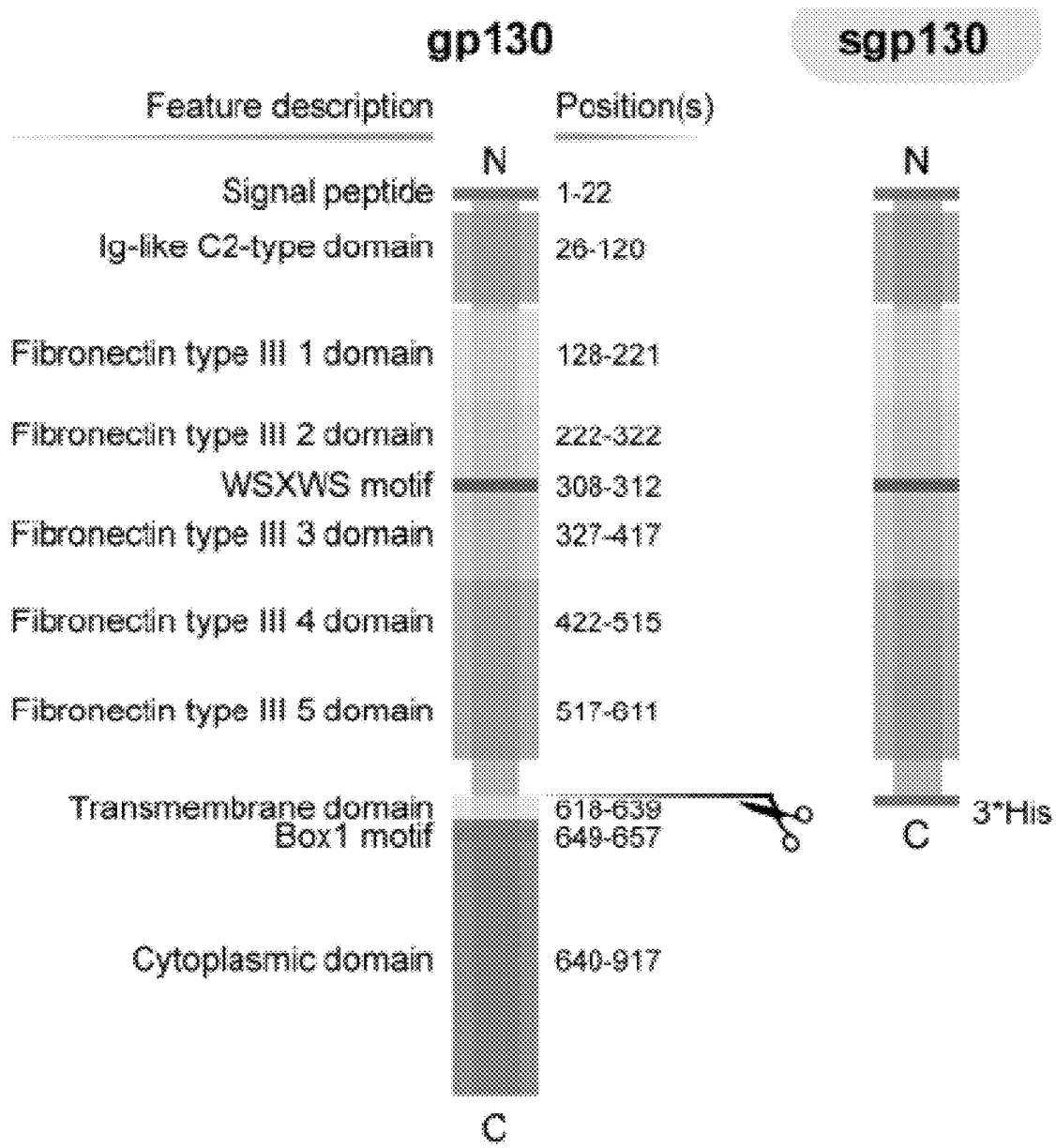
FIGS. 41A to 41E. Schematic, box plots and graph showing that sgp130 expression does not protect mice from WDF-induced liver and obesity phenotypes. (A) Schematic of gp130 protein domain structure and its amino acid position (left) and the domains that were used to construct sgp130 in this study (right). (B-E) Data for WDF-sgp130 in vivo experiments as shown in FIG. 35A. (B) Serum gp130 levels in NC-fed control mice and WDF-fed AAV8-Alb-Null- and AAV8-Alb-sgp130-injected mice. (C) Effect of 16 weeks of WDF on body weight of AAV8-Alb-Null- and AAV8-Alb-sgp130-injected mice. Data are shown as mean±SEM. (D and E) Hepatic mRNA expression of (D) pro-inflammatory markers (Tnfα, Ccl2, Ccl5) and (E) fibrosis markers (Col1a1, Col1a2, Col3a1, Acta2) as shown in FIG. 35O. (B, D-E) Data are shown as box-and-whisker with median (middle line), 25th-75th percentiles (box) and min-max values (whiskers), Tukey-corrected Student's t-test; from left to right, conditions shown are: NC Null, WDF Null, WDF sgp130.
Figure 41B:
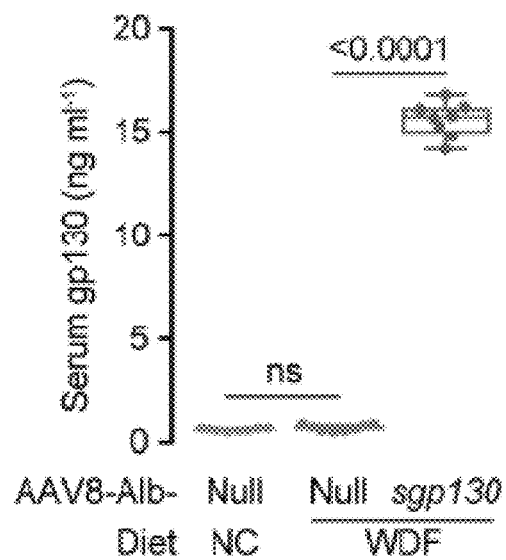
Figure 42A:
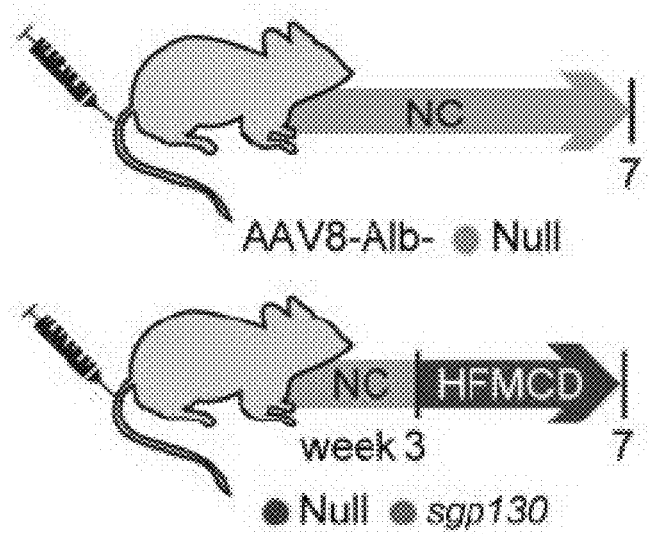
FIGS. 42A to 42N. Schematic, images and box plots showing that inhibition of putative trans-signaling of IL6 family members has no effect on NASH phenotypes in mice on HFMCD diet. (A) Schematic of mice with hepatocyte-specific expression of sgp130 in mice on HFMCD diets for data shown in (B-N). Mice were intravenously injected with either AAV8-Alb-Null or AAV8-Alb-sgp130 and fed HFMCD for 4 weeks. (B) Western blots showing hepatic levels of sgp130, IL11 and IL6 with GAPDH shown as internal control. (C) Serum gp130 levels. (D) Serum IL11 levels. (E) Serum IL6 levels. (F) Representative gross anatomy and H&E stained images of livers. (G) Hepatic triglycerides content. (H) Serum ALT levels. (I) Serum AST levels. (J) Hepatic GSH content. (K) Hepatic collagen levels (L and M) Hepatic mRNA expression of (L) pro-inflammatory markers (Tnfα, Ccl2, Ccl5) and (M) fibrosis markers (Col1a1, Col1a2, Col3a1, Acta2). (N) Western blots of hepatic p-ERK, ERK, p-JNK, JNK, p-STAT3, STAT3. (C-E, G-M) Data are shown as box-and-whisker with median (middle line), $25^{th}$-$75^{th}$ percentiles (box) and min-max values (whiskers), Tukey-corrected Student's t-test; from left to right, conditions shown are: NC Null, HFMCD Null, HFMCD sgp130.

Three weeks prior to starting either the WDF and HFMCD diet, mice were injected with an AAV8 virus encoding either albumin promoter-driven sgp130 (AAV8-Alb-sgp130), which contains the whole extracellular domain of mouse gp130 protein (amino acid 1 to 617), or albumin promoter alone (AAV8-Alb-Null) (FIGS. 35A, 41A, and 42A). AAV8-Alb-sgp130 administration induced high levels of sgp130 in the liver, which was also detectable in the peripheral circulation, suitable for both local and systemic inhibition of putative IL6 or IL11 trans-signaling (FIGS. 35B, 41B, 42B-42C).

Figure 35B:
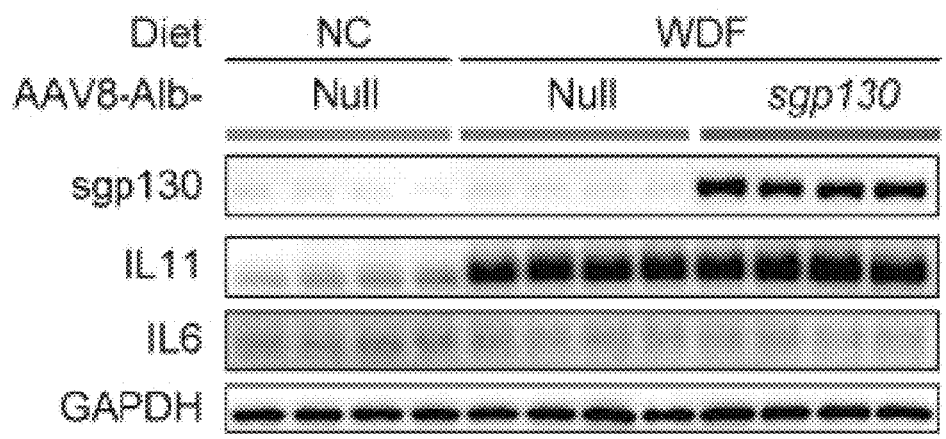
Figure 35C:
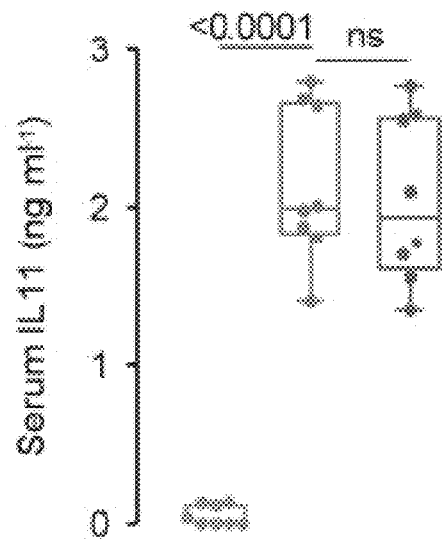
Figure 35D:
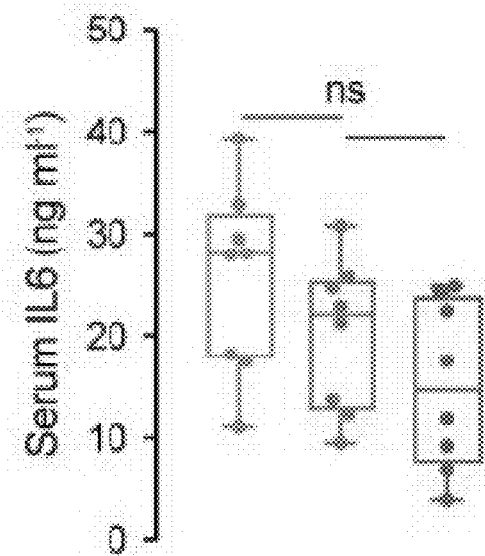
Figure 35E:
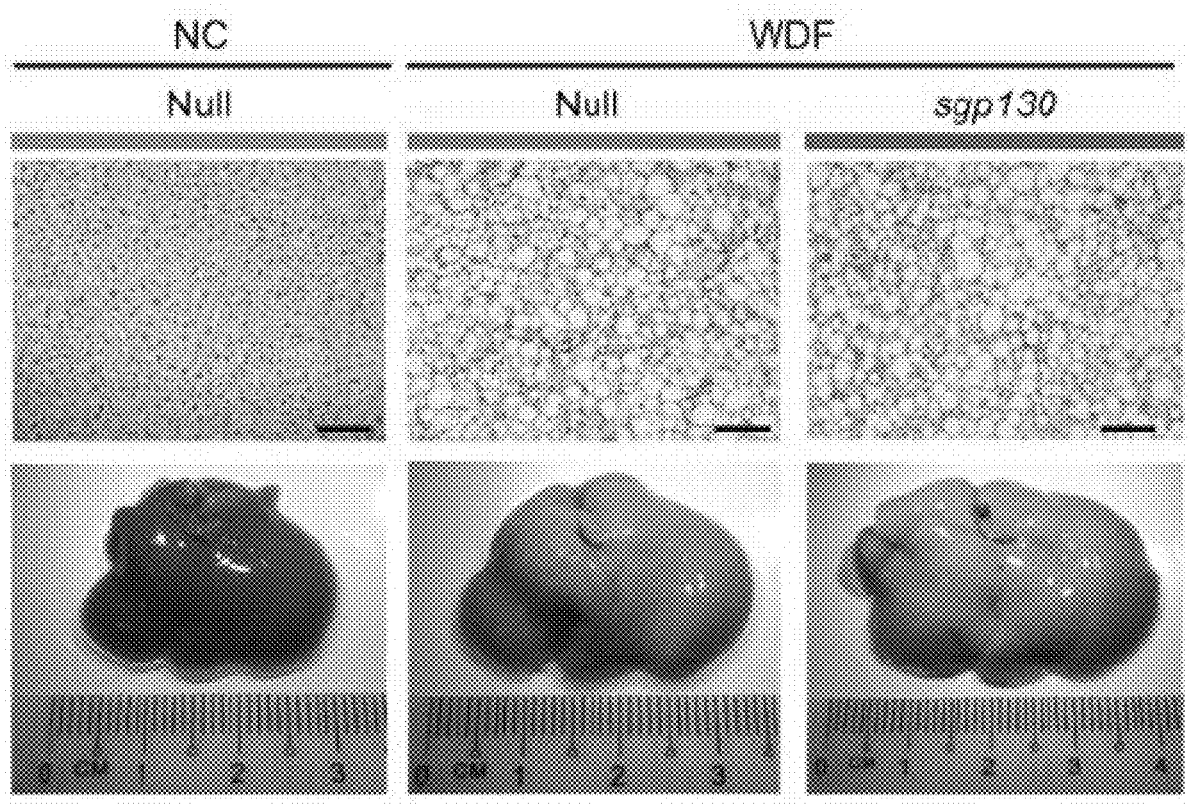
Figure 35F:
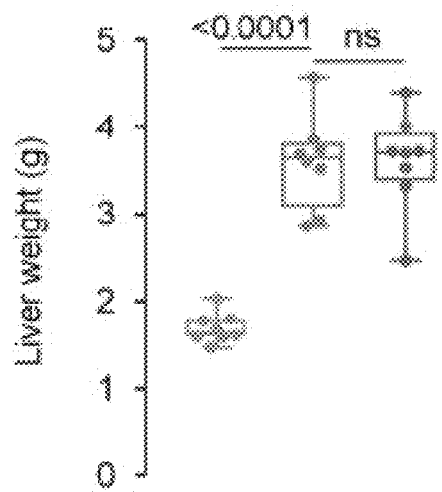
Figure 35G:
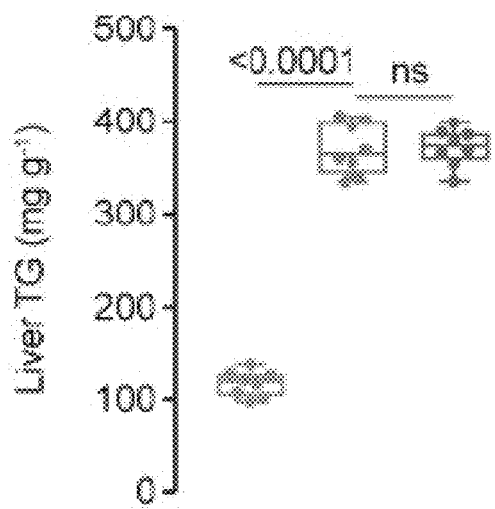
Figure 35H:
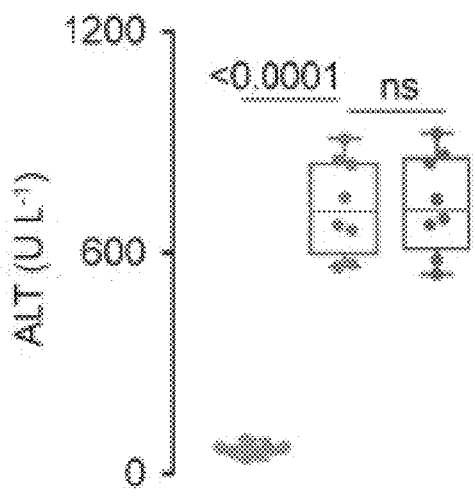
Figure 35I:
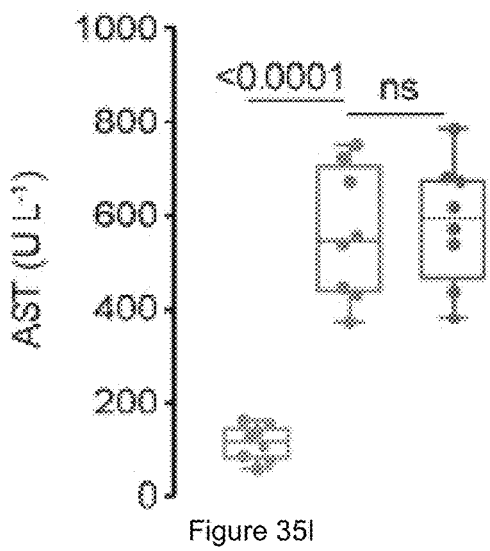
Figure 35J:
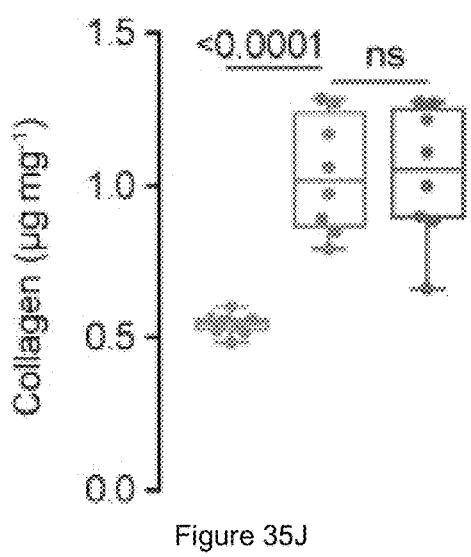
Figure 35K:
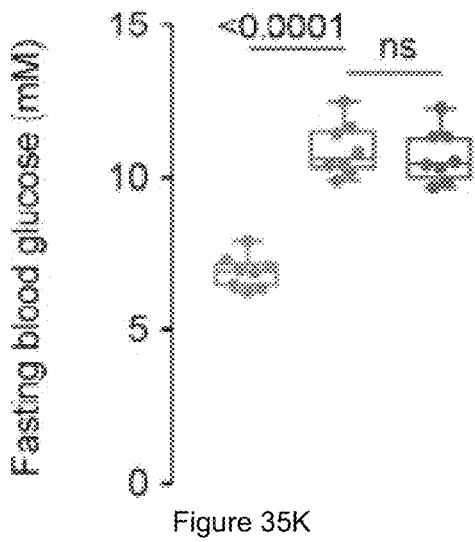
Figure 35L:
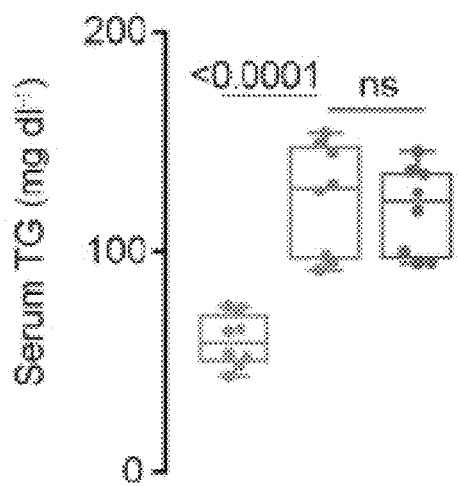
Figure 35M:
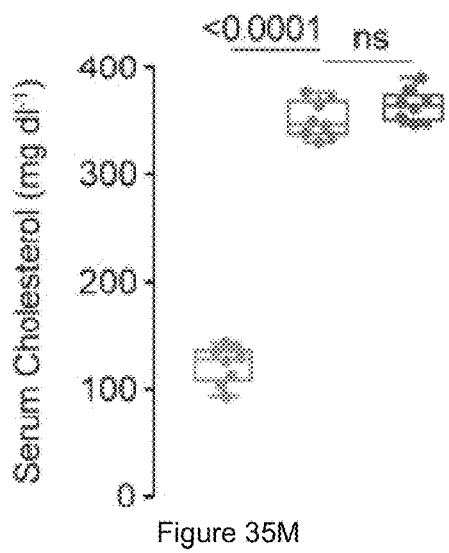
Figure 35N:
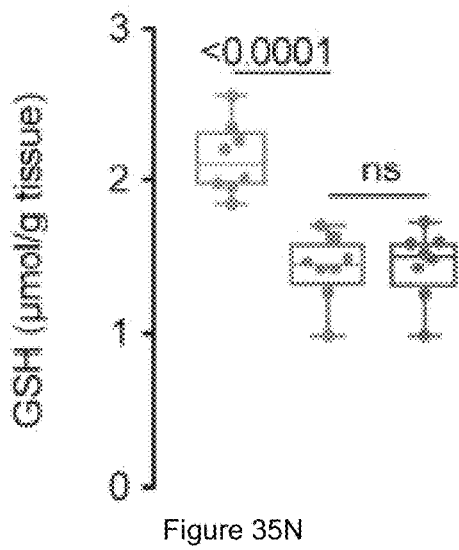
Figure 35O:
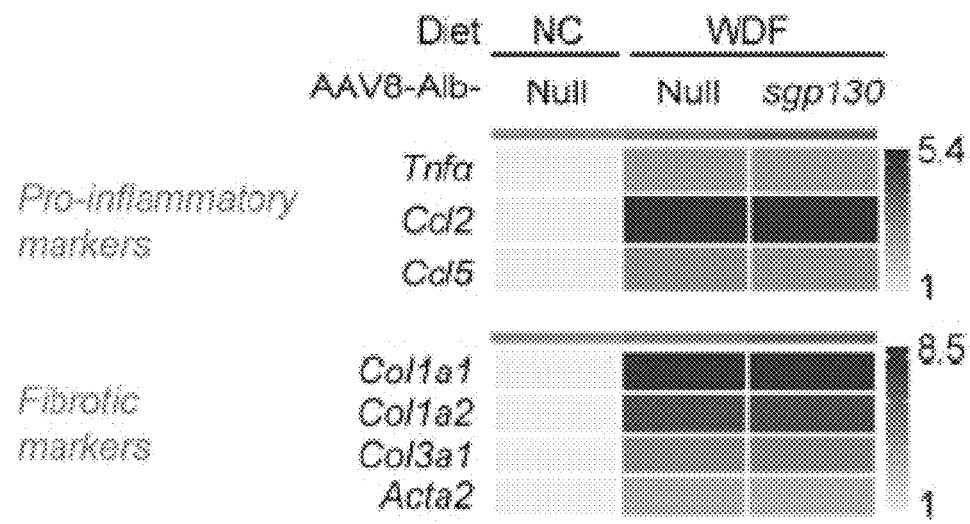
Figure 41C:
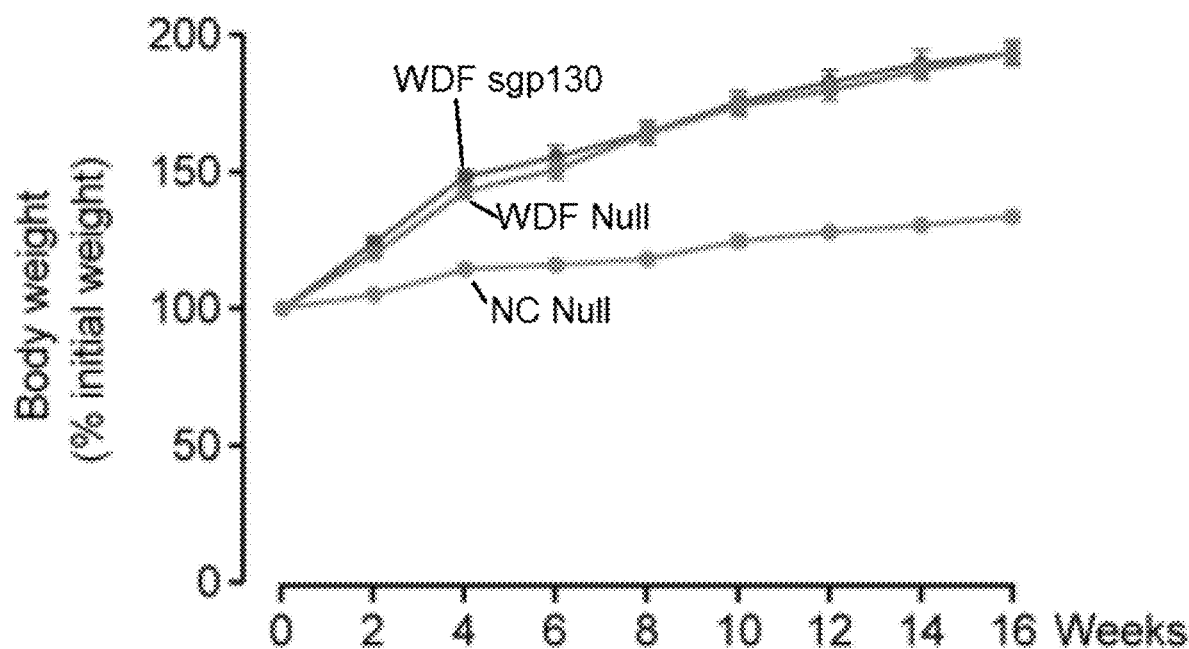
Figure 41D:
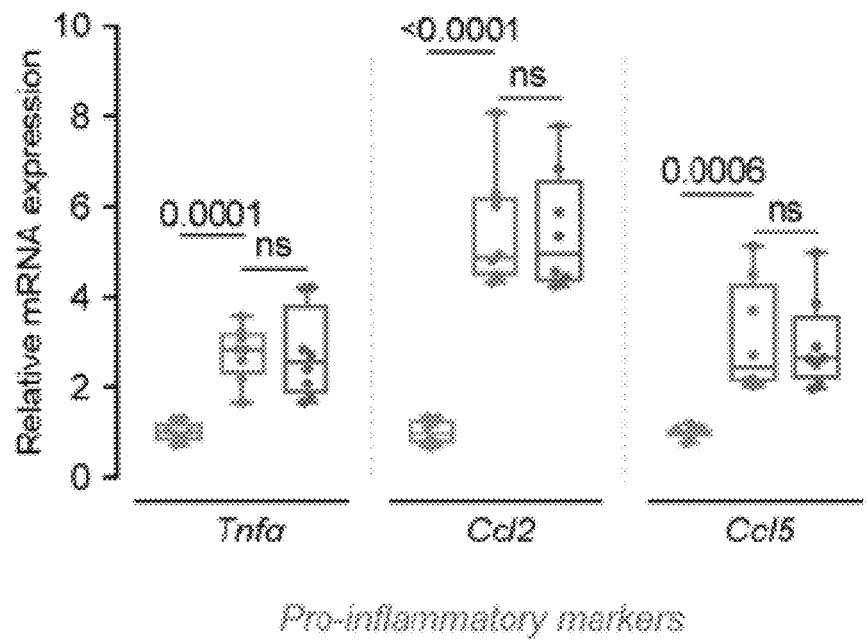
Figure 41E:
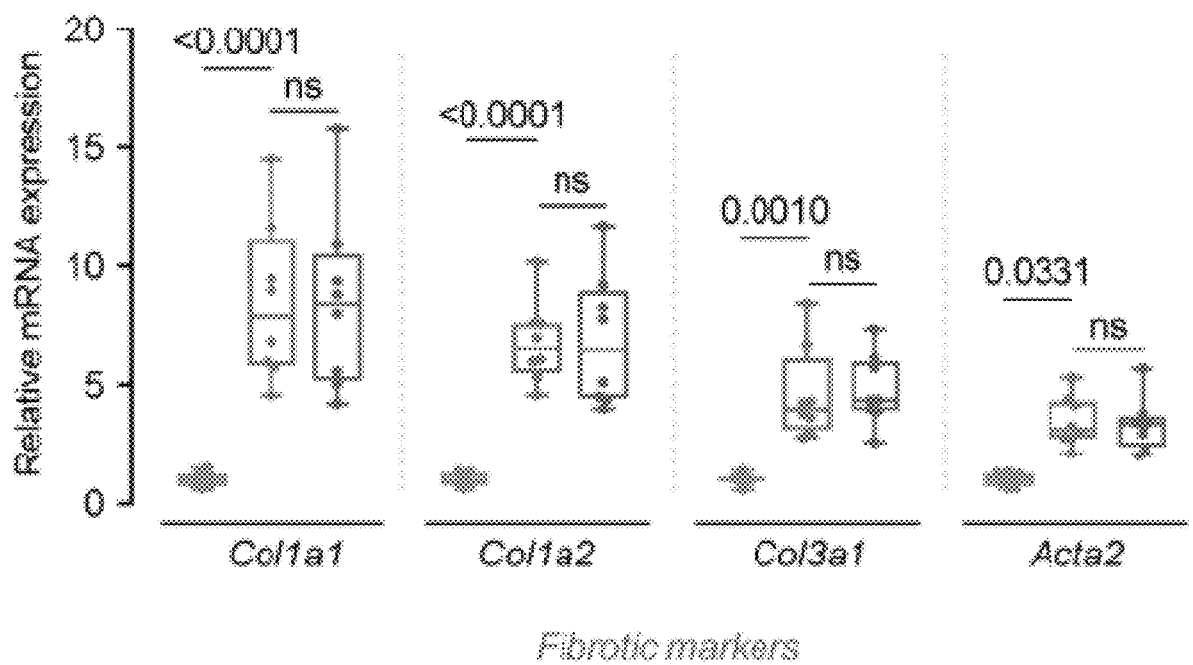

After 16 weeks of WDF, IL11 levels were strongly upregulated in the liver and the periphery but IL6 expression was not affected (FIGS. 35B and 35C). Mice on WDF became obese (FIG. 41C), had an approximate 2-fold increase in liver mass and developed severe steatosis by gross morphology, histology and quantitative analysis of liver triglycerides (FIGS. 35E-35G). These phenotypes were unaffected by high levels of sgp130 expression (FIGS. 35B-35G). Similarly, mice on WDF had elevated levels of ALT, AST, collagen and peripheral cardiovascular risk factors (fasting blood glucose, serum triglycerides and serum cholesterol), along with depleted levels of GSH, but none of these parameters were affected by sgp130 (FIGS. 35H-35N). Livers from mice on WDF diet for 16 weeks showed increased expression of pro-inflammatory and fibrosis genes and this signature was unaffected by sgp130-mediated inhibition of putative trans-signaling (FIGS. 35O and 41D-41E).

Figure 42B:
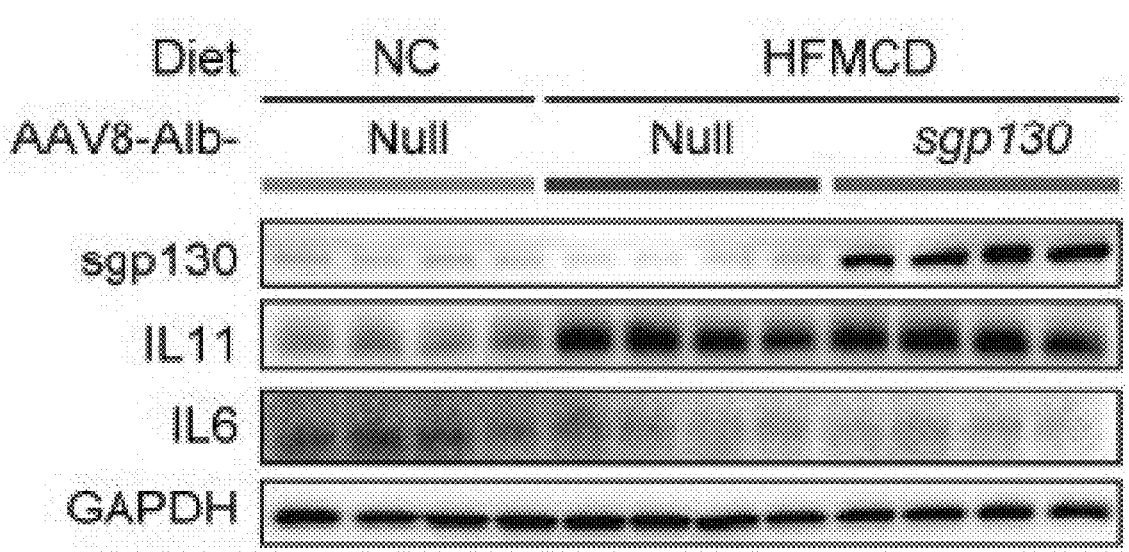
Figure 42C:
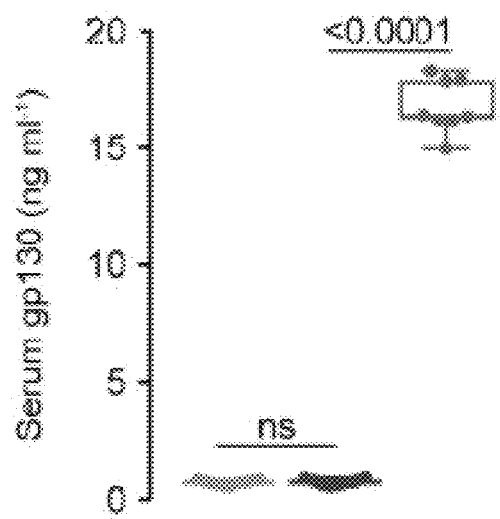
Figure 42D:
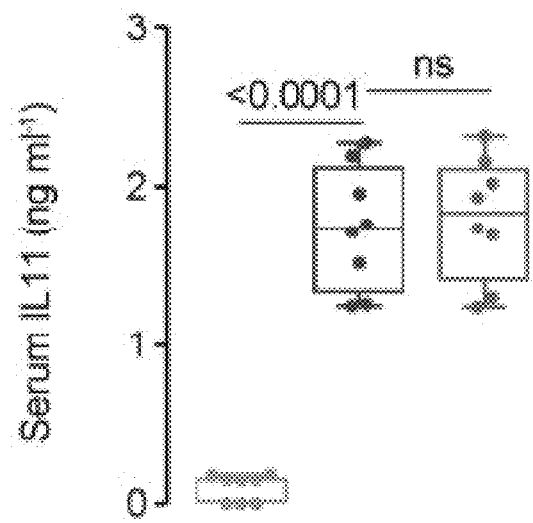
Figure 42E:
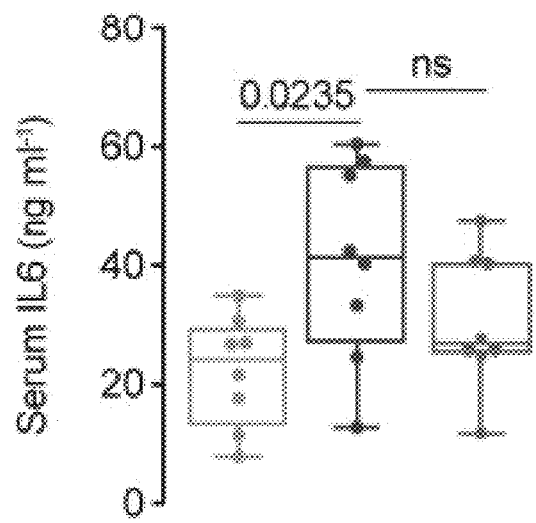
Figure 42F:
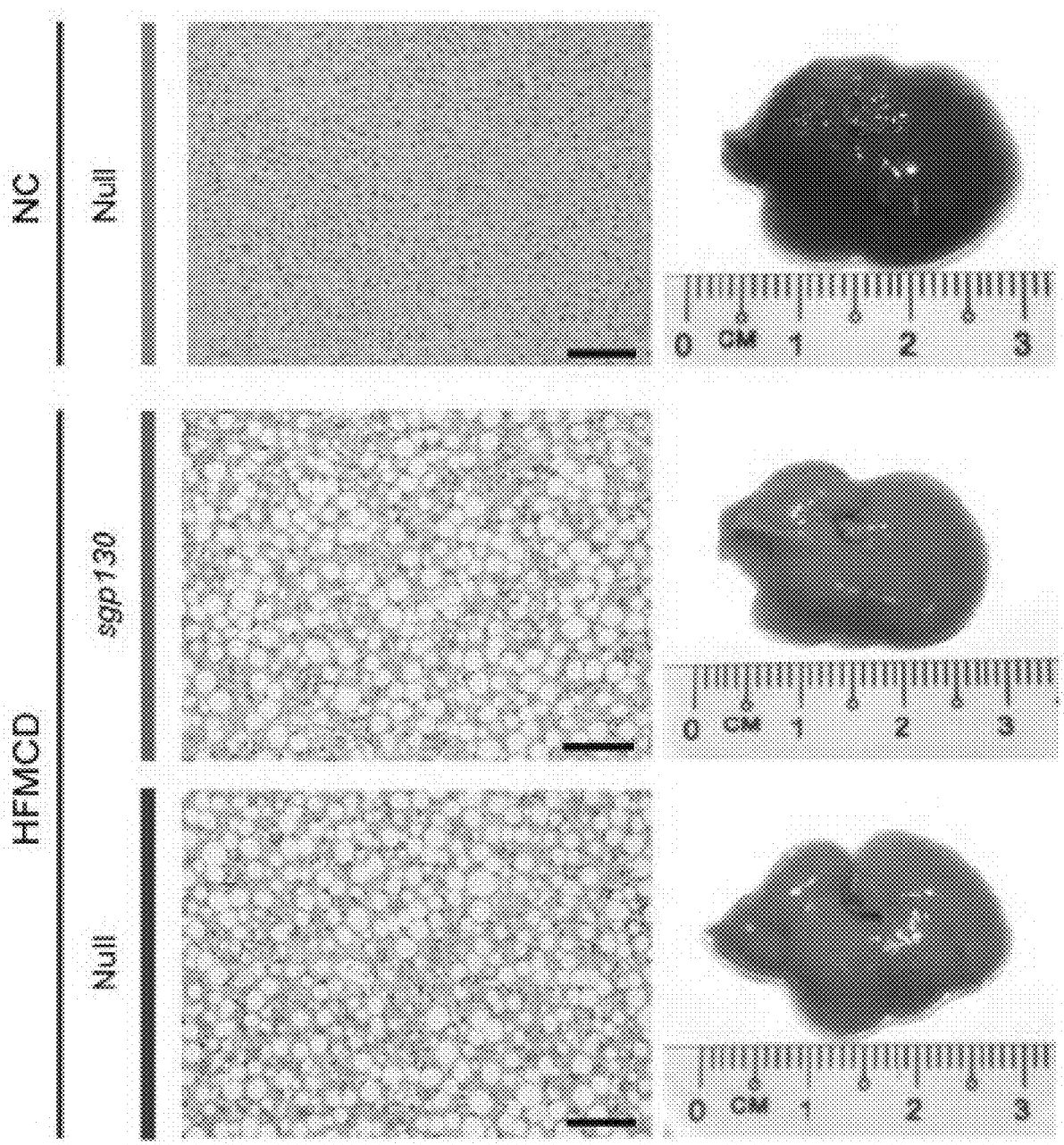
Figure 42G:
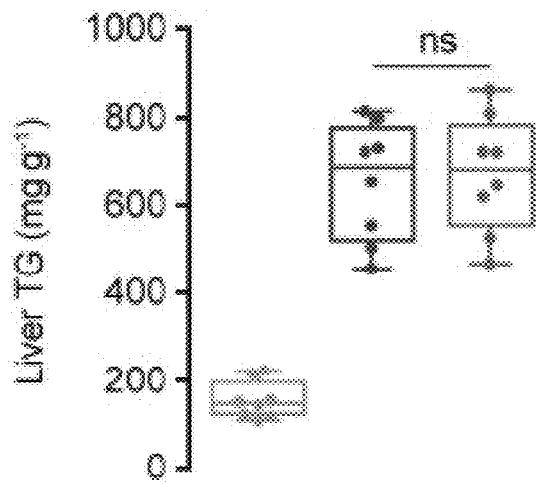
Figure 42H:
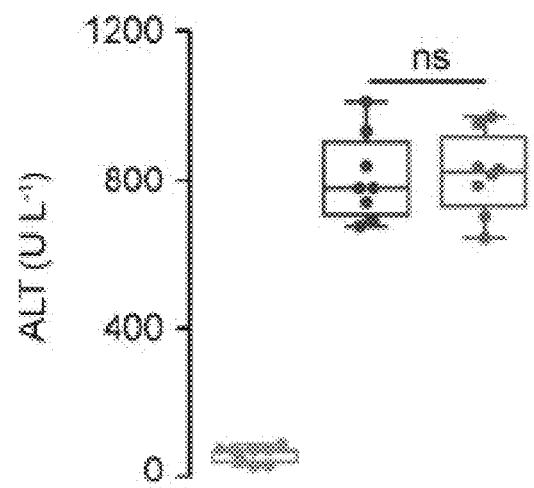
Figure 42I:
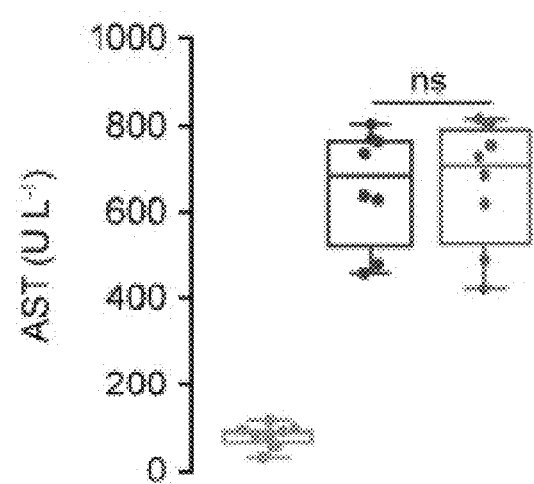
Figure 42J:
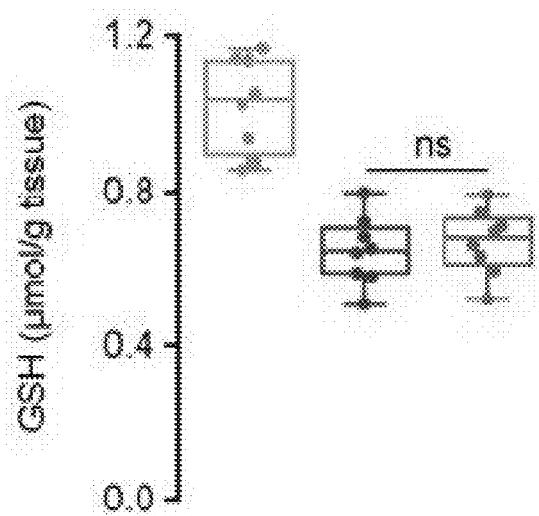
Figure 42K:
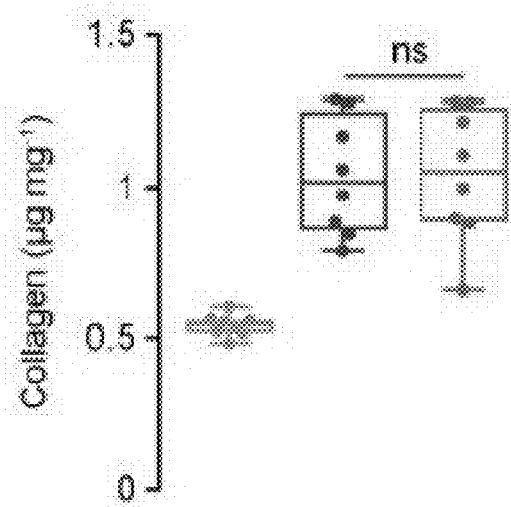
Figure 42L:
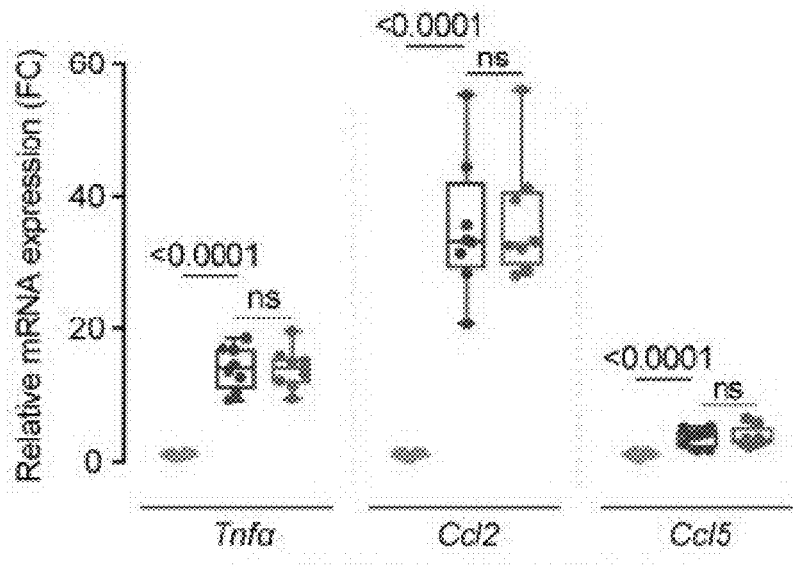
Figure 42M:
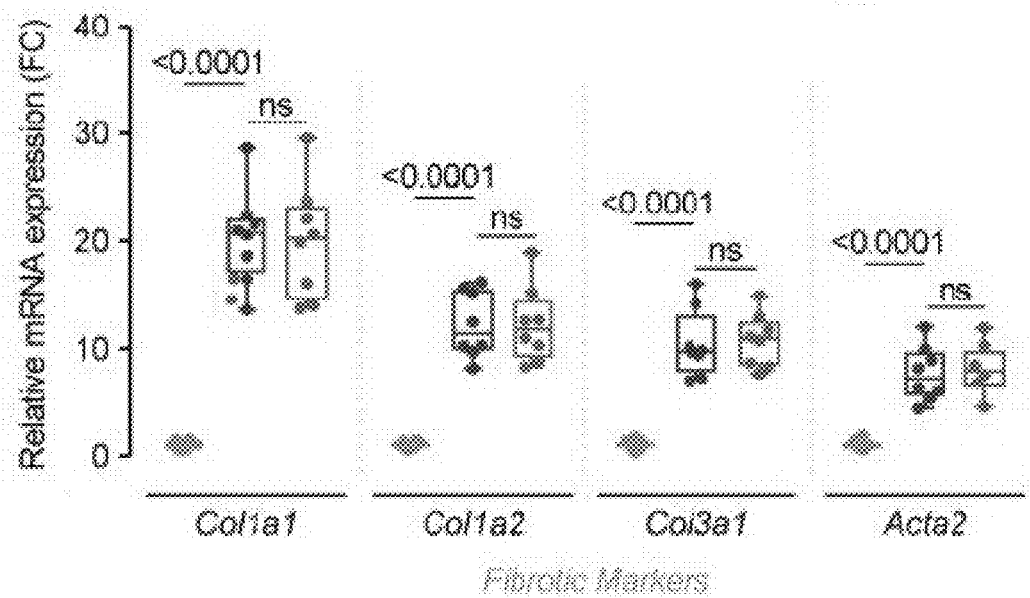

In a second set of experiments NASH was induced using the HFMCD diet (FIG. 42A). HFMCD diet increased IL11 levels in liver and serum, whereas IL6 levels were slightly lower in the liver and were mildly increased in the periphery (FIGS. 42B and 42D-42E). Mice on HFMCD diet developed rapid and profound steatosis by gross morphology, histology, and molecular assays, which was unaltered by sgp130 expression (FIGS. 42F and 42G). Hepatocyte damage markers (ALT and AST) were elevated and GSH depleted by HFMCD diet, irrespective of sgp130 expression (FIGS. 42H-42J). Similarly, HFMCD-induced liver fibrosis was unchanged by sgp130 expression (FIG. 42K). At the RNA level, the HFMCD diet was associated with dysregulated expression of inflammation and fibrosis genes and these molecular phenotypes were unaffected by sgp130 expression (FIGS. 42L and 42M).

Figure 35P:
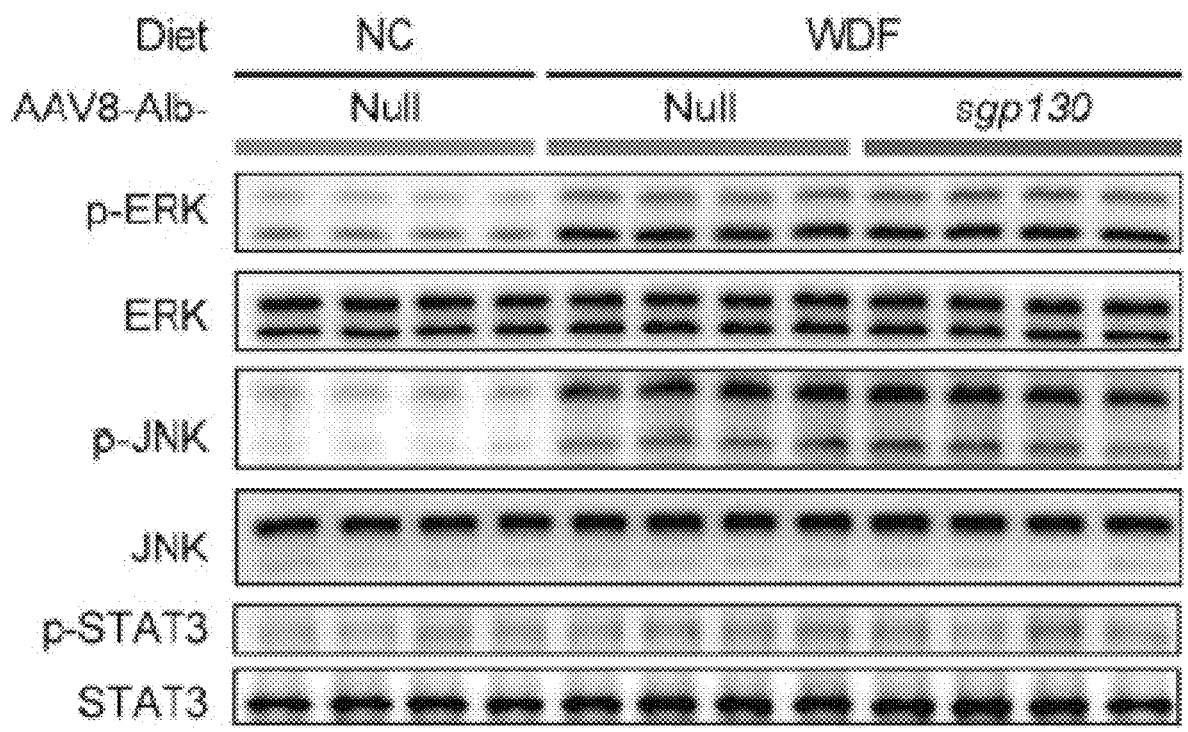
Figure 42N:
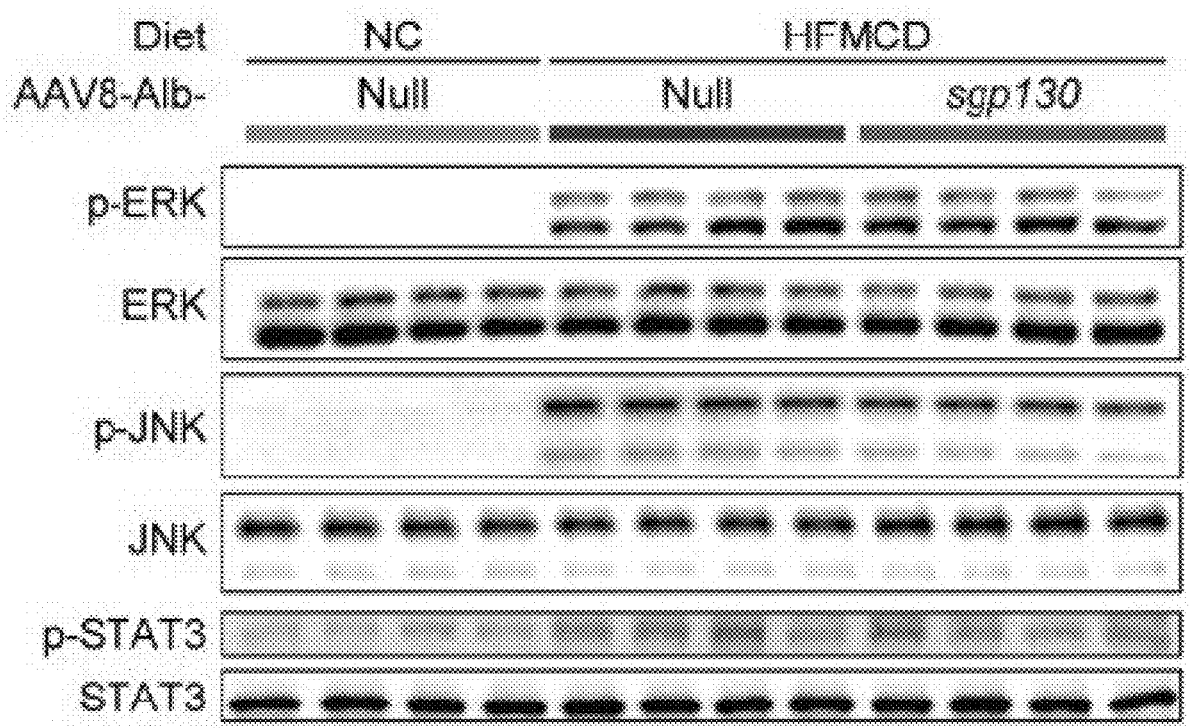
Figure 43A:
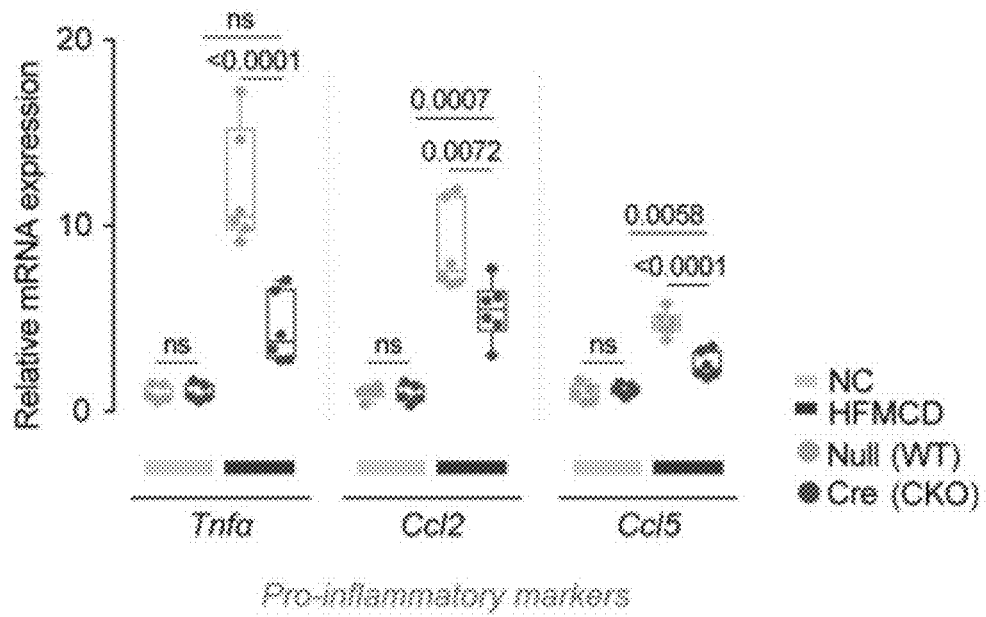
FIGS. 43A and 43B. Box plots showing that mice with hepatocyte-specific deletion of Il11 ra1 are protected from HFMCD-induced gene dysregulation. (A and B) Hepatic mRNA expression of (A) pro-inflammatory markers (Tnfα, Ccl2, Ccl5) and (B) fibrotic markers (Col1a1, Col1a2, Col3a1, Acta2) from control and CKO mice on NC and HFMCD diet as shown in FIG. 36J. (A-B) Data are shown as box-and-whisker with median (middle line), $25^{th}$-$75^{th}$ percentiles (box) and min-max values (whiskers), Sidak-corrected Student's t-test; for each gene, from left to right, conditions shown are: NC WT, NC CKO, HFMCD WT, HFMCD CKO.
Figure 43B:
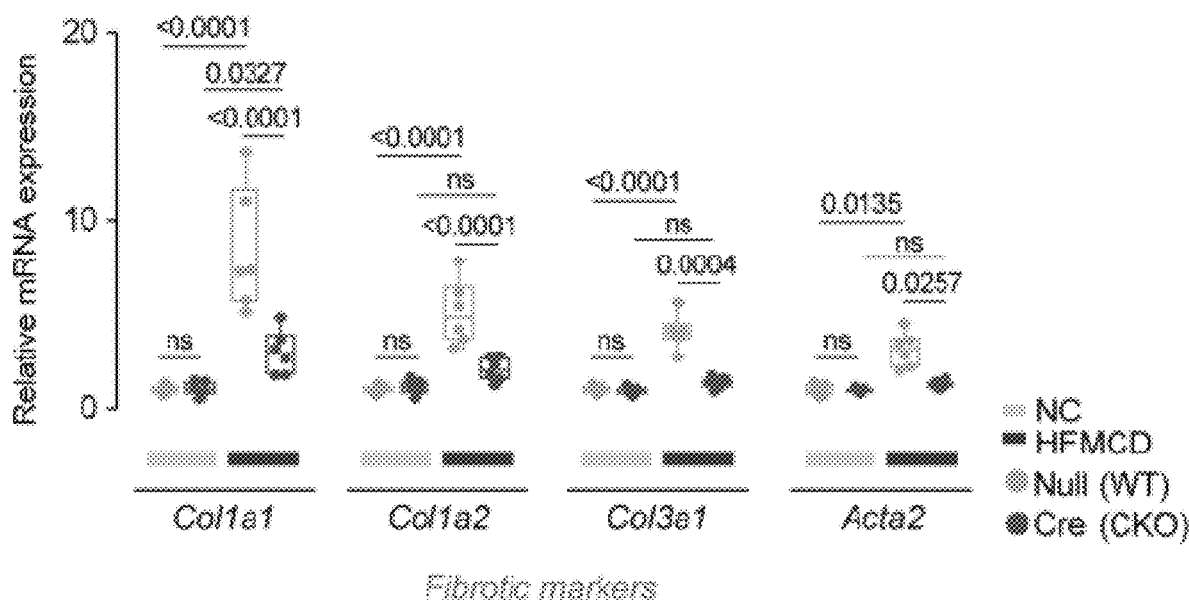

At the signaling level, both WDF and HFMCD diets stimulated ERK and JNK activation, consistent with elevated IL11 cis-signaling (FIGS. 35P and 42N). By contrast, pSTAT3 levels in the liver were not elevated by WDF (FIG. 35P) and appeared mildly elevated in mice on the HFMCD diet (FIG. 42N). In all instances, there was no effect of sgp130 on diet-induced signaling events. Overall, these data suggest that neither IL6 nor IL11 trans-signaling plays a role in NASH, which is consistent with other studies where IL6 family trans-signaling has not been detected (Agthe et al., 2017; Balic et al., 2017; Kammoun et al., 2017; Kraakman et al., 2015).

5.3.4 Hepatocyte-Specific IL11 Cis-Signaling is Required to Initiate NASH

Figure 36A:
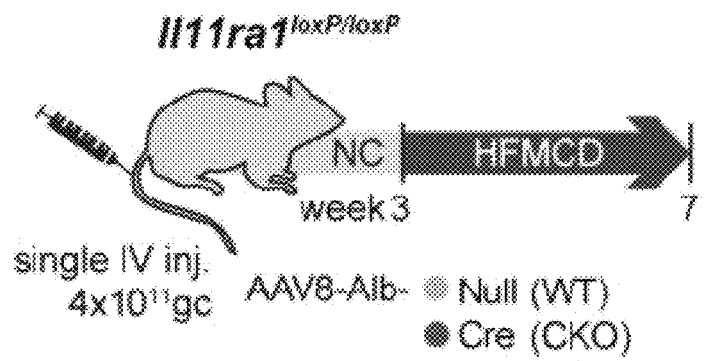
FIGS. 36A to 36K. Schematic, images, graphs and box plots showing that hepatocyte-specific inhibition of IL11 cis-signaling protects against cachexia and NASH in mice on HFMCD diet. (A) Schematic of HFMCD feeding regimen for AAV8-Alb-Cre injected Il11ra1$_{loxP/loxP}$ (conditional knockout; CKO) mice for experiments shown in (B-K). Il11ra1$_{loxP/loxP}$ mice were intravenously injected with either AAV8-Alb-Null or AAV8-Alb-Cre to delete Il11ra1 specifically in hepatocytes three weeks prior to the start of HFMCD diet. (B) Western blots of hepatic IL11 RA and GAPDH. (C) Body weight (shown as a percentage (%) of initial body weight). (D) Representative gross anatomy and H&E stained images of livers. (E) Hepatic triglycerides content. (F) Serum ALT levels. (G) Serum AST levels. (H) Hepatic GSH content. (I) Hepatic collagen levels. (J) Heatmap showing hepatic mRNA expression of pro-inflammatory markers (Tnfα, Ccl2, Ccl5) and fibrotic markers (Col1a1, Col1a2, Col3a1, Acta2). Values are shown in FIGS. 43A and 43B. (K) Western blots showing hepatic ERK and JNK activation status. (C) Data are shown as mean±SEM, 2-way ANOVA with Tukey's multiple comparison test, statistical significance is shown as the P values between HFMCD WT and CKO; (E-I) Data are shown as box-and-whisker with median (middle line), 25th-75th percentiles (box) and min-max values (whiskers), Sidak-corrected Student's t-test; from left to right, conditions shown are: NC WT, NC CKO, HFMCD WT, HFMCD CKO.
Figure 36B:
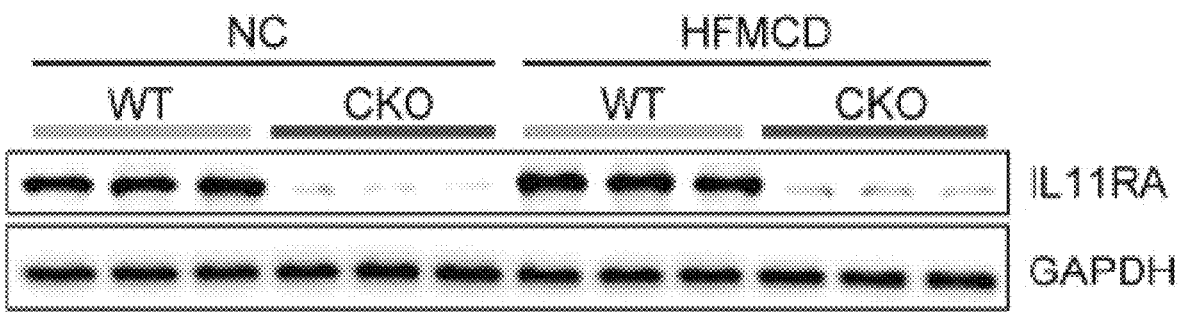
Figure 37A:
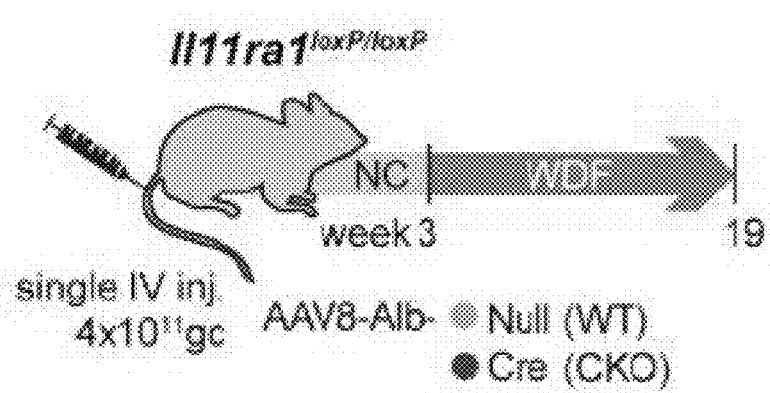
FIGS. 37A to 37M. Schematic, images, graphs and box plots showing that mice with hepatocyte-specific inhibition of IL11 cis-signaling are protected against WDF-induced obesity and NASH. (A) Schematic of WDF-fed control and CKO mice for data shown in (B-M). Three weeks following AAV8-Alb-Null or AAV8-Alb-Cre virus injection, CKO mice were fed WDF for 16 weeks. (B) Western blots showing hepatic levels of IL11 RA and GAPDH. (C) Body weight (shown as a percentage (%) of initial body weight). (D) Fat mass. (E) Representative gross anatomy and H&E stained images of livers. (F) Hepatic triglycerides content. (G) Liver weight. (H) Serum ALT levels. (I) Serum AST levels. (J) Hepatic GSH content. (K) Hepatic collagen levels. (L) Hepatic pro-inflammatory and fibrotic genes expression on heat map (values are shown in FIGS. 44A and 44B). (M) Western blots showing activation status of hepatic ERK and JNK. (C and D) Data are shown as mean±SEM, 2-way ANOVA with Tukey's multiple comparison test, statistical significance is shown as the P values between WDF WT and CKO; (F-K) Data are shown as box-and-whisker with median (middle line), $25^{th}$-$75^{th}$ percentiles (box) and min-max values (whiskers), Sidak-corrected Student's t-test; from left to right, conditions shown are: NC WT, NC CKO, WDF WT, WDF CKO.
Figure 37B:

While no evidence was found to support IL11 trans-signaling in NASH models, overall the data suggested increased IL11 effects in hepatocytes, presumed in cis. To test this premise, the inventors administered AAV8-Alb-Cre to Il11ra$_{loxP/loxP}$ mice to delete Il11ra1 in hepatocytes only (CKO mice). CKO mice were then fed either normal chow (NC), HFMCD diet or WDF (FIGS. 36A and 37A). Liver IL11RA protein was greatly diminished in the CKOs following AAV8-Alb-Cre, showing the model to be effective and suggesting that hepatocytes are the largest hepatic reservoir of Il11ra1 (FIGS. 36B and 37B).

Figure 36C:
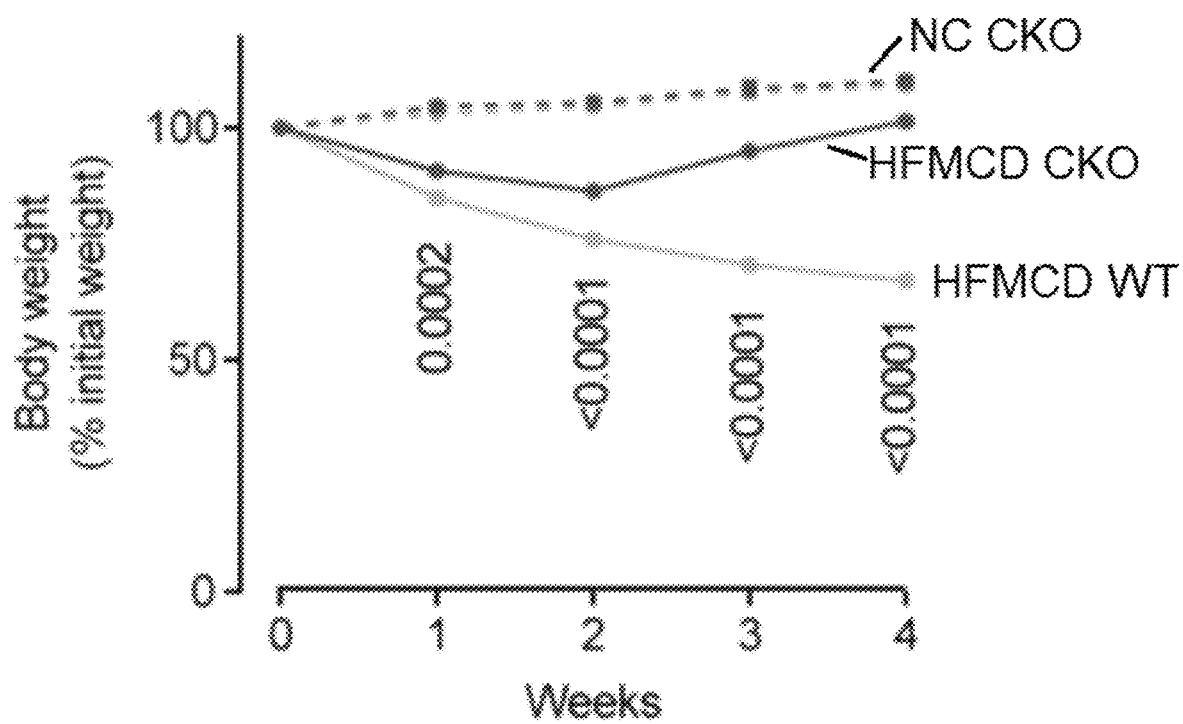
Figure 36D:
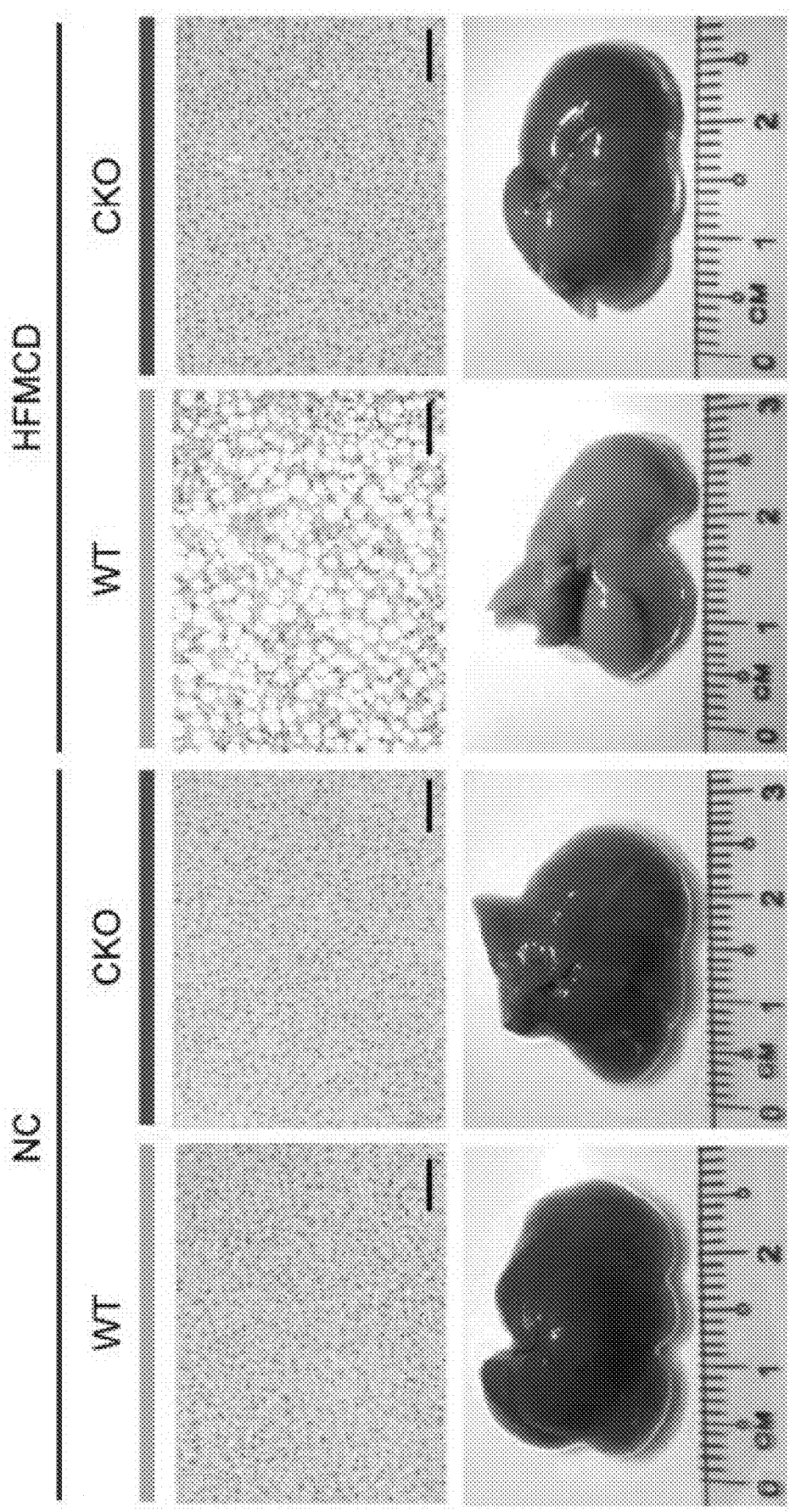
Figure 36E:
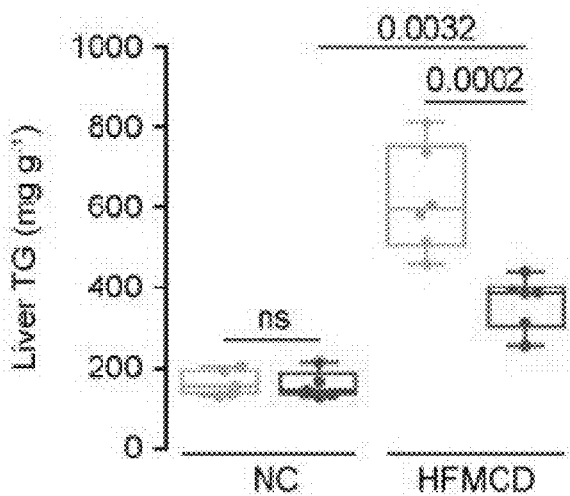
Figure 36F:
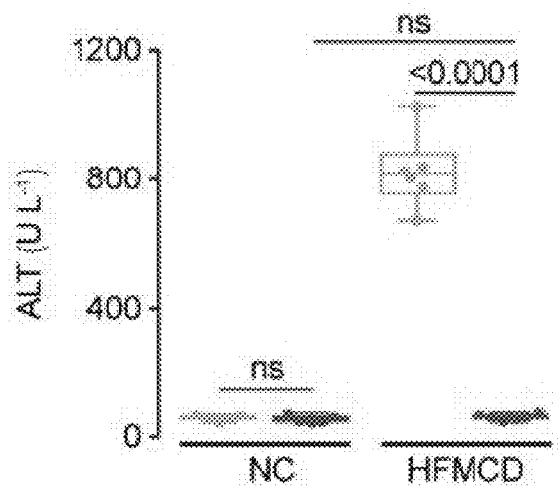
Figure 36G:
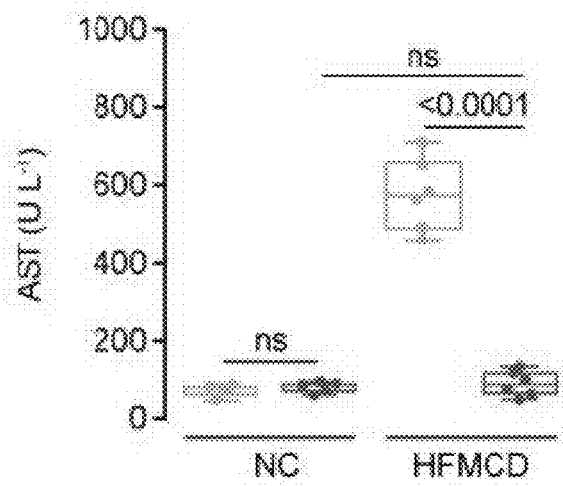
Figure 37C:
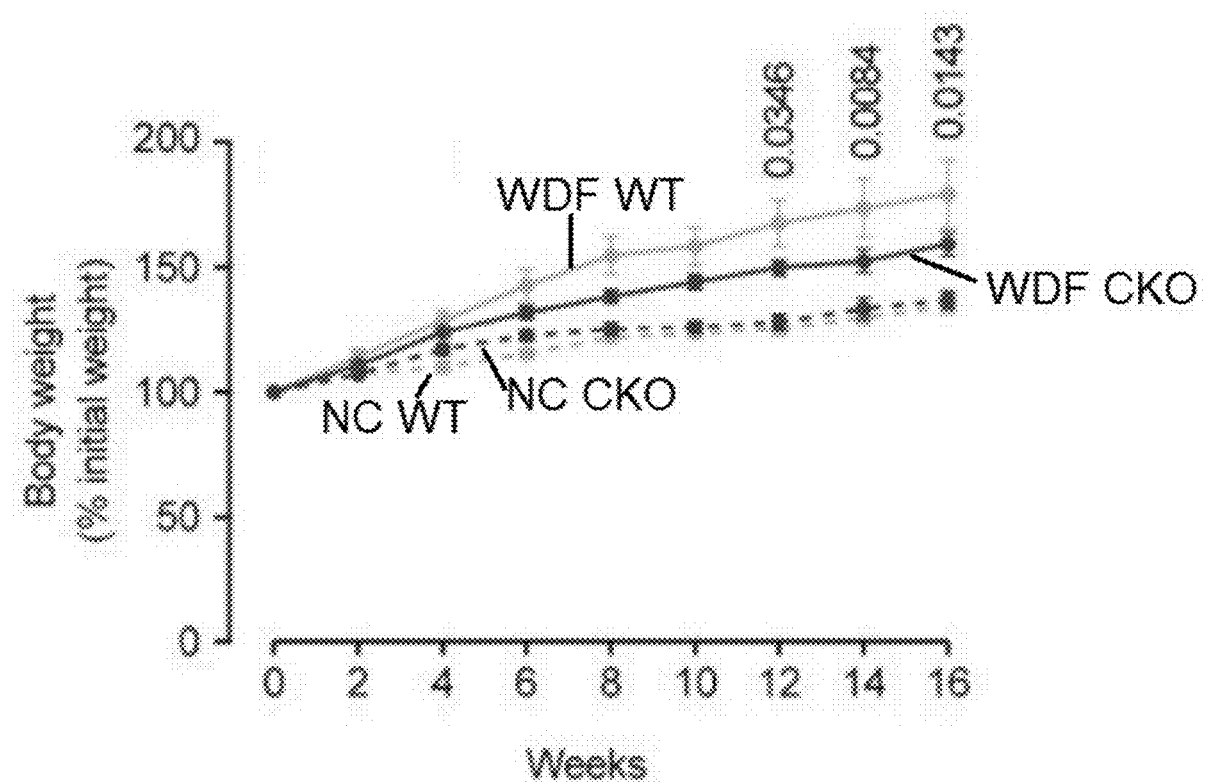
Figure 37D:
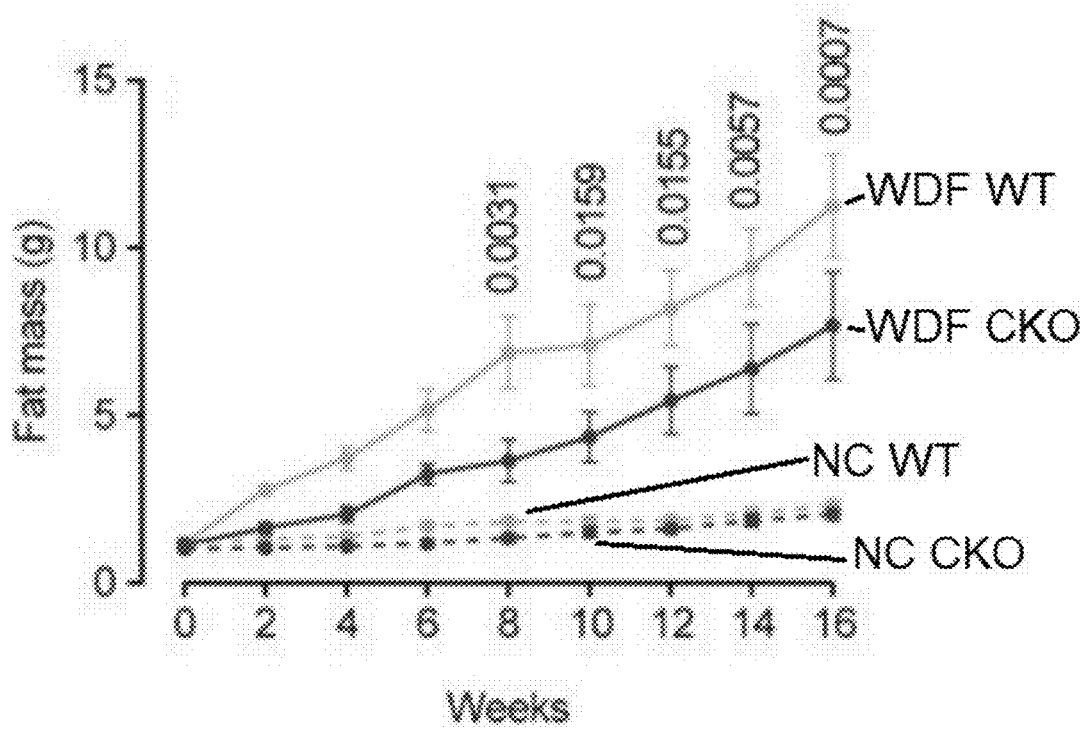
Figure 37E:
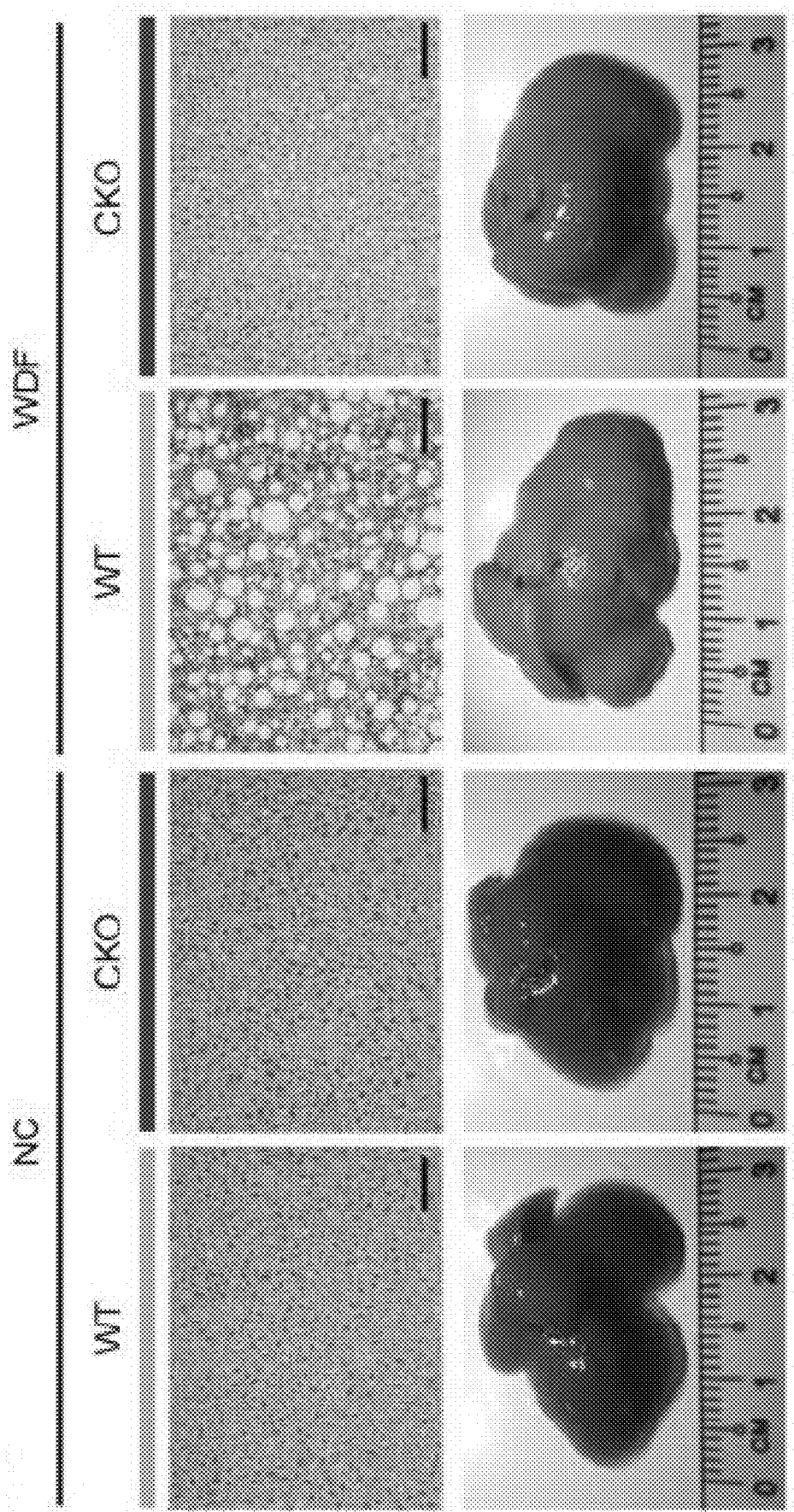
Figure 37F:
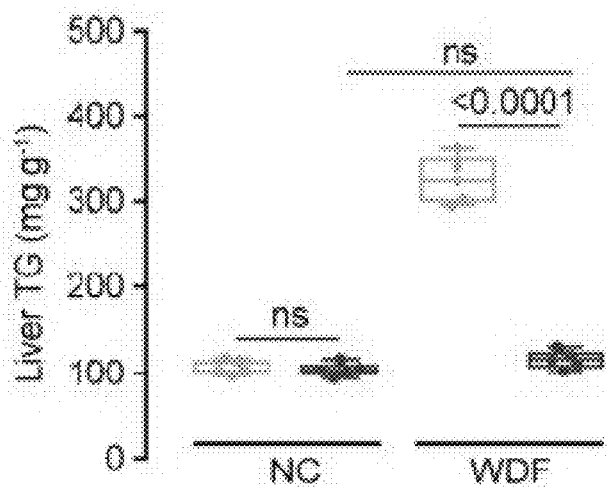

In addition to rapidly stimulating lipotoxicity-driven NASH (Stephenson et al., 2018) the HFMCD diet causes weight loss (Stephenson et al., 2018). Surprisingly, weight loss in mice on the HFMCD diet was initially limited and later reversed in CKO mice (FIG. 36C). Mice on WDF gained weight and fat mass throughout the experimental period, as expected. However, and equally surprising, these obesity phenotypes were mitigated in CKO mice (FIGS. 37C and 37D). These data suggest that inhibition of IL11 signaling is permissive for weight homeostasis, with context-specific anti-cachectic or anti-obesity effects.

Figure 36H:
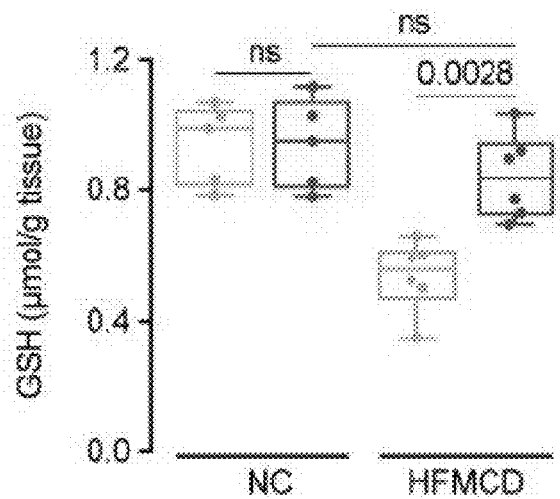
Figure 37G:
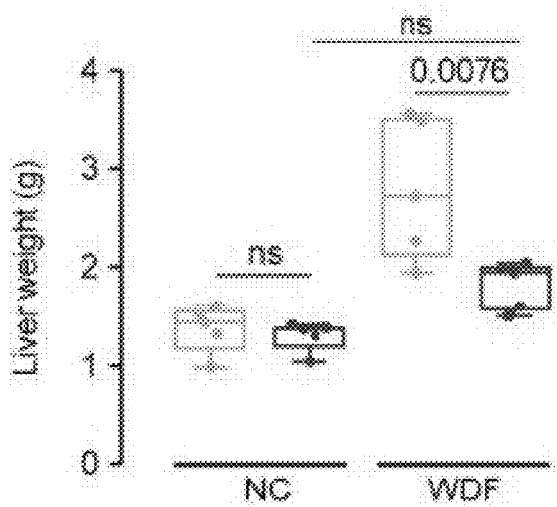
Figure 37H:
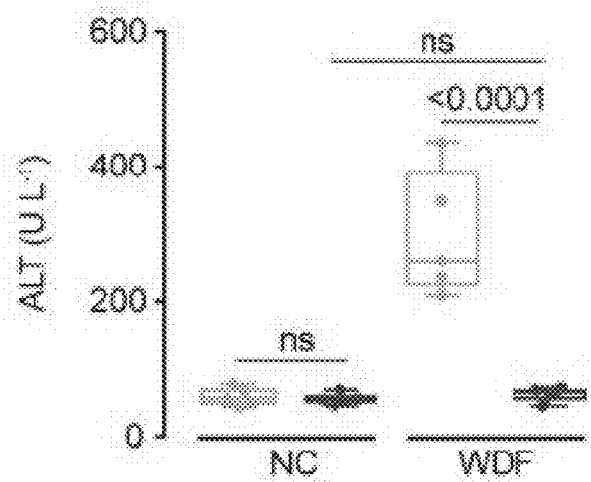
Figure 37I:
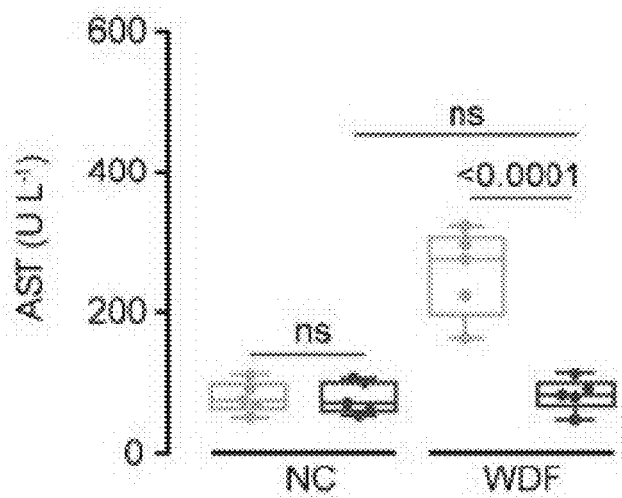
Figure 37J:
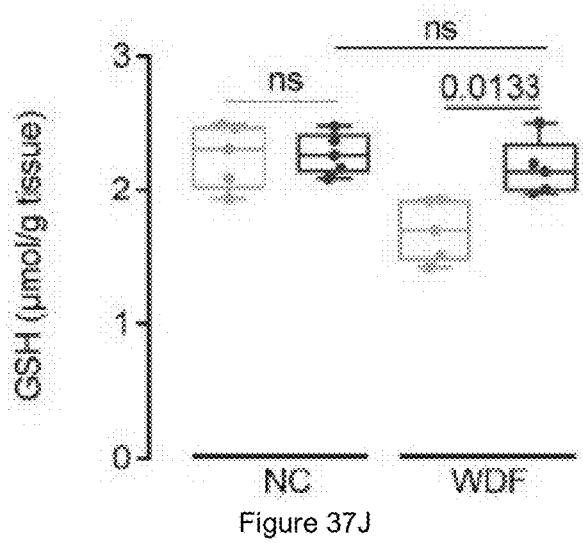
Figure 37K:
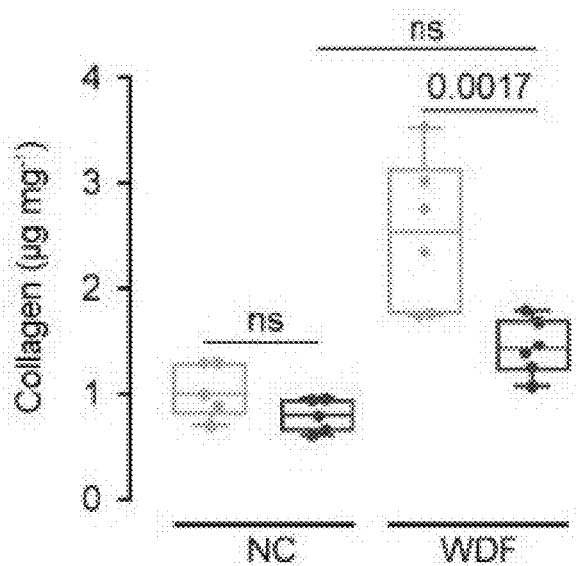
Figure 37L:
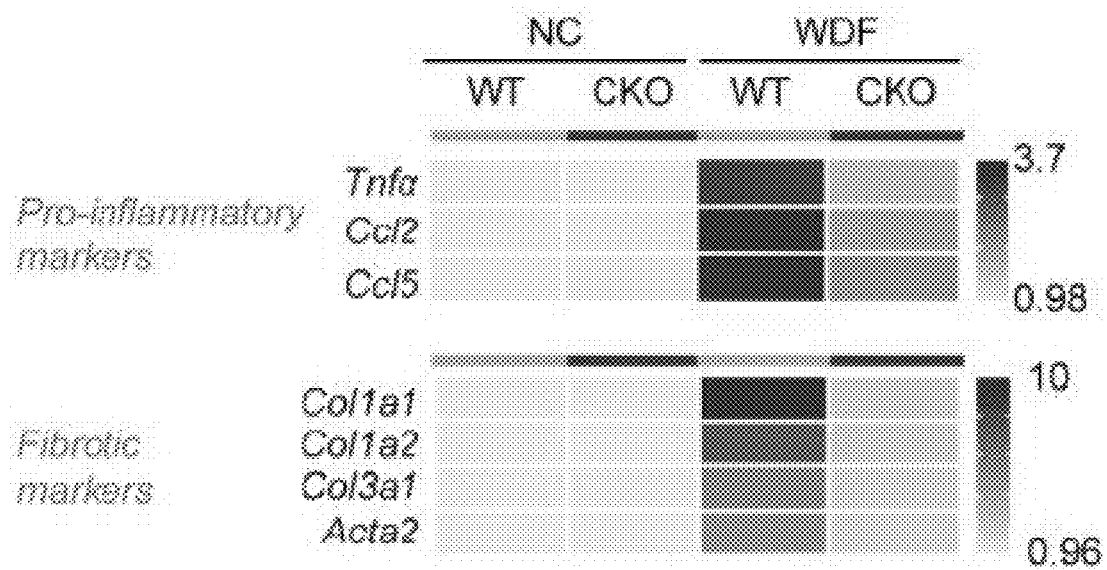

By gross morphology, histology and quantitative triglyceride analysis, the CKO mice on either HFMCD or WDF diet were robustly protected from steatosis (FIGS. 36D and 36E, 37E and 37F) and those on WDF had less hepatomegaly (FIG. 37G). Liver damage markers were markedly reduced in CKO mice fed with either HFMCD diet (reduction: ALT, 99%; AST, 97%; P<0.0001 for both) or WDF (reduction: ALT, 98%; AST, 98%; P<0.0001 for both) and found to be comparable to NC control levels (FIGS. 36F and 36G, 37H and 37I). In both models, GSH levels were diminished in control mice on the NASH diets but normalized in CKOs (FIGS. 36H and 37J).

Figure 36I:
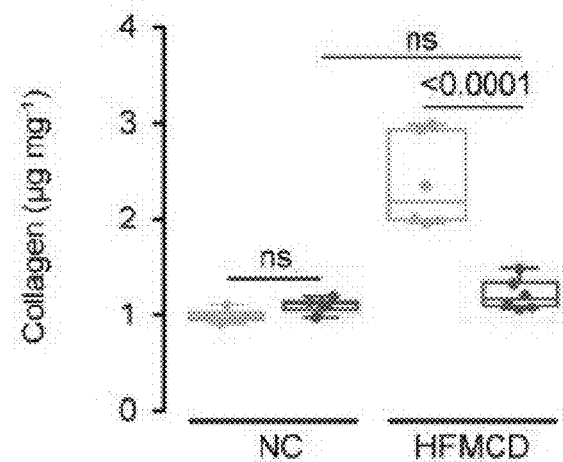
Figure 36J:
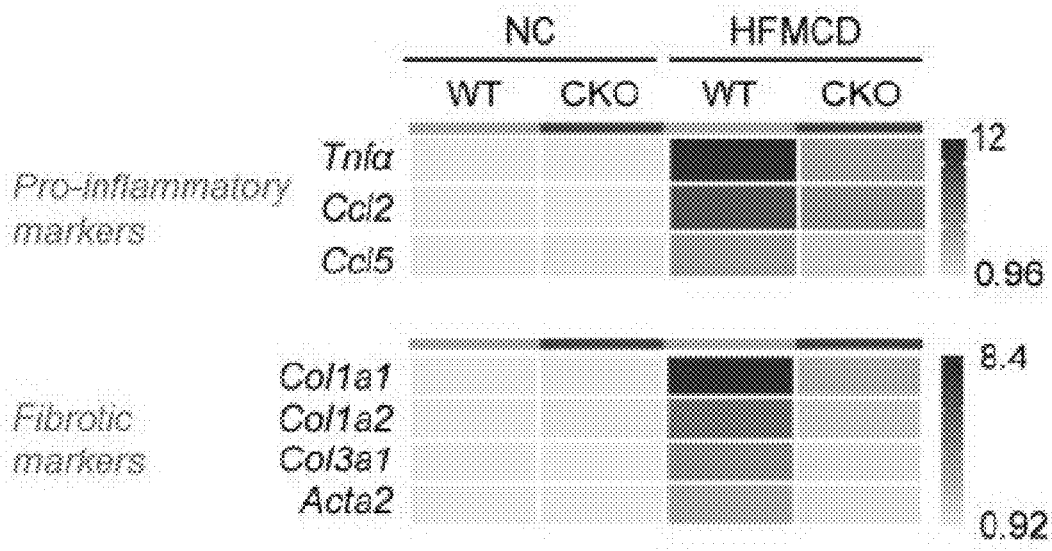
Figure 36K:
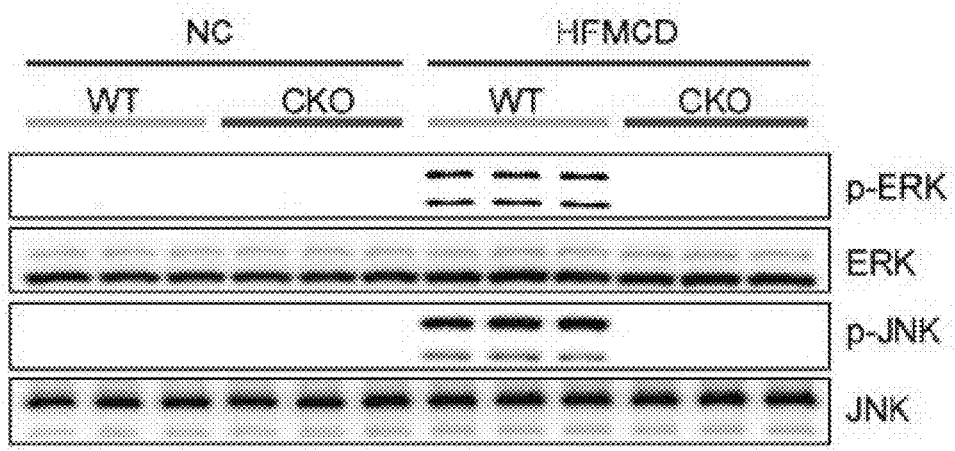
Figure 37M:
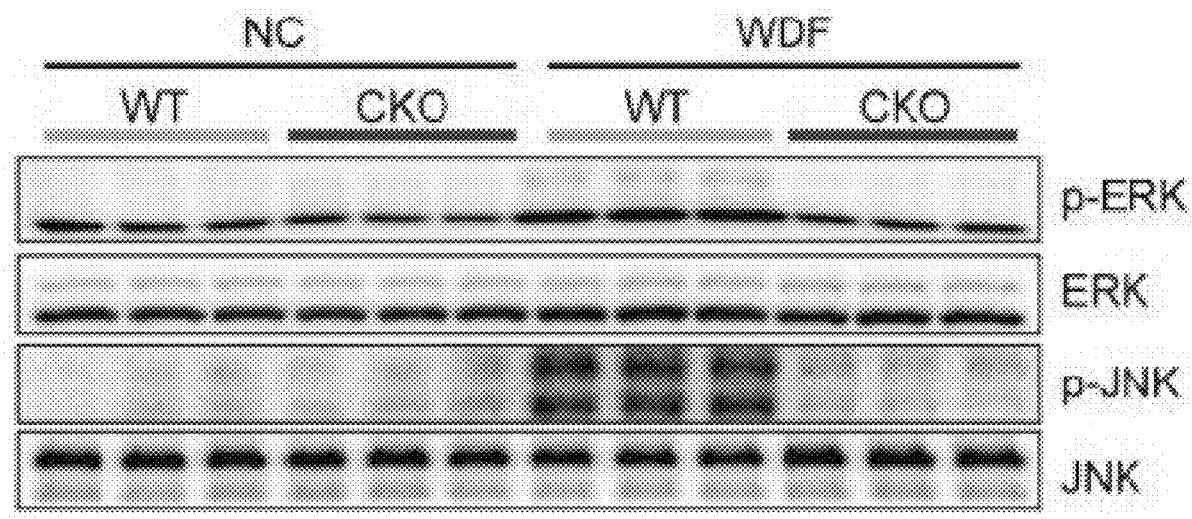
Figure 44A:
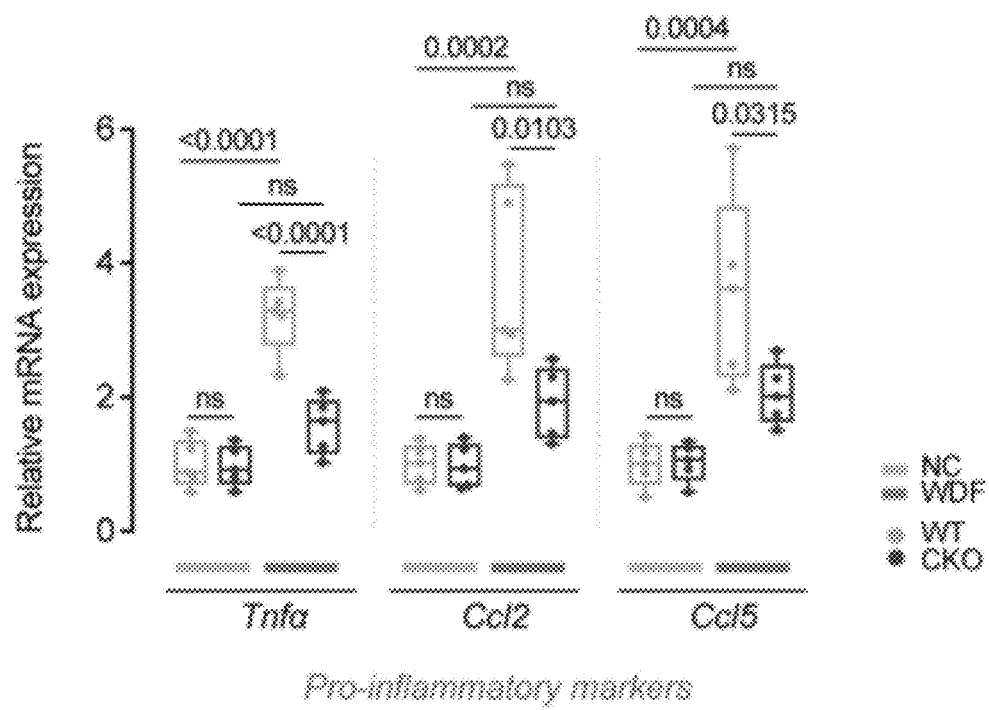
FIGS. 44A to 44E. Box plots showing that hepatocyte-specific Il11ra1 deleted mice are protected from WDF-induced NASH phenotypes. (A-E) Data for control and CKO mice on NC and WDF diet as shown in FIG. 37A. (A and B) Hepatic mRNA expression of (A) pro-inflammatory markers (Tnfα, Ccl2, Ccl5) and (B) fibrotic markers (Col1a1, Col1a2, Col3a1, Acta2) as shown in FIG. 37L. (C) Fasting blood glucose levels. (D) Serum triglycerides levels. (E) Serum cholesterol levels. (A-E) Data are shown as box-and-whisker with median (middle line), 25th-75th percentiles (box) and min-max values (whiskers), Sidak-corrected Student's t-test. (A and B) for each gene, from left to right, conditions shown are: NC WT, NC CKO, WDF WT, WDF CKO. (C-E) from left to right, conditions shown are: NC WT, NC CKO, WDF WT, WDF CKO.
Figure 44B:
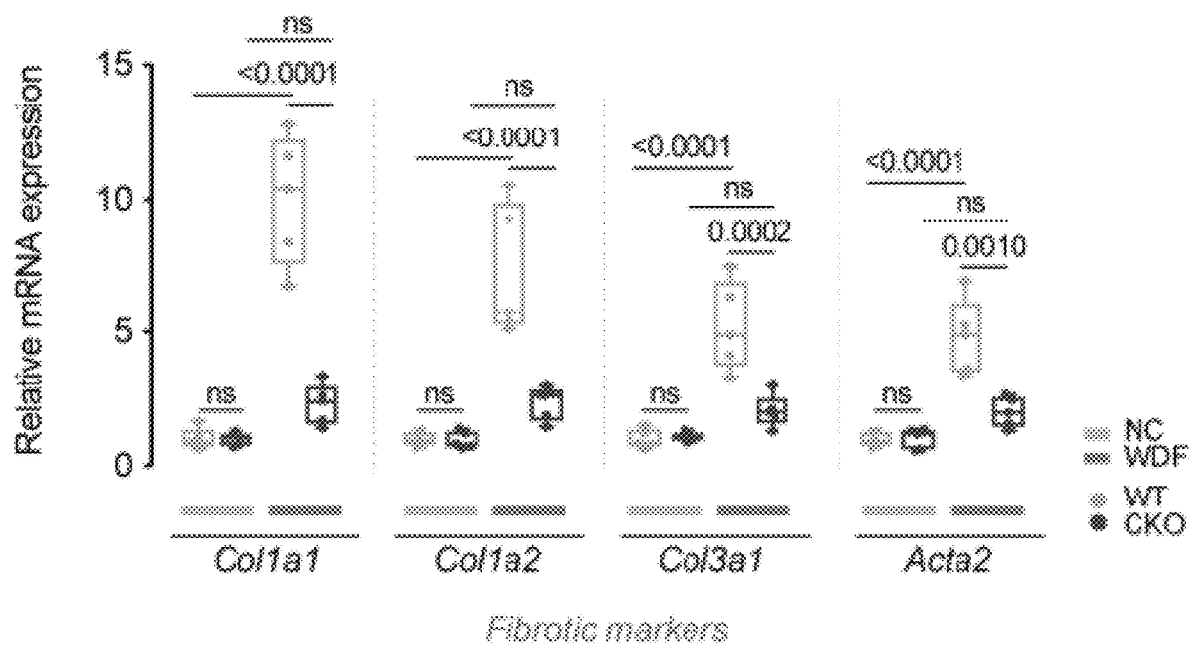
Figure 44C:
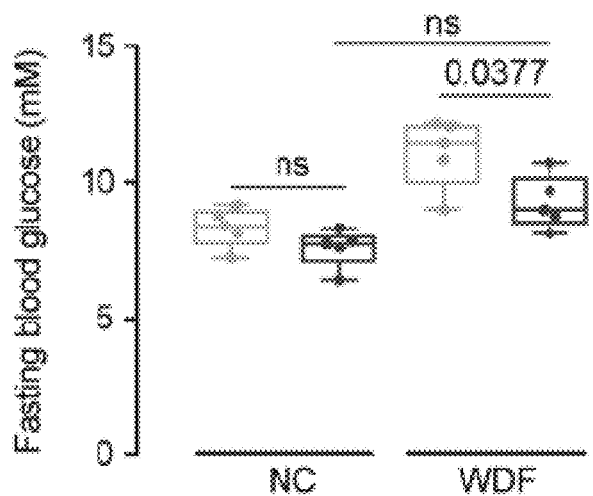
Figure 44D:
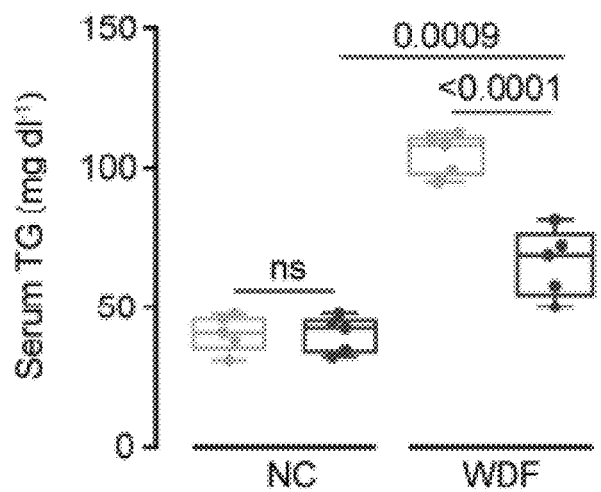
Figure 44E:
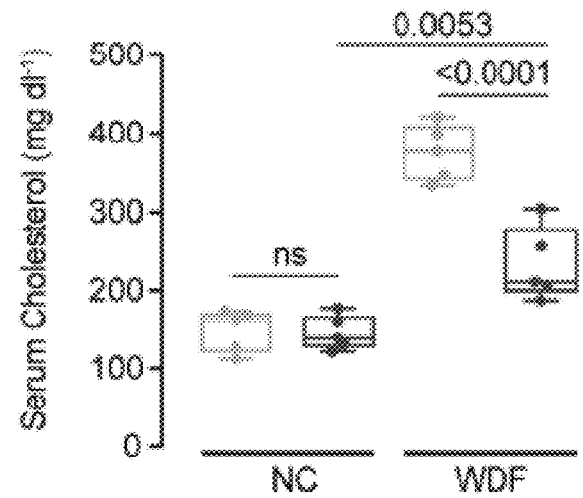

Liver fibrosis was greatly reduced in CKO mice on either NASH diet as compared to controls (reduction: HFMCD, 87%; WDF, 64%; P<0.001 for both) (FIGS. 36I and 36K). Upregulation of pro-inflammatory and fibrosis genes in mice on either the HFMCD or WDF diets was also diminished in the CKOs (FIGS. 36J, 37L, 43A and 43B, 44A and 44B). This suggests that transformation of HSCs to myofibroblasts and activation of immune cells are, in part, secondary to upstream, IL11-driven events in hepatocytes. Mice on WDF also develop hyperglycemia, hypertriglyceridemia, and hypercholesterolemia, all of which were improved in the CKOs, suggesting an important role for hepatocyte-specific IL11 signalling for NASH phenotypes more generally (FIGS. 44C-44E). At the signaling level, both HFMCD diet and WDF resulted in elevated ERK and JNK phosphorylation. This was largely prevented in CKO mice, consistent with inhibition of IL11 signaling in hepatocytes (FIGS. 36K and 37M).

Figure 38A:
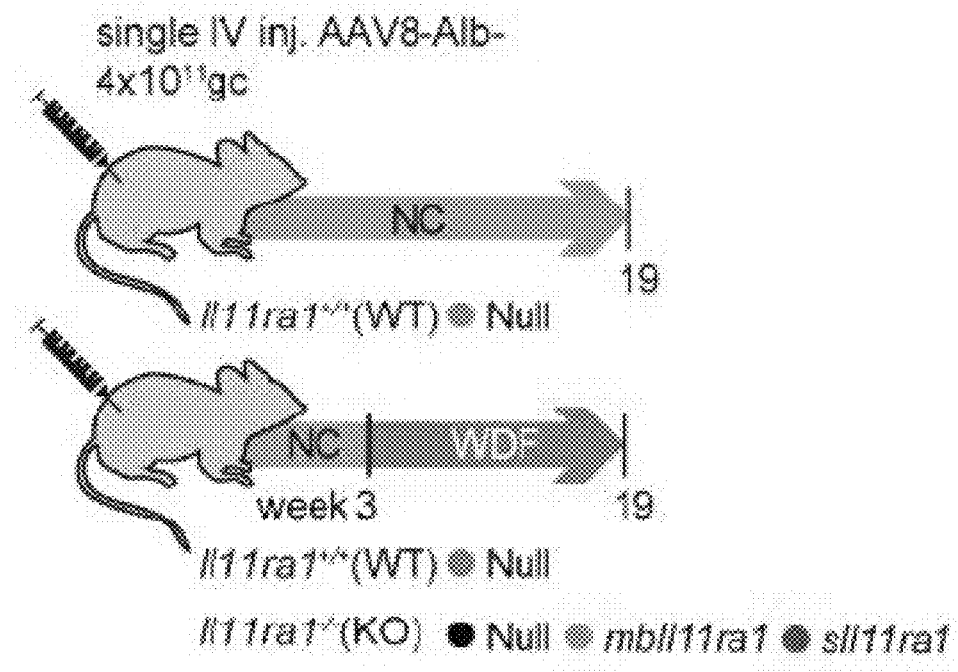
FIGS. 38A to 38N. Schematic, images and box plots showing that hepatocyte-specific IL11 cis-signaling but not IL11 trans-signaling drives steatohepatitis in mice on WDF. (A) Schematic showing WDF feeding regimen of Il11ra1+/+ (WT) and Il11ra1−/− (KO) mice for experiments shown in (B-N). AAV8-Alb-Null, AAV8-Alb-mbIl11ra1 (full length membrane-bound Il11ra1), and AAV8-Alb-sIl11ra1 (soluble form of Il11ra1)-injected KO mice were given 16 weeks of WDF feeding, three weeks following virus administration. (B) Western blots showing hepatic levels of IL11 RA and GAPDH. (C) Representative gross anatomy and H&E stained images of livers. (D) Liver weight. (E) Hepatic triglycerides content. (F) Serum ALT levels. (G) Serum AST levels. (H) Hepatic GSH content. (I) Hepatic collagen content. (J) Hepatic pro-inflammatory and fibrotic genes expression heat map (values are shown in FIGS. 45C and 45D). (K) Western blots showing activation status of hepatic ERK and JNK. (L) Fasting blood glucose levels. (M) Serum triglycerides levels. (N) Serum cholesterol levels. (D-I, L-N) Data are shown as box-and-whisker with median (middle line), $25^{th}$-$75^{th}$ percentiles (box) and min-max values (whiskers), Tukey-corrected Student's t-test; from left to right, conditions shown are: NC Null WT, WDF Null WT, WDF Null KO, WDF mbIl11ra1 KO, WDF sIl11ra1 KO.
Figure 45A:
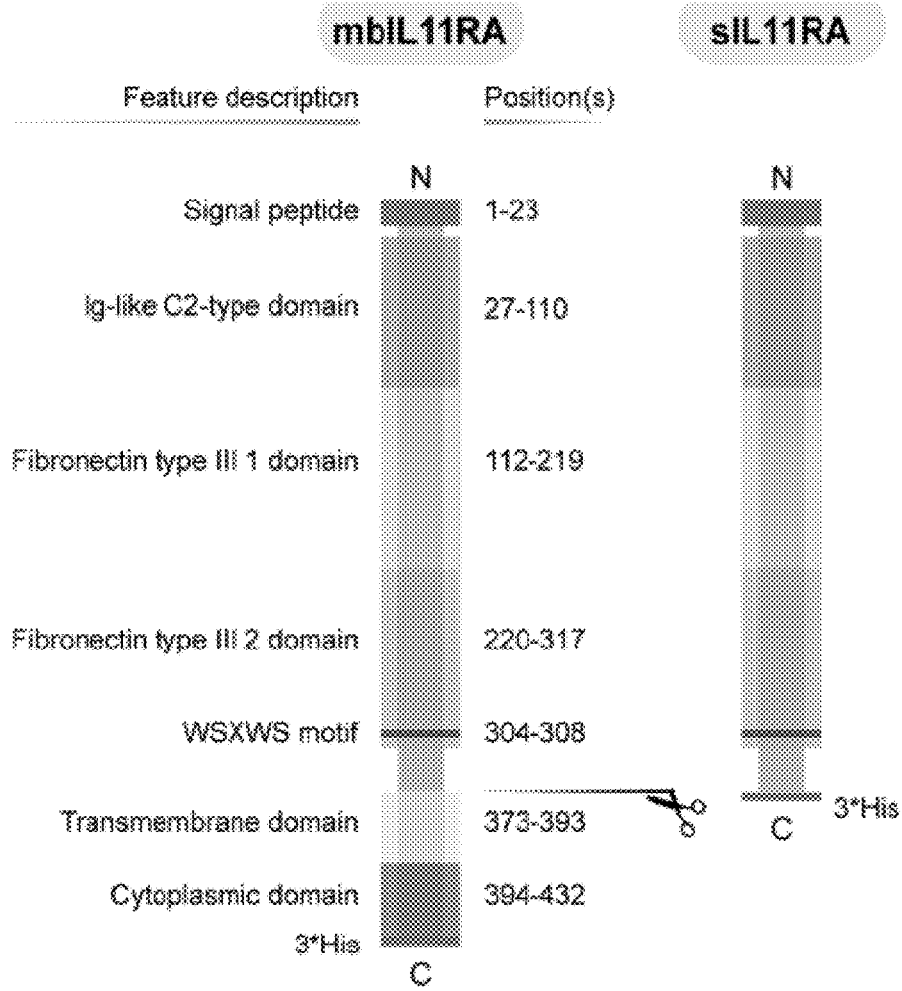
FIGS. 45A to 45D. Schematic and box plots showing that hepatocyte-specific IL11 cis-signaling but not IL11 trans-signaling drives WDF-induced steatohepatitis in mice. (A) Schematic of full-length membrane-bound IL11 RA protein domain structure and its amino acid position (left) and the domains that were used to construct soluble IL11 RA (right). (B-D) Data for WDF feeding regimen on IL11ra1+/+ (WT) mice and mice globally deleted for Il11ra (Il11ra1-/-; KO mice) that had been injected with AAV8-Alb-Null, AAV8-Alb-mbIl11ra1 (full length membrane-bound Il11ra1) or AAV8-Alb-sIl11ra1 (soluble form of Il11ra1) as illustrated in FIG. 38A. (B) Serum IL11 RA levels in AAV8-Alb-Null and AAV8-Alb-sIl11ra1-injected KO mice on WDF. (C and D) Hepatic mRNA expression of (C) pro-inflammatory markers (Tnfα, Ccl2, Ccl5) and (D) fibrotic markers (Coital, Col1a2, Col3a1, Acta2). (B-D) Data are shown as box-and-whisker with median (middle line), $25^{th}$-$75^{th}$ percentiles (box) and min-max values (whiskers), Tukey-corrected Student's t-test. (C and D) for each gene, from left to right, conditions shown are: NC Null WT, WDF Null WT, WDF Null KO, WDF mbIl11 ra1 KO, WDF sIl11 ra1 KO.
Figure 46A:
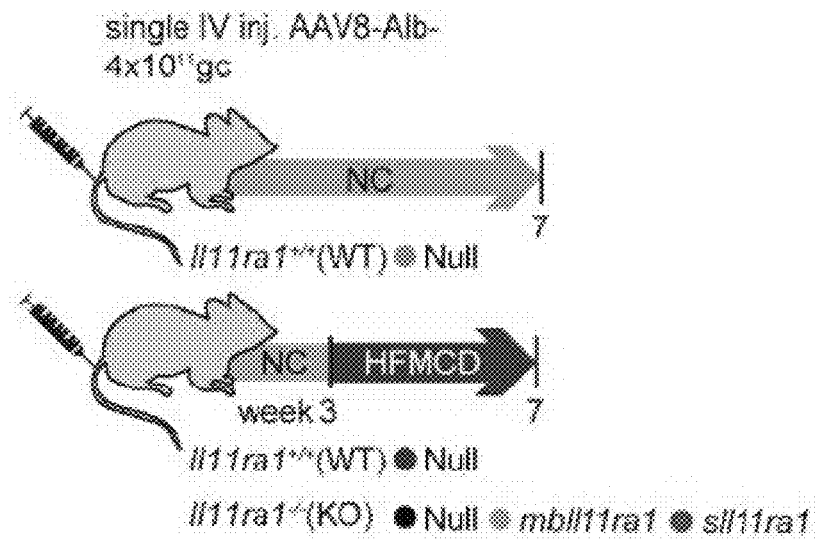
FIGS. 46A to 46L. Schematic, images and box plots showing that hepatocyte-specific IL11 cis-signaling but not IL11 trans-signaling drives steatohepatitis in mice on a HFMCD. (A) Schematic of HFMCD-fed WT and KO mice for experiments shown in (B-L). KO mice were intravenously injected with either AAV8-Alb-Null, AAV8-Alb-mbIl11ra1 or AAV8-ALB-sIl11ra1; WT mice received AAV8-Alb-Null as control. Three weeks following virus administration, mice were started on HFMCD feeding for 4 weeks. (B) Western blots showing hepatic levels of IL11 RA and GAPDH. (C) Serum IL11 RA levels. (D) Representative gross anatomy and H&E stained images of livers. (E) Hepatic triglycerides content. (F) Serum ALT levels. (G) Serum AST levels. (H) Hepatic GSH levels. (I) Hepatic collagen content. (J and K) Hepatic mRNA expression of (J) pro-inflammatory markers (Tnfα, Ccl2, Ccl5) and (K) fibrotic markers (Coital, Col1a2, Col3a1, Acta2). (L) Western blots showing activation status of hepatic ERK and JNK. (C, E-K) Data are shown as box-and-whisker with median (middle line), 25th-75th percentiles (box) and min-max values (whiskers), Tukey-corrected Student's t-test. (E-I) from left to right, conditions shown are: NC Null WT, HFMCD Null WT, HFMCD Null KO, HFMCD mbIl11ra1 KO, HFMCD sIl11ra1 KO. (J and K) for each gene, from left to right, conditions shown are: NC Null WT, HFMCD Null WT, HFMCD Null KO, HFMCD mbIl11ra1 KO, HFMCD sIl11ra1 KO.

5.3.5 Reconstitution of Hepatocyte-Specific IL11 Cis-Signaling in IL11ra1 Null Mice Restores Steatohepatitis but not Liver Fibrosis In vivo gain-of-function experiments were employed to complement loss-of-function experiments using the CKO mice. The inventors investigated whether restoring IL11 cis- or trans-signaling specifically in hepatocytes in mice with global Il11ra1 deletion (Il11ra1−/− knockouts (KOs)) resulted in disease. KO mice were injected with AAV8 encoding either the full length, membrane bound Il11ra1 (mbIl11ra1; to reconstitute cis-signaling) or a secreted/soluble form of Il11ra1 (sIl11ra1, which constitutes the extracellular portion of Il11ra1; to enable trans-signaling) or a control construct and the animals were then fed with NC, HFMCD diet or WDF (FIGS. 38A, 45A, and 46A).

Figure 38B:
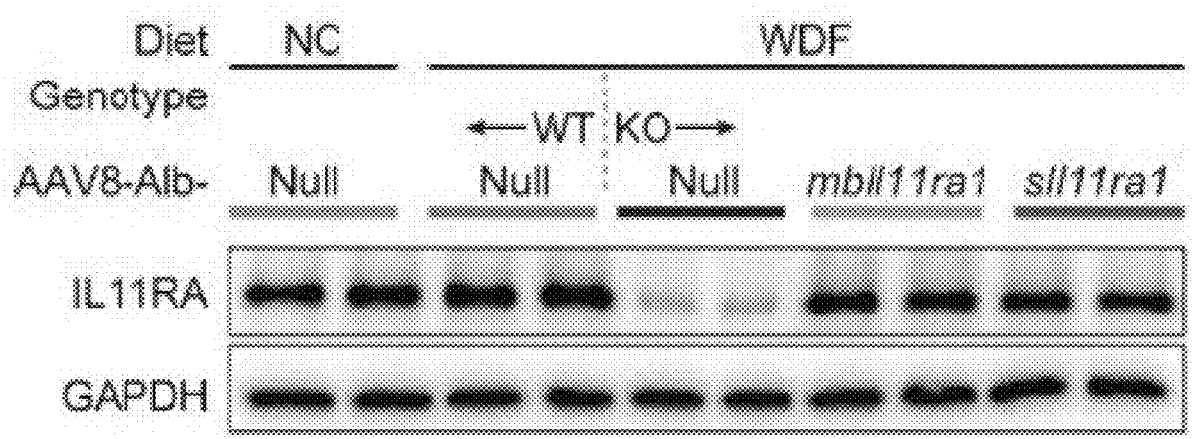
Figure 38C:
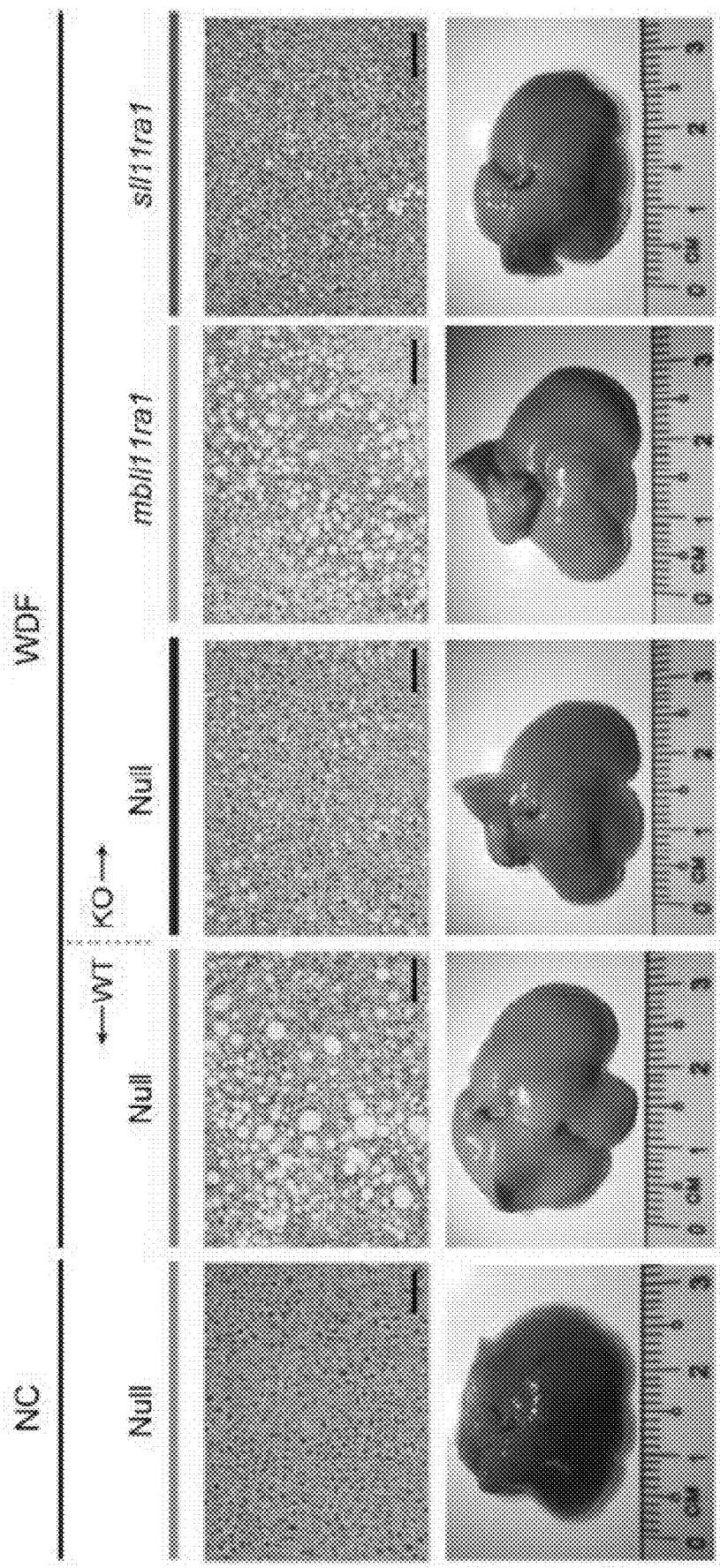
Figure 38D:
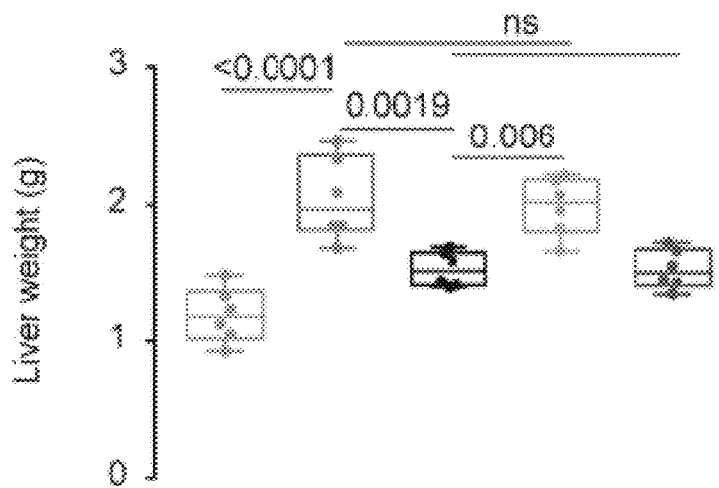
Figure 38E:
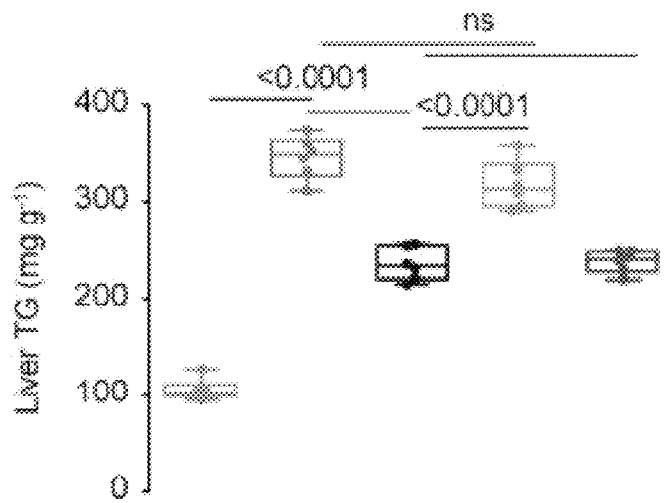
Figure 38F:
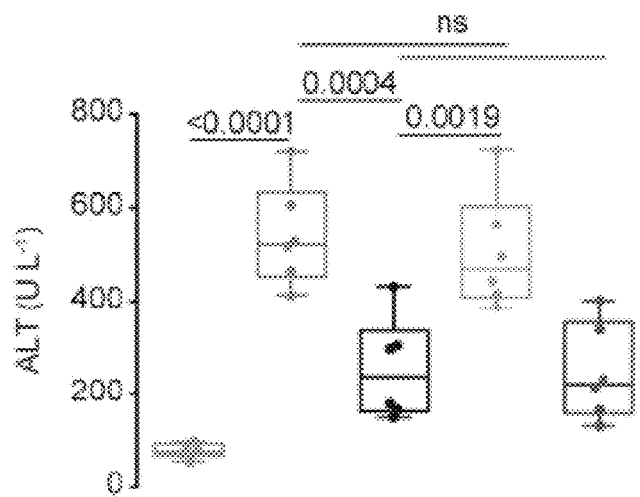
Figure 38G:
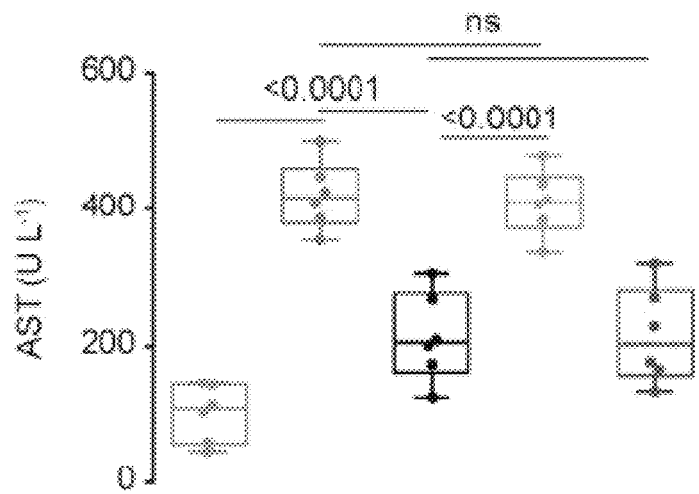
Figure 38H:
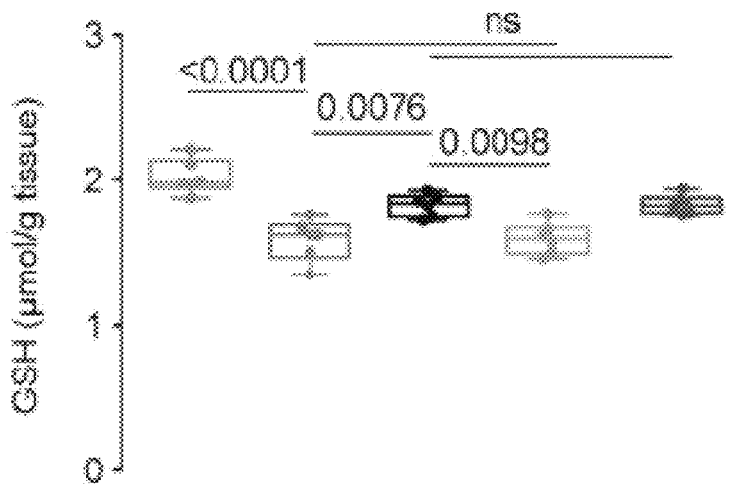
Figure 38I:
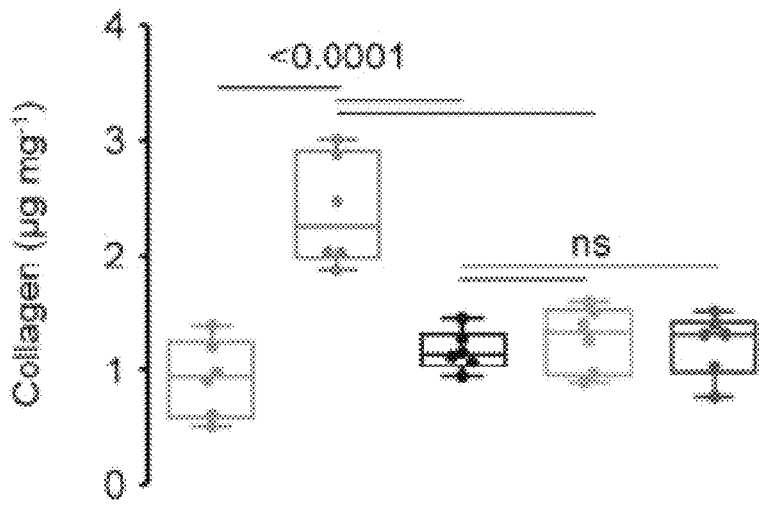
Figure 38J:
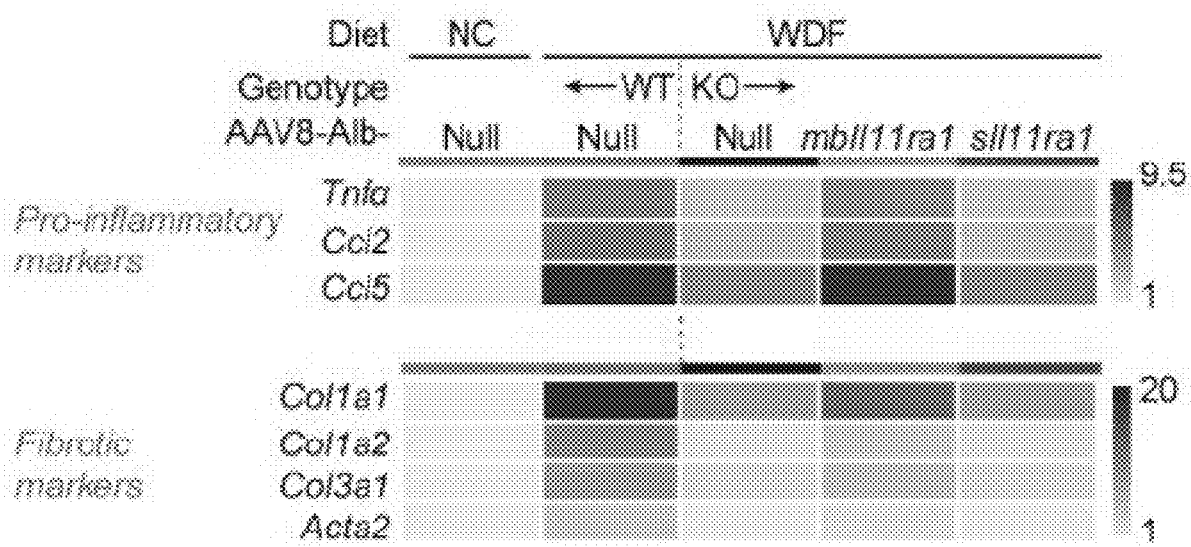
Figure 45B:
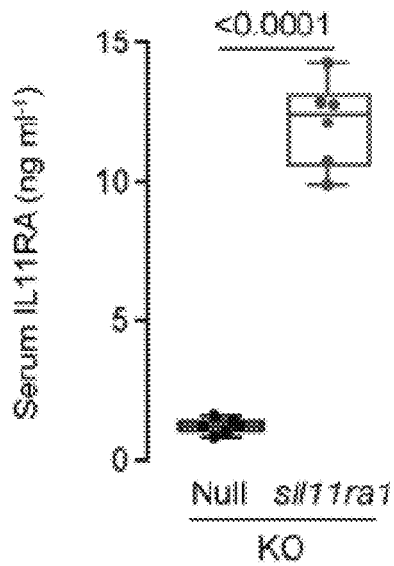
Figure 45C:
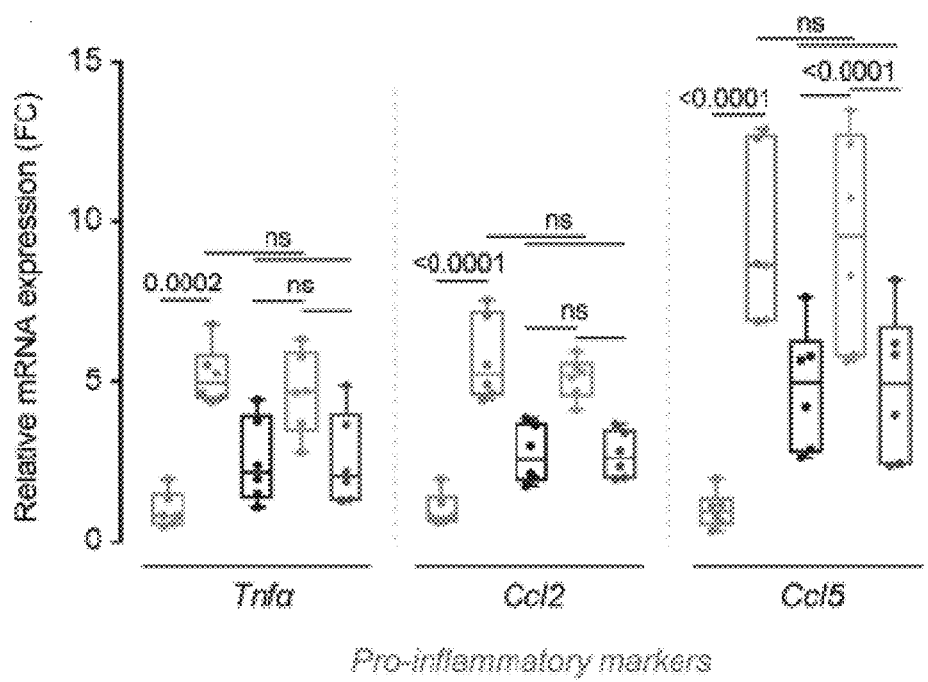
Figure 45D:
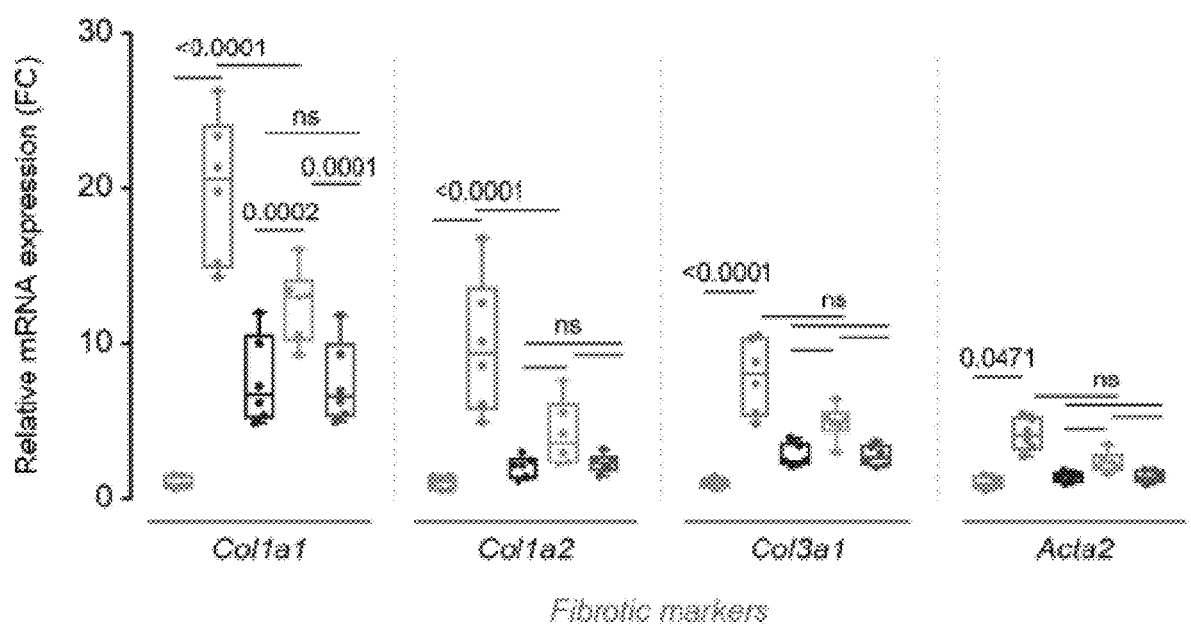
Figure 46B:
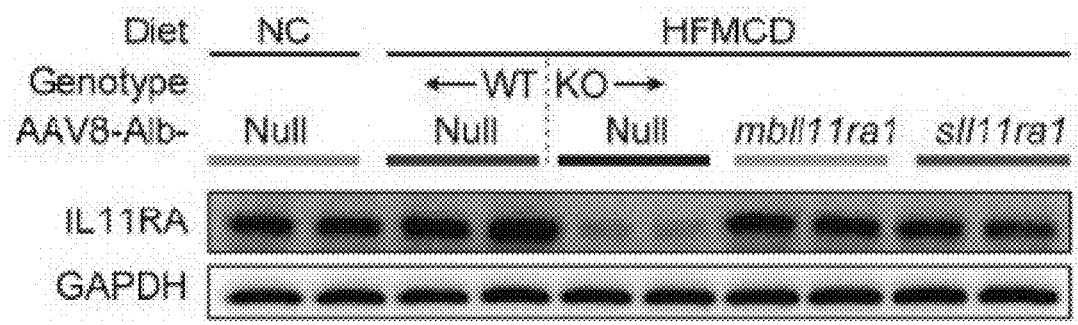
Figure 46C:
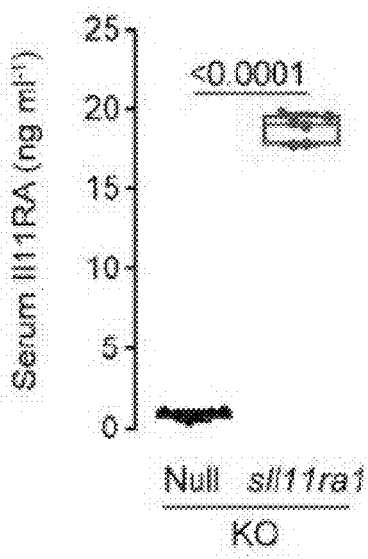
Figure 46D:
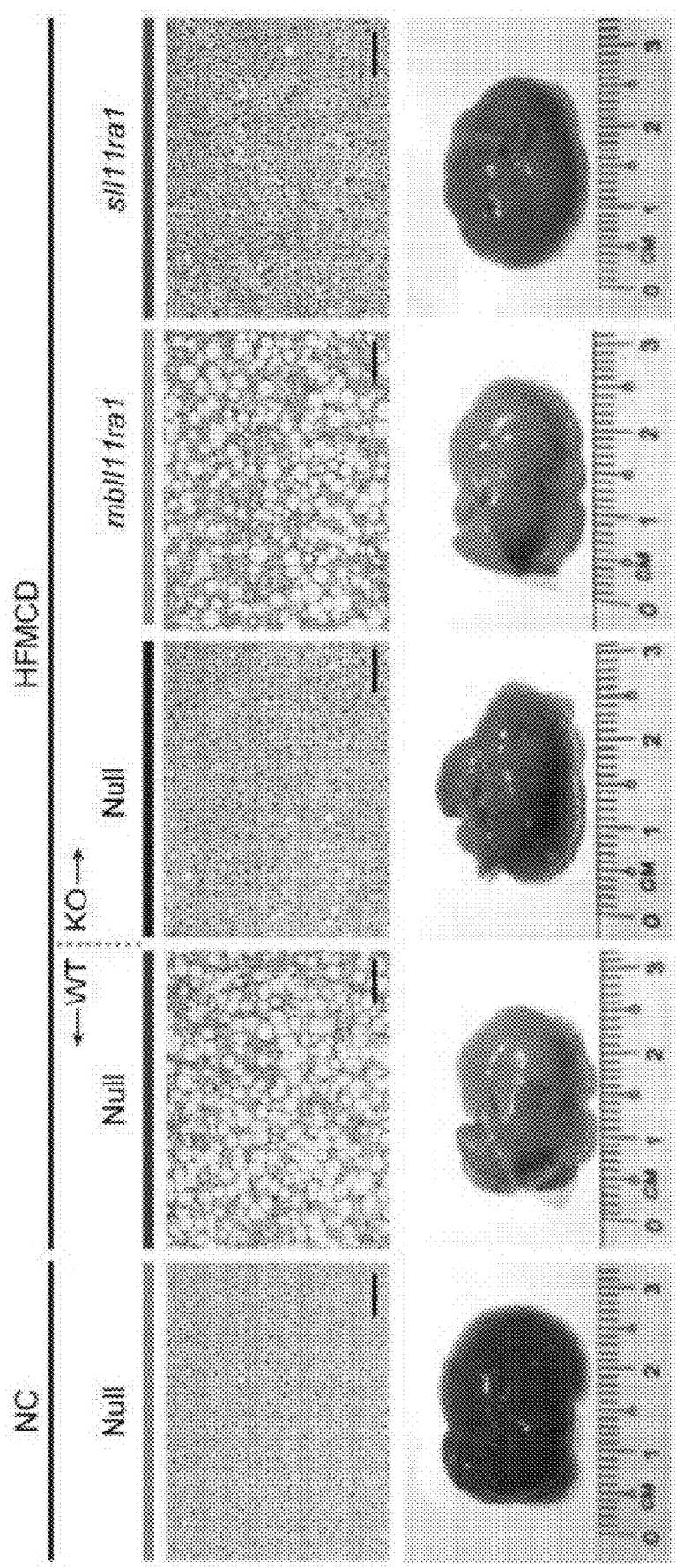
Figure 46E:
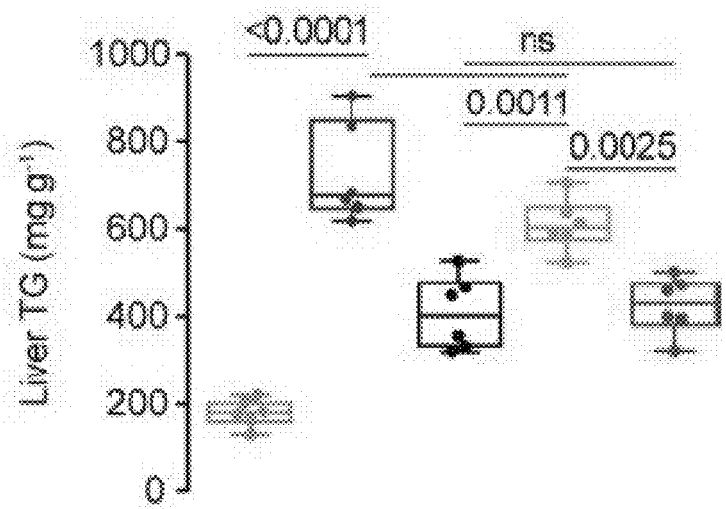
Figure 46F:
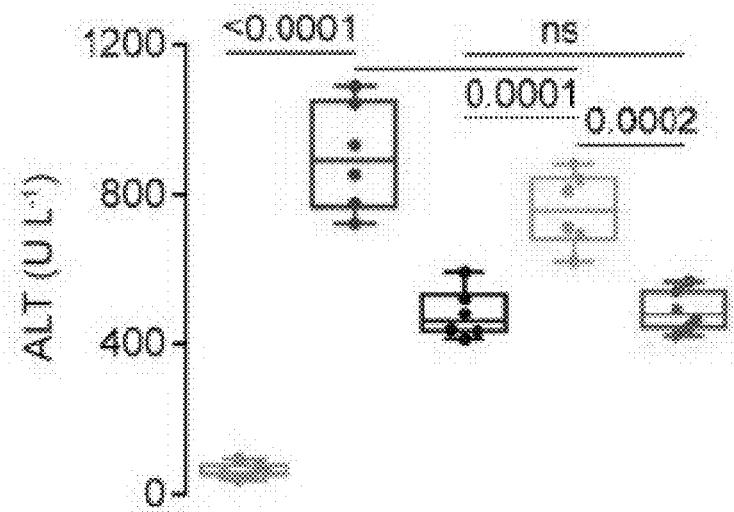
Figure 46G:
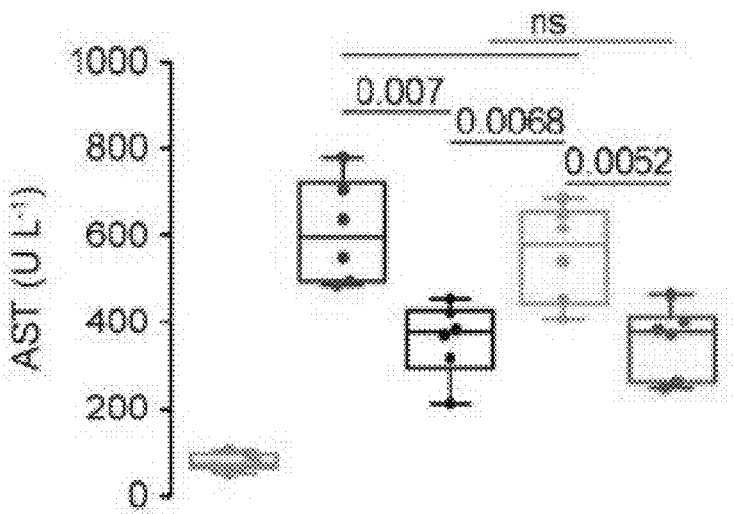
Figure 46H:
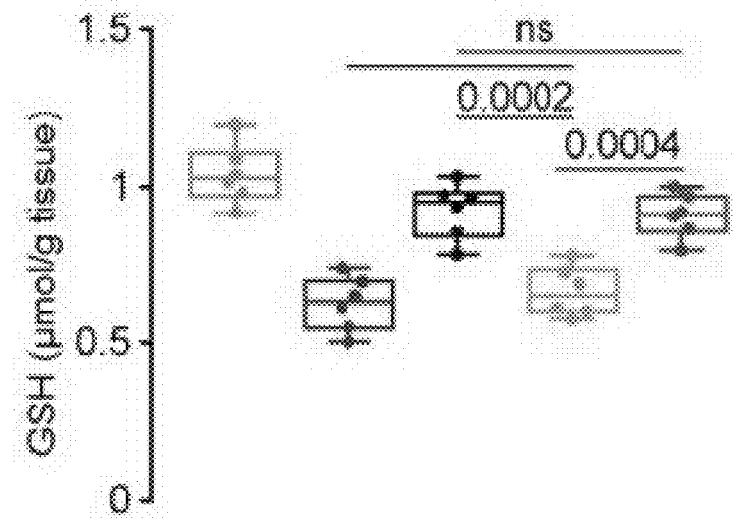
Figure 46I:
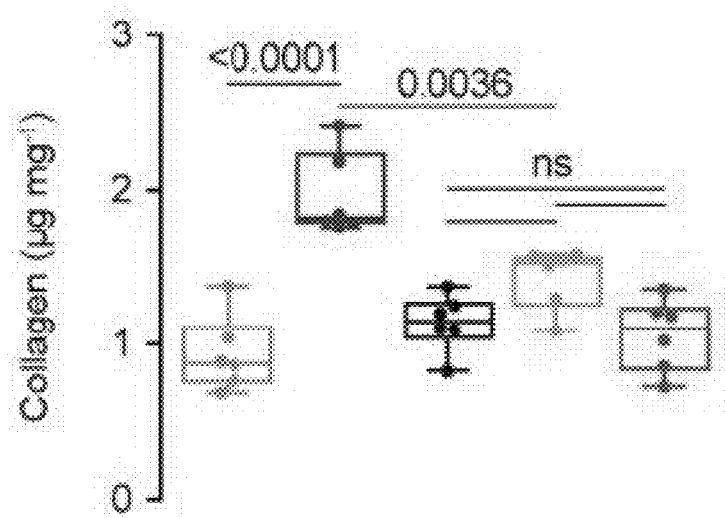
Figure 46J:
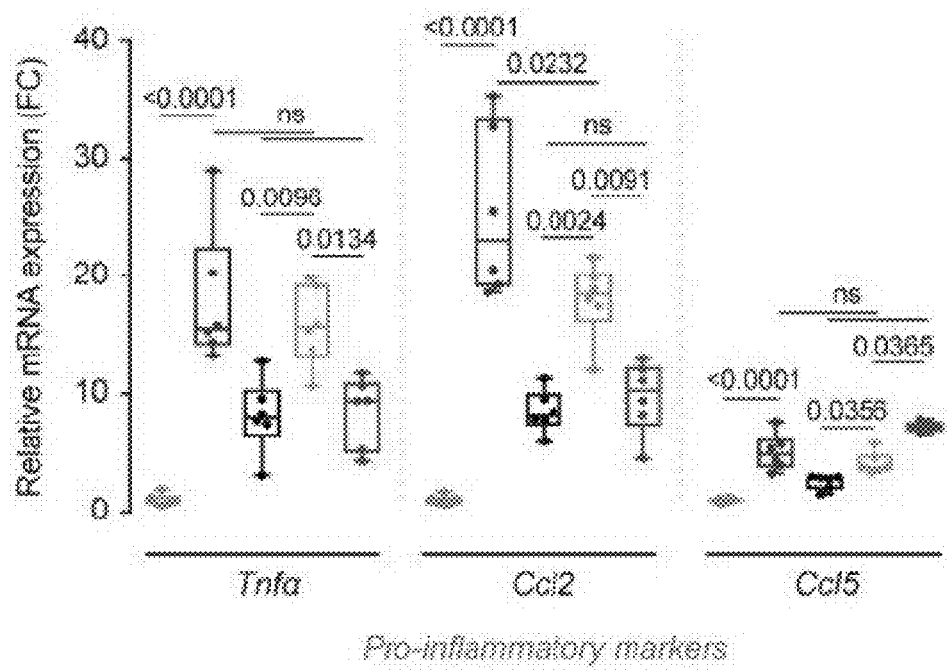
Figure 46K:
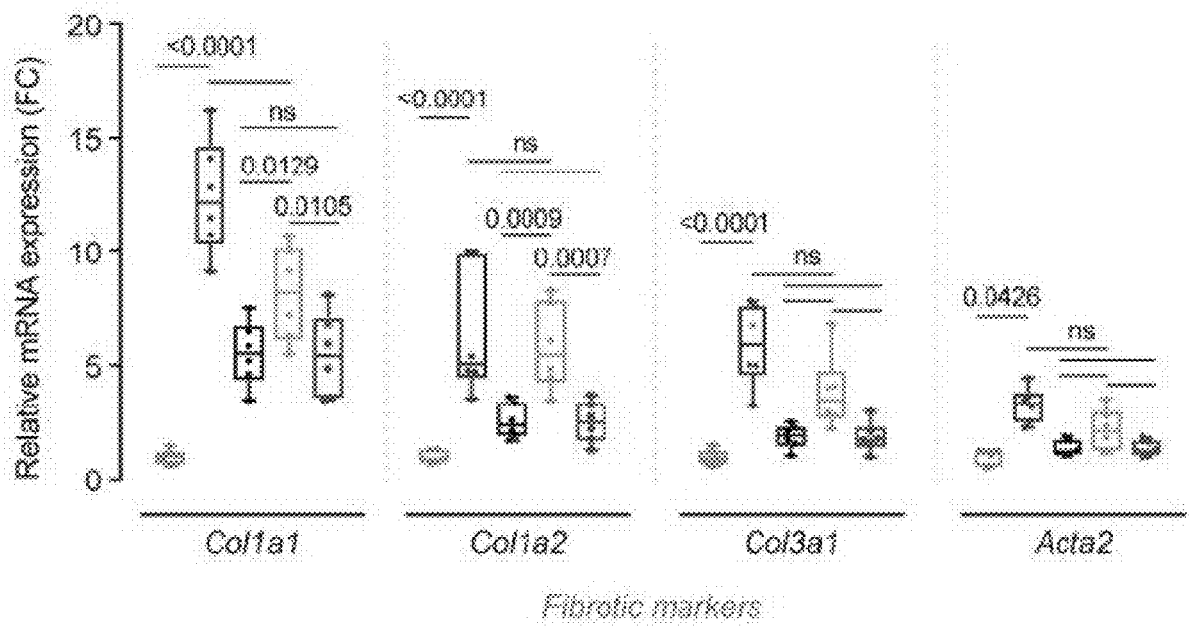

KO mice injected with AAV8-Alb-mbIl11ra1 re-expressed IL11RA1 on hepatocytes and KO mice injected with AAV8-Alb-sIl11ra1 displayed increased expression of sIL11RA1 in both the liver and the circulation (FIGS. 38B, 45B, and 46B). As expected, wild-type mice receiving control AAV8 constructs (AAV8-Alb-Null) on NC had normal livers and, when on either HFMCD diet or WDF, developed steatosis, inflammation and liver damage (FIGS. 38C-38J, 45C and 45D, 46D-46K). KO mice injected with control virus and fed either HFMCD or WDF diets were protected from NASH phenotypes, although protection with germline deletion of Il11ra1 was not as strong as seen in the CKOs.

Figure 38K:
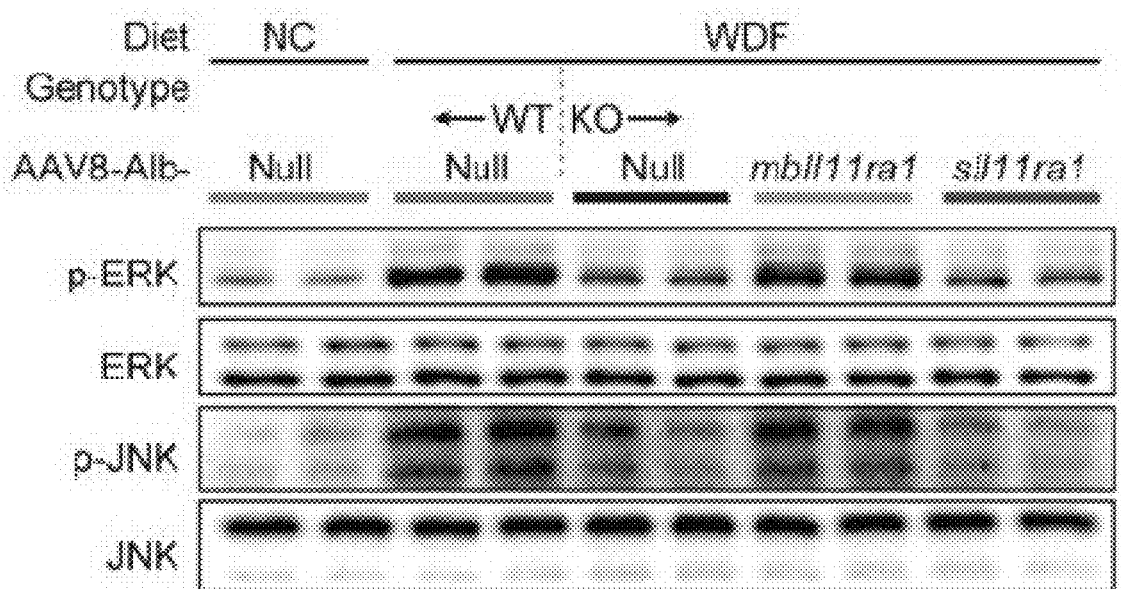
Figure 38L:
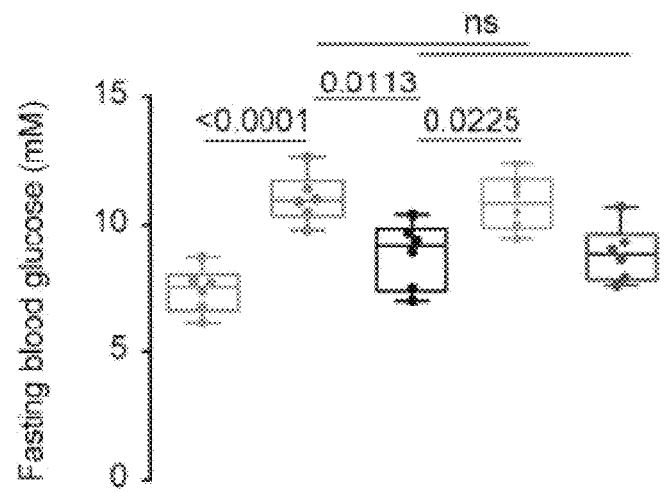
Figure 38M:
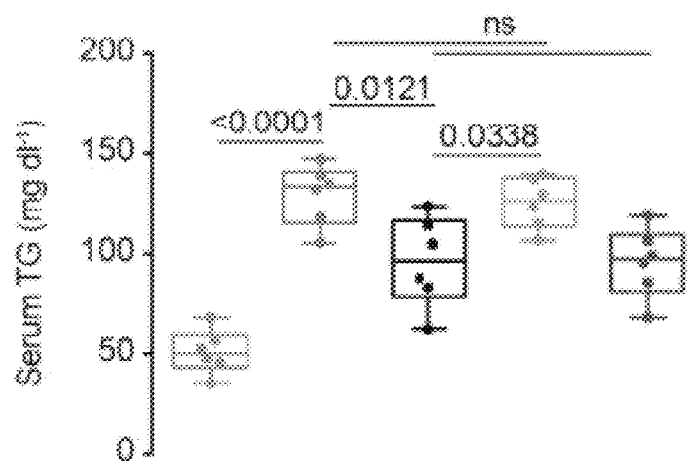
Figure 38N:
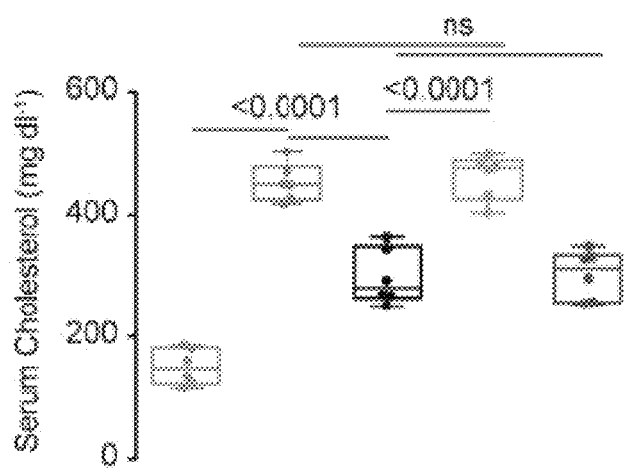
Figure 46L:
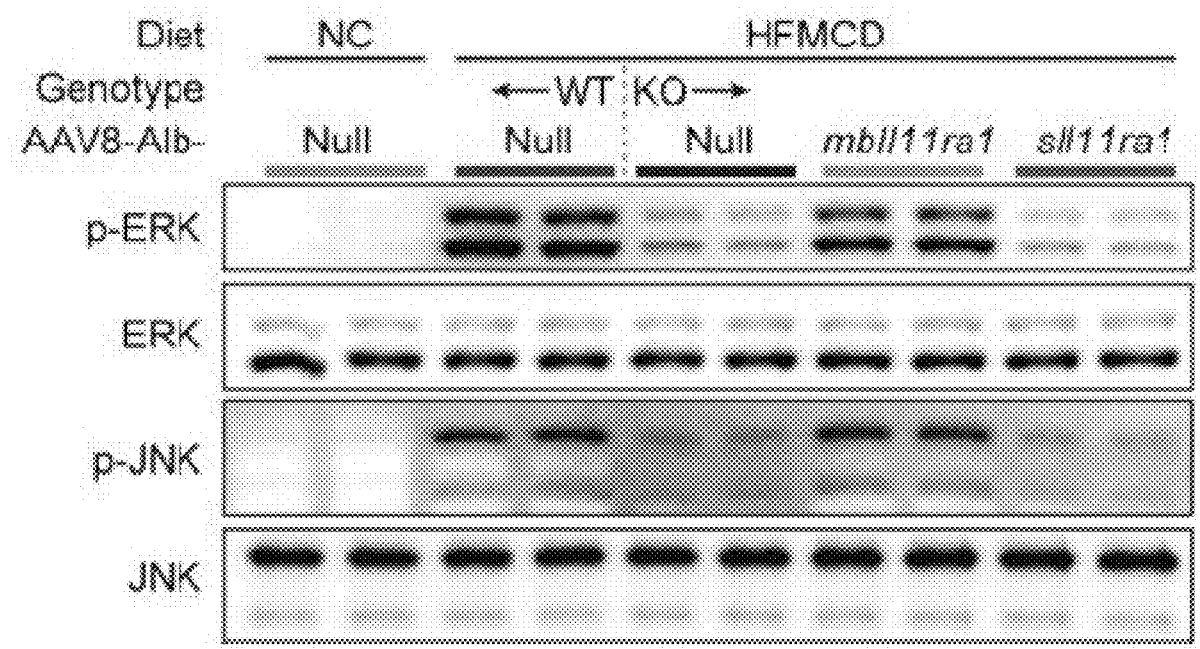

Restoration of IL11 cis-signaling in KO mice using mbIl11ra1 recapitulated hepatic steatosis and inflammation that was evident from gross morphology to molecular patterns of gene expression and signaling (FIGS. 38C-38J, 45C-45D, and 46D-46L). Notably, hepatic collagen content and fibrotic gene expression was not restored (FIGS. 38I and 38J, 45D, 46I and 46K) as IL11 signaling in HSCs, important for HSC-to-myofibroblast transformation (Widjaja et al., 2019), is unaffected by the albumin-driven Il11ra1 expression (i.e. HSCs remain deleted for Il11ra1 in these models). In stark contrast, expression of the sIL11RA in hepatocytes of KOs, which would theoretically activate trans-signaling, had no effect despite high IL11 levels (FIG. 35B) and mice remained protected from all NASH liver pathologies (FIGS. 38C-38J, 45C-45D, and 46D-46K). Signaling changes were consistent in that mIL11RA expression restored ERK and JNK activation in KOs on either diet, whereas sIL11RA1 did not (FIGS. 38K and 46L). In the WDF model, restoration of hepatocyte-specific IL11 cis-signaling in KO mice caused hyperglycemia, hypertriglyceridemia, and hypercholesterolemia but expression of sIl11ra1 did not (FIGS. 38L-38N).

5.4 Discussion

Metabolic liver disease commonly occurs in the context of obesity and type 2 diabetes and manifests initially as NAFLD that can progress to NASH (Friedman et al., 2018; Sanyal, 2019). A key underlying pathology in progression to NASH is "substrate overload", whereby an abundance of metabolites overrun the hepatocyte's ability to process fat, causing lipotoxicity. Cytokines are key NASH factors secreted from lipotoxic hepatocytes (Friedman et al., 2018) and here the inventors establish IL11 as an important component of the lipotoxic milieu and a driver of NAFLD-to-NASH transition.

A large body of evidence supports the idea that IL6 signaling in the liver is beneficial (Kroy et al., 2010; Schmidt-Arras and Rose-John, 2016; Yamaguchi et al., 2010). However, a pathogenic role for IL6 trans-signaling in hepatic steatosis has been proposed (Kammoun et al., 2017; Wieckowska et al., 2008). The inventors found using synthetic constructs that hyperIL11, initiating IL11 trans-signaling, is cytotoxic, whereas hyperIL6 is protective in hepatocytes. However, there was no evidence for trans-signaling in a biologically relevant context in vitro or in vivo, using both gain- and loss-of-function. This suggests that IL6 family member trans-signaling plays no role in NASH, which is in agreement with previous studies outside the liver (Agthe et al., 2017; Balic et al., 2017). The relevance of these findings for other diseases is unclear and clinical trials are underway targeting trans-signaling in ulcerative colitis (Kang et al., 2019). Previous studies have suggested that IL6R is expressed in hepatocytes (Schmidt-Arras and Rose-John, 2016) and so it was surprising that primary human hepatocytes were found to express very little/no IL6R. This may reflect a strong reliance on transformed hepatocyte-like cells (e.g. HepG2) in earlier studies.

Here the inventors show the critical importance of IL11 cis-signaling in hepatocytes for NASH. This effect was established using both hepatocyte-specific loss-of-function on a wildtype genetic background and also hepatocyte-specific gain-of-function on an Il11ra1 null background. This overturns the suggestion in the literature that IL11 is protective for hepatocytes based on the use of rhIL11, ineffective in the mouse, in murine models of liver disease (Maeshima et al., 2004; Nishina et al., 2012; Trepicchio et al., 2001; Zhu et al., 2015). Importantly, while restoration of hepatocyte-specific IL11 cis-signaling causes steatohepatitis in KO mice, fibrosis is not restored whereas it was prevented in the CKO. This demonstrates that IL11 cis-signaling in HSCs is required for liver fibrosis and places hepatocyte dysfunction upstream of HSC activation.

Figure 39:
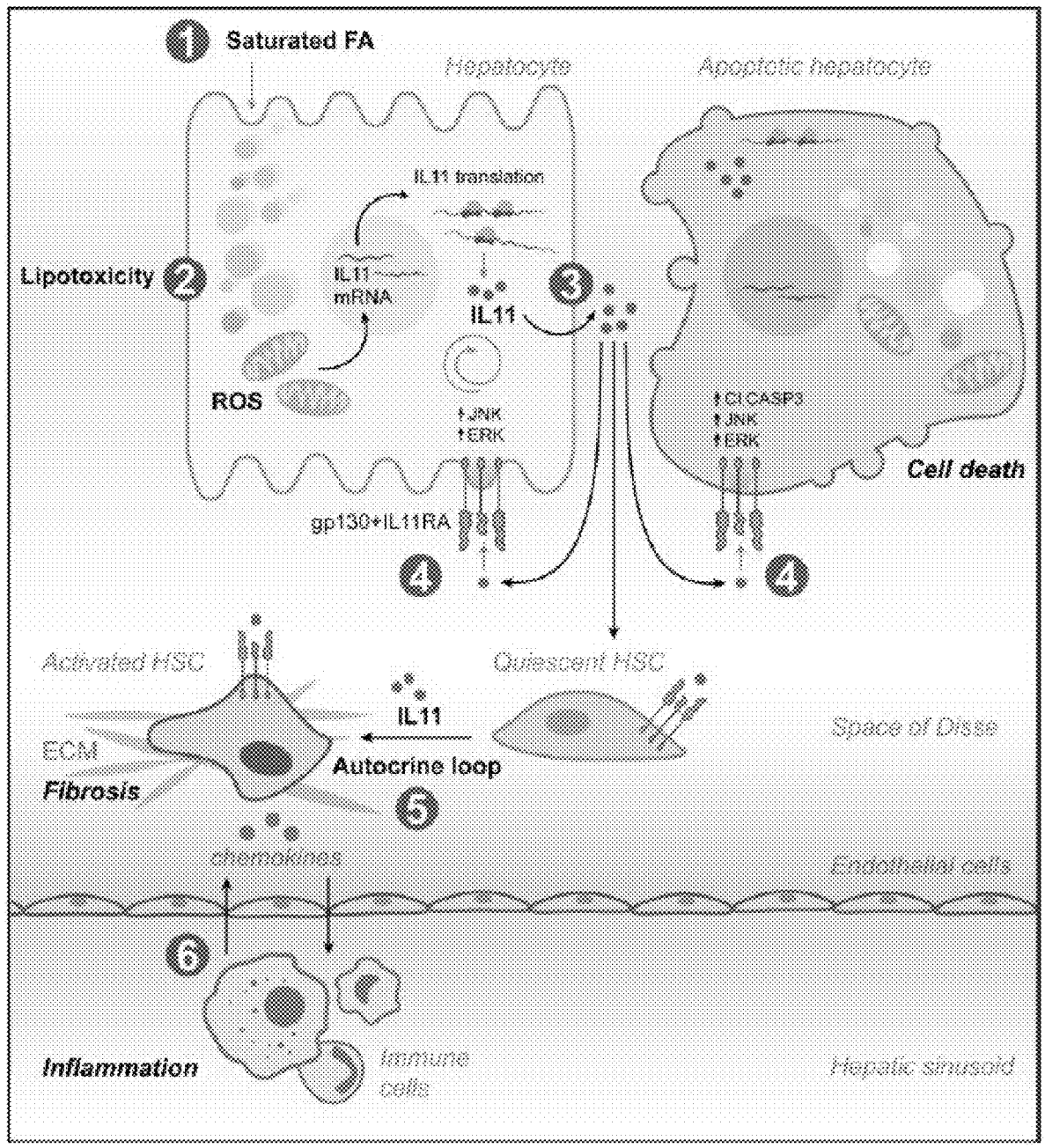
FIG. 39. Schematic of proposed mechanism of IL11 signalling in NASH. Excessive lipid accumulation in hepatocytes results in lipotoxicity leading to reactive oxygen species production that triggers IL11 protein translation and secretion. IL11 binds to IL11 RA and gp130 on hepatocytes to initiate autocrine ERK, JNK, and Caspase3 activation leading to lipoapoptosis. IL11 also acts in a paracrine fashion to drive transformation of quiescent hepatic stellate cells (HSCs) to become activated myofibroblasts. Cytokines and chemokines released from lipotoxic hepatocytes and HSCs activate and recruit immune cells causing inflammation. Thus, autocrine IL11 cis-signaling in hepatocytes is an important initiating event for all NASH pathologies.

The inventors propose a mechanistic model for NASH whereby lipid loaded hepatocytes secrete IL11 leading to autocrine cell death, paracrine activation of HSCs and secondary inflammatory cell activation and infiltration (FIG. 39). Inhibiting IL11 signaling targets an initiating nexus for diet-induced steatohepatitis that impacts subsequent liver fibrosis and inflammation, which suggests a new therapeutic approach for NASH.

5.5 Materials and Methods for Example 5

5.5.1 AAV8 Vectors

All Adeno-associated virus serotype 8 (AAV8) vectors were synthesized by Vector Biolabs. AAV8 vector carrying a mouse membrane-bound Il11ra1 cDNA (NCBI accession number: BC069984), a mouse soluble Il11ra1 cDNA, and a mouse soluble gp130 cDNA driven by Albumin (Alb) promoter is referred to as AAV8-Alb-mbIl11ra1, AAV8-Alb-sIl11ra1, and AAV8-Alb-sgp130, respectively. AAV8-Alb-sgp130 and AAV8-Alb-sIl11ra1 were constructed by removing the transmembrane and cytoplasmic regions of mouse gp130 sequence (NCBI accession number: BC058679) and mouse Il11ra1 sequence, respectively. AAV8-Null vector was used as vector control. To specifically delete Il11ra1 in Albumin-expressing cells, AAV8-Alb-iCre vector was injected to mice homozygous for LoxP-flanked Il11ra1 alleles (Il11ra1$_{loxP/loxP}$ mice).

5.5.2 Antibodies

Albumin (ab207327, Abcam), Alexa Fluor 488 secondary antibody (ab150077, Abcam), Cleaved Caspase-3 (9664, CST), Caspase3 (9662, CST) p-ERK1/2 (4370, CST), ERK1/2 (4695, CST), GAPDH (2118, CST), gp130 (PA5-28932, Thermo Fisher), IL6 (AF506, R&D systems), IL6R (flow cytometry, ab222101, Abcam), IL6R (for immunofluorescence staining, MA1-80456, Thermo Fisher), IL11 (Aldevron), IL11 RA (flow cytometry and immunofluorescence staining, ab125015, Abcam), IL11 RA (western blot, 130920, Santa Cruz), p-JNK (4668, CST), JNK (9258, CST), p-STAT3 (4113, CST), STAT3 (4904, CST), mouse HRP (7076, CST), rabbit HRP (7074, CST), rat HRP (31470, Santa Cruz).

5.5.3 Recombinant Proteins

Commercial recombinant proteins: Human hyperIL6 (IL6R:IL6 fusion protein, 8954-SR, R&D systems), human soluble gp130 Fc (671-GP-100, R&D systems), human IL11 RA (8895-MR-050, R&D systems). Custom recombinant proteins: Human IL11 (UniProtKB:P20809, Genscript). Human hyperIL11 (IL11 RA:IL11 fusion protein), which mimics the trans-signalling complex, was constructed using a fragment of IL11RA (amino acid residues 1-317; UniProtKB: Q14626) and IL11 (amino acid residues 22-199, UniProtKB: P20809) with a 20 amino acid linker (SEQ ID NO:20) (Schafer et al., 2017).

5.5.4 Chemicals

Palmitate (P5585, Sigma), Paraformaldehyde (PFA, 28908; Thermo Fisher), phorbol 12-myristate 13-acetate (PMA, P1585, Sigma), Triton X-100 (T8787, Sigma), and 4',6-diamidino-2-phenylindole (D1306; Thermo Fisher).

5.5.5 Primary Human Hepatocytes Culture

Primary human hepatocytes (5200, ScienCell) were maintained in hepatocyte medium (520, ScienCell) supplemented with 2% fetal bovine serum, 1% Penicillin-streptomycin at 37° C. and 5% CO2. Hepatocytes (P2-P3) were serum-starved overnight unless otherwise specified in the methods prior to 24 hours stimulation with different doses of various recombinant proteins as described.

5.5.6 THP-1 Culture

THP-1 (ATCC) were cultured in RPMI 1640 (A1049101, Thermo Fisher) supplemented with 10% FBS and 0.05 mM β-mercaptoethanol. THP-1 cells were differentiated with 10 ng/ml of PMA in RPMI 1640 for 48 hours.

5.5.7 Palmitate (Saturated Fatty Acid) Treatment In Vitro

Palmitate:BSA conjugated solution in the ratio of 6:1 was prepared as described earlier (Alsabeeh et al., 2018). Palmitate (0.5 mM) conjugated in fatty acids free BSA was used to treated cells as described in figure legends; 0.5% BSA solution was used as control.

5.5.8 Flow Cytometry

For surface IL11RA, IL6R, and gp130 analysis, primary human hepatocytes and THP-1 cells were stained with IL11RA, IL6R, or gp130 antibody and the corresponding Alexa Fluor 488 secondary antibody. Cell death analysis was performed by staining primary human hepatocytes with Dead Cell Apoptosis Kit with Annexin V FITC and PI (V13242, Thermo Fisher). PI+ve cells were then quantified with the flow cytometer (Fortessa, BD Biosciences) and analyzed with FlowJo version X software (TreeStar).

5.5.9 Immunofluorescence

Primary human hepatocytes were seeded on 8-well chamber slides ($1.5 \times 10^4$ cells/well) 24 hours before the staining. Cells were fixed in 4% PFA for 20 minutes, washed with PBS, and non-specific sites were blocked with 5% BSA in PBS for 2 hours. Cells were incubated with IL11RA, IL6R, gp130, or Albumin antibody overnight (4° C.), followed by incubation with the appropriate Alexa Fluor 488 secondary antibody for 1 hour. Chamber slides were dried in the dark and 5 drops of mounting medium with DAPI were added to the slides for 15 minutes prior to imaging by fluorescence microscope (Leica).

5.5.10 Oil Red O Staining

Primary human hepatocytes were seeded on 8-well chamber slides ($1 \times 10^4$ cells/well) Following 24 hours of palmitate treatment, cells were fixed in 10% PFA for 30 minutes, washed with distilled water, and incubated with 60% (v/v) isopropyl alcohol for 5 minutes. Cells were then stained with Oil Red O Solution for 30 minutes and washed with distilled water prior to imaging with bright field microscope (BX53, Olympus). The lipid droplets were identified by their red staining.

5.5.11 Reactive Oxygen Species (ROS) Detection

Primary human hepatocytes were seeded on 8-well chamber slides ($1 \times 10^4$ cells/well). For this experiment, cells were not serum-starved prior to palmitate treatment. 24 hours following palmitate stimulation, cells were washed, incubated with 25 μM of DCFDA solution (ab113851, Abcam) for 45 minutes at 37° C. in the dark, and rinsed with dilution buffer according to the manufacturer's protocol. Live cells with positive DCF staining were imaged with filter set appropriate for fluorescein (FITC) using a fluorescence microscope (Leica).

5.5.12 Animal Models

Animal experiments were performed under the guidelines of SingHealth Institutional Animal Care and Use Committee (IACUC). Mice were maintained in SPF environment and provided with food and water ad libitum.
Mouse Models of Metabolic Liver Disease
HFMCD
6-8 weeks old C57BL/6N, Il11ra1−/− mice, and Il11ra1$_{loxP/loxP}$ and their respective control were fed with methionine- and choline-deficient diet supplemented with 60 kcal % fat (HFMCD, A06071301B16, Research Diets) for 4 weeks. Control mice received normal chow (NC, Specialty Feeds).
WDF
6-8 weeks old C57BL/6N, Il11ra1−/− mice, and Il11ra1$_{loxP/loxP}$ and their respective control were fed western diet (D12079B, Research Diets) supplemented with 15% weight/volume fructose in drinking water (WDF) for 16 weeks. Control mice received NC and tap water.
Il11ra1-Deleted Mice (KO)
6-8-week old male Il11ra1−/− mice (B6.129S1-Il11ratm1Wehi/J, Jackson's Laboratory) were intravenously injected with $4 \times 10^{11}$ genome copies (gc) of AAV8-AlbmbIl11ra1 or AAV8-Alb-sIl11ra1 virus to induce hepatocyte specific expression of mouse Il11ra1 or soluble Il11ra1, respectively. As controls, both Il11ra1−/− mice and their wildtype littermates (Il11ra1+/+) were intravenously injected with $4\times10^{11}$ gc AAV8-Alb-Null virus. 3 weeks after virus injection, mice were fed with HFMCD, WDF, or NC. Durations of diet are described.

In Vivo Administration of Soluble Gp130

6-8-week old male C57BL/6N mice (InVivos) were injected with $4\times10^{11}$ gc AAV8-Alb-sgp130 virus to induce hepatocyte specific expression of soluble gp130; control mice were injected with $4\times10^{11}$ gc AAV8-Alb-Null virus. 3 weeks following virus administration, mice were fed with HFMCD, WDF, or NC for durations that are described.

Il11ra-Floxed Mice (CKO)

Il11ra-floxed mice, in which exons 4 to 7 of the Il11ra1 gene were flanked by loxP sites, were created using CRISPR/Cas9 system as previously described (Ng et al.). To induce the specific deletion of Il11ra1 in hepatocytes, 6-8-week old male homozygous Il11ra1-floxed mice were intravenously injected with AAV8-Alb-Cre virus ($4\times10^{11}$ gc); a similar amount of AAV8-Alb-Null virus were injected into homozygous Il11ra1-floxed mice as controls. The AAV8-injected mice were allowed to recover for three weeks prior to HFMCD, WDF, or NC feeding. Knockdown efficiency was determined by Western blotting of hepatic IL11RA.

5.5.13 RNA-Sequencing (RNA-Seq) and Ribosome Profiling (Ribo-Seq)

RNA-seq and Ribo-Seq library preparations were performed as previously described (Chothani et al., 2019).

Generation of RNA-Seq Libraries

Total RNA was extracted from human hepatocytes using RNeasy columns (Qiagen). RNA was quantified using a Qubit RNA High-Sensitivity Assay kit (Life Technologies) and its quality was assessed on the basis of their RNA integrity number using the LabChip GX RNA Assay Reagent Kit (Perkin Elmer). TruSeq Stranded mRNA Library Preparation kit (Illumina) was used to measure transcript abundance following standard instructions from the manufacturer.

Generation of Ribo-Seq Libraries

Hepatocytes were grown to 90% confluence in a 10 cm culture dish and lysed in 1 mL cold lysis buffer (formulation as in TruSeq® Ribo Profile Mammalian Kit, RPHMR12126, Illumina) supplemented with 0.1 mg/mL cycloheximide. Homogenized and cleared lysates were then footprinted with Truseq Nuclease (Illumina) according to the manufacturer's instructions. Ribosomes were purified using Illustra Sephacryl S400 columns (GE Healthcare), and the protected RNA fragments were extracted with a standard phenol:chloroform:isoamylalcohol technique. Following ribosomal RNA removal (Mammalian RiboZero Magnetic Gold, Illumina), sequencing libraries were then prepared out of the footprinted RNA by using TruSeq® Ribo Profile Mammalian Kit according to the manufacturer's protocol.

The final RNA-seq and ribosome profiling libraries were quantified using KAPA library quantification kits (KAPA Biosystems) on a StepOnePlus Real-Time PCR system (Applied Biosystems) according to the manufacturer's protocol. The quality and average fragment size of the final libraries were determined using a LabChip GX DNA High Sensitivity Reagent Kit (Perkin Elmer). Libraries with unique indexes were pooled and sequenced on a NextSeq 500 benchtop sequencer (Illumina) using NextSeq 500 High Output v2 kit and paired-end 75-bp sequencing chemistry.

Data Processing and Analyses for RNA-Sequencing and Ribosome Profiling

Raw sequencing data were demultiplexed with bcl2fastq V2.19.0.316 and the adaptors were trimmed using Trimmomatic (Bolger et al., 2014) V0.36, retaining reads longer than 20 nt post-clipping. Ribo-seq reads were aligned using bowtie (Langmead et al., 2009) to known mtRNA, rRNA and tRNA sequences (RNACentral(The RNAcentral Consortium, 2017), release 5.0) and only unaligned reads were retained as Ribosome protected fragments (RPFs). Alignment to the human genome (hg38) was carried out using STAR (Dobin et al., 2012). Gene expression was quantified on the CDS (coding sequence) regions for Ribo-seq and exonic regions for RNA-seq using uniquely mapped reads (Ensembl database release GRCh38 v86) with feature counts (Liao et al., 2014). TPM was calculated and visualized using boxplot to compare baseline expression of IL11RA (ENSG00000137070), IL6R (ENSG00000160712), and gp130 (ENSG00000134352). Read coverage using Ribo-seq and RNA-seq reads for IL11RA, IL6R and gp130 was visualized using Gviz R package (Hahne and Ivanek, 2016) with strand specific alignment files.

5.5.14 Colorimetric Assays

Alanine Aminotransferase (ALT) activity in the cell culture supernatant and mouse serum was measured using ALT Activity Assay Kit (ab105134, Abcam). Liver Glutathione (GSH) levels were measured using Glutathione Colorimetric Detection Kit (EIAGSHC, Thermo Fisher). Total hydroxyproline content in mouse livers was measured using Quickzyme Total Collagen assay kit (QZBtotco15, Quickzyme Biosciences). The levels of serum and liver triglycerides were measured using Triglyceride Assay Kit (ab65336, Abcam). Mouse serum levels of Aspartate Aminotransferase (AST) and cholesterol were measured using AST Assay Kit (ab105135, Abcam) and Cholesterol Assay Kit (ab65390; Abcam), respectively. All colorimetric assays were performed according to the manufacturer's protocol.

5.5.15 Enzyme-Linked Immunosorbent Assay (ELISA)

The levels of gp130 in mouse serum were quantified using Mouse gp130 DuoSet ELISA (DY468, R&D systems) according to the manufacturer's protocol.

5.5.16 RT-qPCR

Total RNA was extracted from snap-frozen liver tissues using Trizol (Invitrogen) and RNeasy Mini Kit (Qiagen). PCR amplifications were performed using iScript cDNA Synthesis Kit (Biorad). Gene expression was analyzed in duplicate by TaqMan (Applied Biosystems) or SYBR green (Qiagen) technology using StepOnePlus (Applied Biosystem) over 40 cycles. Expression data were normalized to GAPDH mRNA expression and fold change was calculated using 2-ΔΔCt method. The sequences of specific TaqMan probes and SYBR green primers are available upon request.

5.5.17 Immunoblotting

Western blots were carried out on total protein extracts from hepatocytes and liver tissues. Hepatocyte and liver tissue lysates were homogenized in RIPA Lysis and Extraction Buffer (89901, Thermo Scientific) containing protease and phosphatase inhibitors (Roche). Protein lysates were separated by SDS-PAGE and transferred to PVDF membranes. Protein bands were visualized using the ECL detection system (Pierce) with the appropriate secondary antibodies: anti-rabbit HRP or anti-mouse HRP.

5.5.18 Liver Tissue Processing and Histological Analysis

Liver samples were fixed in 10% neutral formalin, paraffinized, cut into 5-μm sections, stained with hematoxylin and eosin (H&E) according to standard protocol, and examined by light microscopy.

5.5.19 Statistical Analysis

All statistical analyses were performed using Graph Pad Prism software (version 6.07). P values were corrected for multiple testing according to Dunnett's (when several experimental groups were compared to one condition), Tukey (when several conditions were compared to each other within one experiment), Sidak (when several conditions from 2 different genotypes were compared to each other). Analysis for two parameters for comparison of two different groups were performed by two-way ANOVA. The criterion for statistical significance was set at $P<0.05$.

5.6 References to Example 5

Agthe, M., Garbers, Y., Putoczki, T., and Garbers, C. (2017). Interleukin-11 classic but not trans-signaling is essential for fertility in mice. Placenta 57, 13-16.

Alsabeeh, N., Chausse, B., Kakimoto, P. A., Kowaltowski, A. J., and Shirihai, O. (2018). Cell culture models of fatty acid overload: Problems and solutions. Biochim. Biophys. Acta Mol. Cell Biol. Lipids 1863, 143-151.

Balic, J. J., Garbers, C., Rose-John, S., Yu, L., and Jenkins, B. J. (2017). Interleukin-11-driven gastric tumourigenesis is independent of trans-signalling. Cytokine 92, 118-123.

Bettaieb, A., Jiang, J. X., Sasaki, Y., Chao, T.-I., Kiss, Z., Chen, X., Tian, J., Katsuyama, M., Yabe-Nishimura, C., Xi, Y., et al. (2015). Hepatocyte Nicotinamide Adenine Dinucleotide Phosphate Reduced Oxidase 4 Regulates Stress Signaling, Fibrosis, and Insulin Sensitivity During Development of Steatohepatitis in Mice. Gastroenterology 149, 468-480.e10.

Bigaeva, E., Gore, E., Simon, E., Zwick, M., Oldenburger, A., de Jong, K. P., Hofker, H. S., Schlepütz, M., Nicklin, P., Boersema, M., et al. (2019). Transcriptomic characterization of culture-associated changes in murine and human precision-cut tissue slices. Arch. Toxicol.

Bolger, A. M., Lohse, M., and Usadel, B. (2014). Trimmomatic: a flexible trimmer for Illumina sequence data. Bioinformatics 30, 2114-2120.

Bozza, M., Bliss, J. L., Maylor, R., Erickson, J., Donnelly, L., Bouchard, P., Dorner, A. J., and Trepicchio, W. L. (1999). Interleukin-11 reduces T-cell-dependent experimental liver injury in mice. Hepatology 30, 1441-1447.

Chothani, S., Schafer, S., Adami, E., Viswanathan, S., Widjaja, A. A., Langley, S. R., Tan, J., Wang, M., Quaife, N. M., Jian Pua, C., et al. (2019). Widespread Translational Control of Fibrosis in the Human Heart by RNA-Binding Proteins. Circulation 140, 937-951.

Dobin, A., Davis, C. A., Schlesinger, F., Drenkow, J., Zaleski, C., Jha, S., Batut, P., Chaisson, M., and Gingeras, T. R. (2012). STAR: ultrafast universal RNA-seq aligner. Bioinformatics 29, 15-21.

Farrell, G. C., Haczeyni, F., and Chitturi, S. (2018). Pathogenesis of NASH: How Metabolic Complications of Overnutrition Favour Lipotoxicity and Pro-Inflammatory Fatty Liver Disease. Adv. Exp. Med. Biol. 1061, 19-44.

Friedman, S. L., Neuschwander-Tetri, B. A., Rinella, M., and Sanyal, A. J. (2018). Mechanisms of NAFLD development and therapeutic strategies. Nat. Med.

Hahne, F., and Ivanek, R. (2016). Visualizing Genomic Data Using Gviz and Bioconductor. In Statistical Genomics, (Humana Press, New York, N.Y.), pp. 335-351.

Kakisaka, K., Cazanave, S. C., Fingas, C. D., Guicciardi, M. E., Bronk, S. F., Werneburg, N. W., Mott, J. L., and Gores, G. J. (2012). Mechanisms of lysophosphatidylcholine-induced hepatocyte lipoapoptosis. Am. J. Physiol. Gastrointest. Liver Physiol. 302, G77-G84.

Kammoun, H. L., Allen, T. L., Henstridge, D. C., Kraakman, M. J., Peijs, L., Rose-John, S., and Febbraio, M. A. (2017). Over-expressing the soluble gp130-Fc does not ameliorate methionine and choline deficient diet-induced non alcoholic steatohepatitis in mice. PLoS One 12, e0179099.

Kang, S., Tanaka, T., Narazaki, M., and Kishimoto, T. (2019). Targeting Interleukin-6 Signaling in Clinic. Immunity 50, 1007-1023.

Klein, C., Wüstefeld, T., Assmus, U., Roskams, T., Rose-John, S., Müller, M., Manns, M. P., Ernst, M., and Trautwein, C. (2005). The IL-6-gp130-STAT3 pathway in hepatocytes triggers liver protection in T cell-mediated liver injury. J. Clin. Invest. 115, 860-869.

Kleinfeld, A. M., Prothro, D., Brown, D. L., Davis, R. C., Richieri, G. V., and DeMaria, A. (1996). Increases in serum unbound free fatty acid levels following coronary angioplasty. Am. J. Cardiol. 78, 1350-1354.

Kleinfeld, A. M., Prothro, D., Brown, D. L., Davis, R. C., Richieri, G. V., and DeMaria, A. (1996). Increases in serum unbound free fatty acid levels following coronary angioplasty. Am. J. Cardiol. 78, 1350-1354.

Kraakman, M. J., Kammoun, H. L., Allen, T. L., Deswaerte, V., Henstridge, D. C., Estevez, E., Matthews, V. B., Neill, B., White, D. A., Murphy, A. J., et al. (2015). Blocking IL-6 trans-signaling prevents high-fat diet-induced adipose tissue macrophage recruitment but does not improve insulin resistance. Cell Metab. 21, 403-416.

Kroy, D. C., Beraza, N., Tschaharganeh, D. F., Sander, L. E., Erschfeld, S., Giebeler, A., Liedtke, C., Wasmuth, H. E., Trautwein, C., and Streetz, K. L. (2010). Lack of interleukin-6/glycoprotein 130/signal transducers and activators of transcription-3 signaling in hepatocytes predisposes to liver steatosis and injury in mice. Hepatology 51, 463-473.

Langmead, B., Trapnell, C., Pop, M., and Salzberg, S. L. (2009). Ultrafast and memory-efficient alignment of short DNA sequences to the human genome. Genome Biol. 10, R25.

Liao, Y., Smyth, G. K., and Shi, W. (2014). featureCounts: an efficient general purpose program for assigning sequence reads to genomic features. Bioinformatics 30, 923-930.

Maeshima, K., Takahashi, T., Nakahira, K., Shimizu, H., Fujii, H., Katayama, H., Yokoyama, M., Morita, K., Akagi, R., and Sassa, S. (2004). A protective role of interleukin 11 on hepatic injury in acute endotoxemia. Shock 21, 134-138.

Matthews, V. B., Allen, T. L., Risis, S., Chan, M. H. S., Henstridge, D. C., Watson, N., Zaffino, L. A., Babb, J. R., Boon, J., Meikle, P. J., et al. (2010). Interleukin-6-deficient mice develop hepatic inflammation and systemic insulin resistance. Diabetologia 53, 2431-2441.

Ng, B., Dong, J., D'Agostino, G., Viswanathan, S., Widjaja, A. A., Lim, W.-W., Ko, N. S. J., Tan, J., Chothani, S. P., Huang, B., et al. (2019). Interleukin-11 is a therapeutic target in idiopathic pulmonary fibrosis. Sci. Transl. Med. 11.

Ng, B., Dong, J., Viswanathan, S., Widjaja, A. A., Paleja, B. S., Adami, E., Ko, N. S. J., Wang, M., Lim, S., Tan, J., et al. Fibroblast-specific IL11 signaling is required for lung fibrosis and inflammation.

Nishina, T., Komazawa-Sakon, S., Yanaka, S., Piao, X., Zheng, D.-M., Piao, J.-H., Kojima, Y., Yamashina, S., Sano, E., Putoczki, T., et al. (2012). Interleukin-11 links oxidative stress and compensatory proliferation. Sci. Signal. 5, ra5.

Sanyal, A. J. (2019). Past, present and future perspectives in nonalcoholic fatty liver disease. Nat. Rev. Gastroenterol. Hepatol. 16, 377-386.

Schafer, S., Viswanathan, S., Widjaja, A. A., Lim, W.-W., Moreno-Moral, A., DeLaughter, D. M., Ng, B., Patone, G., Chow, K., Khin, E., et al. (2017). IL-11 is a crucial determinant of cardiovascular fibrosis. Nature 552, 110-115.

Schafer, S., Viswanathan, S., Widjaja, A. A., Lim, W.-W., Moreno-Moral, A., DeLaughter, D. M., Ng, B., Patone, G., Chow, K., Khin, E., et al. (2017). IL-11 is a crucial determinant of cardiovascular fibrosis. Nature 552, 110-115.

Schmidt-Arras, D., and Rose-John, S. (2016). IL-6 pathway in the liver: From physiopathology to therapy. J. Hepatol. 64, 1403-1415.

Stephenson, K., Kennedy, L., Hargrove, L., Demieville, J., Thomson, J., Alpini, G., and Francis, H. (2018). Updates on Dietary Models of Nonalcoholic Fatty Liver Disease: Current Studies and Insights. Gene Expr. 18, 5-17.

The RNAcentral Consortium (2017). RNAcentral: a comprehensive database of non-coding RNA sequences. Nucleic Acids Res. 45, D128-D134.

Trepicchio, W. L., Bozza, M., Bouchard, P., and Dorner, A. J. (2001). Protective effect of rhIL-11 in a murine model of acetaminophen-induced hepatotoxicity. Toxicol. Pathol. 29, 242-249.

Widjaja, A. A., Dong, J., Adami, E., Viswanathan, S., Ng, B., Singh, B. K., Lim, W. W., Zhou, J., Pakkiri, L. S., Shekeran, S. G., et al. Redefining Interleukin 11 as a regeneration-limiting hepatotoxin.

Widjaja, A. A., Singh, B. K., Adami, E., Viswanathan, S., Dong, J., D'Agostino, G. A., Ng, B., Lim, W. W., Tan, J., Paleja, B. S., et al. (2019). Inhibiting Interleukin 11 Signaling Reduces Hepatocyte Death and Liver Fibrosis, Inflammation, and Steatosis in Mouse Models of Non-Alcoholic Steatohepatitis. Gastroenterology.

Wieckowska, A., Papouchado, B. G., Li, Z., Lopez, R., Zein, N. N., and Feldstein, A. E. (2008). Increased hepatic and circulating interleukin-6 levels in human nonalcoholic steatohepatitis. Am. J. Gastroenterol. 103, 1372-1379.

Wuestefeld, T., Klein, C., Streetz, K. L., Betz, U., Lauber, J., Buer, J., Manns, M. P., Müller, W., and Trautwein, C. (2003). Interleukin-6/glycoprotein 130-dependent pathways are protective during liver regeneration. J. Biol. Chem. 278, 11281-11288.

Yamaguchi, K., Itoh, Y., Yokomizo, C., Nishimura, T., Niimi, T., Fujii, H., Okanoue, T., and Yoshikawa, T. (2010). Blockade of interleukin-6 signaling enhances hepatic steatosis but improves liver injury in methionine choline-deficient diet-fed mice. Lab. Invest. 90, 1169-1178.

Yu, J., Feng, Z., Tan, L., Pu, L., and Kong, L. (2016). Interleukin-11 protects mouse liver from warm ischemia/reperfusion (WI/Rp) injury. Clin. Res. Hepatol. Gastroenterol. 40, 562-570.

Zhu, M., Lu, B., Cao, Q., Wu, Z., Xu, Z., Li, W., Yao, X., and Liu, F. (2015). IL-11 Attenuates Liver Ischemia/Reperfusion Injury (IRI) through STAT3 Signaling Pathway in Mice. PLoS One 10, e0126296.

Example 6: Dissecting Fibro-Inflammatory Mechanisms in Pancreatitis

Chronic pancreatitis is an aetiologically heterogeneous fibro-inflammatory syndrome, which leads to exocrine and endocrine pancreatic insufficiency.

Pancreatic stellate cells (PSC) exist in two states and are the predominant fibrogenic cell type involved in pancreatic injury. PSCs are part of a wider retinoid-storing cellular network in the body, including cells in liver parenchyma (HSC). IL-11 has recently been shown to have a key role in HSC transformation, a defining pathology in NASH (Widjaja et al., Gastroenterology (2019) 157(3): 777-792).

Figure 47A:
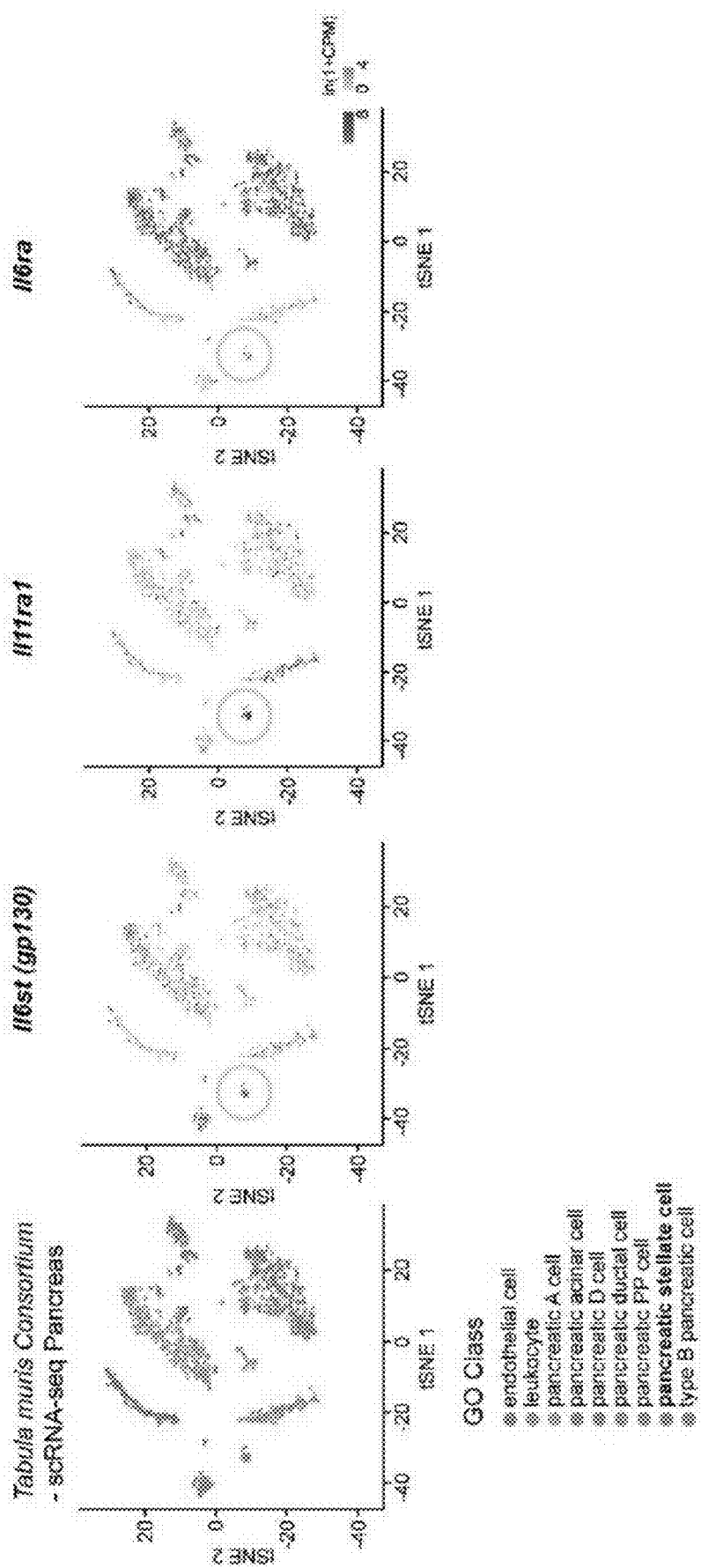
FIGS. 47A and 47B. Graphs and images showing that pancreatic stellate cells (PSCs) express IL-11Rα and gp130, but not IL-6Rα. (A) Single-cell RNA sequencing analysis of expression of Il6st (encoding gp130), Il11ra1 and Il6ra in mouse PSC and ductal cells. (B) Immunofluorescence analysis of expression of gp130, IL11 RA and IL6RA protein by human PSCs.
Figure 47B:
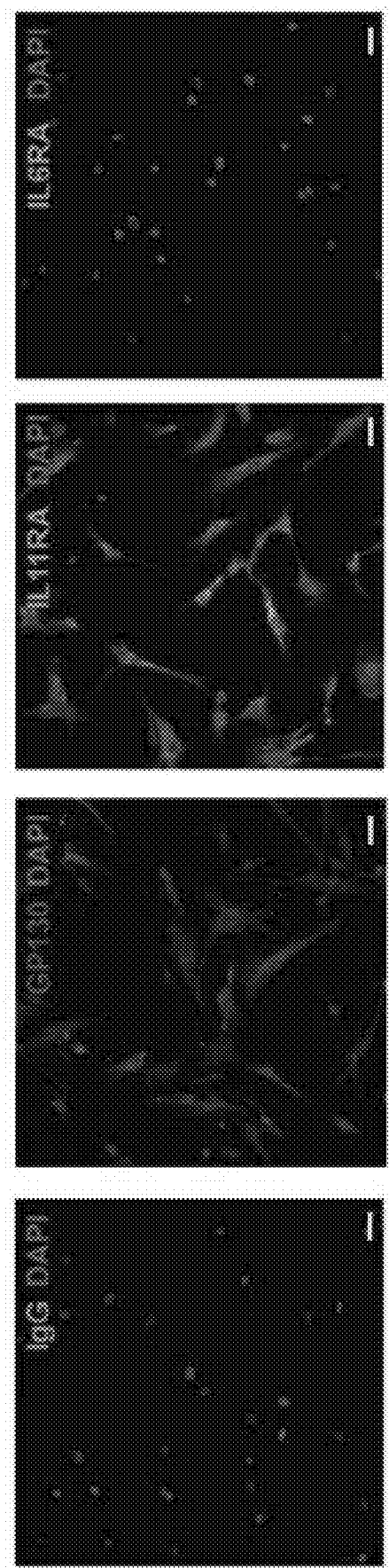

Single-cell RNA sequencing (scRNA-seq) analysis of pancreatic tissue from *Mus musculus* (from the Tabula muris Consortium data—Schaum et al., Nature (2018) 562: 367-372) reveals that PSCs (and ductal cells) display high expression of Il11ra1 but not Il6ra—see FIG. 47A. This result was confirmed at the protein level by immunofluorescence analysis of human PSCs (FIG. 47B).

Figure 48A:
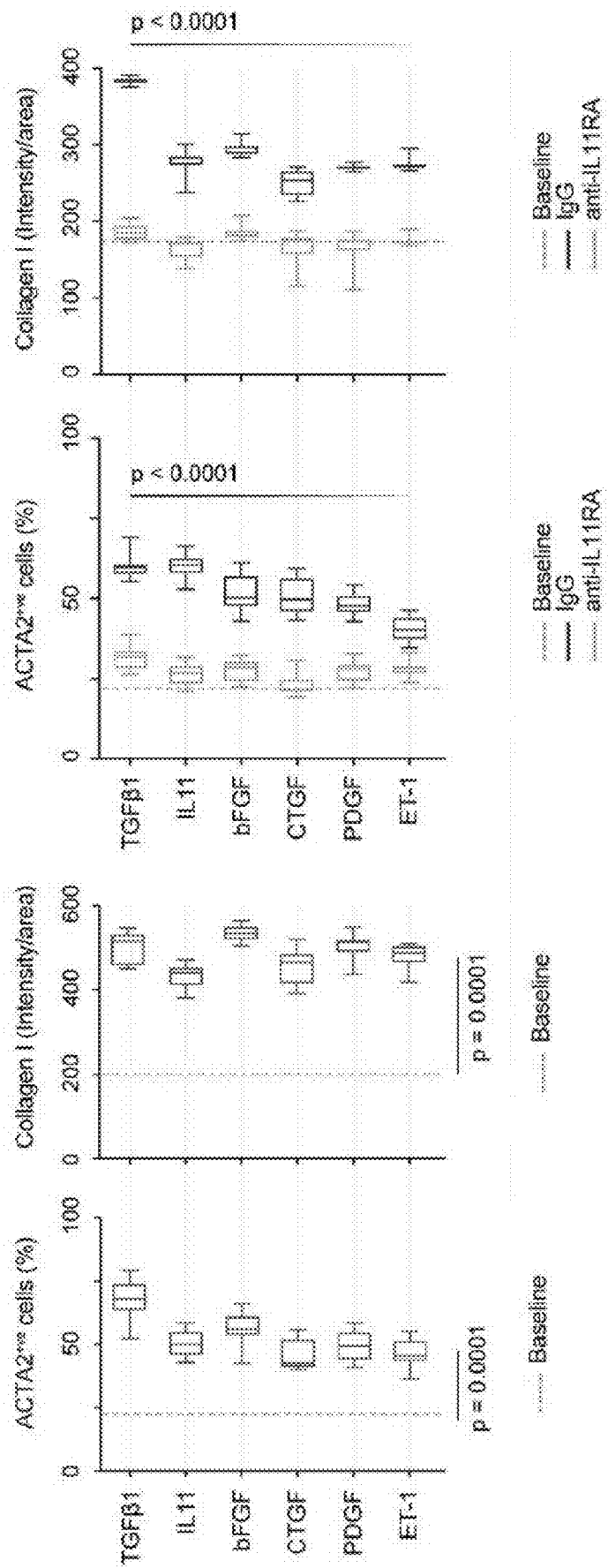
FIGS. 48A and 48B. Box plots and images showing activation of pancreatic stellate cells (PSCs) to a αSMA-positive, collagen-expressing fibrogenic phenotype. (A) Quantification of high-content imaging assays for the percentage of ACTA2-positive cells and collagen I intensity/area following in vitro stimulation of PSCs for 24 hours with the indicated factors, in the presence or absence of neutralising anti-IL-11 RA antibody or IgG isotype control antibody. (B) Representative images for high-content imaging analysis of collagen I intensity/area following in vitro stimulation of PSCs for 24 hours with the indicated factors, in the presence of neutralising anti-IL-11 RA antibody or IgG isotype control antibody.
Figure 48B:
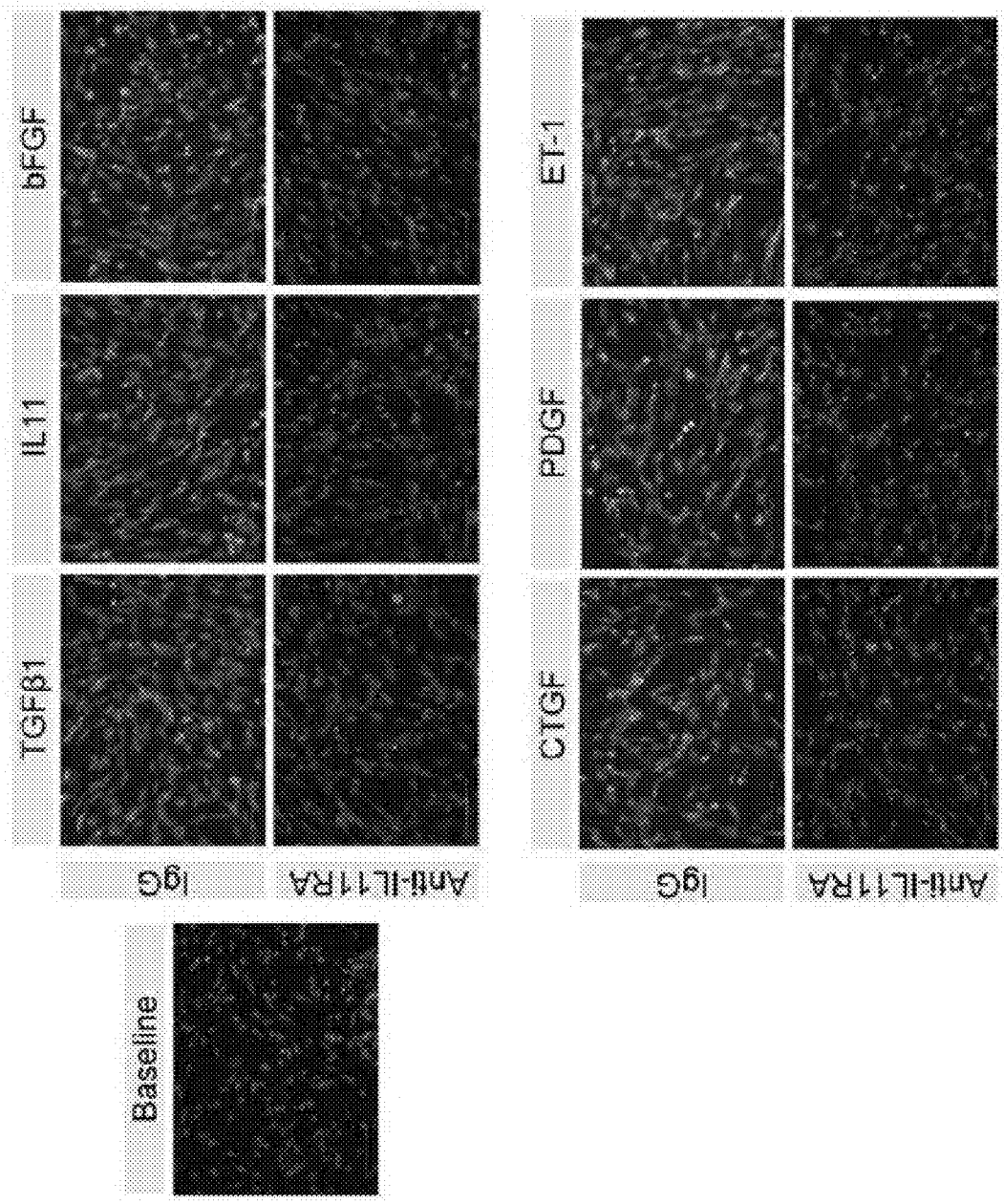

PSC activation was show to be triggered in vitro by treatment with IL-11, and was inhibited by treatment with an anti-IL-11 RA antibody antagonist of IL-11 mediated signalling, irrespective of the stimulus for PSC activation (i.e. TGFβ1, IL-11, bFGF, CTGF, PDGF or ET-1)—see FIGS. 48A and 48B.

Figure 49A:
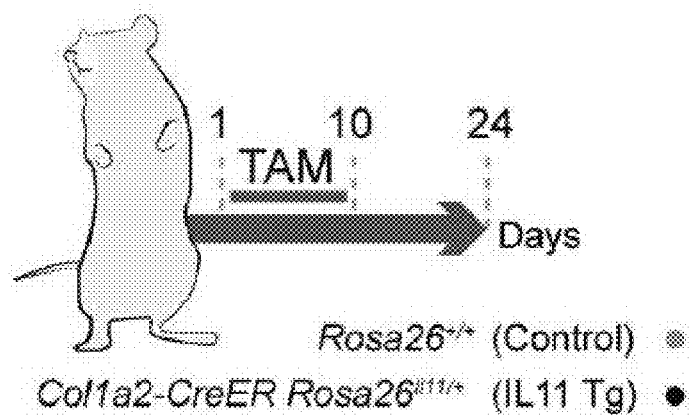
FIGS. 49A to 49C. Schematic, box plot and images relating to induction of pancreatic fibrosis in vivo in transgenic mice having inducible, fibroblast-specific expression of IL-11. (A) Schematic representation of experiment in which transgenic Col1a2-CreER Rosa26Il11/+(IL11 Tg) mice are induced by treatment with tamoxifen to express IL-11 in fibroblasts. (B) Hydroxyproline content of pancreatic tissue of control mice and IL11 Tg mice after 24 days. (C) Representative images of Masson's Trichrome staining of pancreatic tissue from control and IL11 Tg mice after 24 days.
Figure 49B:
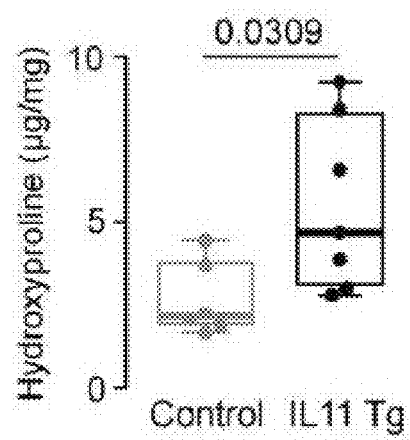
Figure 49C:
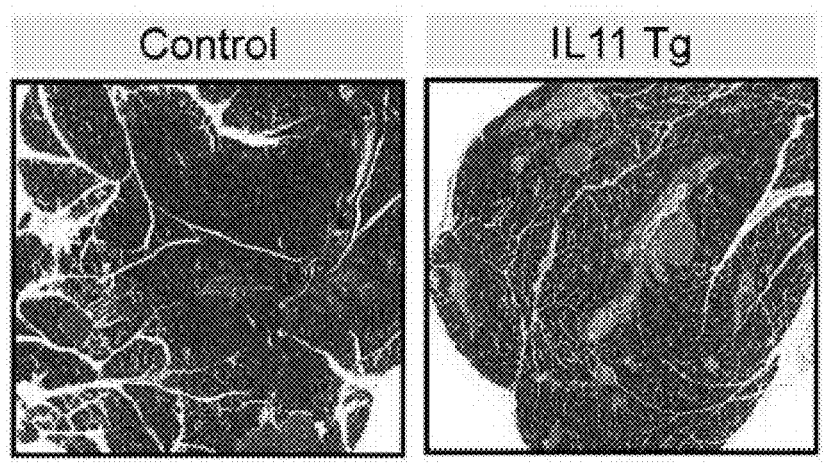

Transgenic mice having inducible, fibroblast-specific expression of IL-11 develop pancreatic fibrosis—see FIGS. 49A to 49C.

Figure 50A:
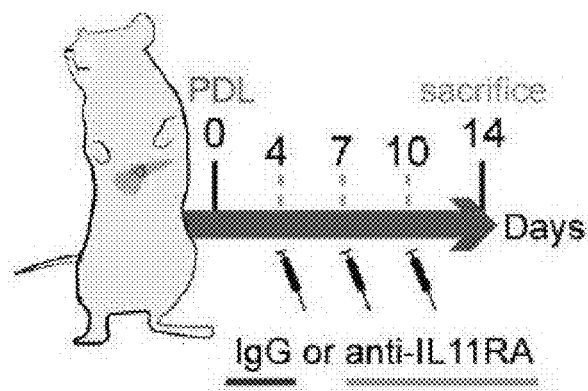
FIGS. 50A to 50C. Schematic, box plot and images relating to the effect of antagonism of IL-11 mediated signalling in a pancreatic duct ligation (PDL) model of pancreatic injury. (A) Schematic representation of experiment in which pancreatic injury is induced by PDL, and wherein mice are subsequently treated with neutralising anti-IL-11 RA antibody or IgG isotype control antibody. (B) Ligated lobe weight for mice treated with neutralising anti-IL-11 RA antibody or IgG isotype control antibody at 14 days. (C) Representative images of Masson's Trichrome staining of pancreatic tissue from mice treated with neutralising anti-IL-11 RA antibody or IgG isotype control antibody at 14 days.
Figure 50B:
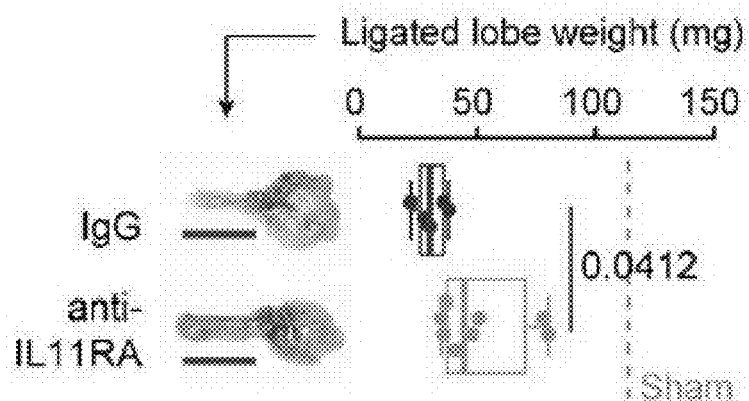
Figure 50C:
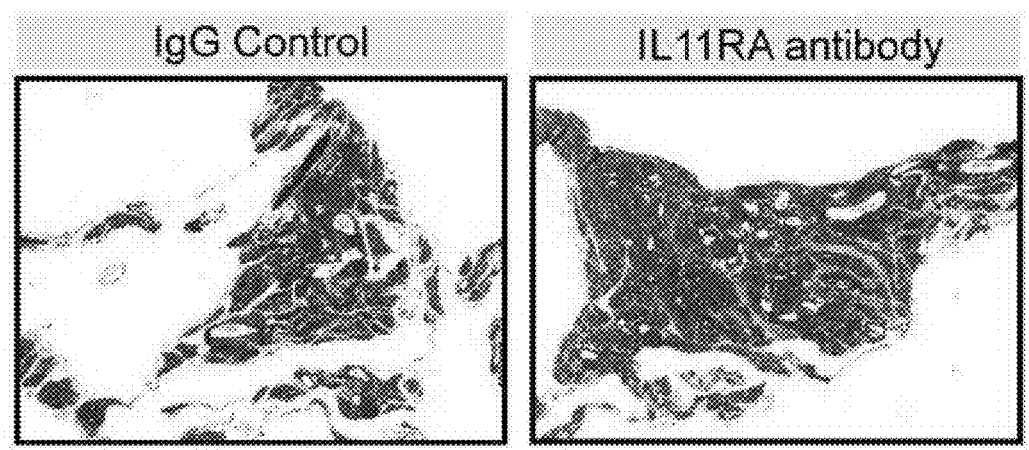

In a pancreatic duct ligation (PDL) model of pancreatic injury, treatment with an anti-IL-11 RA antibody antagonist of IL-11 mediated signalling reduced pancreatic fibrosis and inhibited the reduction in pancreatic tissue associated with PDL—see FIGS. 50A to 50C.

The invention claimed is:

1. A method of treating a metabolic disease, comprising administering a therapeutically or prophylactically effective amount of an agent capable of inhibiting interleukin 11 (IL-11)-mediated signalling to a subject;
wherein the agent is selected from: (i) an anti-IL-11 antibody antagonist of IL-11-mediated signalling, or an antigen-binding fragment thereof, or (ii) an anti-IL-11Rα antibody antagonist of IL-11-mediated signalling, or an antigen-binding fragment thereof;
and wherein the metabolic disease is or comprises: obesity, being overweight, hyperglycaemia, pregnancy-associated hyperglycemia, insulin resistance, pre-diabetes, metabolic syndrome, hyperlipidaemia, hypertriglyceridemia, hypercholesterolemia, pancreatic insufficiency, pancreatitis, acute pancreatitis, chronic pancreatitis, lipotoxicity, or hyperglucagonemia.

2. The method according to claim 1, wherein the agent is an agent capable of preventing or reducing the binding of interleukin 11 (IL-11) to a receptor for interleukin 11 (IL-11R).

3. The method according to claim 1, wherein the method comprises administering the agent to a subject in which expression of interleukin 11 (IL-11) or a receptor for IL-11 (IL-11R) is upregulated.

4. The method according to claim 1, wherein the method comprises administering the agent to a subject in which expression of interleukin 11 (IL-11) or a receptor for interleukin 11 (IL-11R) has been determined to be upregulated.

5. The method according to claim 1, wherein the method comprises determining whether expression of interleukin 11 (IL-11) or a receptor for IL-11 (IL-11R) is upregulated in the subject and administering the agent to a subject in which expression of interleukin 11 (IL-11) or a receptor for IL-11 (IL-11R) is upregulated.

6. The method according to claim 1, wherein the agent is an anti-IL-11 antibody antagonist of IL-11-mediated signalling, or an antigen-binding fragment thereof, comprising:

(i) a VH region incorporating the following CDRs:
HC-CDR1 having the amino acid sequence of SEQ ID NO: 40;
HC-CDR2 having the amino acid sequence of SEQ ID NO: 41;
HC-CDR3 having the amino acid sequence of SEQ ID NO: 42, and
(ii) a VL region incorporating the following CDRs:
LC-CDR1 having the amino acid sequence of SEQ ID NO: 43;
LC-CDR2 having the amino acid sequence of SEQ ID NO: 44;
LC-CDR3 having the amino acid sequence of SEQ ID NO: 45.

7. The method according to claim 1, wherein the agent is an anti-IL-11 antibody antagonist of IL-11-mediated signalling, or an antigen-binding fragment thereof, comprising:
(i) a VH region incorporating the following CDRs:
HC-CDR1 having the amino acid sequence of SEQ ID NO: 34;
HC-CDR2 having the amino acid sequence of SEQ ID NO: 35;
HC-CDR3 having the amino acid sequence of SEQ ID NO: 36,
and
(ii) a VL region incorporating the following CDRs:
LC-CDR1 having the amino acid sequence of SEQ ID NO: 37;
LC-CDR2 having the amino acid sequence of SEQ ID NO: 38;
LC-CDR3 having the amino acid sequence of SEQ ID NO: 39.

8. The method according to claim 1, wherein the agent is an anti-IL-11Rα antibody antagonist of IL-11-mediated signalling, or an antigen-binding fragment thereof, comprising:
(i) a VH region incorporating the following CDRs:
HC-CDR1 having the amino acid sequence of SEQ ID NO: 46;

HC-CDR2 having the amino acid sequence of SEQ ID NO: 47;
HC-CDR3 having the amino acid sequence of SEQ ID NO: 48,
and
(ii) a VL region incorporating the following CDRs:
LC-CDR1 having the amino acid sequence of SEQ ID NO: 49;
LC-CDR2 having the amino acid sequence of SEQ ID NO: 50;
LC-CDR3 having the amino acid sequence of SEQ ID NO: 51.

\* \* \* \* \*

UNITED STATES PATENT AND TRADEMARK OFFICE
CERTIFICATE OF CORRECTION

PATENT NO. : 11,813,311 B2
APPLICATION NO. : 16/865259
DATED : November 14, 2023
INVENTOR(S) : Stuart Alexander Cook et al.

It is certified that error appears in the above-identified patent and that said Letters Patent is hereby corrected as shown below:

On the Title Page

(30) Foreign Application Priority Data:
"May 3, 2019 (GB) ................................ 1906291
Jan. 24, 2020 (GB) ................................ 2001013
Feb. 12, 2020 (GB) ................................ 2001896
Feb. 14, 2020 (GB) ................................ 2002030"

Should be replaced with:
--May 3, 2019 (GB) ................................ 1906291
May 10, 2019 (GB) ................................ 1906597
Jan. 24, 2020 (GB) ................................ 2001013
Feb. 12, 2020 (GB) ................................ 2001896
Feb. 14, 2020 (GB) ................................ 2002030--

Signed and Sealed this
Nineteenth Day of December, 2023

Katherine Kelly Vidal
*Director of the United States Patent and Trademark Office*

SEQUENCE LISTING

```
<160> NUMBER OF SEQ ID NOS: 60

<210> SEQ ID NO 1
<211> LENGTH: 199
<212> TYPE: PRT
<213> ORGANISM: Homo sapiens
<220> FEATURE:
<223> OTHER INFORMATION: IL-11 (UniProt P20809)
```

<400> SEQUENCE: 1

```
Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
            35                  40                  45

Leu Leu Ala Asp Thr Arg Gln Leu Ala Ala Gln Leu Arg Asp Lys Phe
        50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
        195
```

<210> SEQ ID NO 2
<211> LENGTH: 918
<212> TYPE: PRT
<213> ORGANISM: Homo sapiens
<220> FEATURE:
<223> OTHER INFORMATION: gp130 (UniProt P40189-1)

<400> SEQUENCE: 2

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140
```

Glu Trp Asp Gly Gly Arg Glu Thr His Leu Thr Asn Phe Thr Leu
145                 150                 155                 160

Lys Ser Glu Trp Ala Thr His Lys Phe Ala Asp Cys Lys Ala Lys Arg
            165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
        370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu

```
                        565                 570                 575
Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 3
<211> LENGTH: 422
<212> TYPE: PRT
<213> ORGANISM: Homo sapiens
<220> FEATURE:
<223> OTHER INFORMATION: IL11RA (UniProt Q14626)

<400> SEQUENCE: 3

Met Ser Ser Ser Cys Ser Gly Leu Ser Arg Val Leu Val Ala Val Ala
```

-continued

```
  1               5                  10                 15
Thr Ala Leu Val Ser Ala Ser Pro Cys Pro Gln Ala Trp Gly Pro
                 20                 25                 30

Pro Gly Val Gln Tyr Gly Gln Pro Gly Arg Ser Val Lys Leu Cys Cys
                 35                 40                 45

Pro Gly Val Thr Ala Gly Asp Pro Val Ser Trp Phe Arg Asp Gly Glu
 50                 55                 60

Pro Lys Leu Leu Gln Gly Pro Asp Ser Gly Leu Gly His Glu Leu Val
 65                 70                 75                 80

Leu Ala Gln Ala Asp Ser Thr Asp Glu Gly Thr Tyr Ile Cys Gln Thr
                 85                 90                 95

Leu Asp Gly Ala Leu Gly Gly Thr Val Thr Leu Gln Leu Gly Tyr Pro
                100                105                110

Pro Ala Arg Pro Val Val Ser Cys Gln Ala Ala Asp Tyr Glu Asn Phe
                115                120                125

Ser Cys Thr Trp Ser Pro Ser Gln Ile Ser Gly Leu Pro Thr Arg Tyr
                130                135                140

Leu Thr Ser Tyr Arg Lys Lys Thr Val Leu Gly Ala Asp Ser Gln Arg
145                150                155                160

Arg Ser Pro Ser Thr Gly Pro Trp Pro Cys Pro Gln Asp Pro Leu Gly
                165                170                175

Ala Ala Arg Cys Val Val His Gly Ala Glu Phe Trp Ser Gln Tyr Arg
                180                185                190

Ile Asn Val Thr Glu Val Asn Pro Leu Gly Ala Ser Thr Arg Leu Leu
                195                200                205

Asp Val Ser Leu Gln Ser Ile Leu Arg Pro Asp Pro Pro Gln Gly Leu
                210                215                220

Arg Val Glu Ser Val Pro Gly Tyr Pro Arg Arg Leu Arg Ala Ser Trp
225                230                235                240

Thr Tyr Pro Ala Ser Trp Pro Cys Gln Pro His Phe Leu Leu Lys Phe
                245                250                255

Arg Leu Gln Tyr Arg Pro Ala Gln His Pro Ala Trp Ser Thr Val Glu
                260                265                270

Pro Ala Gly Leu Glu Glu Val Ile Thr Asp Ala Val Ala Gly Leu Pro
                275                280                285

His Ala Val Arg Val Ser Ala Arg Asp Phe Leu Asp Ala Gly Thr Trp
                290                295                300

Ser Thr Trp Ser Pro Glu Ala Trp Gly Thr Pro Ser Thr Gly Thr Ile
305                310                315                320

Pro Lys Glu Ile Pro Ala Trp Gly Gln Leu His Thr Gln Pro Glu Val
                325                330                335

Glu Pro Gln Val Asp Ser Pro Ala Pro Pro Arg Pro Ser Leu Gln Pro
                340                345                350

His Pro Arg Leu Leu Asp His Arg Asp Ser Val Glu Gln Val Ala Val
                355                360                365

Leu Ala Ser Leu Gly Ile Leu Ser Phe Leu Gly Leu Val Ala Gly Ala
                370                375                380

Leu Ala Leu Gly Leu Trp Leu Arg Leu Arg Arg Gly Gly Lys Asp Gly
385                390                395                400

Ser Pro Lys Pro Gly Phe Leu Ala Ser Val Ile Pro Val Asp Arg Arg
                405                410                415

Pro Gly Ala Pro Asn Leu
                420
```

<210> SEQ ID NO 4
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 4
ccttccaaag ccagatctt					19

<210> SEQ ID NO 5
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 5
gcctgggcag gaacatata					19

<210> SEQ ID NO 6
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 6
cctgggcagg aacatatat					19

<210> SEQ ID NO 7
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 7
ggttcattat ggctgtgtt					19

<210> SEQ ID NO 8
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 8
ggaccatacc aaaggagat					19

<210> SEQ ID NO 9
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 9
gcgtctttgg gaatccttt					19

<210> SEQ ID NO 10
<211> LENGTH: 18
<212> TYPE: DNA
<213> ORGANISM: Artificial Sequence
<220> FEATURE:

```
<223> OTHER INFORMATION: siRNA target IL-11Ralpha

<400> SEQUENCE: 10
gcaggacagt agatccct                                                        18

<210> SEQ ID NO 11
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 11
gctcaaggaa cgtgtgtaa                                                       19

<210> SEQ ID NO 12
<211> LENGTH: 42
<212> TYPE: RNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 12
ccuuccaaag ccagaucuun naagaucugg cuuuggaagg nn                             42

<210> SEQ ID NO 13
<211> LENGTH: 42
<212> TYPE: RNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 13
gccugggcag gaacauauan nuauauguuc cugcccaggc nn                             42

<210> SEQ ID NO 14
<211> LENGTH: 42
<212> TYPE: RNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 14
ccugggcagg aacauauaun nauauauguu ccugcccagg nn                             42
```

```
<210> SEQ ID NO 15
<211> LENGTH: 42
<212> TYPE: RNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 15
gguucauuau ggcuguguun naacacagcc auaaugaacc nn                              42

<210> SEQ ID NO 16
<211> LENGTH: 42
<212> TYPE: RNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 16
ggaccauacc aaaggagaun naucuccuuu gguauggucc nn                              42

<210> SEQ ID NO 17
<211> LENGTH: 42
<212> TYPE: RNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 17
gcgucuuugg gaauccuuun naaaggauuc ccaaagacgc nn                              42

<210> SEQ ID NO 18
<211> LENGTH: 42
<212> TYPE: RNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 18
gcaggacagu agaucccuan nuagggaucu acguccugc nn                              42
```

```
<210> SEQ ID NO 19
<211> LENGTH: 42
<212> TYPE: RNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymidine
<220> FEATURE:
<221> NAME/KEY: misc_feature
<222> LOCATION: (41)..(42)
<223> OTHER INFORMATION: n = deoxythymidine

<400> SEQUENCE: 19
gcucaaggaa cguguguaan nuuacacacg uuccuugagc nn                42

<210> SEQ ID NO 20
<211> LENGTH: 21
<212> TYPE: PRT
<213> ORGANISM: Artificial Sequence
<220> FEATURE:
<223> OTHER INFORMATION: 20 amino acid linker

<400> SEQUENCE: 20

Gly Pro Ala Gly Gln Ser Gly Gly Gly Gly Ser Gly Gly Gly Ser
1               5                   10                  15

Gly Gly Gly Ser Val
            20

<210> SEQ ID NO 21
<211> LENGTH: 516
<212> TYPE: PRT
<213> ORGANISM: Artificial Sequence
<220> FEATURE:
<223> OTHER INFORMATION: Hyper IL-11 (IL-11RA:IL-11 fusion)

<400> SEQUENCE: 21

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175
```

```
Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
        260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
        290                 295                 300

Ser Thr Trp Ser Pro Glu Ala Trp Gly Thr Pro Ser Thr Gly Pro Ala
305                 310                 315                 320

Gly Gln Ser Gly Gly Gly Gly Ser Gly Gly Ser Gly Gly Gly
                325                 330                 335

Ser Val Pro Gly Pro Pro Gly Pro Pro Arg Val Ser Pro Asp Pro
                340                 345                 350

Arg Ala Glu Leu Asp Ser Thr Val Leu Leu Thr Arg Ser Leu Leu Ala
                355                 360                 365

Asp Thr Arg Gln Leu Ala Ala Gln Leu Arg Asp Lys Phe Pro Ala Asp
        370                 375                 380

Gly Asp His Asn Leu Asp Ser Leu Pro Thr Leu Ala Met Ser Ala Gly
385                 390                 395                 400

Ala Leu Gly Ala Leu Gln Leu Pro Gly Val Leu Thr Arg Leu Arg Ala
                405                 410                 415

Asp Leu Leu Ser Tyr Leu Arg His Val Gln Trp Leu Arg Arg Ala Gly
                420                 425                 430

Gly Ser Ser Leu Lys Thr Leu Glu Pro Glu Leu Gly Thr Leu Gln Ala
        435                 440                 445

Arg Leu Asp Arg Leu Leu Arg Arg Leu Gln Leu Leu Met Ser Arg Leu
450                 455                 460

Ala Leu Pro Gln Pro Pro Asp Pro Pro Ala Pro Pro Leu Ala Pro
465                 470                 475                 480

Pro Ser Ser Ala Trp Gly Gly Ile Arg Ala Ala His Ala Ile Leu Gly
                485                 490                 495

Gly Leu His Leu Thr Leu Asp Trp Ala Val Arg Gly Leu Leu Leu Leu
                500                 505                 510

Lys Thr Arg Leu
        515

<210> SEQ ID NO 22
<211> LENGTH: 119
<212> TYPE: PRT
<213> ORGANISM: Artificial Sequence
<220> FEATURE:
<223> OTHER INFORMATION: Enx203 VH

<400> SEQUENCE: 22

Glu Val Gln Leu Gln Gln Ser Gly Pro Glu Leu Val Lys Pro Gly Ala
1               5                   10                  15
```

Ser Val Lys Ile Pro Cys Lys Ala Ser Gly Tyr Thr Phe Thr Asp Tyr
             20                  25                  30

Asn Met Asp Trp Val Lys Gln Ser His Gly Lys Ser Leu Glu Trp Ile
         35                  40                  45

Gly Asp Ile Asn Pro His Asn Gly Gly Pro Ile Tyr Asn Gln Lys Phe
     50                  55                  60

Thr Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                 85                  90                  95

Ala Arg Gly Glu Leu Gly His Trp Tyr Phe Asp Val Trp Gly Thr Gly
             100                 105                 110

Thr Thr Val Thr Val Ser Ser
             115

<210> SEQ ID NO 23
<211> LENGTH: 111
<212> TYPE: PRT
<213> ORGANISM: Artificial Sequence
<220> FEATURE:
<223> OTHER INFORMATION: Enx203 VL

<400> SEQUENCE: 23

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
             20                  25                  30

Gly Tyr Ser Tyr Ile His Trp Tyr Gln Gln Lys Pro Gly Gln Pro Pro
         35                  40                  45

Lys Leu Leu Ile Tyr Leu Ala Ser Asn Leu Asp Ser Gly Val Pro Ala
     50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                 85                  90                  95

Asp Leu Pro Pro Thr Phe Gly Gly Gly Thr Lys Leu Glu Ile Lys
             100                 105                 110

<210> SEQ ID NO 24
<211> LENGTH: 117
<212> TYPE: PRT
<213> ORGANISM: Artificial Sequence
<220> FEATURE:
<223> OTHER INFORMATION: Enx209 VH

<400> SEQUENCE: 24

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Asn Tyr
             20                  25                  30

Trp Met His Trp Leu Lys Gln Arg Pro Val Gln Gly Leu Glu Trp Ile
         35                  40                  45

Gly Asn Ile Gly Pro Ser Asp Ser Lys Thr His Tyr Asn Gln Lys Phe
     50                  55                  60

Lys Asp Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                 85                  90                  95

```
Ala Arg Gly Asp Tyr Val Leu Phe Thr Tyr Trp Gly Gln Gly Thr Leu
                100                 105                 110

Val Thr Val Ser Ala
        115

<210> SEQ ID NO 25
<211> LENGTH: 107
<212> TYPE: PRT
<213> ORGANISM: Artificial Sequence
<220> FEATURE:
<223> OTHER INFORMATION: Enx209 VL

<400> SEQUENCE: 25

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Ser His Glu Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Ser Phe Ser Ser Leu Glu Thr
65                  70                  75                  80

Glu Asp Phe Ala Val Tyr Phe Cys Gln Gln Ser Tyr Ser Trp Pro Leu
                85                  90                  95

Thr Phe Gly Gln Gly Thr Lys Leu Glu Ile Lys
            100                 105

<210> SEQ ID NO 26
<211> LENGTH: 118
<212> TYPE: PRT
<213> ORGANISM: Artificial Sequence
<220> FEATURE:
<223> OTHER INFORMATION: Enx108A VH

<400> SEQUENCE: 26

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
                100                 105                 110

Leu Val Thr Val Ser Ser
        115

<210> SEQ ID NO 27
<211> LENGTH: 111
<212> TYPE: PRT
<213> ORGANISM: Artificial Sequence
<220> FEATURE:
<223> OTHER INFORMATION: Enx108A VL
```

<400> SEQUENCE: 27

```
Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Thr Lys Val Thr Val Leu Gly
            100                 105                 110
```

<210> SEQ ID NO 28
<211> LENGTH: 445
<212> TYPE: PRT
<213> ORGANISM: Artificial Sequence
<220> FEATURE:
<223> OTHER INFORMATION: Enx108A hIgG4 (L248E, S241P) HC

<400> SEQUENCE: 28

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 29
<211> LENGTH: 216
<212> TYPE: PRT
<213> ORGANISM: Artificial Sequence
<220> FEATURE:
<223> OTHER INFORMATION: Enx108A lambda LC

<400> SEQUENCE: 29

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
        180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 30
<211> LENGTH: 119
<212> TYPE: PRT
<213> ORGANISM: Artificial Sequence
<220> FEATURE:
<223> OTHER INFORMATION: hEnx203 VH

<400> SEQUENCE: 30

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser
        115

<210> SEQ ID NO 31
<211> LENGTH: 111
<212> TYPE: PRT
<213> ORGANISM: Artificial Sequence
<220> FEATURE:
<223> OTHER INFORMATION: hEnx203 VL

<400> SEQUENCE: 31

Asp Ile Val Leu Thr Gln Ser Pro Ala Ser Leu Ala Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys
            100                 105                 110

<210> SEQ ID NO 32
```

<211> LENGTH: 117
<212> TYPE: PRT
<213> ORGANISM: Artificial Sequence
<220> FEATURE:
<223> OTHER INFORMATION: hEnx209 VH

<400> SEQUENCE: 32

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met His Trp Leu Arg Gln Arg Pro Gly Gln Gly Leu Glu Trp Ile
        35                  40                  45
Gly Asn Ile Gly Pro Ser Asp Ser Lys Thr His Tyr Asn Gln Lys Phe
    50                  55                  60
Lys Asp Arg Val Thr Met Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Asp Tyr Val Leu Phe Thr Tyr Trp Gly Gln Gly Thr Leu
            100                 105                 110
Val Thr Val Ser Ser
        115

<210> SEQ ID NO 33
<211> LENGTH: 107
<212> TYPE: PRT
<213> ORGANISM: Artificial Sequence
<220> FEATURE:
<223> OTHER INFORMATION: hEnx209 VL

<400> SEQUENCE: 33

Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Ile Ser Asn Asn
            20                  25                  30
Leu His Trp Tyr Gln Gln Lys Pro Gly Gln Ala Pro Arg Leu Leu Ile
        35                  40                  45
Lys Tyr Ala Ser Gln Ser Ile Ser Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ser Tyr Ser Trp Pro Leu
                85                  90                  95
Thr Phe Gly Gln Gly Thr Lys Leu Glu Ile Lys
            100                 105

<210> SEQ ID NO 34
<211> LENGTH: 5
<212> TYPE: PRT
<213> ORGANISM: Artificial Sequence
<220> FEATURE:
<223> OTHER INFORMATION: Enx108A VH CDR1

<400> SEQUENCE: 34

Ser Tyr Gly Met His
1               5

<210> SEQ ID NO 35
<211> LENGTH: 17

```
<212> TYPE: PRT
<213> ORGANISM: Artificial Sequence
<220> FEATURE:
<223> OTHER INFORMATION: Enx108A VH CDR2

<400> SEQUENCE: 35

Val Ile Ser Tyr Asp Gly Ser Asn Lys Tyr Tyr Ala Asp Ser Val Lys
1               5                   10                  15
Gly

<210> SEQ ID NO 36
<211> LENGTH: 9
<212> TYPE: PRT
<213> ORGANISM: Artificial Sequence
<220> FEATURE:
<223> OTHER INFORMATION: Enx108A VH CDR3

<400> SEQUENCE: 36

Ile Gly Ala Thr Asp Pro Leu Asp Tyr
1               5

<210> SEQ ID NO 37
<211> LENGTH: 14
<212> TYPE: PRT
<213> ORGANISM: Artificial Sequence
<220> FEATURE:
<223> OTHER INFORMATION: Enx108A VL CDR1

<400> SEQUENCE: 37

Thr Gly Thr Ser Ser Asp Val Gly Gly Tyr Asn Tyr Val Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Enx108A VL CDR2

<400> SEQUENCE: 38

Asp Val Asn Glu Arg Ser Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Enx108A VL CDR3

<400> SEQUENCE: 39

Ala Ser Tyr Ala Gly Arg Tyr Thr Trp Met
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Enx203, hEnx203 VH CDR1

<400> SEQUENCE: 40

Asp Tyr Asn Met Asp
1               5

<210> SEQ ID NO 41
```

```
<211> LENGTH: 17
<212> TYPE: PRT
<213> ORGANISM: Artificial Sequence
<220> FEATURE:
<223> OTHER INFORMATION: Enx203, hEnx203 VH CDR2

<400> SEQUENCE: 41

Asp Ile Asn Pro His Asn Gly Gly Pro Ile Tyr Asn Gln Lys Phe Thr
1               5                   10                  15

Gly

<210> SEQ ID NO 42
<211> LENGTH: 10
<212> TYPE: PRT
<213> ORGANISM: Artificial Sequence
<220> FEATURE:
<223> OTHER INFORMATION: Enx203, hEnx203 VH CDR3

<400> SEQUENCE: 42

Gly Glu Leu Gly His Trp Tyr Phe Asp Val
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Enx203, hEnx203 VL CDR1

<400> SEQUENCE: 43

Arg Ala Ser Lys Ser Val Ser Thr Ser Gly Tyr Ser Tyr Ile His
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Enx203, hEnx203 VL CDR2

<400> SEQUENCE: 44

Leu Ala Ser Asn Leu Asp Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Enx203, hEnx203 VL CDR3

<400> SEQUENCE: 45

Gln His Ser Arg Asp Leu Pro Pro Thr
1               5

<210> SEQ ID NO 46
<211> LENGTH: 5
<212> TYPE: PRT
<213> ORGANISM: Artificial Sequence
<220> FEATURE:
<223> OTHER INFORMATION: Enx209, hEnx209 VH CDR1

<400> SEQUENCE: 46

Asn Tyr Trp Met His
1               5
```

```
<210> SEQ ID NO 47
<211> LENGTH: 17
<212> TYPE: PRT
<213> ORGANISM: Artificial Sequence
<220> FEATURE:
<223> OTHER INFORMATION: Enx209, hEnx209 VH CDR2

<400> SEQUENCE: 47

Asn Ile Gly Pro Ser Asp Ser Lys Thr His Tyr Asn Gln Lys Phe Lys
1               5                   10                  15
Asp

<210> SEQ ID NO 48
<211> LENGTH: 8
<212> TYPE: PRT
<213> ORGANISM: Artificial Sequence
<220> FEATURE:
<223> OTHER INFORMATION: Enx209, hEnx209 VH CDR3

<400> SEQUENCE: 48

Gly Asp Tyr Val Leu Phe Thr Tyr
1               5

<210> SEQ ID NO 49
<211> LENGTH: 11
<212> TYPE: PRT
<213> ORGANISM: Artificial Sequence
<220> FEATURE:
<223> OTHER INFORMATION: Enx209, hEnx209 VL CDR1

<400> SEQUENCE: 49

Arg Ala Ser Gln Ser Ile Ser Asn Asn Leu His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Enx209, hEnx209 VL CDR2

<400> SEQUENCE: 50

Tyr Ala Ser Gln Ser Ile Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Enx209, hEnx209 VL CDR3

<400> SEQUENCE: 51

Gln Gln Ser Tyr Ser Trp Pro Leu Thr
1               5

<210> SEQ ID NO 52
<211> LENGTH: 330
<212> TYPE: PRT
<213> ORGANISM: Homo sapiens
<220> FEATURE:
<223> OTHER INFORMATION: IGHG1 constant (K214R, D356E, L358M)

<400> SEQUENCE: 52

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 327
<212> TYPE: PRT
<213> ORGANISM: Homo sapiens
<220> FEATURE:
<223> OTHER INFORMATION: IGHG4 constant (L248E, S241P)

<400> SEQUENCE: 53

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 54
<211> LENGTH: 107
<212> TYPE: PRT
<213> ORGANISM: Homo sapiens
<220> FEATURE:
<223> OTHER INFORMATION: IGKC constant

<400> SEQUENCE: 54

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
 65                 70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 106
<212> TYPE: PRT
<213> ORGANISM: Homo sapiens
<220> FEATURE:
<223> OTHER INFORMATION: IGLC2 constant

<400> SEQUENCE: 55

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 56
<211> LENGTH: 449
<212> TYPE: PRT
<213> ORGANISM: Artificial Sequence
<220> FEATURE:
<223> OTHER INFORMATION: hEnx203 hIgG1 HC

<400> SEQUENCE: 56

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 57
<211> LENGTH: 218
<212> TYPE: PRT
<213> ORGANISM: Artificial Sequence
<220> FEATURE:
<223> OTHER INFORMATION: hEnx203 kappa LC

<400> SEQUENCE: 57

Asp Ile Val Leu Thr Gln Ser Pro Ala Ser Leu Ala Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Thr Ile Ser
65                  70                  75                  80
```

```
Ser Leu Glu Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215
```

<210> SEQ ID NO 58
<211> LENGTH: 444
<212> TYPE: PRT
<213> ORGANISM: Artificial Sequence
<220> FEATURE:
<223> OTHER INFORMATION: hEnx209 hIgG4 (L248E, S241P) HC

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220
```

```
Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 59
<211> LENGTH: 214
<212> TYPE: PRT
<213> ORGANISM: Artificial Sequence
<220> FEATURE:
<223> OTHER INFORMATION: hEnx209 kappa LC

<400> SEQUENCE: 59

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Trp Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 60
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 60

Gly Pro Ala Gly Gln Ser Gly Gly Gly Gly Ser Gly Gly Gly Ser
1               5                   10                  15

Gly Gly Gly Ser Val
            20
```